United States Patent
Kanouni et al.

(10) Patent No.: US 9,617,242 B2
(45) Date of Patent: Apr. 11, 2017

(54) HISTONE DEMETHYLASE INHIBITORS

(71) Applicant: Quanticel Pharmaceuticals, Inc., San Diego, CA (US)

(72) Inventors: Toufike Kanouni, La Jolla, CA (US); Jeffrey Alan Stafford, San Diego, CA (US); James Marvin Veal, Apex, CA (US); Michael Brennan Wallace, San Diego, CA (US)

(73) Assignee: CELGENE QUANTICEL RESEARCH, INC., San Diego, CA (US)

( * ) Notice: Subject to any disclaimer, the term of this patent is extended or adjusted under 35 U.S.C. 154(b) by 85 days.

(21) Appl. No.: 14/653,818

(22) PCT Filed: Dec. 19, 2013

(86) PCT No.: PCT/US2013/076666
§ 371 (c)(1),
(2) Date: Aug. 28, 2015

(87) PCT Pub. No.: WO2014/100463
PCT Pub. Date: Jun. 26, 2014

(65) Prior Publication Data
US 2016/0060247 A1    Mar. 3, 2016

Related U.S. Application Data

(60) Provisional application No. 61/792,930, filed on Mar. 15, 2013, provisional application No. 61/739,521, filed on Dec. 19, 2012.

(51) Int. Cl.
| | | |
|---|---|---|
| *C07D 401/00* | (2006.01) |
| *C07D 401/12* | (2006.01) |
| *C07D 401/14* | (2006.01) |
| *C07D 403/12* | (2006.01) |
| *C07D 405/14* | (2006.01) |
| *C07D 413/12* | (2006.01) |
| *C07D 471/04* | (2006.01) |
| *C07D 413/14* | (2006.01) |

(52) U.S. Cl.
CPC ......... *C07D 401/12* (2013.01); *C07D 401/14* (2013.01); *C07D 403/12* (2013.01); *C07D 405/14* (2013.01); *C07D 413/12* (2013.01); *C07D 413/14* (2013.01); *C07D 471/04* (2013.01)

(58) Field of Classification Search
None
See application file for complete search history.

(56) References Cited

U.S. PATENT DOCUMENTS

| | | |
|---|---|---|
| 8,299,057 B2 | 10/2012 | Lombardi et al. |
| 8,969,343 B2 | 3/2015 | Kanouni et al. |
| 2004/0110956 A1 | 6/2004 | Lesuisse et al. |
| 2008/0070960 A1 | 3/2008 | Bertin et al. |
| 2011/0237590 A1 | 9/2011 | Kitamura et al. |

FOREIGN PATENT DOCUMENTS

| | | |
|---|---|---|
| WO | WO02/074388 | 9/2002 |
| WO | WO-2005009978 A1 | 2/2005 |
| WO | WO-2011140325 A1 | 11/2011 |
| WO | WO2012/118812 | 9/2012 |
| WO | WO-2014100463 A1 | 6/2014 |

OTHER PUBLICATIONS

CAPLUS 1973:492089.*
Klose et al. JmjC-domain-containing proteins and histone demethylation. Nature Reviews Genetics 7:715-727 (Sep. 2006).
Lachner et al. An epigenetic road map for histone lysine methylation. Journal of Cell Science 116:2117-2124 (Jun. 1, 2003).
Lin et al. Loss of the retinoblastoma binding protein 2 (RBP2) histone demethylase supresses tumorigenesis in mice lacking RB1 or Men1.PNAS108(33):13379-13386 (2011).
Mangueron et al. The key to development: interpreting the histone code? Current Opinion Genet. Dev.15:163-176 (2005).
PCT/US2013/076666 International Preliminary Report on Patentability dated Jul. 2, 2015.
PCT/US2013/76666 International Search Report and Written Opinion Dated Apr. 21, 2014.

* cited by examiner

*Primary Examiner* — Heidi Reese
(74) *Attorney, Agent, or Firm* — Wiley Rein LLP

(57) ABSTRACT

The present invention relates generally to compositions and methods for treating cancer and neoplastic disease. Provided herein are substituted 3-aminopyridine derivative compounds, substituted 3-aminopyridazine derivative compounds, and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like.

3 Claims, No Drawings

HISTONE DEMETHYLASE INHIBITORS

CROSS REFERENCE

This application is the National Phase entry of International Application No. PCT/US2013/076666 filed Dec. 19, 2013, which claims the benefit of U.S. Provisional Application No. 61/792,930, filed Mar. 15, 2013, and U.S. Provisional Application No. 61/739,521, filed Dec. 19, 2012, the contents of which are hereby incorporated by reference in their entireties.

BACKGROUND

A need exists in the art for an effective treatment of cancer and neoplastic disease.

BRIEF SUMMARY OF THE INVENTION

Provided herein are substituted aminopyridine and substituted aminopyridazine derivative compounds and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like. The substituted aminopyridine and aminopyridazine derivative compounds described herein are based upon a disubstituted pyridine or pyridazine ring bearing at the 4-position a carboxylic acid, a carboxylic acid ester, or a carboxylic acid bioisostere thereof, and at the 3-position a substituted amino group.

One embodiment provides a compound of Formula (I) or a tautomer, stereoisomer, geometric isomer, N-oxide, or pharmaceutically acceptable salt thereof,

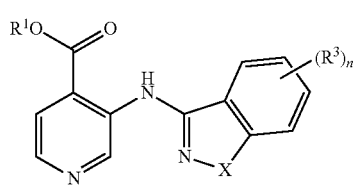

Formula (I)

wherein,
X is O or $NR^5$;
$R^1$ is hydrogen or alkyl;
each $R^3$ is independently selected from hydroxy, halogen, cyano, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;
each $R^4$ is independently selected from alkyl, aryl, aralkyl, carbocyclyl, heterocyclyl, heteroaryl, carbocyclylalkyl, heterocyclylalkyl, or heteroarylalkyl;
$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and
n is an integer selected from 0, 1, 2, 3, or 4.

One embodiment provides a compound of Formula (II) or a tautomer, stereoisomer, geometric isomer, N-oxide, or pharmaceutically acceptable salt thereof,

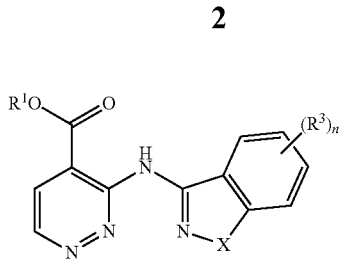

Formula (II)

wherein,
X is O or $NR^5$;
$R^1$ is hydrogen or alkyl;
each $R^3$ is independently selected from hydroxy, halogen, cyano, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;
each $R^4$ is independently selected from alkyl, aryl, aralkyl, carbocyclyl, heterocyclyl, heteroaryl, carbocyclylalkyl, heterocyclylalkyl, or heteroarylalkyl;
$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and
n is an integer selected from 0, 1, 2, 3, or 4.

One embodiment provides a pharmaceutical composition comprising a pharmaceutically acceptable carrier and a compound of Formula (I) or Formula (II), or a tautomer, stereoisomer, geometric isomer, N-oxide, or pharmaceutically acceptable salt thereof.

One embodiment provides a method for treating cancer in subject comprising administering to the subject in need thereof a composition comprising a compound of Formula (I) or Formula (II), or a tautomer, stereoisomer, geometric isomer, N-oxide, or pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a" "and" and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising"

(and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

DEFINITIONS

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butyryl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula $-O-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

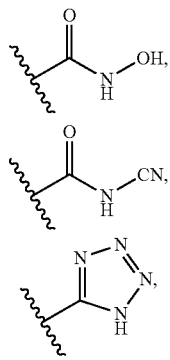

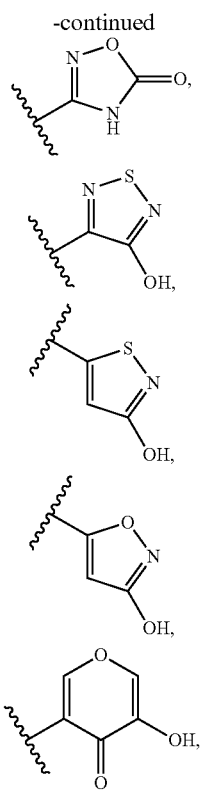

and the like.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (5)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "stereoisomer" refers to a compound made up of the same atoms bonded by the same bonds but having different three-dimensional structures, which are not interchangeable. It is therefore contemplated that various stereoisomers and mixtures thereof and includes "enantiomers" which refers to two stereoisomers whose molecular structures are nonsuperimposeable mirror images of one another.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

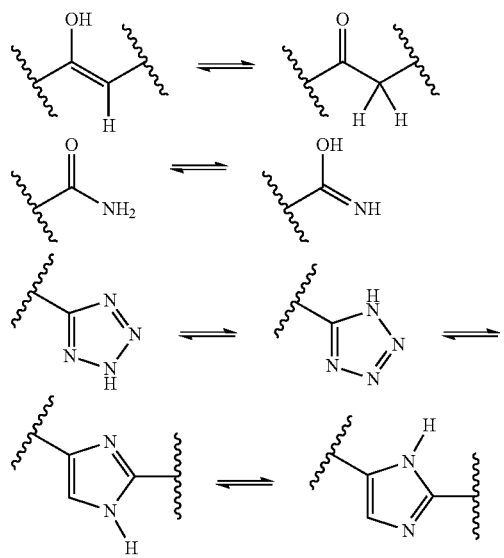
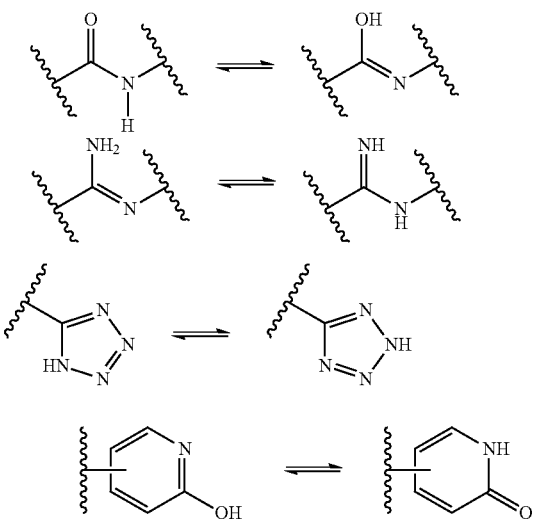

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted 3-aminopyridine derivative compounds or substituted 3-aminopyridazine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted 3-Aminopyridine Derivative Compounds & Substituted 3-Aminopyridazine Derivative Compounds Substituted 3-aminopyridine derivative compounds and substituted 3-aminopyridazine derivative compounds are described herein that inhibit a histone demethylase enzyme. These compounds, and compositions comprising these compounds, are useful for the treatment of cancer and neoplastic disease. The compounds described herein may, therefore, be useful for treating prostate cancer, breast cancer, bladder cancer, lung cancer and/or melanoma and the like.

One embodiment provides a compound of Formula (I) or a tautomer, stereoisomer, geometric isomer, N-oxide, or pharmaceutically acceptable salt thereof,

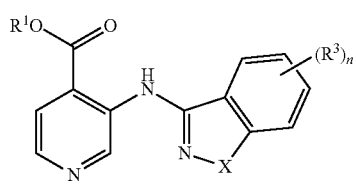

Formula (I)

wherein,
X is O or $NR^5$;
$R^1$ is hydrogen or alkyl;

each $R^3$ is independently selected from hydroxy, halogen, cyano, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;

each $R^4$ is independently selected from alkyl, aryl, aralkyl, carbocyclyl, heterocyclyl, heteroaryl, carbocyclylalkyl, heterocyclylalkyl, or heteroarylalkyl;

$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and n is an integer selected from 0, 1, 2, 3, or 4.

Another embodiment provides a compound of Formula (I), wherein $R^1$ is hydrogen. Another embodiment provides a compound of Formula (I), wherein $R^1$ is alkyl. Another embodiment provides a compound of Formula (I), wherein $R^5$ is alkyl, carbocyclylalkyl, aralkyl, heterocyclylalkyl, or heteroarylalkyl. Another embodiment provides a compound of Formula (I), wherein X is O. Another embodiment provides a compound of Formula (I), wherein X is $NR^5$.

Another embodiment provides a compound of Formula (I), wherein $R^5$ is alkyl, and the alkyl group is optionally substituted with hydroxy, halo, cyano, alkenyl, alkynyl, alkoxy, aryloxy, (alkoxy)alkoxy, aminoalkoxy, hydroxalkoxy, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, $C(O)NHR^4$, $C(O)N(R^4)_2$, $C(O)R^4$, $C(O)OR^4$, $S(O)_2R^4$, $S(O)_2NHR^4$, $S(O)_2N(R^4)_2$; and each $R^4$ is independently selected from alkyl, aryl, aralkyl, carbocyclyl, heterocyclyl, heteroaryl, carbocyclylalkyl, heterocyclylalkyl, or heteroarylalkyl.

Another embodiment provides a compound of Formula (I), wherein n is 0 or 1. Another embodiment provides a compound of Formula (I), wherein $R^3$ is halogen, alkyl, or alkoxy.

One embodiment provides a compound of Formula (II) or a tautomer, stereoisomer, geometric isomer, N-oxide, or pharmaceutically acceptable salt thereof,

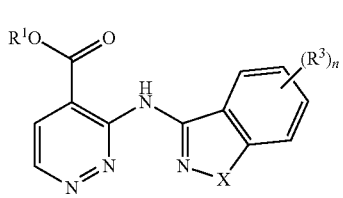

Formula (II)

wherein,
X is O or $NR^5$;
$R^1$ is hydrogen or alkyl;
each $R^3$ is independently selected from hydroxy, halogen, cyano, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;

each $R^4$ is independently selected from alkyl, aryl, aralkyl, carbocyclyl, heterocyclyl, heteroaryl, carbocyclylalkyl, heterocyclylalkyl, or heteroarylalkyl;

$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and n is an integer selected from 0, 1, 2, 3, or 4.

Another embodiment provides a compound of Formula (II), wherein X is O.

Another embodiment provides a compound of Formula (II), wherein X is $NR^5$.

One embodiment provides a compound of Formula (III) or a tautomer, stereoisomer, geometric isomer, N-oxide, or pharmaceutically acceptable salt thereof,

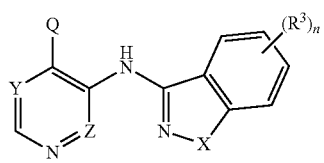

Formula (III)

wherein,

X is O or $NR^5$;

Y is COH and Z is CH; or

Y is CH and Z is CH or N; and

Q is —$CO_2R^1$, —C(O)N(H)CN, —C(O)N(H)OH, or tetrazolyl;

$R^1$ is hydrogen or alkyl;

each $R^3$ is independently selected from hydroxy, halogen, cyano, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;

each $R^4$ is independently selected from alkyl, aryl, aralkyl, carbocyclyl, heterocyclyl, heteroaryl, carbocyclylalkyl, heterocyclylalkyl, or heteroarylalkyl;

$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and n is an integer selected from 0, 1, 2, 3, or 4;

with the provision:

if Y is CH, then Q is not —$CO_2R^1$.

Another embodiment provides the compound of Formula (III), wherein Y is is COH and Z is CH. Another embodiment provides the compound of Formula (III), wherein Y is CH and Z is CH. Another embodiment provides the compound of Formula (III), wherein Y is CH and Z is N. Another embodiment provides the compound of Formula (III), wherein Q is —$CO_2R^1$. Another embodiment provides the compound of Formula (III), wherein Q is —C(O)N(H)CN. Another embodiment provides the compound of Formula (III), wherein Q is —C(O)N(H)OH. Another embodiment provides the compound of Formula (III), wherein Q is tetrazolyl. Another embodiment provides the compound of Formula (III), wherein Q is —$CO_2R^1$, Y is COH, and Z is CH. Another embodiment provides the compound of Formula (III), wherein Q is —C(O)N(H)CN, Y is COH, and Z is CH. Another embodiment provides the compound of Formula (III), wherein Q is —C(O)N(H)CN, Y is CH, and Z is CH. Another embodiment provides the compound of Formula (III), wherein Q is —C(O)N(H)CN, Y is CH, and Z is N. Another embodiment provides the compound of Formula (III), wherein Q is —C(O)N(H)OH, Y is COH, and Z is CH. Another embodiment provides the compound of Formula (III), wherein Q is —C(O)N(H)OH, Y is CH, and Z is CH. Another embodiment provides the compound of Formula (III), wherein Q is —C(O)N(H)OH, Y is CH, and Z is N. Another embodiment provides the compound of Formula (III), wherein Q is tetrazolyl, Y is COH, and Z is CH. Another embodiment provides the compound of Formula (III), wherein Q is tetrazolyl, Y is CH, and Z is CH. Another embodiment provides the compound of Formula (III), wherein Q is tetrazolyl, Y is CH, and Z is N.

Another embodiment provides a compound of Formula (III), wherein $R^1$ is hydrogen. Another embodiment provides a compound of Formula (III), wherein $R^1$ is alkyl. Another embodiment provides a compound of Formula (III), wherein $R^5$ is alkyl, carbocyclylalkyl, aralkyl, heterocyclylalkyl, or heteroarylalkyl. Another embodiment provides a compound of Formula (III), wherein X is O. Another embodiment provides a compound of Formula (III), wherein X is $NR^5$.

Another embodiment provides a compound of Formula (III), wherein $R^5$ is alkyl, and the alkyl group is optionally substituted with hydroxy, halo, cyano, alkenyl, alkynyl, alkoxy, aryloxy, (alkoxy)alkoxy, aminoalkoxy, hydroxalkoxy, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, C(O)$NHR^4$, C(O)N($R^4$)$_2$, C(O)$R^4$, C(O)$OR^4$, S(O)$_2R^4$, S(O)$_2NHR^4$, S(O)$_2N(R^4)_2$; and each $R^4$ is independently selected from alkyl, aryl, aralkyl, carbocyclyl, heterocyclyl, heteroaryl, carbocyclylalkyl, heterocyclylalkyl, or heteroarylalkyl.

Another embodiment provides a compound of Formula (III), wherein n is 0 or 1. Another embodiment provides a compound of Formula (III), wherein $R^3$ is halogen, alkyl, or alkoxy.

One embodiment provides a compound of Formula (IIIa) or a tautomer, stereoisomer, geometric isomer, N-oxide, or pharmaceutically acceptable salt thereof,

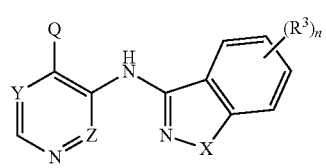

Formula (IIIa)

wherein,

X is O or $NR^5$;

Y is CH and Z is CH or N; and

Q is —C(O)N(H)CN, —C(O)N(H)OH, or tetrazolyl;

each $R^3$ is independently selected from hydroxy, halogen, cyano, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;

each $R^4$ is independently selected from alkyl, aryl, aralkyl, carbocyclyl, heterocyclyl, heteroaryl, carbocyclylalkyl, heterocyclylalkyl, or heteroarylalkyl;

$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and n is an integer selected from 0, 1, 2, 3, or 4.

Another embodiment provides the compound of Formula (IIIa), wherein Y is CH and Z is CH. Another embodiment provides the compound of Formula (IIIa), wherein Y is CH and Z is N. Another embodiment provides the compound of Formula (IIIa), wherein Q is —C(O)N(H)CN. Another embodiment provides the compound of Formula (IIIa), wherein Q is —C(O)N(H)OH. Another embodiment provides the compound of Formula (IIIa), wherein Q is tetrazolyl. Another embodiment provides the compound of Formula (IIIa), wherein Q is —C(O)N(H)CN, Y is CH, and Z is CH. Another embodiment provides the compound of Formula (IIIa), wherein Q is —C(O)N(H)CN, Y is CH, and Z is N. Another embodiment provides the compound of Formula (IIIa), wherein Q is —C(O)N(H)OH, Y is CH, and Z is CH. Another embodiment provides the compound of Formula (IIIa), wherein Q is —C(O)N(H)OH, Y is CH, and Z is N. Another embodiment provides the compound of Formula (IIIa), wherein Q is tetrazolyl, Y is CH, and Z is CH. Another embodiment provides the compound of Formula (IIIa), wherein Q is tetrazolyl, Y is CH, and Z is N.

Another embodiment provides a compound of Formula (IIIa), wherein $R^5$ is alkyl, carbocyclylalkyl, aralkyl, heterocyclylalkyl, or heteroarylalkyl. Another embodiment provides a compound of Formula (IIIa), wherein X is O. Another embodiment provides a compound of Formula (IIIa), wherein X is $NR^5$.

Another embodiment provides a compound of Formula (IIIa), wherein $R^5$ is alkyl, and the alkyl group is optionally substituted with hydroxy, halo, cyano, alkenyl, alkynyl, alkoxy, aryloxy, (alkoxy)alkoxy, aminoalkoxy, hydroxalkoxy, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, $C(O)NHR^4$, $C(O)N(R^4)_2$, $C(O)R^4$, $C(O)OR^4$, $S(O)_2R^4$, $S(O)_2NHR^4$, $S(O)_2N(R^4)_2$; and each $R^4$ is independently selected from alkyl, aryl, aralkyl, carbocyclyl, heterocyclyl, heteroaryl, carbocyclylalkyl, heterocyclylalkyl, or heteroarylalkyl.

Another embodiment provides a compound of Formula (IIIa), wherein n is 0 or 1. Another embodiment provides a compound of Formula (IIIa), wherein $R^3$ is halogen, alkyl, or alkoxy.

One embodiment provides a compound of Formula (IIIb), or a pharmaceutically acceptable salt thereof,

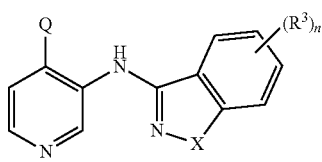

Formula (IIIb)

wherein,
Q is —$CO_2R^1$, —C(O)N(H)CN, —C(O)N(H)OH, or tetrazolyl;
X is O or $NR^5$;
$R^1$ is hydrogen or alkyl;
each $R^3$ is independently selected from hydroxy, halogen, cyano, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;
each $R^4$ is independently selected from alkyl, aryl, aralkyl, carbocyclyl, heterocyclyl, heteroaryl, carbocyclylalkyl, heterocyclylalkyl, or heteroarylalkyl;
$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and
n is an integer selected from 0, 1, 2, 3, or 4.

Another embodiment provides a compound of Formula (IIIb), or a pharmaceutically acceptable salt thereof, wherein Q is —$CO_2R^1$. Another embodiment provides a compound of Formula (IIIb), or a pharmaceutically acceptable salt thereof, wherein Q is —C(O)N(H)CN. Another embodiment provides a compound of Formula (IIIb), or a pharmaceutically acceptable salt thereof, wherein Q is —C(O)N(H)OH. Another embodiment provides a compound of Formula (IIIb), or a pharmaceutically acceptable salt thereof, wherein Q is tetrazolyl. Another embodiment provides a compound of Formula (IIIb), or a pharmaceutically acceptable salt thereof, wherein X is O. Another embodiment provides a compound of Formula (IIIb), or a pharmaceutically acceptable salt thereof, wherein X is $NR^5$. Another embodiment provides a compound of Formula (IIIb), or a pharmaceutically acceptable salt thereof, wherein $R^1$ is hydrogen. Another embodiment provides a compound of Formula (IIIb), or a pharmaceutically acceptable salt thereof, wherein $R^1$ is alkyl. Another embodiment provides a compound of Formula (IIIb), or a pharmaceutically acceptable salt thereof, wherein $R^5$ is alkyl, carbocyclylalkyl, aralkyl, heterocyclylalkyl, or heteroarylalkyl. Another embodiment provides a compound of Formula (IIIb), or a pharmaceutically acceptable salt thereof, wherein $R^5$ is alkyl, and the alkyl group is optionally substituted with hydroxy, halo, cyano, alkenyl, alkynyl, alkoxy, aryloxy, (alkoxy)alkoxy, aminoalkoxy, hydroxalkoxy, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, $C(O)NHR^4$, $C(O)N(R^4)_2$, $C(O)R^4$, $C(O)OR^4$, $S(O)_2R^4$, $S(O)_2NHR^4$, $S(O)_2N(R^4)_2$; and each $R^4$ is independently selected from alkyl, aryl, aralkyl, carbocyclyl, heterocyclyl, heteroaryl, carbocyclylalkyl, heterocyclylalkyl, or heteroarylalkyl. Another embodiment provides a compound of Formula (IIIb), or a pharmaceutically acceptable salt thereof, wherein $R^5$ is alkyl, and the alkyl group is optionally substituted with hydroxy, halo, —$N(R^4)_2$, $C_1$-$C_3$ alkoxy, —$OCH_2CH_2$—$N(R^4)_2$; and each $R^4$ is hydrogen or $C_1$-$C_3$ alkyl. Another embodiment provides a compound of Formula (IIIb), or a pharmaceutically acceptable salt thereof, wherein $R^5$ is carbocyclylalkyl, aralkyl, heterocyclylalkyl, or heteroarylalkyl. Another embodiment provides a compound of Formula (IIIb), or a pharmaceutically acceptable salt thereof, wherein $R^5$ is alkenyl, or alkynyl.

Another embodiment provides a compound of Formula (IIIb), or a pharmaceutically acceptable salt thereof, wherein $R^5$ is carbocyclyl. Another embodiment provides a compound of Formula (IIIb), or a pharmaceutically acceptable salt thereof, wherein $R^5$ is heterocyclyl. Another embodiment provides a compound of Formula (IIIb), or a pharmaceutically acceptable salt thereof, wherein $R^5$ is aryl. Another embodiment provides a compound of Formula (IIIb), or a pharmaceutically acceptable salt thereof, wherein $R^5$ is heteroaryl.

Another embodiment provides a compound of Formula (IIIb), or a pharmaceutically acceptable salt thereof, wherein n is 0 or 1. Another embodiment provides a compound of Formula (IIIb), or a pharmaceutically acceptable salt thereof, wherein n is 2, 3, or 4. Another embodiment provides a compound of Formula (IIIb), or a pharmaceutically acceptable salt thereof, wherein $R^3$ is halogen, alkyl, or alkoxy.

One embodiment provides a compound of Formula (IV), or a tautomer, stereoisomer, geometric isomer, N-oxide, or pharmaceutically acceptable salt thereof,

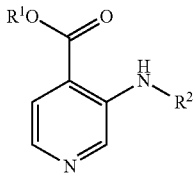

Formula (IV)

wherein,
R$^1$ is hydrogen or alkyl; and
R$^2$ is heteroaryl;
with the provision that R$^2$ is not selected from the group consisting of:

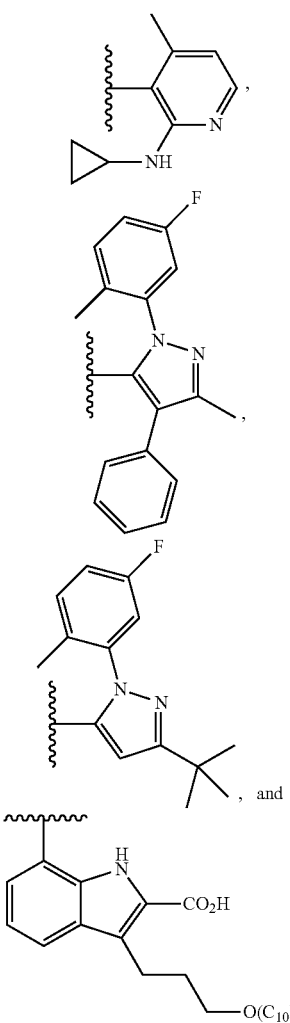

, and

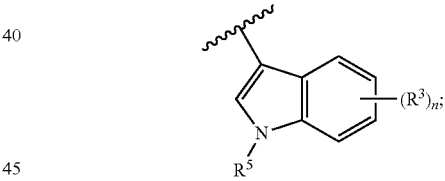

Another embodiment provides a compound of Formula (IV), wherein the heteroaryl is pyrazolyl, oxazolyl, thiazolyl, or benzoxazolyl. Another embodiment provides a compound of Formula (IV), wherein the heteroaryl is optionally substituted with alkyl or aralkyl.

Another embodiment provides the compound of Formula (IV), wherein the heteroaryl is

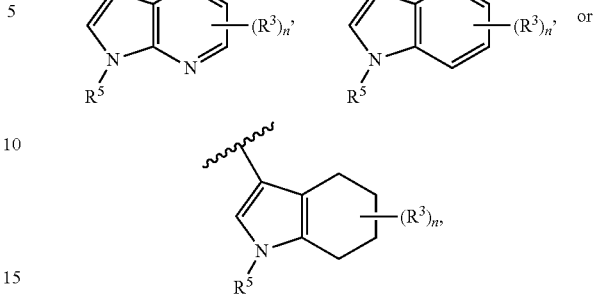

wherein each R$^3$ is independently selected from hydroxy, halogen, cyano, NH$_2$, NHR$^4$, N(R$^4$)$_2$, NHC(O)R$^4$, NHC(O)OR$^4$, NHC(O)NHR$^4$, NHC(O)N(R$^4$)$_2$, NHS(O)$_2$R$^4$, NR$^4$C(O)R$^4$, NR$^4$C(O)OR$^4$, NR$^4$C(O)NHR$^4$, NR$^4$C(O)N(R$^4$)$_2$, NR$^4$S(O)$_2$R$^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;

each R$^4$ is independently selected from alkyl, aryl, aralkyl, carbocyclyl, heterocyclyl, heteroaryl, carbocyclylalkyl, heterocyclylalkyl, or heteroarylalkyl;

R$^5$ is alkyl, alkenyl, alkynyl, aryl, aralkyl, carbocyclyl, heterocyclyl, heteroaryl, carbocyclylalkyl, heterocyclylalkyl, or heteroarylalkyl; and n is an integer selected from 0, 1, 2, 3, or 4.

Another embodiment provides the compound of Formula (IV), wherein the heteroaryl is wherein each R$^3$ is independently selected from hydroxy, halogen, cyano, NH$_2$, NHR$^4$, N(R$^4$)$_2$, NHC(O)R$^4$, NHC(O)OR$^4$, NHC(O)NHR$^4$, NHC(O)N(R$^4$)$_2$, NHS(O)$_2$R$^4$, NR$^4$C(O)R$^4$, NR$^4$C(O)OR$^4$, NR$^4$C(O)NHR$^4$, NR$^4$C(O)N(R$^4$)$_2$, NR$^4$S(O)$_2$R$^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;

each R$^4$ is independently selected from alkyl, aryl, aralkyl, carbocyclyl, heterocyclyl, heteroaryl, carbocyclylalkyl, heterocyclylalkyl, or heteroarylalkyl;

R$^5$ is alkyl, alkenyl, alkynyl, aryl, aralkyl, carbocyclyl, heterocyclyl, heteroaryl, carbocyclylalkyl, heterocyclylalkyl, or heteroarylalkyl; and n is an integer selected from 0, 1, 2, 3, or 4.

One embodiment provides a compound of Formula (V) or a tautomer, stereoisomer, geometric isomer, N-oxide, or pharmaceutically acceptable salt thereof,

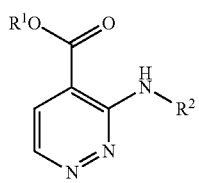

Formula (V)

wherein,

R¹ is hydrogen or alkyl; and

R² is carbocyclyl, heterocyclyl, aryl, or heteroaryl;

with the provision:

if the aryl is phenyl, then the phenyl is substituted with at least one substituent independently selected from $C_2$-$C_8$ alkyl, hydroxy, halogen, cyano, alkoxy, aryl, aryloxy, aralkyl, carbocyclyl, heterocyclyl, heteroaryl, carbocyclylalkyl, heterocyclylalkyl, heteroarylalkyl, $NH_2$, NHC(O)$R^4$, NHC(O)O$R^4$, NHC(O)NH$R^4$, NHC(O)N($R^4$)$_2$, NHS(O)$_2$$R^4$, $NR^4$C(O)$R^4$, $NR^4$C(O)O$R^4$, $NR^4$C(O)NH$R^4$, $NR^4$C(O)N($R^4$)$_2$, or $NR^4$S(O)$_2$$R^4$; or two adjacent substituents together form a carbocyclic, heterocyclic, aryl, or heteroaryl ring; and each $R^4$ is independently selected from alkyl, aryl, aralkyl, carbocyclyl, heterocyclyl, heteroaryl, carbocyclylalkyl, heterocyclylalkyl, or heteroarylalkyl.

Another embodiment provides the compound of Formula (V), wherein $R^2$ is heteroaryl and the heteroaryl is

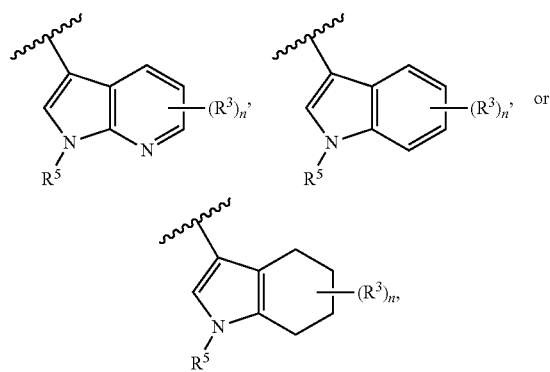

wherein each $R^3$ is independently selected from hydroxy, halogen, cyano, $NH_2$, NH$R^4$, N($R^4$)$_2$, NHC(O)$R^4$, NHC(O)O$R^4$, NHC(O)NH$R^4$, NHC(O)N($R^4$)$_2$, NHS(O)$_2$$R^4$, $NR^4$C(O)$R^4$, $NR^4$C(O)O$R^4$, $NR^4$C(O)NH$R^4$, $NR^4$C(O)N($R^4$)$_2$, $NR^4$S(O)$_2$$R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;

each $R^4$ is independently selected from alkyl, aryl, aralkyl, carbocyclyl, heterocyclyl, heteroaryl, carbocyclylalkyl, heterocyclylalkyl, or heteroarylalkyl;

$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and n is an integer selected from 0, 1, 2, 3, or 4.

Another embodiment provides the compound of Formula (V), wherein the heteroaryl is

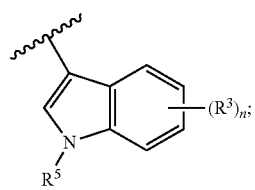

wherein each $R^3$ is independently selected from hydroxy, halogen, cyano, $NH_2$, NH$R^4$, N($R^4$)$_2$, NHC(O)$R^4$, NHC(O)O$R^4$, NHC(O)NH$R^4$, NHC(O)N($R^4$)$_2$, NHS(O)$_2$$R^4$, $NR^4$C(O)$R^4$, $NR^4$C(O)O$R^4$, $NR^4$C(O)NH$R^4$, $NR^4$C(O)N($R^4$)$_2$, $NR^4$S(O)$_2$$R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;

each $R^4$ is independently selected from alkyl, aryl, aralkyl, carbocyclyl, heterocyclyl, heteroaryl, carbocyclylalkyl, heterocyclylalkyl, or heteroarylalkyl;

$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and n is an integer selected from 0, 1, 2, 3, or 4.

One embodiment provides a compound of Formula (VI) or a tautomer, stereoisomer, geometric isomer, N-oxide, or pharmaceutically acceptable salt thereof,

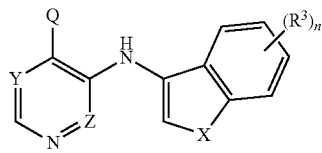

Formula (VI)

wherein,

X is $NR^5$;

Y is CH and Z is CH or N; and

Q is —C(O)N(H)CN, —C(O)N(H)OH, or tetrazolyl;

each $R^3$ is independently selected from hydroxy, halogen, cyano, $NH_2$, NH$R^4$, N($R^4$)$_2$, NHC(O)$R^4$, NHC(O)O$R^4$, NHC(O)NH$R^4$, NHC(O)N($R^4$)$_2$, NHS(O)$_2$$R^4$, $NR^4$C(O)$R^4$, $NR^4$C(O)O$R^4$, $NR^4$C(O)NH$R^4$, $NR^4$C(O)N($R^4$)$_2$, $NR^4$S(O)$_2$$R^4$, alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl;

each $R^4$ is independently selected from alkyl, aryl, aralkyl, carbocyclyl, heterocyclyl, heteroaryl, carbocyclylalkyl, heterocyclylalkyl, or heteroarylalkyl;

$R^5$ is alkyl, alkenyl, alkynyl, aryl, aralkyl, carbocyclyl, heterocyclyl, heteroaryl, carbocyclylalkyl, heterocyclylalkyl, or heteroarylalkyl; and n is an integer selected from 0, 1, 2, 3, or 4.

Another embodiment provides the compound of Formula (VI), wherein Y is CH and Z is CH. Another embodiment provides the compound of Formula (VI), wherein Y is CH and Z is N. Another embodiment provides the compound of Formula (VI), wherein Q is —C(O)N(H)CN. Another embodiment provides the compound of Formula (VI), wherein Q is —C(O)N(H)OH. Another embodiment provides the compound of Formula (VI), wherein Q is tetrazolyl. Another embodiment provides the compound of Formula (VI), wherein Q is —C(O)N(H)CN, Y is CH, and Z is CH. Another embodiment provides the compound of Formula (VI), wherein Q is —C(O)N(H)CN, Y is CH, and Z is N. Another embodiment provides the compound of Formula (VI), wherein Q is —C(O)N(H)OH, Y is CH, and Z is CH. Another embodiment provides the compound of Formula (VI), wherein Q is —C(O)N(H)OH, Y is CH, and Z is N. Another embodiment provides the compound of Formula (VI), wherein Q is tetrazolyl, Y is CH, and Z is CH. Another embodiment provides the compound of Formula (VI), wherein Q is tetrazolyl, Y is CH, and Z is N.

Another embodiment provides a compound of Formula (VI), wherein $R^5$ is alkyl, carbocyclylalkyl, aralkyl, heterocyclylalkyl, or heteroarylalkyl.

Another embodiment provides a compound of Formula (VI), wherein $R^5$ is alkyl, and the alkyl group is optionally substituted with hydroxy, halo, cyano, alkenyl, alkynyl, alkoxy, aryloxy, (alkoxy)alkoxy, aminoalkoxy, hydroxalkyl, $NH_2$, $NHR^4$, $N(R^4)_2$, $NHC(O)R^4$, $NHC(O)OR^4$, $NHC(O)NHR^4$, $NHC(O)N(R^4)_2$, $NHS(O)_2R^4$, $NR^4C(O)R^4$, $NR^4C(O)OR^4$, $NR^4C(O)NHR^4$, $NR^4C(O)N(R^4)_2$, $NR^4S(O)_2R^4$, $C(O)NHR^4$, $C(O)N(R^4)_2$, $C(O)R^4$, $C(O)OR^4$, $S(O)_2R^4$, $S(O)_2NHR^4$, $S(O)_2N(R^4)_2$; and each $R^4$ is independently selected from alkyl, aryl, aralkyl, carbocyclyl, heterocyclyl, heteroaryl, carbocyclylalkyl, heterocyclylalkyl, or heteroarylalkyl.

Another embodiment provides a compound of Formula (VI), wherein n is 0 or 1. Another embodiment provides a compound of Formula (VI), wherein $R^3$ is halogen, alkyl, or alkoxy.

In some embodiments, the substituted aminopyridine derivative compound as described herein, has the structure provided below:

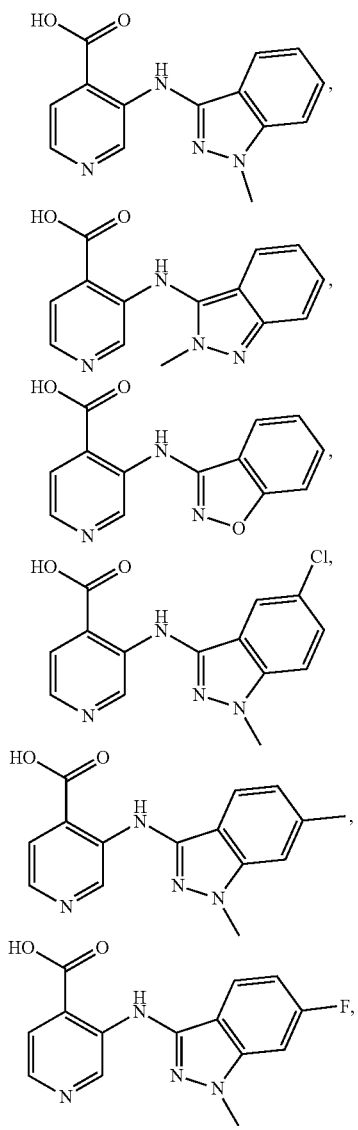

-continued

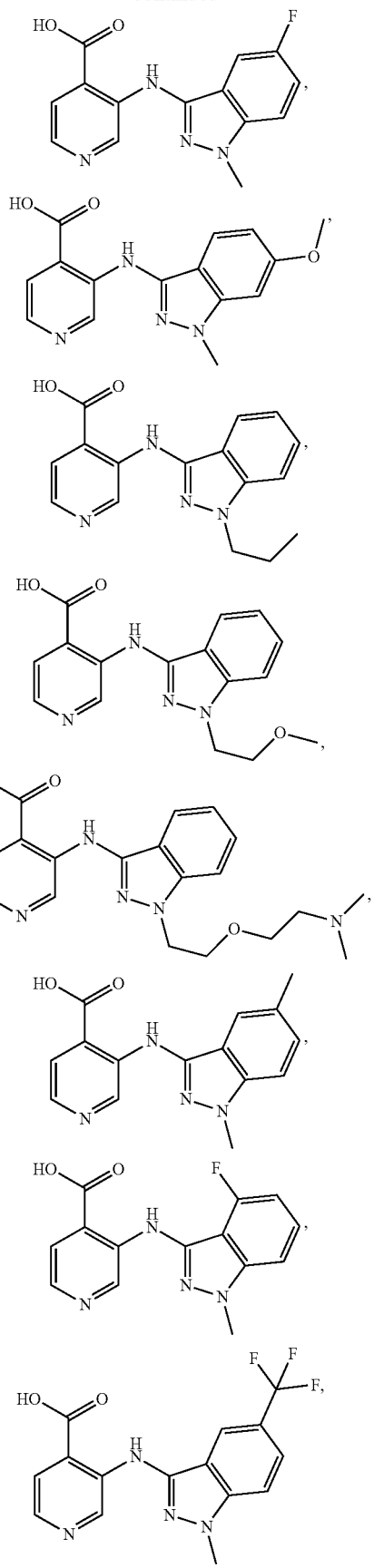

-continued
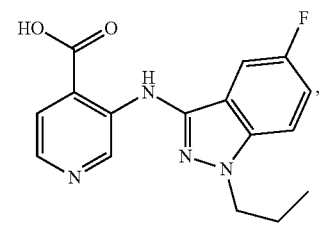
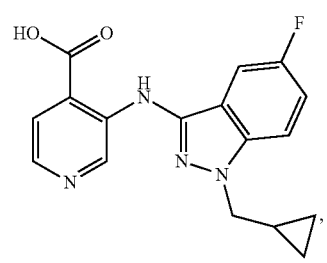
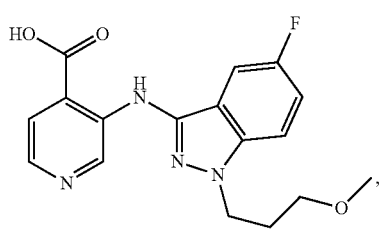
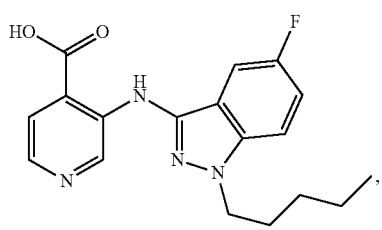
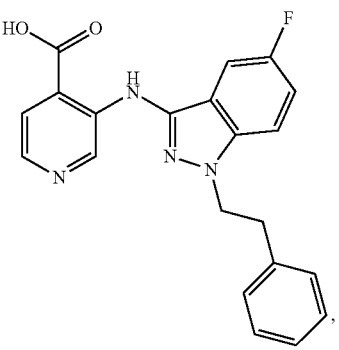
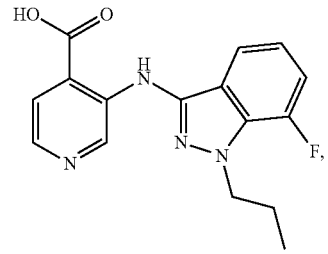
-continued
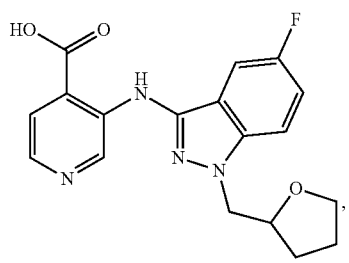
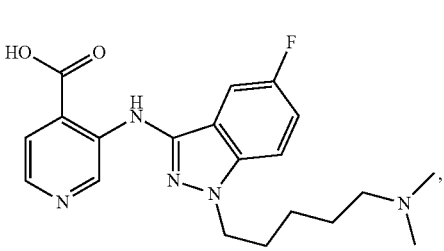
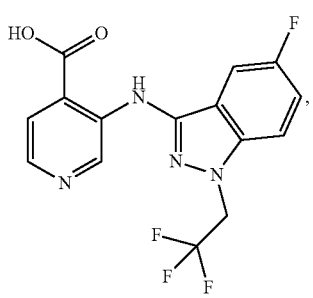
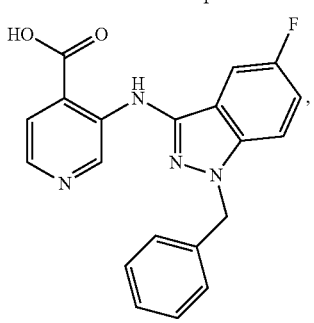
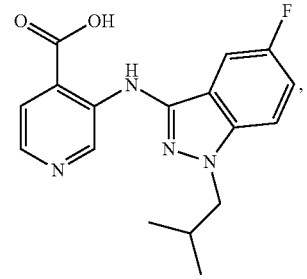
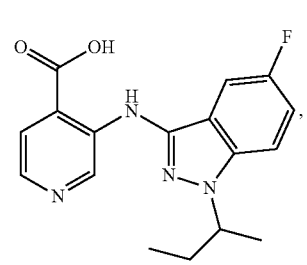

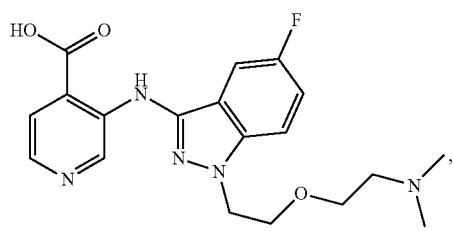
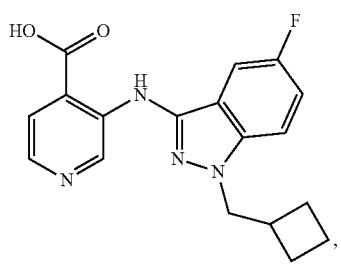
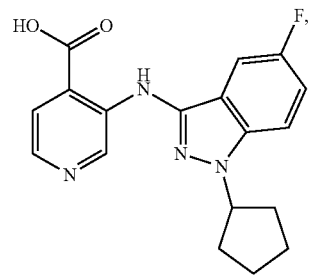
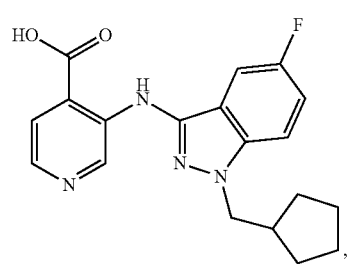
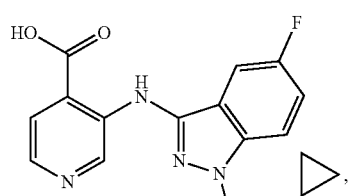
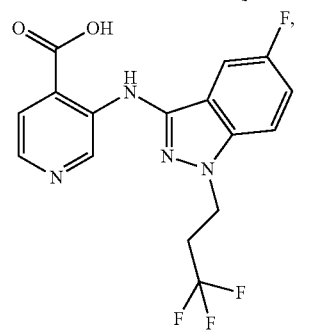
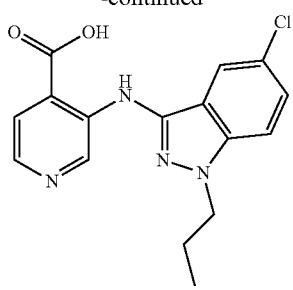
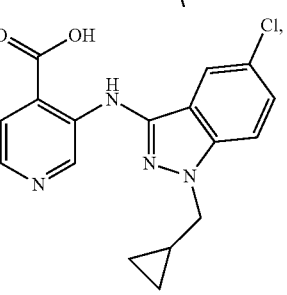
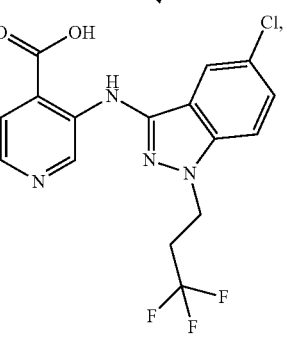
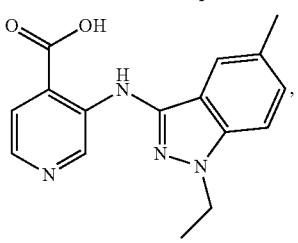
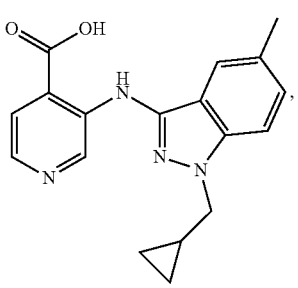
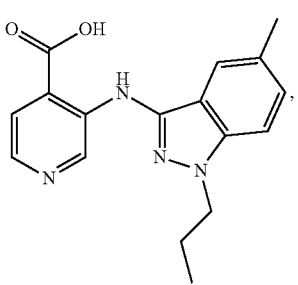

29
-continued
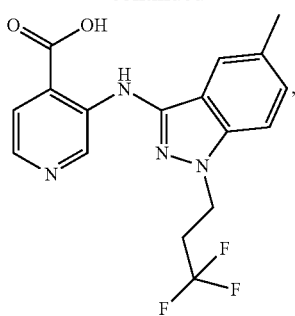
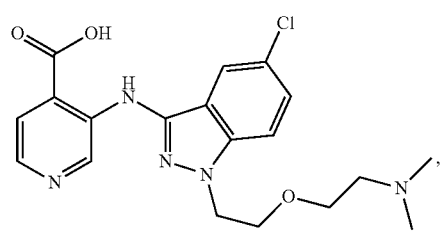
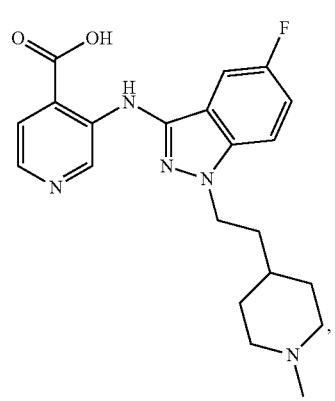
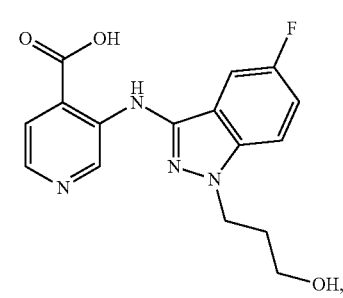
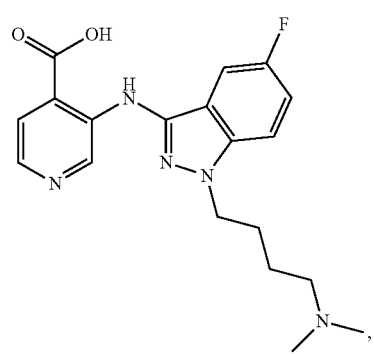
30
-continued
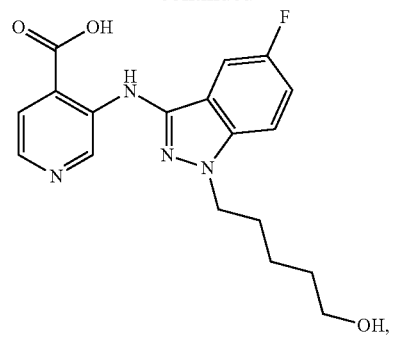
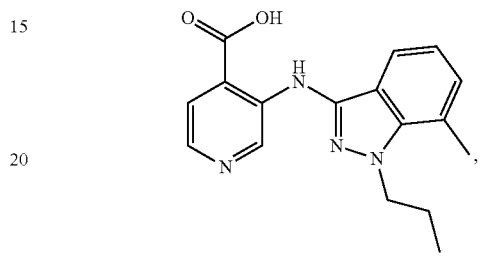
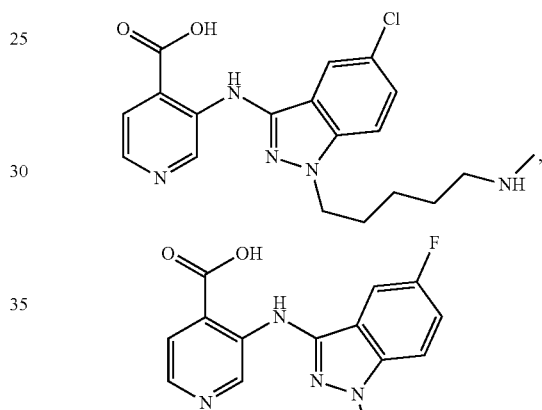
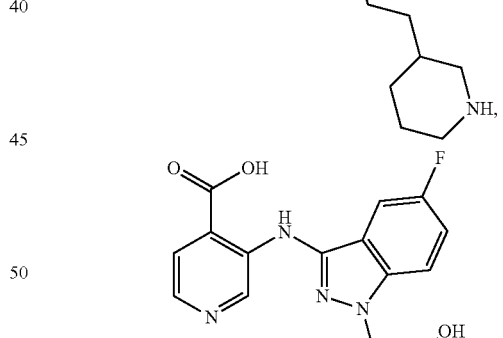
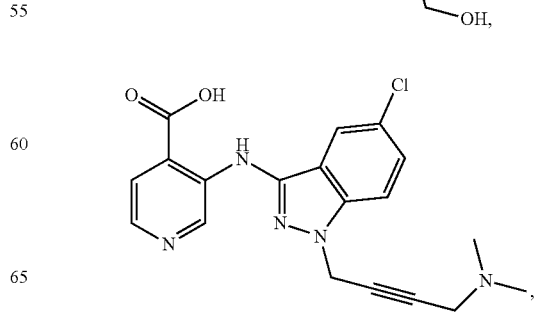

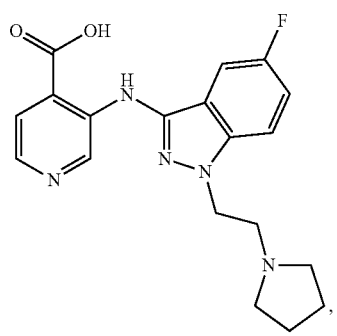
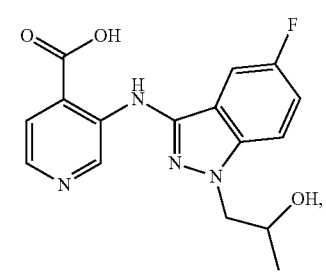
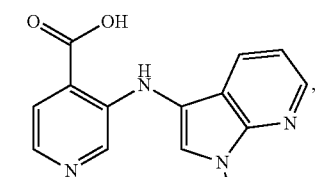
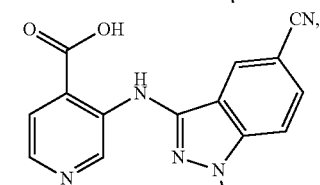
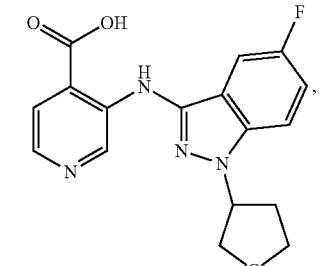
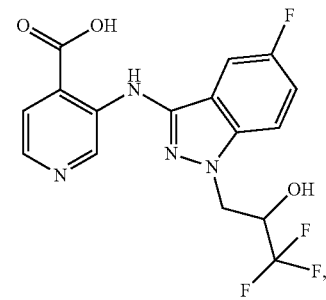
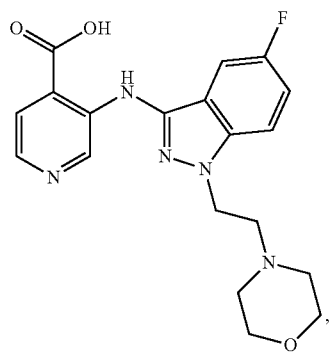
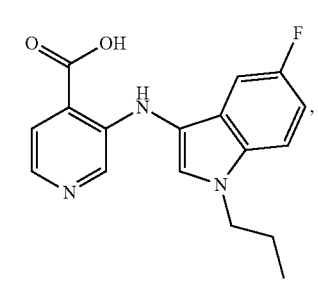
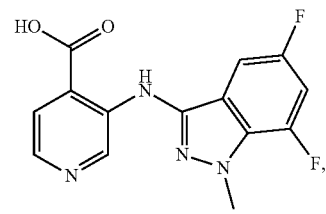
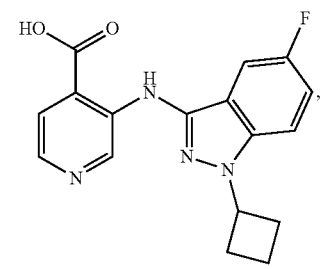
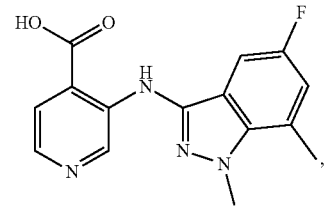
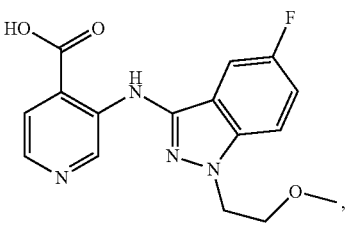

33
-continued
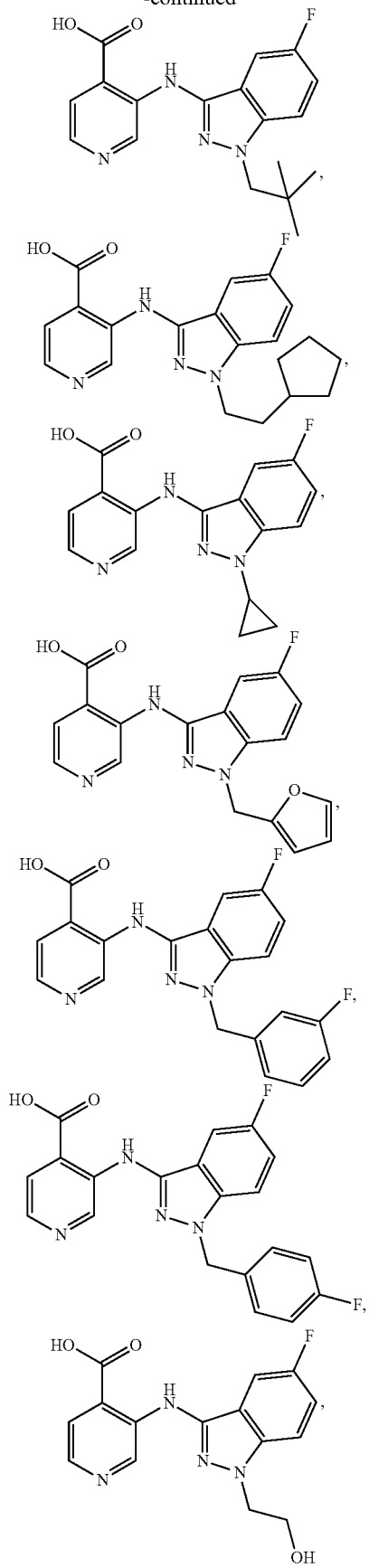
34
-continued
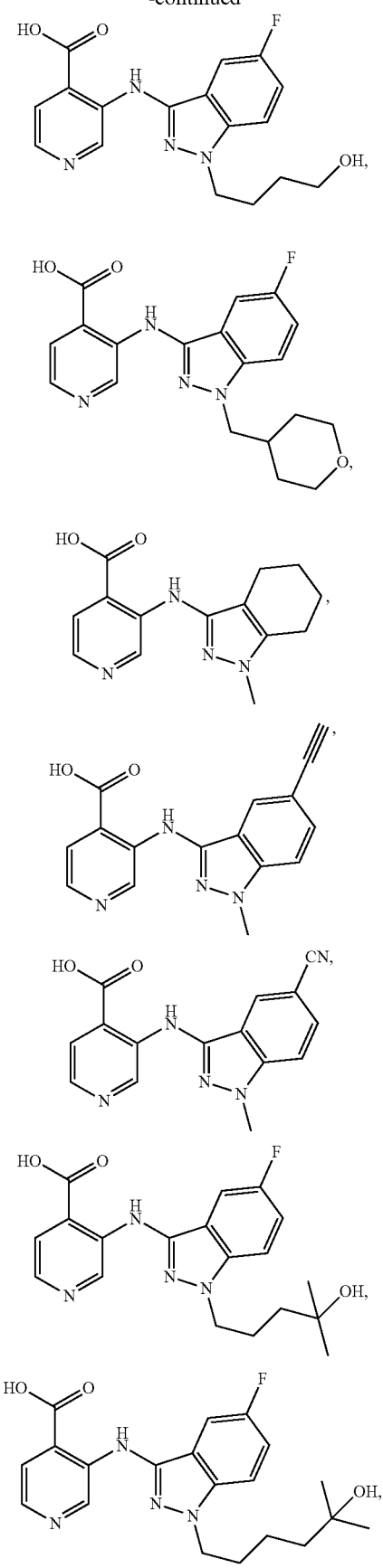

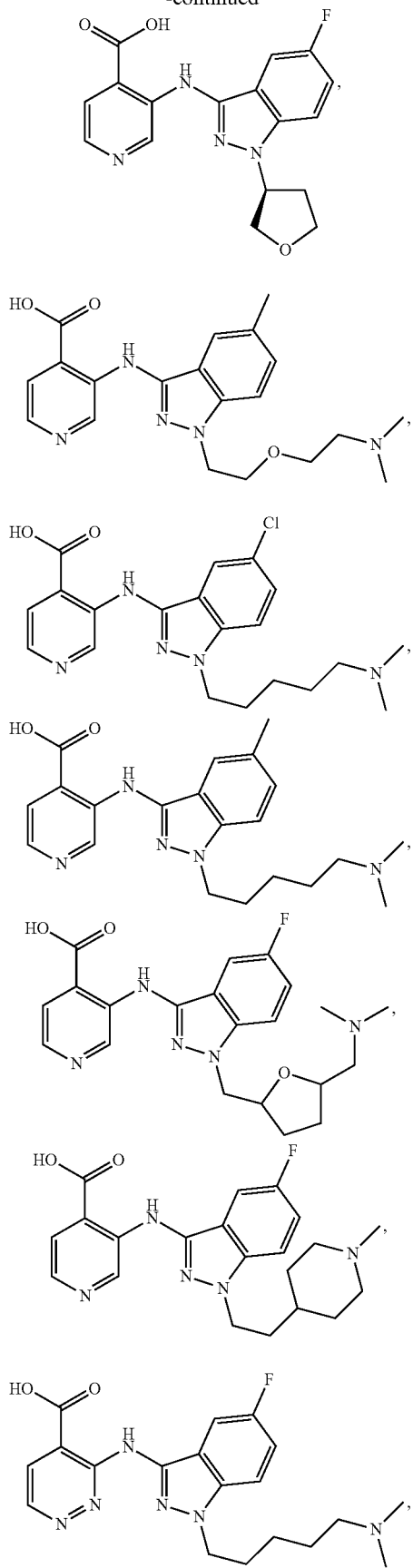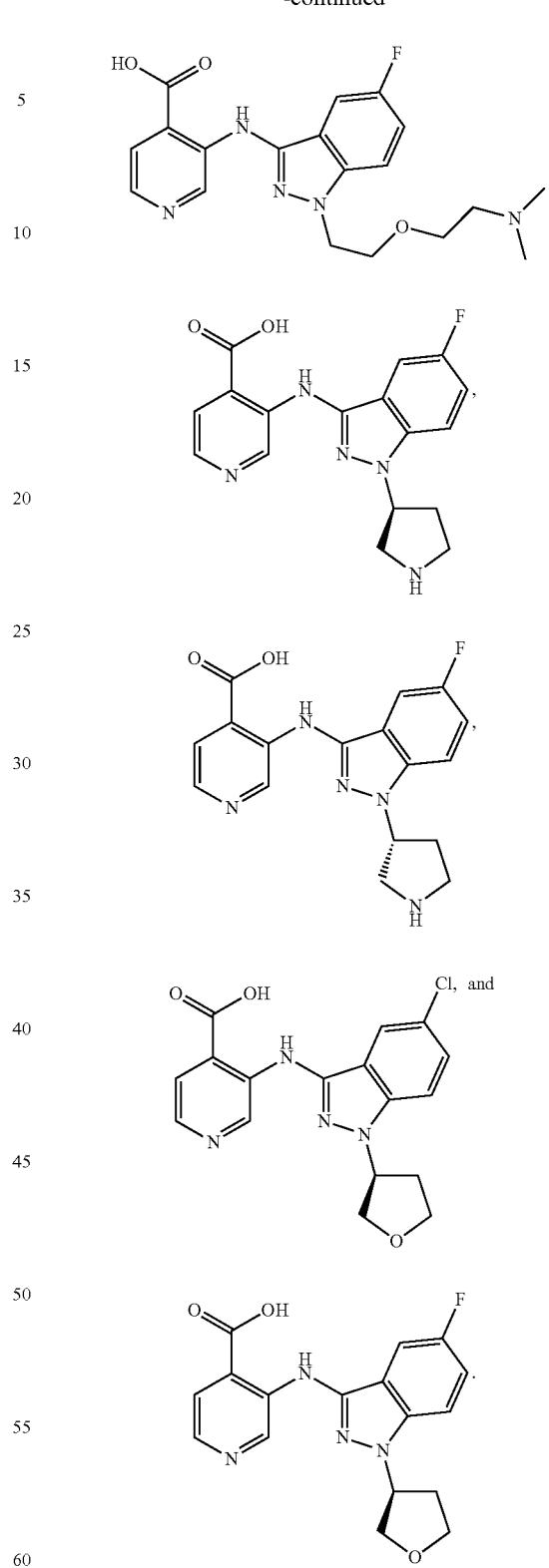
In some embodiments, the substituted aminopyridine derivative compound as described herein, or a carboxylic acid ester, or carboxylic acid bioisostere thereof, has the structure provided in Table 1.

TABLE 1

| Chemical Synthesis Example | Structure | Name |
|---|---|---|
| 1 | 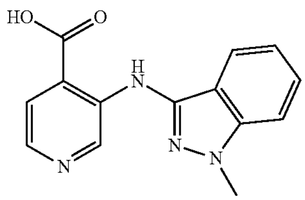 [SMILES: Cn1nc(Nc2cnccc2C(=O)O)c2ccccc21] | 3-[(1-methyl-1H-indazol-3-yl)amino]pyridine-4-carboxylic acid |
| 2 | 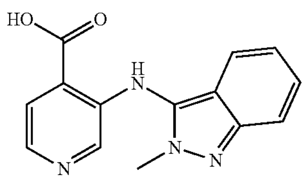 [SMILES: Cn1nc2ccccc2c1Nc1cnccc1C(=O)O] | 3-[(2-methyl-2H-indazol-3-yl)amino]pyridine-4-carboxylic acid |
| 3 | 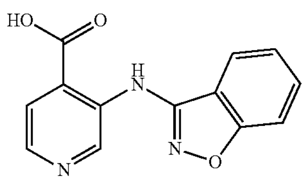 [SMILES: O=C(O)c1ccncc1Nc1noc2ccccc12] | 3-(1,2-benzoxazol-3-ylamino)pyridine-4-carboxylic acid |
| 4 | 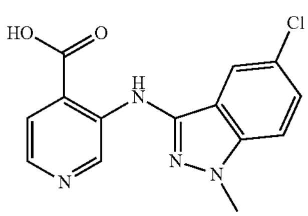 [SMILES: Cn1nc(Nc2cnccc2C(=O)O)c2cc(Cl)ccc21] | 3-[(5-chloro-1-methyl-1H-indazol-3-yl)amino]pyridine-4-carboxylic acid |
| 5 | 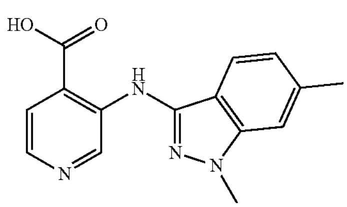 [SMILES: Cc1ccc2c(Nc3cnccc3C(=O)O)nn(C)c2c1] | 3-[(1,6-dimethyl-1H-indazol-3-yl)amino]pyridine-4-carboxylic acid |
| 6 | 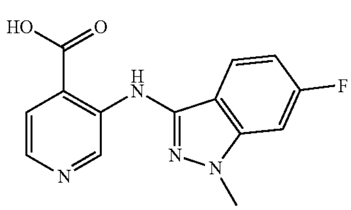 [SMILES: Cn1nc(Nc2cnccc2C(=O)O)c2ccc(F)cc21] | 3-[(6-fluoro-1-methyl-1H-indazol-3-yl)amino]pyridine-4-carboxylic acid |
| 7 | 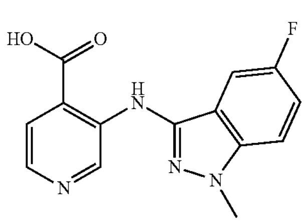 [SMILES: Cn1nc(Nc2cnccc2C(=O)O)c2cc(F)ccc21] | 3-[(5-fluoro-1-methyl-1H-indazol-3-yl)amino]pyridine-4-carboxylic acid |

TABLE 1-continued

| Chemical Synthesis Example | Structure | Name |
|---|---|---|
| 8 | 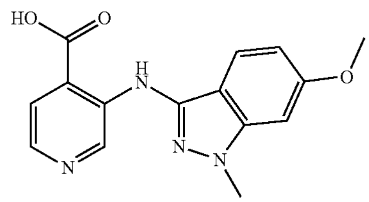 [SMILES: COc1ccc2c(Nc3cnccc3C(=O)O)nn(C)c2c1] | 3-[(6-methoxy-1-methyl-1H-indazol-3-yl)amino]pyridine-4-carboxylic acid |
| 9 | 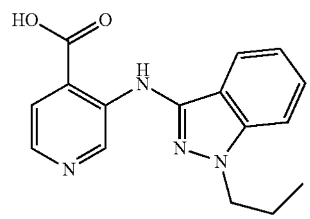 [SMILES: CCCn1nc(Nc2cnccc2C(=O)O)c2ccccc21] | 3-[(1-propyl-1H-indazol-3-yl)amino]pyridine-4-carboxylic acid |
| 10 | 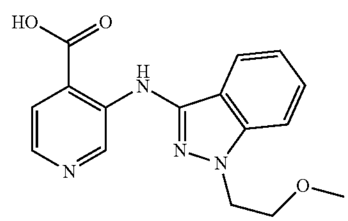 [SMILES: COCCn1nc(Nc2cnccc2C(=O)O)c2ccccc21] | 3-{[1-(2-methoxyethyl)-1H-indazol-3-yl]amino}pyridine-4-carboxylic acid |
| 11 | 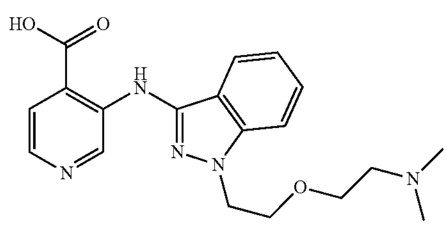 [SMILES: CN(C)CCOCCn1nc(Nc2cnccc2C(=O)O)c2ccccc21] | 3-[(1-{2-[2-(dimethylamino)ethoxy]ethyl}-1H-indazol-3-yl)amino]pyridine-4-carboxylic acid |
| 12 | 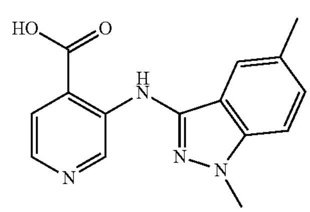 [SMILES: Cc1ccc2c(c1)c(Nc1cnccc1C(=O)O)nn2C] | 3-[(1,5-dimethyl-1H-indazol-3-yl)amino]pyridine-4-carboxylic acid |
| 13 | 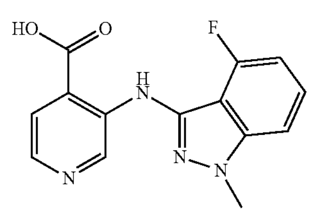 [SMILES: Cn1nc(Nc2cnccc2C(=O)O)c2c(F)cccc21] | 3-[(4-fluoro-1-methyl-1H-indazol-3-yl)amino]pyridine-4-carboxylic acid |
| 14 | 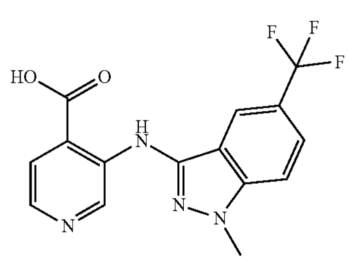 [SMILES: Cn1nc(Nc2cnccc2C(=O)O)c2cc(C(F)(F)F)ccc21] | 3-[(5-trifluoromethyl-1-methyl-1H-indazol-3-yl)amino]pyridine-4-carboxylic acid |

TABLE 1-continued

| Chemical Synthesis Example | Structure | Name |
| --- | --- | --- |
| 15 | 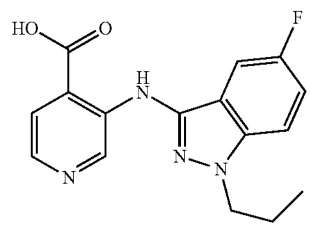 [SMILES: CCCn1nc(Nc2cnccc2C(=O)O)c2cc(F)ccc21] | 3-[(5-fluoro-1-propyl-1H-indazol-3-yl)amino]pyridine-4-carboxylic acid |
| 16 | 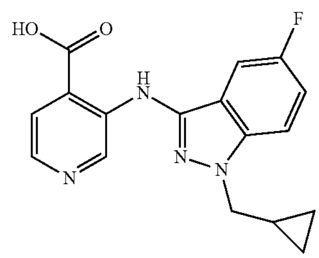 [SMILES: O=C(O)c1ccncc1Nc1nn(CC2CC2)c2ccc(F)cc12] | 3-{[1-(cyclopropylmethyl)-5-fluoro-1H-indazol-3-yl]amino}pyridine-4-carboxylic acid |
| 17 | 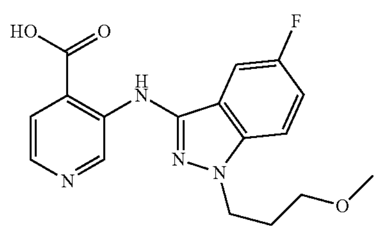 [SMILES: COCCCn1nc(Nc2cnccc2C(=O)O)c2cc(F)ccc21] | 3-{[5-fluoro-1-(methoxypropyl)-1H-indazol-3-yl]amino}pyridine-4-carboxylic acid |
| 18 | 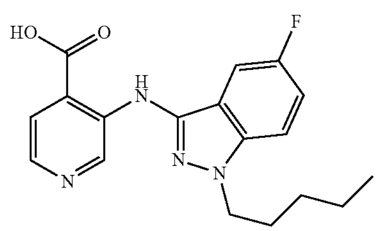 [SMILES: CCCCCn1nc(Nc2cnccc2C(=O)O)c2cc(F)ccc21] | 3-[(5-fluoro-1-pentyl-1H-indazol-3-yl)amino]pyridine-4-carboxylic acid |
| 19 | 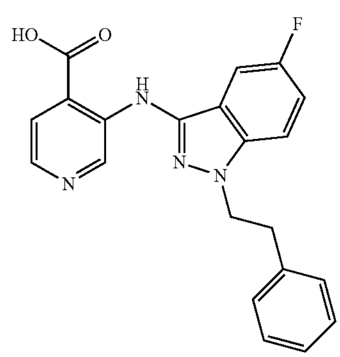 [SMILES: O=C(O)c1ccncc1Nc1nn(CCc2ccccc2)c2ccc(F)cc12] | 3-{[5-fluoro-1-(2-phenethyl)-1H-indazol-3-yl]amino}pyridine-4-carboxylic acid |
| 20 | 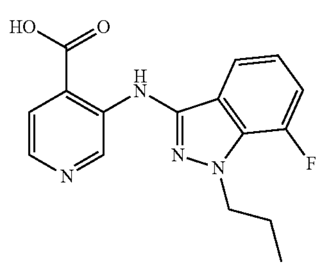 [SMILES: CCCn1nc(Nc2cnccc2C(=O)O)c2cccc(F)c21] | 3-[(7-fluoro-1-propyl-1H-indazol-3-yl)amino]pyridine-4-carboxylic acid |

TABLE 1-continued

| Chemical Synthesis Example | Structure | Name |
|---|---|---|
| 21 | 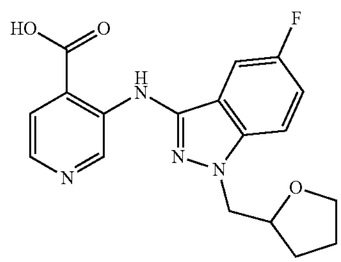 [SMILES: O=C(O)c1ccncc1Nc1nn(CC2CCCO2)c2ccc(F)cc12] | 3-{[5-fluoro-1-(tetrahydrofuran-2-ylmethyl)-1H-indazol-3-yl]amino}pyridine-4-carboxylic acid |
| 22 | 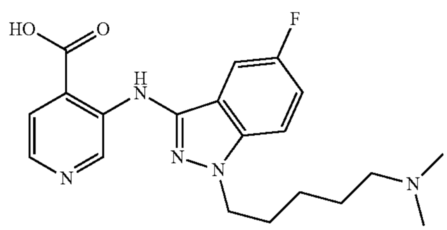 [SMILES: CN(C)CCCCCn1nc(Nc2cnccc2C(=O)O)c2cc(F)ccc21] | 3-({1-[2-(dimethylamino)pentyl]-5-fluoro-1H-indazol-3-yl}amino)pyridine-4-carboxylic acid |
| 23 | 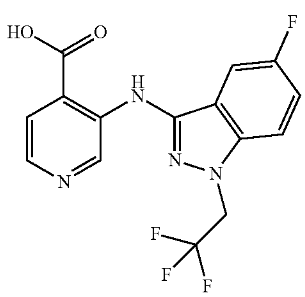 [SMILES: O=C(O)c1ccncc1Nc1nn(CC(F)(F)F)c2ccc(F)cc12] | 3-{[5-fluoro-1-(2,2,2-trifluoroethyl)-1H-indazol-3-yl]amino}pyridine-4-carboxylic acid |
| 24 | 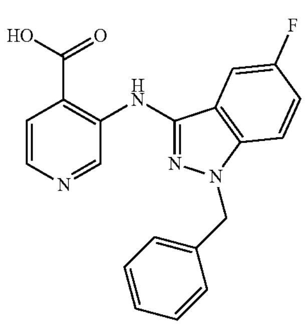 [SMILES: O=C(O)c1ccncc1Nc1nn(Cc2ccccc2)c2ccc(F)cc12] | 3-[(1-benzyl-5-fluoro-1H-indazol-3-yl)amino]pyridine-4-carboxylic acid |
| 25 | 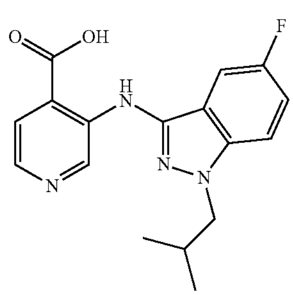 [SMILES: CC(C)Cn1nc(Nc2cnccc2C(=O)O)c2cc(F)ccc21] | 3-{[5-fluoro-1-(2-methylpropyl)-1H-indazol-3-yl]amino}pyridine-4-carboxylic acid |

TABLE 1-continued

| Chemical Synthesis Example | Structure | Name |
|---|---|---|
| 26 | 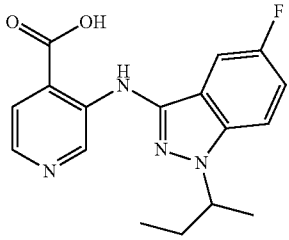 [SMILES: CCC(C)n1nc(Nc2cnccc2C(=O)O)c2cc(F)ccc21] | 3-{[5-fluoro-1-(butan-2-yl)-1H-indazol-3-yl]amino}pyridine-4-carboxylic acid |
| 27 | 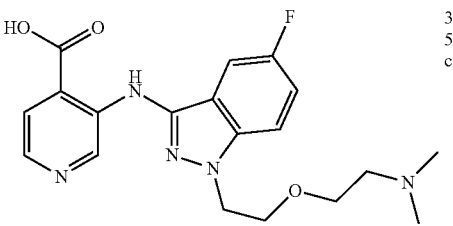 | 3-[(1-{2-[2-(dimethylamino)ethoxy]ethyl}-5-fluoro-1H-indazol-3-yl)amino]pyridine-4-carboxylic acid |
| 28 | 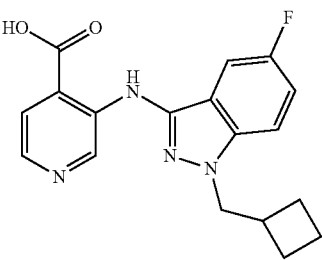 [SMILES: O=C(O)c1ccncc1Nc1nn(CC2CCC2)c2ccc(F)cc12] | 3-{[1-(cyclobutylmethyl)-5-fluoro-1H-indazol-3-yl]amino}pyridine-4-carboxylic acid |
| 29 | 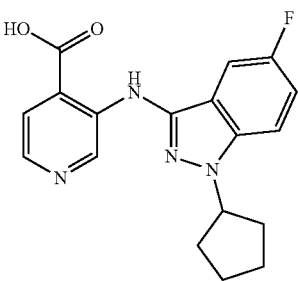 [SMILES: O=C(O)c1ccncc1Nc1nn(C2CCCC2)c2ccc(F)cc12] | 3-[(1-cyclopentyl-5-fluoro-1H-indazol-3-yl)amino]pyridine-4-carboxylic acid |
| 30 | 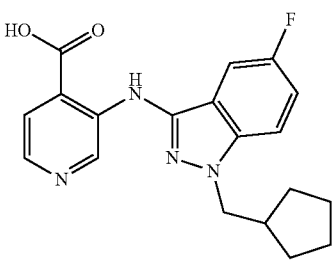 [SMILES: O=C(O)c1ccncc1Nc1nn(CC2CCCC2)c2ccc(F)cc12] | 3-{[1-(cyclopentylmethyl)-5-fluoro-1H-indazol-3-yl]amino}pyridine-4-carboxylic acid |
| 31 | 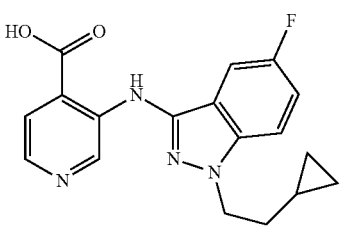 [SMILES: O=C(O)c1ccncc1Nc1nn(CCC2CC2)c2ccc(F)cc12] | 3-{[1-(cyclopropylethyl)-5-fluoro-1H-indazol-3-yl]amino}pyridine-4-carboxylic acid |

| Chemical Synthesis Example | Structure | Name |
|---|---|---|
| 32 | 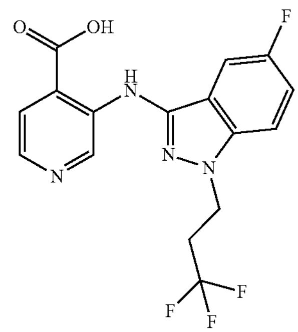 [SMILES: O=C(O)c1ccncc1Nc1nn(CCC(F)(F)F)c2ccc(F)cc12] | 3-{[5-fluoro-1-(3,3,3-trifluoropropyl)-1H-indazol-3-yl]amino}pyridine-4-carboxylic acid |
| 33 | 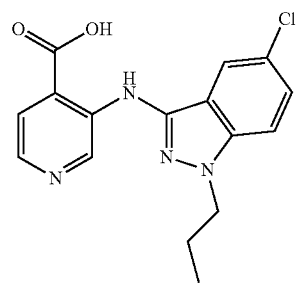 [SMILES: CCCn1nc(Nc2cnccc2C(=O)O)c2cc(Cl)ccc21] | 3-[(5-chloro-1-propyl-1H-indazol-3-yl)amino]pyridine-4-carboxylic acid |
| 34 | 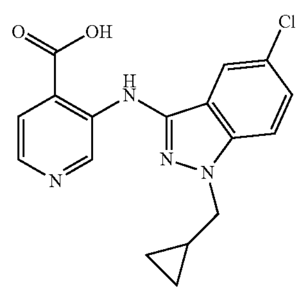 [SMILES: O=C(O)c1ccncc1Nc1nn(CC2CC2)c2ccc(Cl)cc12] | 3-{[5-chloro-1-(cyclopropylmethyl)-1H-indazol-3-yl]amino}pyridine-4-carboxylic acid |
| 35 | 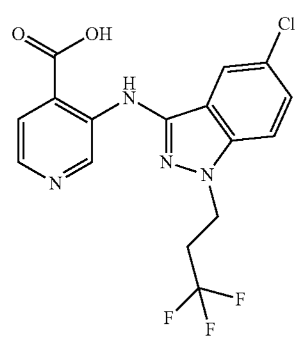 [SMILES: O=C(O)c1ccncc1Nc1nn(CCC(F)(F)F)c2ccc(Cl)cc12] | 3-{[5-chloro-1-(3,3,3-trifluoropropyl)-1H-indazol-3-yl]amino}pyridine-4-carboxylic acid |
| 36 | 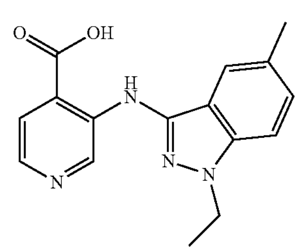 [SMILES: CCn1nc(Nc2cnccc2C(=O)O)c2cc(C)ccc21] | 3-[(1-ethyl-5-methyl-1H-indazol-3-yl)amino]pyridine-4-carboxylic acid |

TABLE 1-continued

| Chemical Synthesis Example | Structure | Name |
|---|---|---|
| 37 | 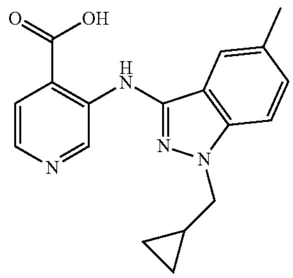 [SMILES: Cc1ccc2c(c1)c(Nc1cnccc1C(=O)O)nn2CC1CC1] | 3-{[1-(cyclopropylmethyl)-5-methyl-1H-indazol-3-yl]amino}pyridine-4-carboxylic acid |
| 38 | 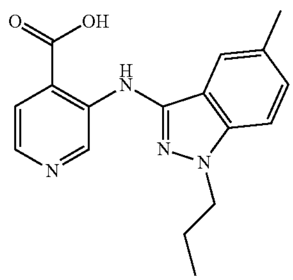 [SMILES: CCCn1nc(Nc2cnccc2C(=O)O)c2cc(C)ccc21] | 3-[(5-methyl-1-propyl-1H-indazol-3-yl)amino]pyridine-4-carboxylic acid |
| 39 | 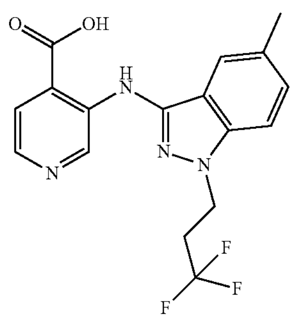 [SMILES: Cc1ccc2c(c1)c(Nc1cnccc1C(=O)O)nn2CCC(F)(F)F] | 3-{[5-methyl-1-(3,3,3-trifluoropropyl)-1H-indazol-3-yl]amino}pyridine-4-carboxylic acid |
| 40 | 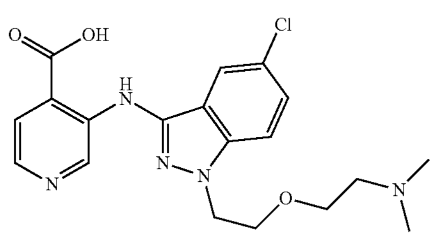 [SMILES: CN(C)CCOCCn1nc(Nc2cnccc2C(=O)O)c2cc(Cl)ccc21] | 3-[(1-{2-[2-(dimethylamino)ethoxy]ethyl}-5-chloro-1H-indazol-3-yl)amino]pyridine-4-carboxylic acid |
| 41 | 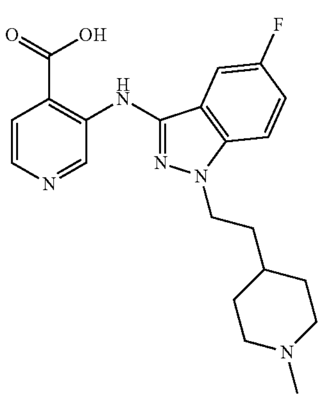 [SMILES: CN1CCC(CCn2nc(Nc3cnccc3C(=O)O)c3cc(F)ccc32)CC1] | 3-({5-fluoro-1-{2-(1-methylpiperidin-4-yl)ethyl]-1H-indazol-3-yl}amino)pyridine-4-carboxylic acid |

TABLE 1-continued

| Chemical Synthesis Example | Structure | Name |
|---|---|---|
| 42 | 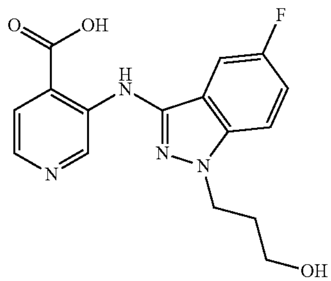 [SMILES: O=C(O)c1ccncc1Nc1nn(CCCO)c2ccc(F)cc12] | 3-{[5-fluoro-1-(3-hydroxypropyl)-1H-indazol-3-yl]amino}pyridine-4-carboxylic acid |
| 43 | 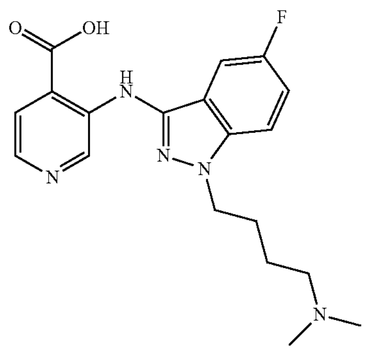 [SMILES: CN(C)CCCCn1nc(Nc2cnccc2C(=O)O)c2cc(F)ccc21] | 3-({1-[4-(dimethylamino)butyl]-5-fluoro-1H-indazol-3-yl}amino)pyridine-4-carboxylic acid |
| 44 | 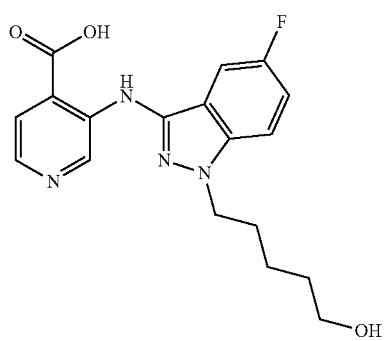 [SMILES: O=C(O)c1ccncc1Nc1nn(CCCCCO)c2ccc(F)cc12] | 3-{[5-fluoro-1-(5-hydroxypentyl)-1H-indazol-3-yl]amino}pyridine-4-carboxylic acid |
| 45 | 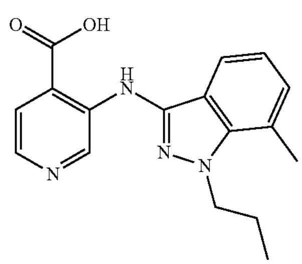 [SMILES: CCCn1nc(Nc2cnccc2C(=O)O)c2cccc(C)c21] | 3-[(5-methyl-1-propyl-1H-indazol-3-yl)amino]pyridine-4-carboxylic acid |
| 46 | 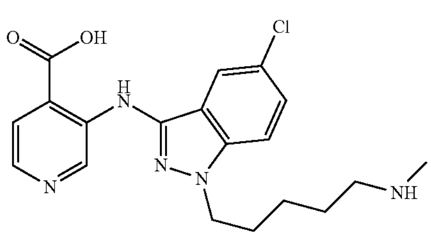 [SMILES: CNCCCCCn1nc(Nc2cnccc2C(=O)O)c2cc(Cl)ccc21] | 3-({5-fluoro-1-[5-(methylamino)pentyl]-1H-indazol-3-yl}amino)pyridine-4-carboxylic acid |

TABLE 1-continued

| Chemical Synthesis Example | Structure | Name |
|---|---|---|
| 47 | 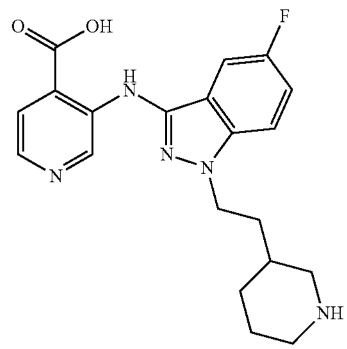 [SMILES: O=C(O)c1ccncc1Nc1nn(CCC2CCCNC2)c2ccc(F)cc12] | 3-({5-fluoro-1-[2-(piperidin-3-yl)ethyl]-1H-indazol-3-yl}amino)pyridine-4-carboxylic acid |
| 48 | 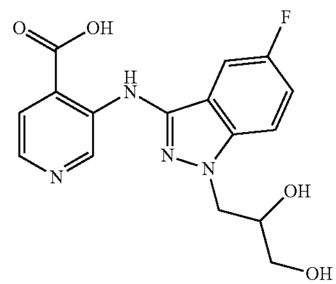 [SMILES: O=C(O)c1ccncc1Nc1nn(CC(O)CO)c2ccc(F)cc12] | 3-{[1-(2,3-dihydroxypropyl)-5-fluoro-1H-indazol-3-yl]amino}pyridine-4-carboxylic acid |
| 49 | 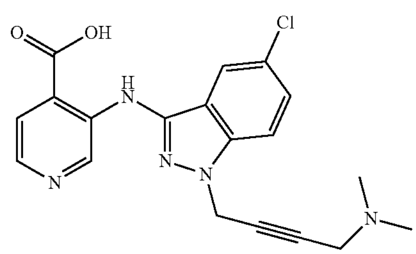 [SMILES: CN(C)CC#CCn1nc(Nc2cnccc2C(=O)O)c2cc(Cl)ccc21] | 3-({1-[4-(dimethylamino)but-2-yn-1-yl]-5-fluoro-1H-indazol-3-yl}amino)pyridine-4-carboxylic acid |
| 50 | 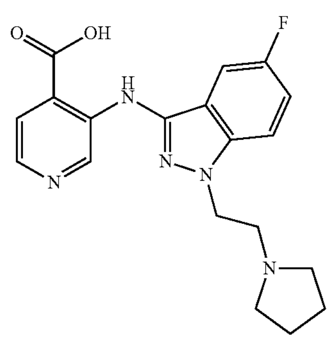 [SMILES: O=C(O)c1ccncc1Nc1nn(CCN2CCCC2)c2ccc(F)cc12] | 3-({5-fluoro-1-[2-(pyrrolidin-1-yl)ethyl]-1H-indazol-3-yl}amino)pyridine-4-carboxylic acid |
| 51 | 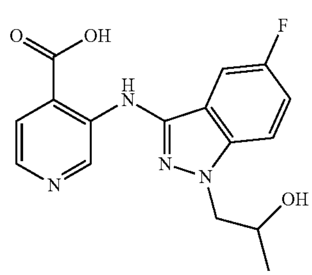 [SMILES: CC(O)Cn1nc(Nc2cnccc2C(=O)O)c2cc(F)ccc21] | 3-{[5-fluoro-1-(2-hydroxypropyl)-1H-indazol-3-yl]amino}pyridine-4-carboxylic acid |

TABLE 1-continued

| Chemical Synthesis Example | Structure | Name |
|---|---|---|
| 52 | 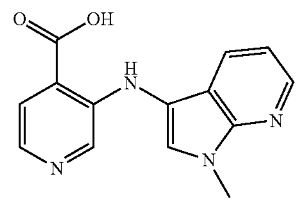 [SMILES: Cn1cc(Nc2cnccc2C(=O)O)c2cccnc21] | 3-[(1-methyl-1H-pyrrolo[2,3-b]pyridine-3-yl)amino]pyridine-4-carboxylic acid |
| 53 | 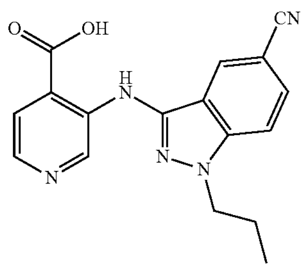 [SMILES: CCCn1nc(Nc2cnccc2C(=O)O)c2cc(C#N)ccc21] | 3-[(5-cyano-1H-indol-3-yl)amino]pyridine-4-carboxylic acid |
| 54 | 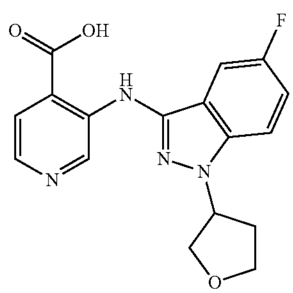 | 3-{[5-fluoro-1-(tetrahydrofuran-3-yl)-1H-indazol-3-yl]amino}pyridine-4-carboxylic acid |
| 55 | 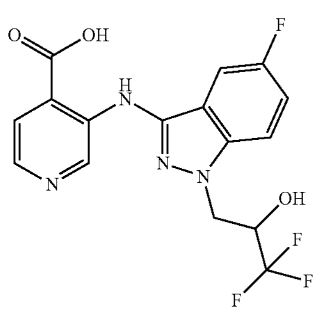 [SMILES: O=C(O)c1ccncc1Nc1nn(CC(O)C(F)(F)F)c2ccc(F)cc12] | 3-{[5-fluoro-1-(3,3,3-trifluoro-2-hydroxypropyl)-1H-indazol-3-yl]amino}pyridine-4-carboxylic acid |
| 56 | 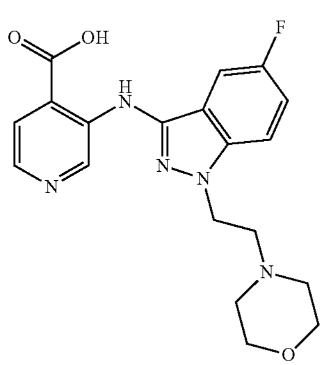 [SMILES: O=C(O)c1ccncc1Nc1nn(CCN2CCOCC2)c2ccc(F)cc12] | 3-({5-fluoro-1-[2-(morpholin-1-yl)ethyl]-1H-indazol-3-yl}amino)pyridine-4-carboxylic acid |

TABLE 1-continued

| Chemical Synthesis Example | Structure | Name |
|---|---|---|
| 57 | 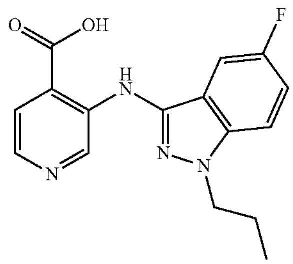 [SMILES: CCCn1nc(Nc2cnccc2C(=O)O)c2cc(F)ccc21] | 3-[(5-fluoro-1-propyl-1H-indol-3-yl)amino]pyridine-4-carboxylic acid |
| 58 | 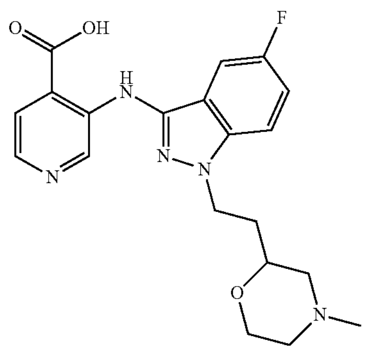 [SMILES: CN1CCOC(CCn2nc(Nc3cnccc3C(=O)O)c3cc(F)ccc32)C1] | 3-({5-fluoro-1-[2-(4-methylmorpholin-2-yl)ethyl]-1H-indazol-3-yl}amino)pyridine-4-carboxylic acid |
| 59 | 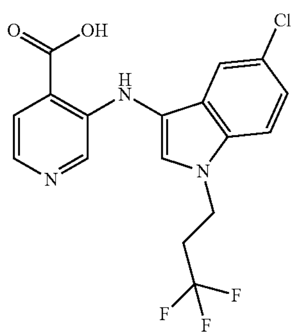 [SMILES: O=C(O)c1ccncc1Nc1cn(CCC(F)(F)F)c2ccc(Cl)cc12] | 3-{[5-chloro-1-(3,3,3-trifluoropropyl)-1H-indol-3-yl]amino}pyridine-4-carboxylic acid |
| 60 | 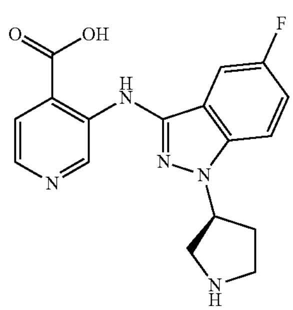 [SMILES: O=C(O)c1ccncc1Nc1nn([C@H]2CCNC2)c2ccc(F)cc12] | 3-({5-fluoro-1-[(3S)-pyrrolidin-3-yl]-1H-indazol-3-yl}amino)pyridine-4-carboxylic acid |
| 61 | 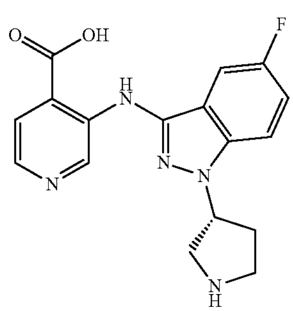 [SMILES: O=C(O)c1ccncc1Nc1nn([C@@H]2CCNC2)c2ccc(F)cc12] | 3-({5-fluoro-1-[(3R)-pyrrolidin-3-yl]-1H-indazol-3-yl}amino)pyridine-4-carboxylic |

TABLE 1-continued

| Chemical Synthesis Example | Structure | Name |
|---|---|---|
| 62 | 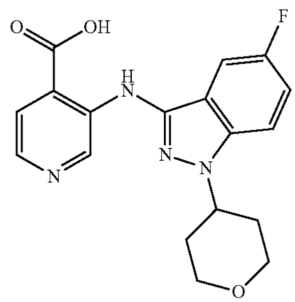 [SMILES: O=C(O)c1ccncc1Nc1nn(C2CCOCC2)c2ccc(F)cc12] | 3-{[5-fluoro-1-(tetrahydro-2H-pyran-4-yl)-1H-indazol-3-yl]amino}pyridine-4-carboxylic acid |
| 63 | 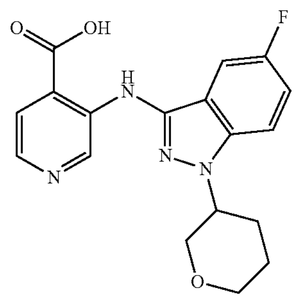 [SMILES: O=C(O)c1ccncc1Nc1nn(C2CCCOC2)c2ccc(F)cc12] | 3-{[5-fluoro-1-(tetrahydro-2H-pyran-3-yl)-1H-indazol-3-yl]amino}pyridine-4-carboxylic acid |
| 64 | 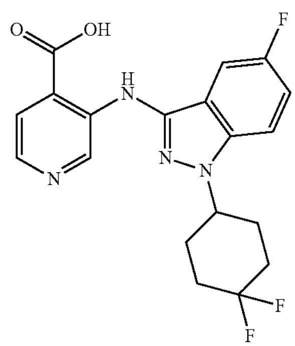 [SMILES: O=C(O)c1ccncc1Nc1nn(C2CCC(F)(F)CC2)c2ccc(F)cc12] | 3-{[1-(4,4-difluorocyclohexyl)-5-fluoro-1H-indazol-3-yl]amino}pyridine-4-carboxylic acid |
| 65 | 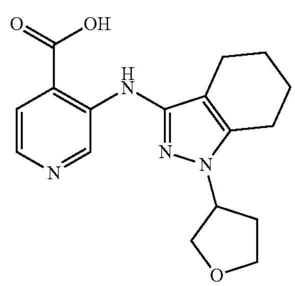 [SMILES: O=C(O)c1ccncc1Nc1nn(C2CCOC2)c2c1CCCC2] | 3-{[1-(tetrahydrofuran-3-yl)-4,5,6,7-tetrahydro-1H-indazol-3-yl]amino}pyridine-4-carboxylic acid |
| 66 | 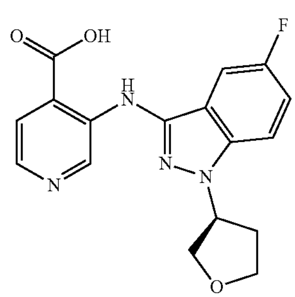 [SMILES: O=C(O)c1ccncc1Nc1nn([C@H]2CCOC2)c2ccc(F)cc12] | 3-({5-fluoro-1-[(3S)-tetrahydrofuran-3-yl]-1H-indazol-3-yl}amino)pyridine-4-carboxylic acid |

TABLE 1-continued
| Chemical Synthesis Example | Structure | Name |
|---|---|---|
| 67 | 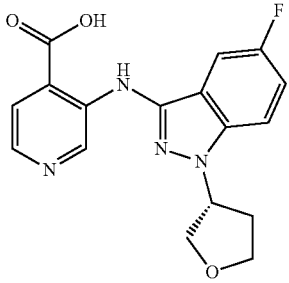 [SMILES: O=C(O)c1ccncc1Nc1nn([C@@H]2CCOC2)c2ccc(F)cc12] | 3-({5-fluoro-1-[(3R)-tetrahydrofuran-3-yl]-1H-indazol-3-yl}amino)pyridine-4-carboxylic acid |
| 68 | 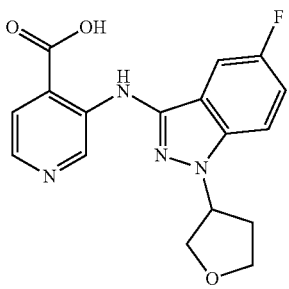 [SMILES: O=C(O)c1ccncc1Nc1nn(C2CCOC2)c2ccc(F)cc12] | 3-{[5-fluoro-1-(tetrahydrofuran-3-yl)-1H-indol-3-yl]amino}pyridine-4-carboxylic acid |
| 69 | 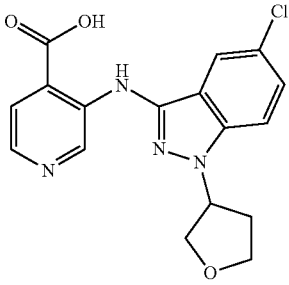 [SMILES: O=C(O)c1ccncc1Nc1nn(C2CCOC2)c2ccc(Cl)cc12] | 3-{[5-chloro-1-(tetrahydrofuran-3-yl)-1H-indazol-3-yl]amino}pyridine-4-carboxylic acid |
| 70 | 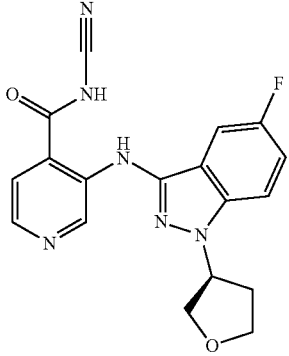 [SMILES: N#CNC(=O)c1ccncc1Nc1nn([C@H]2CCOC2)c2ccc(F)cc12] | N-cyano-3-({5-fluoro-1-[(3S)-tetrahydrofuran-3-yl]-1H-indazol-3-yl}amino)pyridine-4-carboxamide |

TABLE 1-continued

| Chemical Synthesis Example | Structure | Name |
|---|---|---|
| 71 | 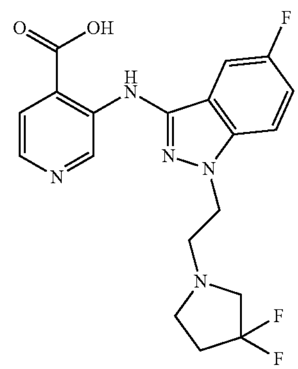 [SMILES: O=C(O)c1ccncc1Nc1nn(CCN2CCC(F)(F)C2)c2ccc(F)cc12] | 3-({1-[2-(3,3-difluoropyrrolidin-1yl)ethyl]-5-fluoro-1H-indazol-3-yl}amino)pyridine-4-carboxylic acid |
| 72 | 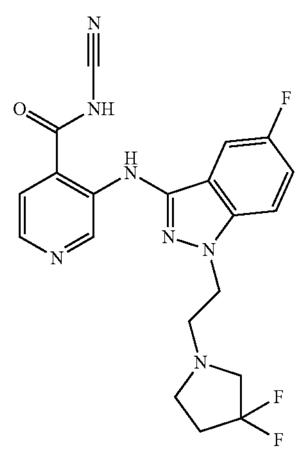 [SMILES: N#CNC(=O)c1ccncc1Nc1nn(CCN2CCC(F)(F)C2)c2ccc(F)cc12] | N-cyano-3-({1-[2-(3,3-difluoropyrrolidin-1yl)ethyl]-5-fluoro-1H-indazol-3-yl}amino)pyridine-4-carboxamide |
| 73 | 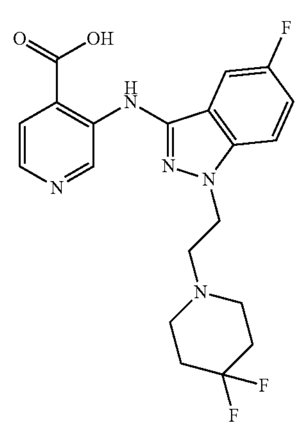 [SMILES: O=C(O)c1ccncc1Nc1nn(CCN2CCC(F)(F)CC2)c2ccc(F)cc12] | 3-({1-[2-(4,4-difluoropiperidin-1yl)ethyl]-5-fluoro-1H-indazol-3-yl}amino)pyridine-4-carboxylic acid |

TABLE 1-continued
| Chemical Synthesis Example | Structure | Name |
|---|---|---|
| 74 | 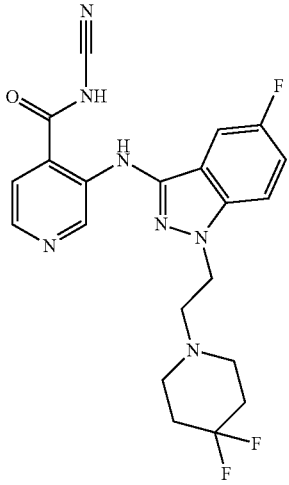 [SMILES: N#CNC(=O)c1ccncc1Nc1nn(CCN2CCC(F)(F)CC2)c2ccc(F)cc12] | N-cyano-3-({1-[2-(4,4-difluoropiperidin-1yl)ethyl]-5-fluoro-1H-indazol-3-yl}amino)pyridine-4-carboxamide |
| 75 | 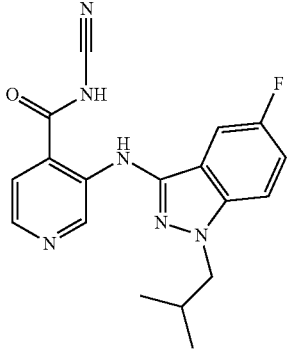 [SMILES: CC(C)Cn1nc(Nc2cnccc2C(=O)NC#N)c2cc(F)ccc21] | N-cyano-3-{[5-fluoro-1-(2-methylpropyl)-1H-indazol-3-yl]amino}pyridine-4-carboxamide |
| 76 | 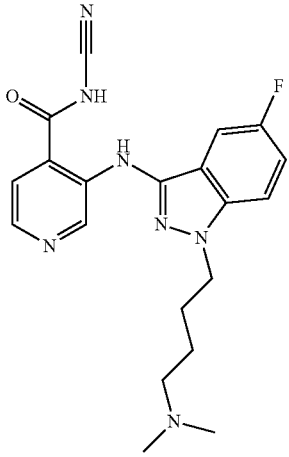 [SMILES: CN(C)CCCCn1nc(Nc2cnccc2C(=O)NC#N)c2cc(F)ccc21] | N-cyano-3-({1-[4-(dimethylamino)butyl]-5-fluoro-1H-indazol-3-yl}amino)pyridine-4-carboxamide |

TABLE 1-continued

| Chemical Synthesis Example | Structure | Name |
|---|---|---|
| 77 | 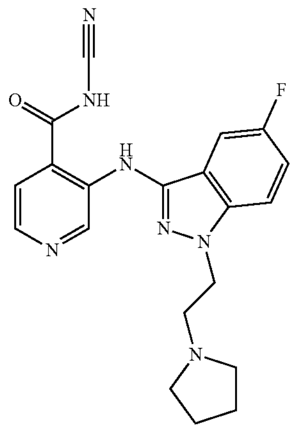 [SMILES: N#CNC(=O)c1ccncc1Nc1nn(CCN2CCCC2)c2ccc(F)cc12] | N-cyano-3-({5-fluoro-1-[2-(pyrrolidin-1-yl)ethyl]-1H-indazol-3-yl}amino)pyridine-4-carboxamide |
| 78 | 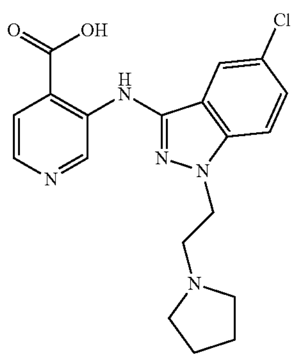 [SMILES: O=C(O)c1ccncc1Nc1nn(CCN2CCCC2)c2ccc(Cl)cc12] | 3-({5-chloro-1-[2-(pyrrolidin-1-yl)ethyl]-1H-indazol-3-yl}amino)pyridine-4-carboxylic acid |
| 79 | 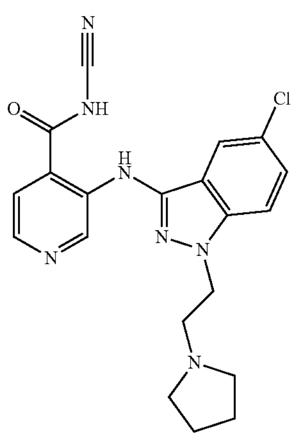 [SMILES: N#CNC(=O)c1ccncc1Nc1nn(CCN2CCCC2)c2ccc(Cl)cc12] | N-cyano-3-({5-chloro-1-[2-(pyrrolidin-1-yl)ethyl]-1H-indazol-3-yl}amino)pyridine-4-carboxamide |

In some embodiments, the substituted aminopyridine derivative compound as described herein, or a carboxylic acid ester, or carboxylic acid bioisostere thereof, has the structure provided in Table 2.

TABLE 2

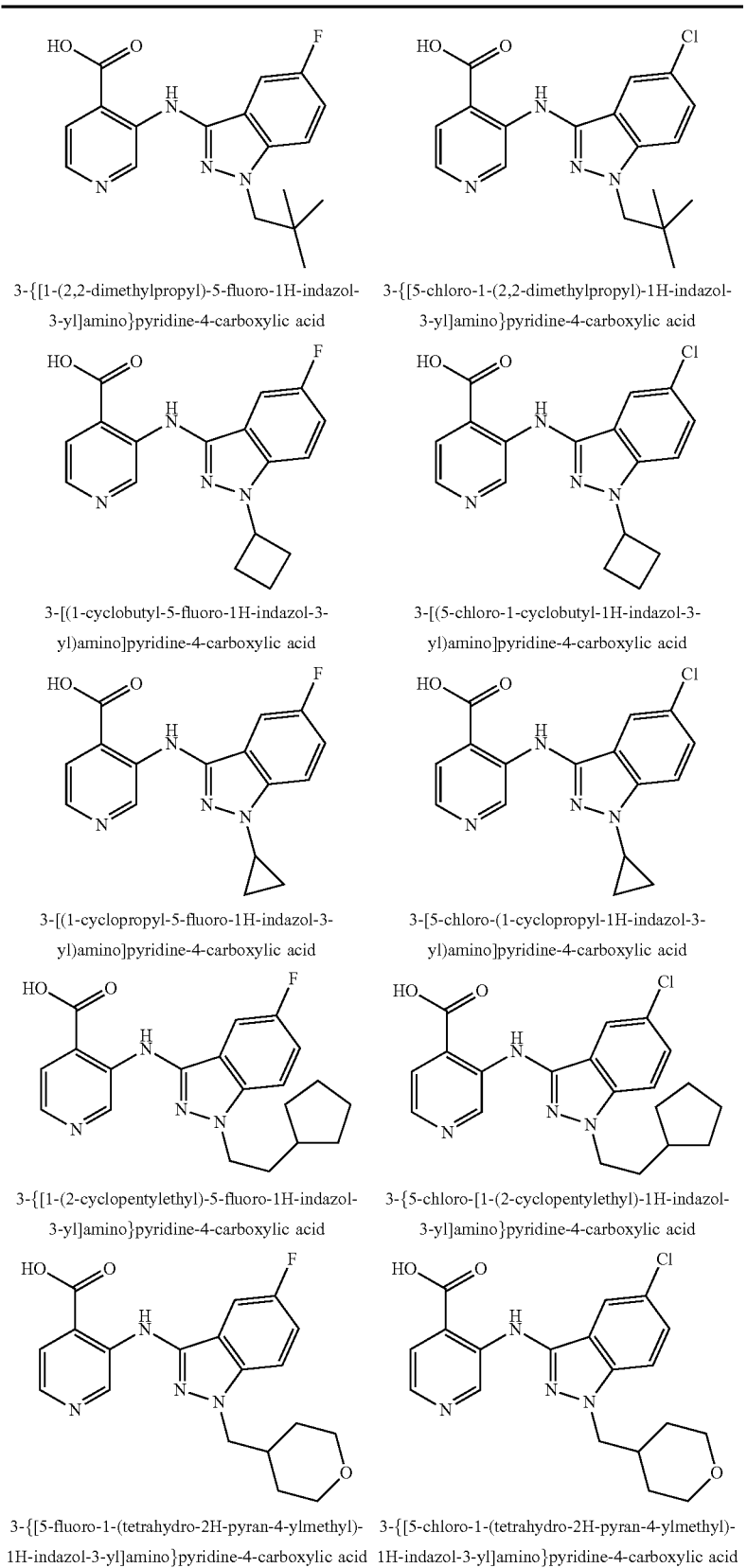

3-{[1-(2,2-dimethylpropyl)-5-fluoro-1H-indazol-3-yl]amino}pyridine-4-carboxylic acid 3-{[5-chloro-1-(2,2-dimethylpropyl)-1H-indazol-3-yl]amino}pyridine-4-carboxylic acid 3-[(1-cyclobutyl-5-fluoro-1H-indazol-3-yl)amino]pyridine-4-carboxylic acid 3-[(5-chloro-1-cyclobutyl-1H-indazol-3-yl)amino]pyridine-4-carboxylic acid 3-[(1-cyclopropyl-5-fluoro-1H-indazol-3-yl)amino]pyridine-4-carboxylic acid 3-[5-chloro-(1-cyclopropyl-1H-indazol-3-yl)amino]pyridine-4-carboxylic acid 3-{[1-(2-cyclopentylethyl)-5-fluoro-1H-indazol-3-yl]amino}pyridine-4-carboxylic acid 3-{5-chloro-[1-(2-cyclopentylethyl)-1H-indazol-3-yl]amino}pyridine-4-carboxylic acid 3-{[5-fluoro-1-(tetrahydro-2H-pyran-4-ylmethyl)-1H-indazol-3-yl]amino}pyridine-4-carboxylic acid 3-{[5-chloro-1-(tetrahydro-2H-pyran-4-ylmethyl)-1H-indazol-3-yl]amino}pyridine-4-carboxylic acid TABLE 2-continued

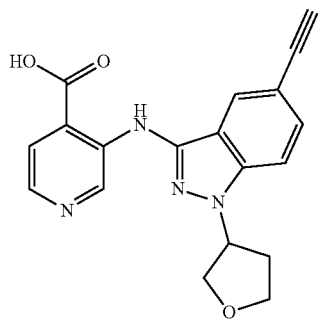 [SMILES: C#Cc1ccc2c(c1)c(Nc1cnccc1C(=O)O)nn2C1CCOC1]

3-{[5-ethynyl-1-(tetrahydrofuran-3-yl)-1H-indazol-3-yl]amino}pyridine-4-carboxylic acid

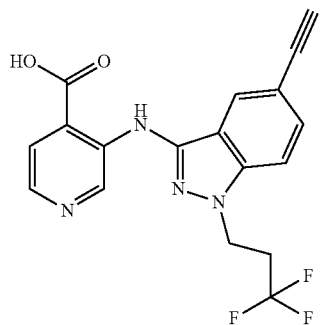 [SMILES: C#Cc1ccc2c(c1)c(Nc1cnccc1C(=O)O)nn2CCC(F)(F)F]

3-{[5-ethynyl-1-(3,3,3-trifluoropropyl)-1H-indazol-3-yl]amino}pyridine-4-carboxylic acid Preparation of the Substituted 3-Aminopyridine Derivative Compounds and Substituted 3-Aminopyridazine Derivative Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted 3-aminopyridine derivative compounds and the substituted 3-aminopyridazine derivative compounds described herein is P. H. Stahl & C. G. Wermuth "Handbook of Pharmaceutical Salts", Verlag Helvetica Chimica Acta, Zurich, 2002.

The substituted 3-aminopyridine derivative compounds and substituted 3-aminopyridazine derivative compounds are prepared by the general synthetic routes described below in Schemes 1-6.

Scheme 1

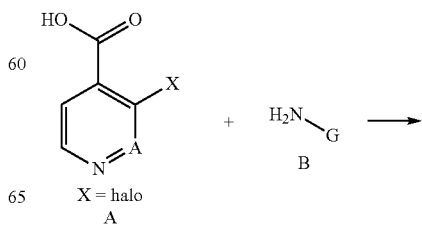

-continued

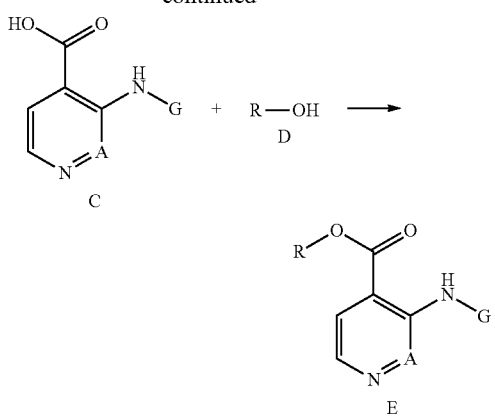

A = CH, N

Referring to Scheme 1, compound A and an amino compound B are mixed and treated under a variety of conditions to form compound C. For example, compound A can be added to a mixture of aniline B and an appropriate base, such as LiHMDS, in an appropriate solvent, at temperatures ranging from −78° C. to 0° C. The ester compound E can be prepared from compound C and an alcohol D using a coupling reagent, such as HATU, in the presence of a base.

Scheme 2

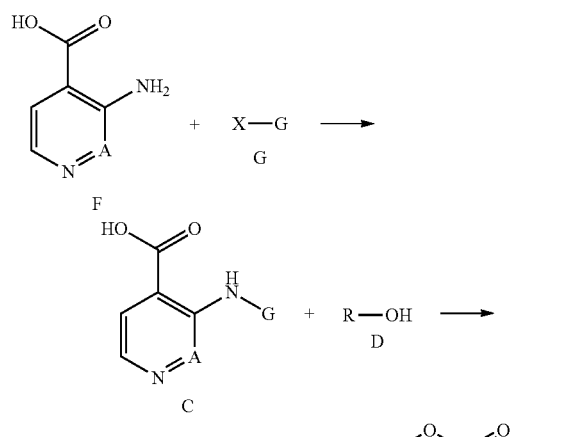

A = CH, N

Referring to Scheme 2, compound F and electrophile X-G (G) are mixed and treated under a variety of conditions to produce compound C. For example, aryl halide compound G can be added to a solution of F and LiHMDS in an appropriate solvent, at temperatures ranging from −78° C. to 0° C. The ester compound E can be prepared from compound C and an alcohol D using a coupling reagent, such as HATU, in the presence of a base.

Scheme 3

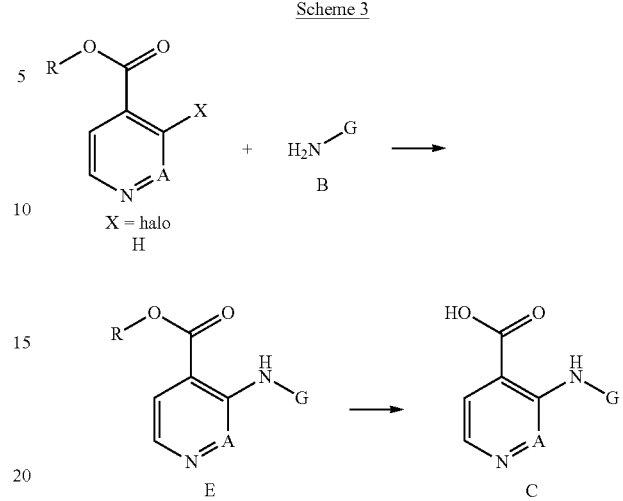

A = CH, N

Referring to Scheme 3, compound H and amino compound B are mixed and treated under a variety of conditions to form compound E. For example, the mixture of compound H and an aniline B can be subjected to a Buchwald reaction under microwave irradiation in an appropriate solvent, at temperatures ranging from 100° C. to 120° C. The ester compound E can be hydrolyzed to give compound C, using basic conditions such as 1N aq. NaOH.

Scheme 4

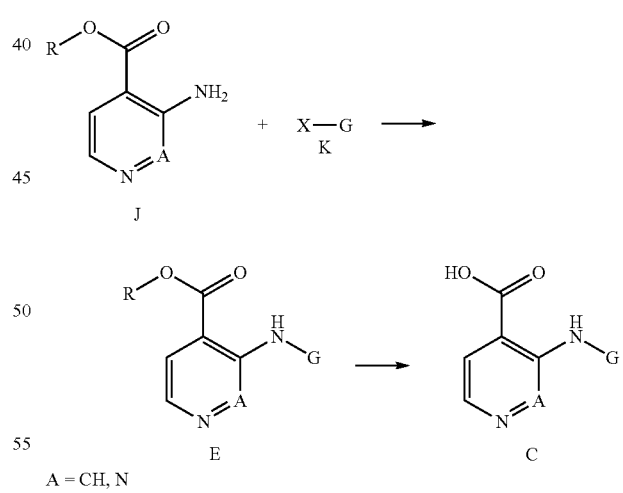

A = CH, N

Referring to Scheme 4, compound J and electrophile X-G (K) are mixed and treated under a variety of conditions to form compound E. For example, the mixture of compound J and an aryl halide K can be subjected to a Buchwald reaction under microwave irradiation in an appropriate solvent, at temperatures ranging from 100° C. to 120° C. The ester compound E can be hydrolyzed to give compound C, using basic conditions such as 1N aq. NaOH.

Scheme 5

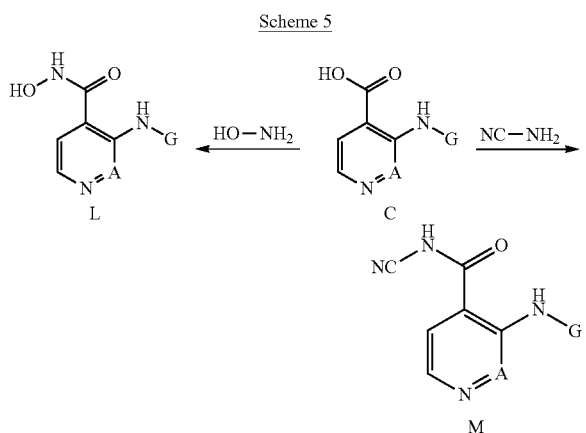

Methods for preparing compounds L and M are provided in Scheme 5. Treatment of acid compound C with hydroxylamine hydrochloride in the presence of a coupling reagent, such as HATU, in a solvent, such as DMF, at room temperature for 1 to 24 hours provides compound L. Compound C can also be used to prepare N-acylcyanamides such as compound M. Treatment of compound C with cyanamide in the presence of an acid coupling reagent, such as HATU, in a solvent, such as DMF, at room temperature for 1 to 24 hours provides compound M.

Scheme 6

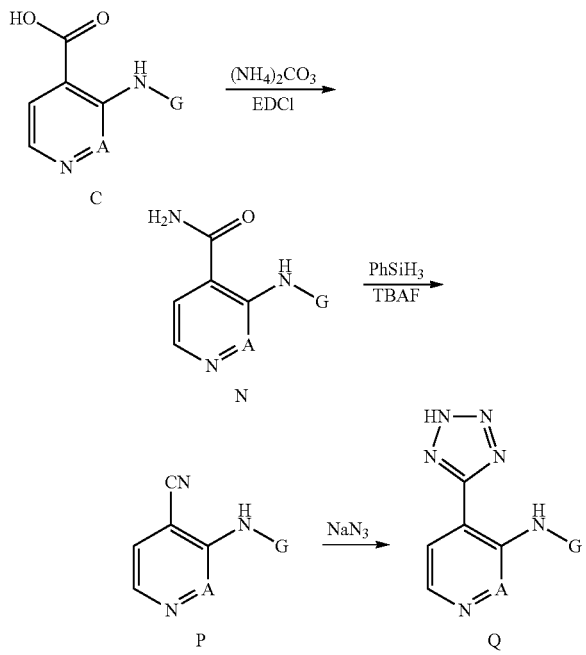

A method for preparing compounds Q is provided in Scheme 6. Treatment of acid compound C with ammonium carbonate in the presence of a coupling reagent, such as EDCI, in a solvent, such as THF, at room temperature for 1 to 24 hours provides compound N. Amide dehydration, with reagents such as a silane and TBAF, affords nitrile P. Treatment of the nitrile P with sodium azide and ammonium chloride in DMF followed by heating to 90° C. for 2 to 24 hours provides the desired tetrazole compound Q.

In each of the above reaction procedures or schemes, the various substituents may be selected from among the various substituents otherwise taught herein.

Pharmaceutical Compositions

In certain embodiments, a substituted 3-aminopyridine derivative compound or a substituted 3-aminopyridazine derivative compound as described herein is administered as a pure chemical. In other embodiments, the substituted 3-aminopyridine derivative compound or the substituted 3-aminopyridazine derivative compound as described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)), the disclosure of which is hereby incorporated herein by reference, in its entirety.

Accordingly, provided herein is a pharmaceutical composition comprising at least one substituted 3-aminopyridine derivative compound or substituted 3-aminopyridazine derivative compound, or a stereoisomer, pharmaceutically acceptable salt, hydrate, solvate, or N-oxide thereof, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), Formula (II), Formula (III), Formula (IIIa), Formula (IIIb), Formula (IV), Formula (V), or Formula (VI) or a tautomer, stereoisomer, geometric isomer, N-oxide, or pharmaceutically acceptable salt thereof.

One embodiment provides a pharmaceutical composition comprising a pharmaceutically acceptable carrier and a compound having the structure of a compound provided in Table 1 or Table 2, or an alkyl ester derivative thereof, or a tautomer, stereoisomer, geometric isomer, N-oxide, or pharmaceutically acceptable salt thereof.

In certain embodiments, the substituted 3-aminopyridine derivative compound or the substituted 3-aminopyridazine derivative compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

The dose of the composition comprising at least one substituted 3-aminopyridine derivative compound or substituted 3-aminopyridazine derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenyosyl methionine (SAM) to histones. Histone methylation is known to participate in a diverse range of biological processes including heterochromatin formation, X-chromosome inactivation, and transcriptional regulation (Lachner et al., (2003) J. Cell Sci. 116:2117-2124; Margueron et al., (2005) Curr. Opin. Genet. Dev. 15:163-176).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas mono-methylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 family of proteins are a family of histone-demethylases known to demethylate tri- and di-methylated H3-K9, and were the first identified histone tri-methyl demethylases. In particular, ectopic expression of JMJD2 family members was found to dramatically decrease levels of tri- and di-methylated H3-K9, while increasing levels of mono-methylated H3-K9, which delocalized Heterochromatin Protein 1 (HP1) and reduced overall levels of heterochromatin in vivo. Members of the JMJD2 subfamily of jumonji proteins include JMJD2C and its homologues JMJD2A, JMJD2B, JMJD2D and JMJD2E. Common structural features found in the JMJD2 subfamily of Jumonji proteins include the JmjN, JmjC, PHD and Tdr sequences.

JMJD2C, also known as GASC1 and KDM4C, is known to demethylate tri-methylated H3K9 and H3K36. Histone demethylation by JMJD2C occurs via a hydroxylation reaction dependent on iron and $\alpha$-ketoglutarate, wherein oxidative decarboxylation of $\alpha$-ketoglutarate by JMJD2C produces carbon dioxide, succinate, and ferryl and ferryl subsequently hydroxylates a methyl group of lysine H3K9, releasing formaldehyde. JMJD2C is known to modulate regulation of adipogenesis by the nuclear receptor PPARγ and is known to be involved in regulation of self-renewal in embryonic stem cells.

JARID Family

As used herein, a "JARID protein" includes proteins in the JARID1 subfamily (e.g., JARID1A, JARID1B, JARID1C and JARID1D proteins) and the JARID2 subfamily, as well as homologues thereof. A further description and listing of JARID proteins can be found in Klose et al. (2006) Nature Reviews/Genetics 7:715-727. The JARID1 family contains several conserved domains: JmjN, ARID, JmjC, PHD and a C5HC2 zing finger.

JARID1A, also called KDM5A or RBP2, was initially found as a binding partner of retinoblastoma (Rb) protein. JARID1A was subsequently found to function as a demethylase of tri- and di-methylated H3K4, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastome binding protein 2 (RBP2) histone demethylase suppresses tumorigenesis in mice lacking Rb1 or Men1 (Lin et al. Proc. Natl. Acad. Sci. USA, Aug. 16, 2011, 108(33),13379-86; doi: 10.1073/pnas.1110104108) and the authors of the study concluded that RBP2-inhibitory drugs would have anti-cancer activity.

JARID1B, also referred to as KDM5B and PLU1, was originally found in experiments to discover genes regulated by the HER2 tyrosine kinase. JARID1B has consistently been found to be expressed in breast cancer cell lines, although restriction of JARID1B has been found in normal adult tissues, with the exception of the testis. In addition, 90% of invasive ductal carcinomas have been found to express JARID1B. In addition, JARID1B has been found to be up-regulated in prostate cancers, while having more limited expression in benign prostate, and has also been found to be up-regulated in bladder cancer and lung cancer (both SCLC and NSCLC). JARID1B has also been found to repress tumor suppressor genes such as BRCA1, CAV1 and 14-3-3σ, and knockdown of JARID1B was found to increase the levels of tri-methylated H3K4 at these genes.

One embodiment provides a method for inhibiting histone demethylase comprising the use of a compound of Formula (I), Formula (II), Formula (III), Formula (IIIa), Formula (IIIb), Formula (IV), Formula (V), or Formula (VI), or a tautomer, stereoisomer, geometric isomer, N-oxide, or pharmaceutically acceptable salt thereof.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the invention provides a method of treating a disease regulated by histone methylation and/or demethylation in a subject in need thereof by modulating the activity of a demethylase comprising a JmjC domain (e.g., a histone demethylase such as a JHDM protein(s)).

One embodiment provides a method for treating cancer in subject comprising administering to the subject in need thereof a composition comprising a compound of Formula (I), Formula (II), Formula (III), Formula (IIIa), Formula (IIIb), Formula (IV), Formula (V), or Formula (VI), or a tautomer, stereoisomer, geometric isomer, N-oxide, or pharmaceutically acceptable salt thereof. One embodiment provides a method for treating cancer in subject comprising administering to the subject in need thereof a composition comprising a compound of Formula (I), Formula (II), Formula (III), Formula (IIIa), Formula (IIIb), Formula (IV), Formula (V), or Formula (VI), or a tautomer, stereoisomer, geometric isomer, N-oxide, or pharmaceutically acceptable salt thereof. One embodiment provides a method for treating cancer in subject comprising administering to the subject in need thereof a composition comprising a compound of Formula (I), Formula (II), Formula (III), Formula (IIIa), Formula (IIIb), Formula (IV), Formula (V), or Formula (VI), or a tautomer, stereoisomer, geometric isomer, N-oxide, or pharmaceutically acceptable salt thereof, wherein the compound of Formula (I), Formula (II), Formula (III), Formula (IIIa), Formula (IIIb), Formula (IV), Formula (V), or Formula (VI), is selected from Table 1 or Table 2, as provided herein.

In a further embodiment is the method for treating cancer in a subject wherein the cancer is selected from prostate cancer, breast cancer, bladder cancer, lung cancer or melanoma.

In an additional embodiment is a method for inhibiting the growth of a tumor comprising administering a composition comprising a compound of Formula (I), Formula (II), Formula (III), Formula (IIIa), Formula (IIIb), Formula (IV), Formula (V), or Formula (VI), or a pharmaceutically acceptable salt thereof, wherein the tumor is characterized by a loss of retinoblastoma gene (RB1) function.

In an additional embodiment is a method for inhibiting the growth of a tumor comprising administering a composition comprising a compound of Formula (I), Formula (II), Formula (III), Formula (IIIa), Formula (IIIb), Formula (IV), Formula (V), or Formula (VI), or a pharmaceutically acceptable salt thereof, wherein the tumor is characterized by a loss of multiple endocrine neoplasia type 1 gene (Men1) function.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

$^1$H NMR spectra were recorded on Bruker Avance III plus 400 MHz and TMS was used as an internal standard.

LCMS was taken on a quadrupole Mass Spectrometer on Agilent LC/MSD 1200 Series (Column: Welchrom XB-C18 (50×4.6 mm, 5 μm) operating in ES (+) or (−) ionization mode; T=30° C.; flow rate=1.5 mL/min.

Prep-HPLC was performed at conditions: (Flash: Welchrom C18, 150×20 mm); Wavelength 220 nm; Mobile phase: A MeCN (0.1% TFA); B water (0.1% TFA); Flow rate: 25 mL/min; Injection volume: 2 mL; Run time: 30 min; Equilibration: 5 min Preparation 1A and 1B:
3-iodo-1-methyl-1H-indazole and
3-iodo-2-methyl-2H-indazole

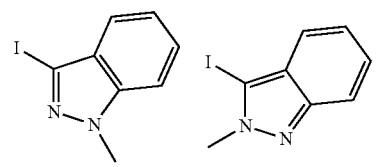

3-iodo-indazole (2.0 g, 8.2 mmol) was stirred in THF (20 mL) at 0° C. under N$_2$. NaH (60%, 394 mg, 9.8 mmol) was added, and the reaction stirred 30 min. Iodomethane (1.4 g, 9.8 mmol) was added, and the reaction stirred overnight while warming to rt. The solution was quenched with water and extracted with EtOAc. Organics were washed with brine, dried (Na$_2$SO$_4$) and concentrated. Purification by silica gel chromatography (10%-40% EtOAc/hexanes gave two isomers:

3-iodo-1-methyl-1H-indazole (1.2 g, 57%) was isolated as the major isomer eluting first. $^1$H NMR (400 MHz, CDCl$_3$): δ 4.10 (3H, s), 7.18-7.22 (1H, m), 7.35 (1H, d, J=8.4 Hz), 7.42-7.46 (2H, m).

3-iodo-2-methyl-2H-indazole (300 mg, 14%) was isolated as the minor isomer eluting second. $^1$H NMR (400 MHz, CDCl$_3$): δ 4.26 (3H, s), 7.12 (1H, t, J=7.6 Hz), 7.31 (1H, t, J=7.6 Hz), 7.38 (1H, d, J=8.4 Hz), 7.65 (1H, d, J=8.8 Hz).

Preparation 1C: Methyl 3-[(1-methyl-1H-indazol-3-yl)amino]pyridine-4-carboxylate

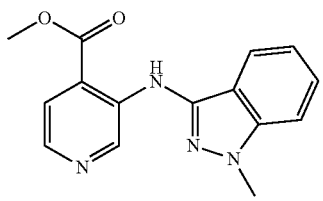 [SMILES: COC(=O)c1ccncc1Nc1nn(C)c2ccccc12]

To a suspension of compound Preparation 1A (100 mg, 0.39 mmol), methyl-3-aminoisonicotinate (83 mg, 0.54 mmol), Cs$_2$CO$_3$ (176 mg, 0.54 mmol), and Xantphos (68 mg, 0.12 mmol) in dioxane (10 mL) was added Pd$_2$(dba)$_3$ (36 mg, 0.039 mmol) under N$_2$ at rt. The suspension was heated at 110° C. overnight. The reaction was filtered and concentrated. Purification by silica gel chromatography (20%-60% EtOAc/hexanes) gave 75 mg (69%) of the title compound as a yellow solid. $^1$H NMR (400 MHz, DMSO-d$_6$): δ 3.97 (3H, s), 4.00 (3H, s), 7.13 (1H, t, J=7.6 Hz), 7.33 (1H, d, J=8.5 Hz), 7.43 (1H, t, J=7.6 Hz), 7.69 (1H, d, J=8.1 Hz), 7.79 (1H, br s), 8.18 (1H, br s), 9.76 (1H, s), 10.16 (1H, s). [M+H] calc'd for C$_{15}$H$_{14}$N$_4$O$_2$, 283; found 283.

Example 1

3-[(1-methyl-1H-indazol-3-yl)amino]pyridine-4-carboxylic acid

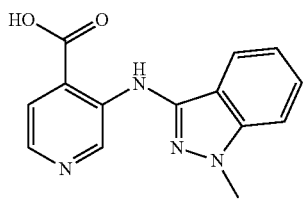

Preparation 1C (75 mg, 0.27 mmol) was stirred in MeOH (2 mL) with 2N NaOH (2 mL) at 50° C. for 30 min. The solution was cooled and acidified with 1N HCl to pH 5, and then filtered to give 50 mg (69%) of the title compound as an orange solid. $^1$H NMR (400 MHz, DMSO-d$_6$): δ 4.00 (3H, s), 7.16 (1H, t, J=7.6 Hz), 7.45-7.49 (1H, m), 7.59-7.63 (2H, m), 7.80 (1H, d, J=4.8 Hz), 7.17 (1H, d, J=4.8 Hz), 9.68 (1H, s), 10.54 (1H, br s). [M+H] calc'd for C$_{14}$H$_{12}$N$_4$O$_2$, 269; found, 269.

Example 2

3-[(2-methyl-2H-indazol-3-yl)amino]pyridine-4-carboxylic acid

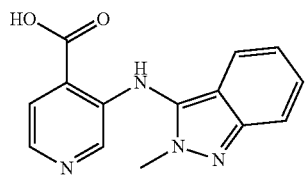 [SMILES: Cn1nc2ccccc2c1Nc1cnccc1C(=O)O]

The title compound was prepared in 20% yield from Preparation 1B and methyl 3-aminoisonicotinate according to the procedure for Preparation 1C, followed by hydrolysis according to Example 1. $^1$H NMR (400 MHz, DMSO-d$_6$): δ 4.00 (3H, s), 6.97-7.01 (1H, m), 7.23-7.27 (1H, m), 7.32 (1H, d, J=8.0 Hz), 7.59 (1H, d, J=8.4 Hz), 7.72-7.75 (2H, m), 8.07 (1H, d, J=7.2 Hz), 9.26 (1H, s), 13.90 (1H, br s). [M+H] calc'd for C$_{14}$H$_{12}$N$_4$O$_2$, 268; found, 269.

Example 3

3-(1,2-benzoxazol-3-ylamino]pyridine-4-carboxylic acid

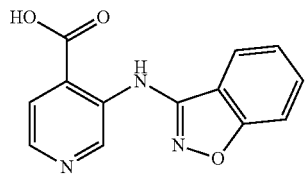

The title compound was prepared in 2% yield from 1,2-benzoxazol-3-amine and methyl 3-aminoisonicotinate according to the procedure for Preparation 1C, followed by hydrolysis according to Example 1. $^1$H NMR (400 MHz, DMSO-d$_6$): δ 7.49 (1H, s), 7.73-7.90 (4H, m), 8.38 (1H, s), 9.62 (1H, s), 11.32 (1H, br s). [M+H] calc'd for C$_{13}$H$_9$N$_3$O$_3$, 256; found 256.

Preparation 4A and 4B: 5-chloro-3-iodo-1-methyl-1H-indazole and 5-chloro-3-iodo-2-methyl-2H-indazole

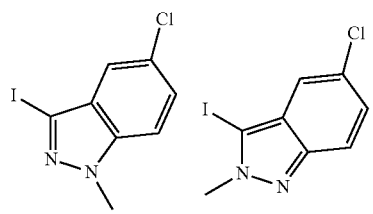

5-Chloro-3-iodo-indazole (1.0 g, 3.6 mmol) was stirred in DMF (8 mL) at 0° C. under N$_2$. NaH (60%, 159 mg, 3.96 mmol) was added, and the reaction stirred 45 min. Iodomethane (260 μL, 4.14 mmol) was added, and the reaction stirred 45 min while warming to rt. The solution was quenched with MeOH and concentrated. Purification by silica gel chromatography (10%-40% EtOAc/hexanes gave two isomers:

5-chloro-3-iodo-1-methyl-1H-indazole (740 mg, 70%) was isolated as the major isomer eluting first. $^1$H NMR (400 MHz, CDCl$_3$): δ 4.09 (3H, s), 7.30 (1H, d, J=8.9 Hz), 7.39 (1H, dd, J=8.9, 1.6 Hz), 7.47 (1H, d, J=1.6 Hz). [M+H] calc'd for $C_8H_6ClIN_2$, 293, 295; found 293, 295.

5-chloro-3-iodo-2-methyl-2H-indazole (268 mg, 25%) was isolated as the minor isomer eluting second. $^1$H NMR (400 MHz, CDCl$_3$): δ 4.24 (3H, s), 7.24 (1H, dd, J=9.1, 2.0 Hz), 7.38 (d, 1H, J=1.9 Hz), 7.59 (1H, d, J=9.1 Hz). [M+H] calc'd for $C_8H_6ClIN_2$, 293, 295; found 293, 295.

Preparation 4C: methyl 3-[(5-chloro-1-methyl-1H-indazol-3-yl)amino]pyridine-4-carboxylate

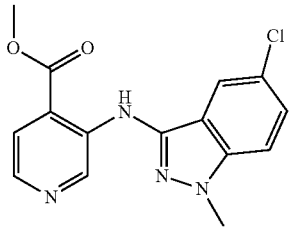 [SMILES: COC(=O)c1ccncc1Nc1nn(C)c2ccc(Cl)cc12]

The title compound was prepared in 25% yield from methyl 3-aminoisonicotinate and Preparation 4A according to the general procedure for Preparation 1C. $^1$H NMR (400 MHz, DMSO-d$_6$): δ 4.00 (3H, s), 4.02 (3H, s), 7.26 (1H, d, J=8.8 Hz), 7.37 (1H, dd, J=8.8, 1.8 Hz), 7.67 (1H, d, J=1.8 Hz), 7.80 (1H, d, J=5.2 Hz), 8.18 (1H, d, J=5.2 Hz), 9.74 (1H, s), 10.15 (1H, br s). [M+H] calc'd for $C_{15}H_{13}ClN_4O_2$, 317, 319; found 317, 319.

Example 4

3-[(5-chloro-1-methyl-1H-indazol-3-yl)amino]pyridine-4-carboxylic acid

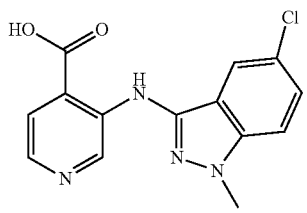 [SMILES: Cn1nc(Nc2cnccc2C(=O)O)c2cc(Cl)ccc21]

The title compound was prepared in 82% yield from Preparation 4C according to the procedure for Example 1. $^1$H NMR (400 MHz, DMSO-d$_6$): δ 4.00 (3H, s), 7.47 (1H, dd, J=8.9, 1.9 Hz), 7.63 (1H, d, J=1.7 Hz), 7.67 (1H, d, J=8.9 Hz), 7.78 (1H, d, J=5.1 Hz), 8.17 (1H, d, J=5.1 Hz), 9.56 (1H, s), 10.52 (1H, br s), 14.22 (1H, br s). [M+H] calc'd for $C_{14}H_{11}ClN_4O_2$, 303, 305; found 303, 305.

Preparation 5A and 5B:
3-iodo-1,6-dimethyl-1H-indazole and 3-iodo-1,6-dimethyl-1H-indazole

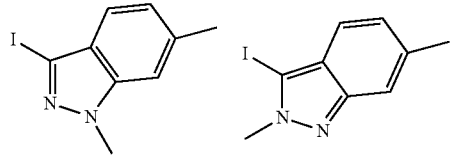

The title compounds were prepared from 3-iodo-6-methyl-indazole according to the procedure for Preparation 4A and 4B.

3-iodo-1,6-dimethyl-1H-indazole (78%) was isolated as the major isomer eluting first. $^1$H NMR (400 MHz, CDCl$_3$): δ 2.51 (3H, s), 4.05 (3H, s), 7.02 (1H, dd, J=8.3, 0.8 Hz), 7.13 (1H, s), 7.33 (1H, d, J=8.3 Hz). [M+H] calc'd for $C_9H_9IN_2$, 273; found 273.

3-iodo-1,6-dimethyl-1H-indazole (11%) was isolated as the minor isomer eluting second. $^1$H NMR (400 MHz, CDCl$_3$): δ 2.45 (3H, s), 4.21 (3H, s), 6.95 (1H, dd, J=8.6, 0.9 Hz), 7.26 (d, 1H, J=8.5 Hz), 7.39 (1H, s). [M+H] calc'd for $C_9H_9IN_2$, 273; found 273.

Example 5

3-[(1,6-dimethyl-1H-indazol-3-yl)amino]pyridine-4-carboxylic acid

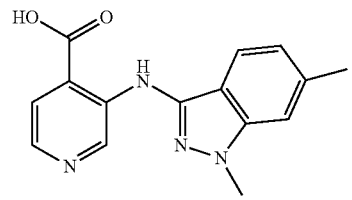

The title compound was prepared in 18% yield from methyl 3-aminoisonicotinate and Preparation 5A according to the general procedure for Preparation 1A, followed by hydrolysis according to Example 1. $^1$H NMR (400 MHz, DMSO-d$_6$): δ 2.47 (3H, s), 3.95 (3H, s), 6.98 (1H, d, J=8.2 Hz), 7.37 (1H, s), 7.49 (1H, d, J=8.2 Hz), 7.78 (1H, d, J=5.0 Hz), 8.15 (1H, d, J=5.0 Hz), 9.67 (1H, s), 10.68 (1H, br s), 14.16 (1H, br s). [M+H] calc'd for $C_{15}H_{14}N_4O_2$, 283; found 283.

Example 6

3-[(6-fluoro-1-methyl-1H-indazol-3-yl)amino]pyridine-4-carboxylic acid

To a suspension of methyl 3-bromoisonicotinate (220 mg, 1.02 mmol), 3-amino-6-fluoro-1-methyl-indazole (220 mg, 1.33 mmol), Cs$_2$CO$_3$ (500 mg, 1.53 mmol), and Xantphos (89 mg, 0.15 mmol) in dioxane (5 mL) was added Pd$_2$(dba)$_3$ (47 mg, 0.051 mmol) under N$_2$ at rt. The suspension was heated at 116° C. in a microwave for 90 min. The reaction was filtered and concentrated. Purification by silica gel chromatography (10%-40% EtOAc/DCM) gave 228 mg (75%) of the intermediate ester as a yellow solid.

The ester was hydrolyzed in 1N NaOH (1 mL) in MeOH (5 mL) at 35° C. for 1 h. The solution was neutralized with HOAc and concentrated. The residue was taken up in water, sonicated, and the solid was collected by filtration. The solid was taken up in MeOH and collected by filtration to give 148 mg (71%) of the title compound as a yellow solid. $^1$H NMR (400 MHz, DMSO-d$_6$): δ 3.96 (3H, s), 7.02 (1H, td, J=8.9, 1.6 Hz), 7.50 (1H, d, J=8.2 Hz), 7.63 (1H, dd, J=8.7, 5.0 Hz), 7.79 (1H, d, J=5.0 Hz), 8.18 (1H, d, J=5.0 Hz), 9.67 (1H, s), 10.59 (1H, br s), 14.20 (1H, br s). [M+H] calc'd for C$_{14}$H$_{11}$FN$_4$O$_2$, 287; found 287.

Example 7

3-[(5-fluoro-1-methyl-1H-indazol-3-yl)amino]pyridine-4-carboxylic acid

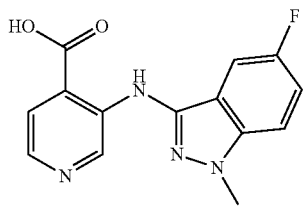

The title compound was prepared in 23% yield from methyl 3-bromoisonicotinate and 3-amino-5-fluoro-1-methyl-indazole according to the general procedure for Example 6. $^1$H NMR (400 MHz, DMSO-d$_6$): δ 4.01 (3H, s), 7.31-7.41 (2H, m), 7.67 (1H, dd, J=9.1, 4.1 Hz), 7.78 (1H, d, J=5.0 Hz), 8.16 (1H, d, J=5.0 Hz), 9.49 (1H, s), 10.33 (1H, br s). [M+H] calc'd for C$_{14}$H$_{11}$FN$_4$O$_2$, 287; found 287.

Preparation 8A and 8B: 3-iodo-6-methoxy-1-methyl-1H-indazole and 3-iodo-6-methoxy-2-methyl-2H-indazole

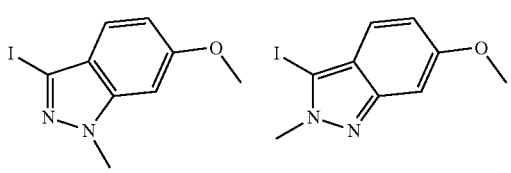

The title compounds were prepared from 3-iodo-6-methoxy-indazole according to the procedure for Preparation 4A and 4B.

3-iodo-6-methoxy-1-methyl-1H-indazole (68%) was isolated as the major isomer eluting first. $^1$H NMR (400 MHz, CDCl$_3$): δ 3.90 (3H, s), 4.03 (3H, s), 6.67 (1H, d, J=2.0 Hz), 6.84 (1H, dd, J=8.9, 2.0 Hz), 7.31 (1H, d, J=8.9 Hz). [M+H] calc'd for C$_9$H$_9$IN$_2$O, 289. found 289.

3-iodo-6-methoxy-2-methyl-2H-indazole (18%) was isolated as the minor isomer eluting second. $^1$H NMR (400 MHz, CDCl$_3$): δ 3.86 (3H, s), 4.18 (3H, s), 6.80 (1H, dd, J=9.1, 2.0 Hz), 6.90 (d, 1H, J=2.0 Hz), 7.23 (1H, d, J=9.1 Hz). [M+H] calc'd for C$_9$H$_9$IN$_2$O, 289. found 289.

Example 8

3-[(6-methoxy-1-methyl-1H-indazol-3-yl)amino]pyridine-4-carboxylic acid

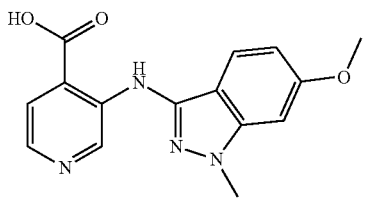 [SMILES: COc1ccc2c(Nc3cnccc3C(=O)O)nn(C)c2c1]

The title compound was prepared in 21% yield from methyl 3-aminoisonicotinate and Preparation 8A according to the general procedure for Preparation 1A, followed by hydrolysis according to Example 1. $^1$H NMR (400 MHz, DMSO-d$_6$): δ 3.86 (3H, s), 3.90 (3H, s), 6.71 (1H, dd, J=8.7, 2.0 Hz), 6.99 (1H, d, J=1.9 Hz), 7.46 (1H, d, J=8.7 Hz), 7.75 (1H, d, J=4.8 Hz), 8.02 (1H, d, J=4.8 Hz), 9.60 (1H, s), 12.29 (1H, br s). [M+H] calc'd for C$_{15}$H$_{14}$N$_4$O$_3$, 299; found 299.

Preparation 9A: 3-iodo-1-propyl-1H-indazole

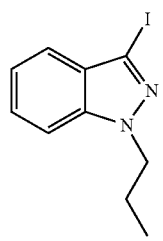

NaH (60%, 197 mg, 4.92 mmol) was added to a solution of 3-iodoindazole (1.0 g, 4.1 mmol) in THF (20 mL) at 0° C., and the reaction stirred further for 30 min. Bromopropane (605 mg, 4.9 mmol) was added to the reaction at 0° C. The solution was heated to reflux and stirred overnight. It was then cooled, diluted with water, extracted with EtOAc (3×30 mL), and the organics were washed with brine, dried (Na$_2$SO$_4$), and concentrated. Purification by silica gel chromatography (10%-30% EtOAc/hexanes) gave 650 mg (56%) of the title compound as a yellow solid. The minor isomer was not isolated or characterized. $^1$H NMR (400 MHz, CDCl$_3$): δ 0.93 (3H, t, J=7.2 Hz), 1.93-1.98 (2H, m), 4.35 (2H, t, J=7.2 Hz), 7.20 (1H, t, J=7.6 Hz), 7.36-7.49 (3H, m).

Example 9

3-[(1-propyl-1H-indazol-3-yl)amino]pyridine-4-carboxylic acid

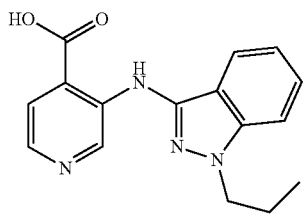

To a suspension of 3-iodo-1-propyl-1H-indazole (500 mg, 1.8 mmol), methyl 3-aminoisonicotinate (372 mg, 2.5 mmol), $Cs_2CO_3$ (1.14 g, 3.5 mmol), and Xantphos (152 mg, 0.26 mmol) in dioxane (20 mL) was added $Pd_2(dba)_3$ (80 mg, 0.088 mmol) under $N_2$ at rt. The suspension was heated at 110° C. overnight. The reaction was filtered and concentrated. The residue was purified by silica gel chromatography (30%-60% EtOAc/hexanes) to give semi-pure ester intermediate. The intermediate was added to 2N NaOH (5 mL) and stirred at 50° C. for 30 min, acidified with 1N HCl to pH 5, and collected by filtration to 200 mg (39%) of the title compound as an orange solid. $^1H$ NMR (400 MHz, DMSO-$d_6$): δ 0.86 (3H, t, J=7.5 Hz), 1.83-1.90 (2H, m), 4.32 (2H, t, J=6.6 Hz), 7.15 (1H, t, J=7.8 Hz), 7.45 (1H, t, J=7.5 Hz), 7.42-7.47 (2H, m), 7.79 (1H, d, J=5.1 Hz), 8.16 (1H, d, J=5.1 Hz), 9.69 (1H, s), 10.55 (1H, br s). [M+H] calc'd for $C_{16}H_{16}N_4O_2$, 297; found 297.

Preparation 9B: methyl 3-[(1-propyl-1H-indazol-3-yl)amino]pyridine-4-carboxylate

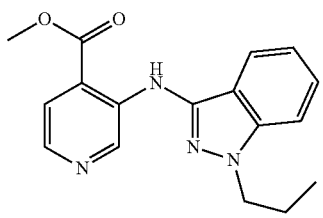 [SMILES: CCCn1nc(Nc2cnccc2C(=O)OC)c2ccccc21]

To a suspension of compound Example 9 (50 mg, 0.17 mmol) in ether (2 mL) was added 1N $CH_2N_2$ (2 mL) in ether at rt. The reaction stirred further for 10 min, and then was filtered and concentrated to give 30 mg (57%) of the title compound as a yellow solid. $^1H$ NMR (400 MHz, DMSO-$d_6$): δ 0.87 (3H, t, J=7.2 Hz), 1.84-1.90 (2H, m), 3.96 (3H, s), 4.33 (2H, t, J=6.8 Hz), 7.16 (1H, t, J=7.6 Hz), 7.46 (1H, t, J=6.8 Hz), 7.65-7.67 (2H, m), 7.77 (1H, d, J=4.8 Hz), 8.17 (1H, d, J=5.2 Hz), 9.64 (1H, s), 10.03 (1H, br s). [M+H] calc'd for $C_{17}H_{18}N_4O_2$, 311; found, 311.

Preparation 10A: 3-iodo-1-(3-methoxy-ethyl)-1H-indazole

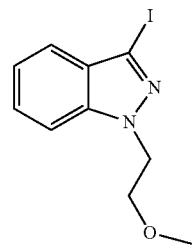

Potassium carbonate (791 mg, 5.7 mmol) was added to a solution of 3-iodoindazole (700 mg, 2.9 mmol) and 2-chloroethyl methyl ether (406 mg, 4.3 mmol) in ACN (20 mL) at rt. The reaction was heated to reflux overnight, and then was filtered and concentrated. The residue was purified by silica gel chromatography (15%-50% EtOAc/hexanes) to give 530 mg (63%) of the title compound as a light yellow oil. $^1H$ NMR (400 MHz, $CDCl_3$): δ 3.28 (3H, s), 3.82 (2H, t, J=5.6 Hz), 4.55 (2H, t, J=5.6 Hz), 7.19 (1H, td, J=1.2, 7.6 Hz), 7.43-7.47 (3H, m).

Example 10

3-{[1-(2-methoxyethyl)-1H-indazol-3-yl]amino}pyridine-4-carboxylic acid

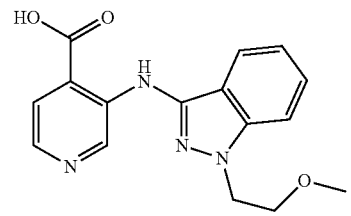 [SMILES: COCCn1nc(Nc2cnccc2C(=O)O)c2ccccc21]

The title compound was prepared in 37% yield using Preparation 10A in the general procedure for the preparation of Example 9. $^1H$ NMR (400 MHz, DMSO-$d_6$): δ 3.17 (3H, s), 3.78 (2H, t, J=5.1 Hz), 4.52 (2H, t, J=5.4 Hz), 7.16 (1H, t, J=7.2 Hz), 7.46 (1H, t, J=7.5 Hz), 7.60-7.65 (2H, m), 7.79 (1H, d, J=4.8 Hz), 8.17 (1H, d, J=5.1 Hz), 9.71 (1H, s), 10.59 (1H, br s). [M+H] calc'd for $C_{16}H_{16}N_4O_3$, 312; found, 313.

Preparation 10B: methyl 3-{[1-(2-methoxyethyl)-1H-indazol-3-yl]amino}pyridine-4-carboxylic acid

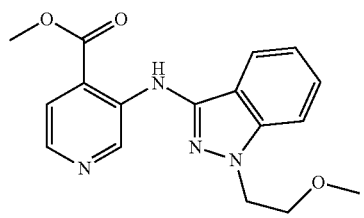

To a suspension of compound Example 10 (100 mg, 0.32 mmol) in ether (5 mL) was added 1N $CH_2N_2$ (5 mL) in ether at rt. The reaction was stirred further for 10 min, filtered, and concentrated to give 50 mg (48%) of the title compound as a yellow solid. $^1$H NMR (400 MHz, DMSO-d$_6$): δ 3.21 (3H, s), 3.78 (2H, t, J=5.2 Hz), 3.96 (3H, s), 4.52 (2H, t, J=5.2 Hz), 7.16 (1H, t, J=7.6 Hz), 7.45 (1H, t, J=7.6 Hz), 7.63-7.67 (2H, m), 7.77 (1H, d, J=5.2 Hz), 8.18 (1H, d, J=5.2 Hz), 9.66 (1H, s), 10.05 (1H, s). [M+H] Calc'd for C$_{17}$H$_{18}$N$_4$O$_3$, 326; Found, 327.

Preparation 11A:
1-[2-(2-chloroethoxy)ethyl]-3-iodo-1H-indazole

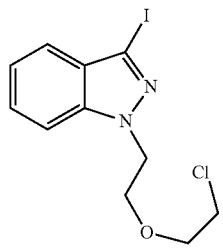 [SMILES: ClCCOCCn1nc(I)c2ccccc21]

Potassium carbonate (1.1 g, 8.2 mmol) was added to a solution of 3-iodoindazole (1.0 g, 4.1 mmol) and bis(2-chloroethyl) ether (1.5 g, 10.3 mmol) in ACN (20 mL) at rt. The reaction was heated to reflux overnight, and the filtered and concentrated. The residue was purified by silica gel chromatography to give 800 mg (56%) of the title compound as a yellow oil. $^1$H NMR (400 MHz, CDCl$_3$): δ 3.47 (2H, t, J=5.6 Hz), 3.60 (2H, t, J=5.6 Hz), 3.94 (2H, t, J=5.2 Hz), 4.58 (2H, t, J=5.6 Hz), 7.20 (1H, t, J=7.6 Hz), 7.41-7.49 (3H, m). The minor isomer was not isolated or characterized.

Preparation 11B: 2-[2-(3-iodo-1H-indazol-1-yl)ethoxy]-N,N-dimethylethanamine

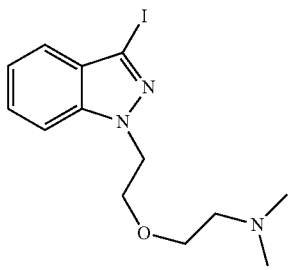 [SMILES: CN(C)CCOCCn1nc(I)c2ccccc21]

Potassium carbonate (5.6 g, 40.6 mmol) and potassium iodide (1.3 g, 8.1 mmol) were added to a solution of Preparation 11A (700 mg, 2.0 mmol) and dimethylamine hydrochloride (2.5 g, 30.5 mmol) in THF (10 mL) at rt. The reaction was heated to 90° C. overnight in a sealed tube and then allowed to cool to rt. The reaction was filtered and concentrated. Purification by silica gel chromatography gave 650 mg (89%) of the title compound as a yellow oil. $^1$H NMR (400 MHz, CDCl$_3$): δ 2.17 (6H, s), 2.38 (2H, t, J=6.0 Hz), 3.45 (2H, t, J=5.6 Hz), 3.89 (2H, t, J=5.6 Hz), 4.57 (2H, t, J=5.6 Hz), 7.18 (1H, t, J=7.6 Hz), 7.40-7.49 (3H, m).

Example 11

3-[(1-{2-[2-(dimethylamino)ethoxy]ethyl}-1H-indazol-3-yl)amino]pyridine-4-carboxylic acid

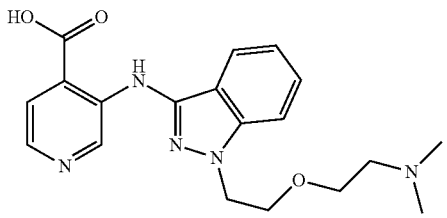 [SMILES: CN(C)CCOCCn1nc(Nc2cnccc2C(=O)O)c2ccccc21]

The title compound was prepared in 30% yield using Preparation 11B in the general procedure for the preparation of Example 9. $^1$H NMR (400 MHz, DMSO-d$_6$): δ 2.58 (6H, s), 3.12 (2H, t, J=4.8 Hz), 3.69 (2H, t, J=5.2 Hz), 3.92 (2H, t, J=4.8 Hz), 4.51 (2H, t, J=5.2 Hz), 7.09 (1H, t, J=7.6 Hz), 7.39 (1H, t, J=7.6 Hz), 7.56-7.63 (2H, m), 7.75 (1H, d, J=4.8 Hz), 8.03 (1H, d, J=4.8 Hz), 9.63 (1H, s), 12.80 (1H, br s). [M+H] calc'd for C$_{19}$H$_{23}$N$_5$O$_3$, 370; found, 370.

Preparation 11C: methyl 3-[(1-{2-[2-(dimethylamino)ethoxy]ethyl}-1H-indazol-3-yl)amino]pyridine-4-carboxylate

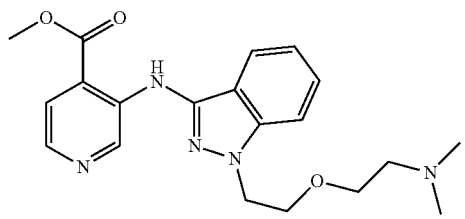

The title compound was prepared in 19% yield from Example 11 according to the general procedure for Preparation 9B. $^1$H NMR (400 MHz, DMSO-d$_6$): δ 2.69 (6H, s), 3.22 (2H, t, J=4.8 Hz), 3.73 (2H, t, J=5.2 Hz), 4.04 (2H, t, J=4.8 Hz), 4.06 (3H, s), 4.61 (2H, t, J=5.2 Hz), 7.21 (1H, t, J=7.6 Hz), 7.49 (1H, t, J=7.6 Hz), 7.58 (1H, d, J=9.2 Hz), 7.71 (1H, d, J=8.0 Hz), 8.07 (1H, d, J=5.6 Hz), 8.19 (1H, d, J=5.6 Hz), 9.78 (1H, s). [M+H] calc'd for C$_{20}$H$_{25}$N$_5$O$_3$, 384; found, 384.

Preparation 12A and 12B:
3-iodo-1,5-dimethyl-1H-indazole and
3-iodo-2,5-dimethyl-2H-indazole

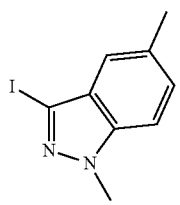 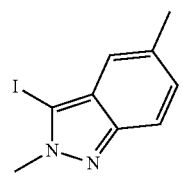

The title compounds were prepared from 3-iodo-5-methyl-indazole according to the procedure for Preparation 4A and 4B.

3-iodo-1,5-dimethyl-1H-indazole (78%) was isolated as the major isomer eluting first. $^1$H NMR (400 MHz, CDCl$_3$): δ 2.47 (3H, s), 4.05 (3H, s), 7.21-7.27 (3H, m). [M+H] calc'd for C$_9$H$_9$IN$_2$, 273; found 273.

3-iodo-2,5-dimethyl-2H-indazole (11%) was isolated as the minor isomer eluting second. $^1$H NMR (400 MHz, CDCl$_3$): δ 2.43 (3H, s), 4.22 (3H, s), 7.11-7.26 (2H, m), 7.55 (d, 1H, J=8.8 Hz). [M+H] calc'd for C$_9$H$_9$IN$_2$, 273; found 273.

Example 12

3-[(1,5-dimethyl-1H-indazol-3-yl)amino]pyridine-4-carboxylic acid

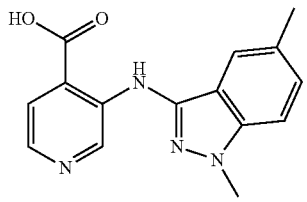 [SMILES: Cc1ccc2c(c1)c(Nc1cnccc1C(=O)O)nn2C]

The title compound was prepared in 22% yield from methyl 3-aminoisonicotinate and Preparation 12A according to the general procedure for Preparation 1A, followed by hydrolysis according to Example 1. $^1$H NMR (400 MHz, DMSO-d$_6$): δ 2.45 (3H, s), 3.97 (3H, s), 7.30 (1H, d, J=8.6 Hz), 7.36 (1H, s), 7.50 (1H, d, J=8.6 Hz), 7.78 (1H, d, J=5.0 Hz), 8.15 (1H, d, J=5.0 Hz), 9.61 (1H, s), 10.49 (1H, br s), 14.19 (1H, br s). [M+H] calc'd for C$_{15}$H$_{14}$N$_4$O$_2$, 283; found 283.

Example 13

3-[(4-fluoro-1-methyl-1H-indazol-3-yl)amino]pyridine-4-carboxylic acid

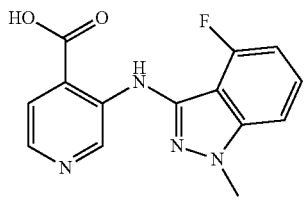 [SMILES: Cn1nc(Nc2cnccc2C(=O)O)c2c(F)cccc21]

The title compound was prepared in 34% yield from methyl 3-bromoisonicotinate and 3-amino-4-fluoro-1-methyl-indazole according to the general procedure for Example 6. $^1$H NMR (400 MHz, DMSO-d$_6$): δ 4.00 (3H, s), 6.84-6.89 (1H, m), 7.39-7.42 (2H, m), 7.80 (1H, d, J=5.0 Hz), 8.21 (1H, d, J=5.0 Hz), 9.90 (1H, s), 10.88 (1H, br s), 14.22 (1H, br s). [M+H] calc'd for C$_{14}$H$_{11}$FN$_4$O$_2$, 287; found 287.

Example 14

3-[(5-trifluoromethyl-1-methyl-1H-indazol-3-yl)amino]pyridine-4-carboxylic acid

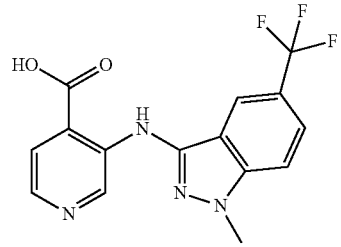 [SMILES: Cn1nc(Nc2cnccc2C(=O)O)c2cc(C(F)(F)F)ccc21]

The title compound was prepared in 44% yield from methyl 3-bromoisonicotinate and 3-amino-5-trifluoromethyl-1-methyl-indazole according to the general procedure for Example 6. $^1$H NMR (400 MHz, DMSO-d$_6$): δ 4.05 (3H, s), 7.72-7.83 (3H, m), 7.99 (1H, s), 8.21 (1H, d, J=5.0 Hz), 9.64 (1H, s), 10.69 (1H, br s), 14.12 (1H, br s). [M+H] calc'd for C$_{15}$H$_{11}$F$_3$N$_4$O$_2$, 337; found 337.

Preparation 15A and 15B: 5-fluoro-3-iodo-1-propyl-1H-indazole and 5-fluoro-3-iodo-2-propyl-2H-indazole

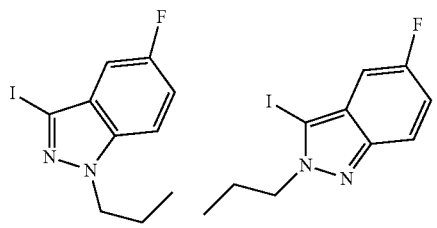

The title compounds were prepared from 3-iodo-5-fluoro-indazole according to the procedure for Preparation 4A and 4B.

5-fluoro-3-iodo-1-propyl-1H-indazole (62%) was isolated as the major isomer eluting first. $^1$H NMR (400 MHz, CDCl$_3$): δ 0.91 (3H, t, J=7.4 Hz), 1.91-1.99 (2H, m), 4.33 (2H, t, J=7.1 Hz), 7.09-7.21 (2H, m), 7.30-7.35 (1H, m). [M+H] calc'd for C$_{10}$H$_{10}$FIN$_2$, 305; found 305.

5-fluoro-3-iodo-2-propyl-2H-indazole (11%) was isolated as the minor isomer eluting second. $^1$H NMR (400 MHz, CDCl$_3$): δ 0.95 (3H, t, J=7.4 Hz), 1.95-2.05 (2H, m), 4.44 (2H, t, J=7.1 Hz), 6.97-7.12 (2H, m), 7.62-7.67 (1H, m). [M+H] calc'd for C$_{10}$H$_{10}$FIN$_2$, 305; found 305.

Example 15C methyl 3-[(5-fluoro-1-propyl-1H-indazol-3-yl)amino]pyridine-4-carboxylate

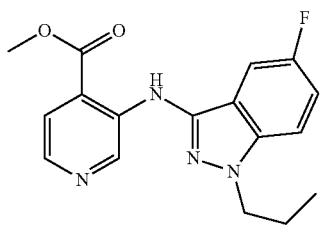 [SMILES: CCCn1nc(Nc2cnccc2C(=O)OC)c2cc(F)ccc21]

The title compound was prepared in 70% yield from methyl 3-aminoisonicotinate and Preparation 15A according to the general procedure for Preparation 1A. $^1$H NMR (400 MHz, CDCl$_3$): δ 0.95 (3H, t, J=7.4 Hz), 1.94-2.00 (2H, m), 4.00 (3H, s), 4.25 (2H, t, J=7.0 Hz), 7.17-7.21 (1H, m), 7.29-7.33 (2H, m), 7.75 (1H, d, J=5.1 Hz), 8.15 (1H, d, J=5.1 Hz), 9.61 (1H, s), 10.00 (1H, s). [M+H] calc'd for C$_{17}$H$_{17}$FN$_4$O$_2$, 329; found 329.

Example 15

3-[(5-fluoro-1-propyl-1H-indazol-3-yl)amino]pyridine-4-carboxylic acid

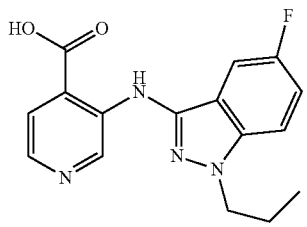 [SMILES: CCCn1nc(Nc2cnccc2C(=O)O)c2cc(F)ccc21]

The title compound was prepared in 92% yield from Preparation 15C according to the general hydrolysis procedure for Example 1. $^1$H NMR (400 MHz, DMSO-d$_6$): δ 0.86 (3H, t, J=7.3 Hz), 1.83-1.89 (2H, m), 4.32 (2H, t, J=6.8 Hz), 7.32-7.39 (2H, m), 7.70-7.78 (2H, m), 8.15 (1H, d, J=5.0 Hz), 9.48 (1H, s), 10.23 (1H, s), 14.10 (1H, s). [M+H] calc'd for C$_{16}$H$_{15}$FN$_4$O$_2$, 315; found 315.

Preparation 16A and 16B: 1-(cyclopropylmethyl)-5-fluoro-3-iodo-1H-indazole and 2-(cyclopropylmethyl)-5-fluoro-3-iodo-2H-indazole

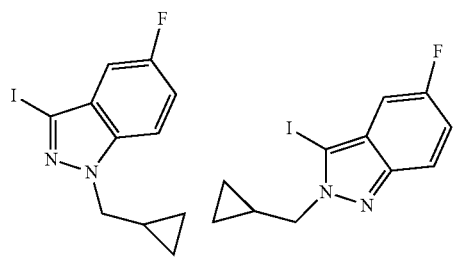

The title compounds were prepared from 3-iodo-5-fluoroindazole according to the procedure for Preparation 4A and 4B.

1-(cyclopropylmethyl)-5-fluoro-3-iodo-1H-indazole (47%) was isolated as the major isomer eluting first. $^1$H NMR (400 MHz, CDCl$_3$): δ 0.60 (6H, m), 1.30-1.36 (1H, m), 4.25 (2H, d, J=6.8 Hz), 7.09-7.22 (2H, m), 7.33-7.37 (1H, m). [M+H] calc'd for C$_{11}$H$_{10}$FIN$_2$, 317; found 317.

2-(cyclopropylmethyl)-5-fluoro-3-iodo-2H-indazole (20%) was isolated as the minor isomer eluting second. $^1$H NMR (400 MHz, CDCl$_3$): δ 0.55-0.64 (6H, m), 1.46-1.49 (1H, m), 4.36 (2H, d, J=7.2 Hz), 6.99-7.13 (2H, m), 7.64-7.68 (1H, m). [M+H] calc'd for C$_{11}$H$_{10}$FIN$_2$, 317; found 317.

Example 16C methyl 3-{[1-(cyclopropylmethyl)-5-fluoro-1H-indazol-3-yl]amino}pyridine-4-carboxylate

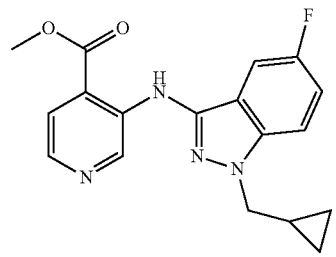 [SMILES: COC(=O)c1ccncc1Nc1nn(CC2CC2)c2ccc(F)cc12]

The title compound was prepared in 65% yield from methyl 3-aminoisonicotinate and Preparation 16A according to the general procedure for Preparation 1A. $^1$H NMR (400 MHz, CDCl$_3$): δ 0.43-0.46 (2H, m), 0.57-0.61 (2H, m), 1.32-1.36 (1H, m), 3.99 (3H, s), 4.17 (2H, d, J=6.8 Hz), 7.16-7.20 (1H, m), 7.28-7.33 (2H, m), 7.74 (1H, d, J=5.1 Hz), 8.15 (1H, s, J=5.1 Hz), 9.64 (1H, s), 10.01 (1H, s). [M+H] calc'd for C$_{18}$H$_{17}$FN$_4$O$_2$, 341; found 341.

Example 16

3-{[1-(cyclopropylmethyl)-5-fluoro-1H-indazol-3-yl]amino}pyridine-4-carboxylic acid

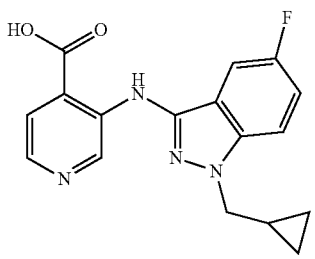 [SMILES: O=C(O)c1ccncc1Nc1nn(CC2CC2)c2ccc(F)cc12]

The title compound was prepared in 81% yield from Preparation 16C according to the general hydrolysis procedure for Example 1. $^1$H NMR (400 MHz, DMSO-d$_6$): δ 0.42-0.52 (4H, m), 1.33-1.37 (1H, m), 4.26 (2H, d, J=6.5 Hz), 7.32-7.38 (2H, m), 7.73-7.78 (2H, m), 8.16 (1H, s, J=5.1 Hz), 9.53 (1H, s), 10.21 (1H, s), 14.16 (1H, br s). [M+H] calc'd for C$_{17}$H$_{15}$FN$_4$O$_2$, 327; found 327.

Preparation 17A and 17B: 5-fluoro-3-iodo-1-(methoxypropyl)-1H-indazole and 5-fluoro-3-iodo-2-(methoxypropyl)-2H-indazole

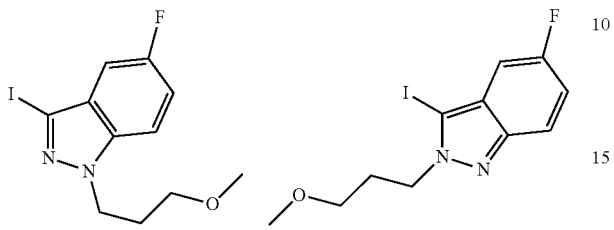

The title compounds were prepared from 5-fluoro-3-iodo-indazole and 1-bromo-3-methoxypropane according to the procedure for Preparation 4A and 4B.

5-fluoro-3-iodo-1-(methoxypropyl)-1H-indazole (47%) was isolated as the major isomer eluting first. $^1$H NMR (400 MHz, CDCl$_3$): δ 2.12-2.19 (2H, m), 3.23-3.33 (5H, m), 4.48 (2H, t, J=6.6 Hz), 7.09 (1H, dd, J=8.3, 2.3 Hz), 7.18 (1H, td, J=8.9, 2.4 Hz), 7.38 (1H, dd, J=9.1, 4.0 Hz). [M+H] calc'd for C$_{11}$H$_{12}$FIN$_2$O, 335. found 335.

5-fluoro-3-iodo-2-(methoxypropyl)-2H-indazole (17%) was isolated as the minor isomer eluting second. $^1$H NMR (400 MHz, CDCl$_3$): δ 2.21-2.28 (2H, m), 3.34-3.39 (5H, m), 4.60 (2H, t, J=7.0 Hz), 7.00 (1H, dd, J=8.7, 2.4 Hz), 7.10 (1H, td, J=9.1, 2.4 Hz), 7.64 (1H, dd, J=9.2, 4.5 Hz). [M+H] calc'd for C$_{11}$H$_{12}$FIN$_2$O, 335. found 335.

Example 17C methyl 3-{[5-fluoro-1-(methoxypropyl)-1H-indazol-3-yl]amino}pyridine-4-carboxylate

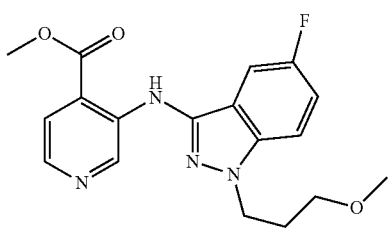

The title compound was prepared in 38% yield from methyl 3-aminoisonicotinate and Preparation 17A according to the general procedure for Preparation 1A. [M+H] calc'd for C$_{18}$H$_{19}$FN$_4$O$_3$, 359; found 359.

Example 17

3-{[5-fluoro-1-(methoxypropyl)-1H-indazol-3-yl]amino}pyridine-4-carboxylic acid

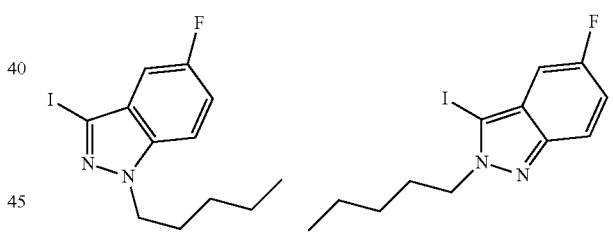

The title compound was prepared in 78% yield from Preparation 17C according to the general hydrolysis procedure for Example 1. $^1$H NMR (400 MHz, DMSO-d$_6$): δ 2.06 (2H, m), 3.25 (3H, s), 3.28 (2H, t, J=6.1 Hz), 4.40 (2H, d, J=6.7 Hz), 7.32-7.40 (2H, m), 7.65 (1H, dd, J=9.1, 4.0 Hz), 7.78 (1H, d, J=5.0 Hz), 8.16 (1H, d, J=5.0 Hz), 9.51 (1H, s), 10.44 (1H, s), 14.19 (1H, br s). [M+H] calc'd for C$_{17}$H$_{17}$FN$_4$O$_3$, 345; found 345.

Preparation 18A and 18B: 5-fluoro-3-iodo-1-pentyl-1H-indazole and 5-fluoro-3-iodo-2-pentyl-2H-indazole The title compounds were prepared from 5-fluoro-3-iodo-indazole and 1-bromopentane according to the procedure for Preparation 4A and 4B.

5-fluoro-3-iodo-1-pentyl-1H-indazole (54%) was isolated as the major isomer eluting first. $^1$H NMR (400 MHz, CDCl$_3$): δ 0.88 (3H, t, J=6.9 Hz), 1.27-1.38 (4H, m), 1.87-1.95 (2H, m), 4.36 (2H, d, J=7.2 Hz), 7.11 (1H, dd, J=8.4, 2.3 Hz), 7.19 (1H, td, J=8.9, 2.4 Hz), 7.32 (1H, dd, J=9.1, 4.0 Hz). [M+H] calc'd for C$_{12}$H$_{14}$FIN$_2$, 333; found 333.

5-fluoro-3-iodo-2-pentyl-2H-indazole (15%) was isolated as the minor isomer eluting second. $^1$H NMR (400 MHz, CDCl$_3$): δ 0.92 (3H, t, J=6.8 Hz), 1.32-1.42 (4H, m), 1.94-2.01 (2H, m), 4.47 (2H, d, J=7.4 Hz), 7.00 (1H, dd, J=8.7, 2.3 Hz), 7.09 (1H, td, J=9.2, 2.4 Hz), 7.64 (1H, dd, J=9.3, 4.5 Hz). [M+H] calc'd for C$_{12}$H$_{14}$FIN$_2$, 333; found 333.

Example 18C methyl 3-[(5-fluoro-1-pentyl-1H-indazol-3-yl)amino]pyridine-4-carboxylate

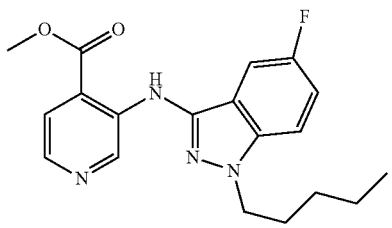 [SMILES: CCCCCn1nc(Nc2cnccc2C(=O)OC)c2cc(F)ccc21]

The title compound was prepared in 56% yield from methyl 3-aminoisonicotinate and Preparation 18A according to the general procedure for Preparation 1A. [M+H] calc'd for $C_{19}H_{21}FN_4O_2$, 357; found 357.

Example 18

3-[(5-fluoro-1-pentyl-1H-indazol-3-yl)amino]pyridine-4-carboxylic acid

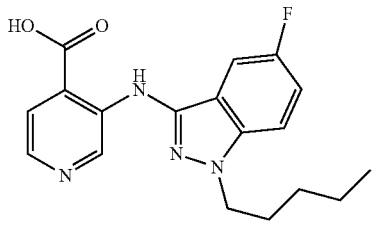 [SMILES: CCCCCn1nc(Nc2cnccc2C(=O)O)c2cc(F)ccc21]

The title compound was prepared in 84% yield from Preparation 18C according to the general hydrolysis procedure for Example 1. $^1$H NMR (400 MHz, DMSO-$d_6$): δ 0.84 (3H, t, J=6.8 Hz), 1.21-1.34 (4H, m), 1.80-1.91 (2H, m), 4.36 (2H, d, J=6.8 Hz), 7.32-7.39 (2H, m), 7.72 (1H, dd, J=9.0, 4.1 Hz), 7.78 (1H, d, J=5.0 Hz), 8.15 (1H, d, J=5.0 Hz), 9.48 (1H, s), 10.30 (1H, s), 14.15 (1H, br s). [M+H] calc'd for $C_{18}H_{19}FN_4O_2$, 343; found 343.

Preparation 19A and 19B: 5-fluoro-3-iodo-1-(2-phenethyl)-1H-indazole and 5-fluoro-3-iodo-2-(2-phenethyl)-2H-indazole

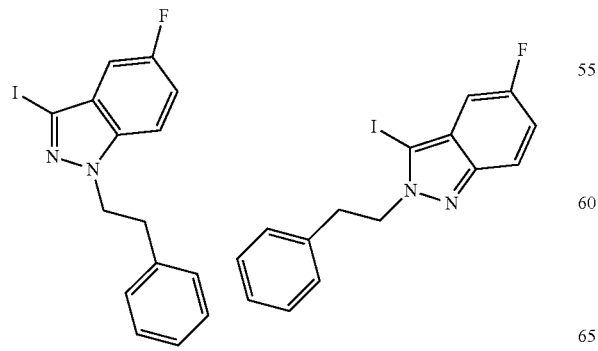

The title compounds were prepared from 5-fluoro-3-iodo-indazole and (2-bromoethyl)benzene according to the procedure for Preparation 4A and 4B.

5-fluoro-3-iodo-1-(2-phenethyl)-1H-indazole (61%) was isolated as the major isomer eluting first. $^1$H NMR (400 MHz, CDCl$_3$): δ 3.18 (2H, m, J=7.4 Hz), 4.55 (2H, t, J=7.4 Hz), 6.97-7.07 (5H, m), 7.17-7.24 (3H, m). [M+H] calc'd for $C_{15}H_{12}FIN_2$, 367; found 367.

5-fluoro-3-iodo-2-(2-phenethyl)-2H-indazole (17%) was isolated as the minor isomer eluting second. $^1$H NMR (400 MHz, CDCl$_3$): δ 3.27 (2H, m, J=7.7 Hz), 4.70 (2H, t, J=7.7 Hz), 6.99 (1H, dd, J=9.6, 2.4 Hz), 7.10-7.17 (3H, m), 7.24-7.32 (3H, m), 7.67 (1H, dd, J=9.3, 4.5 Hz). [M+H] calc'd for $C_{15}H_{12}FIN_2$, 367; found 367.

Example 19C methyl 3-{[5-fluoro-1-(2-phenethyl)-1H-indazol-3-yl]amino}pyridine-4-carboxylate

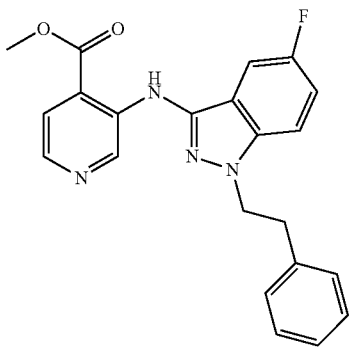 [SMILES: COC(=O)c1ccncc1Nc1nn(CCc2ccccc2)c2ccc(F)cc12]

The title compound was prepared in 82% yield from methyl 3-aminoisonicotinate and Preparation 19A according to the general procedure for Preparation 1A. [M+H] calc'd for $C_{22}H_{19}FN_4O_2$, 391; found 391.

Example 19

3-{[5-fluoro-1-(2-phenethyl)-1H-indazol-3-yl]amino}pyridine-4-carboxylic acid

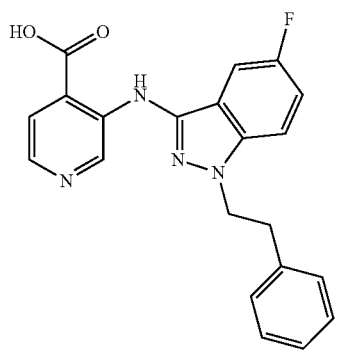 [SMILES: O=C(O)c1ccncc1Nc1nn(CCc2ccccc2)c2ccc(F)cc12]

The title compound was prepared in 78% yield from Preparation 19C according to the general hydrolysis procedure for Example 1. $^1$H NMR (400 MHz, DMSO-$d_6$): δ 3.16 (2H, t, J=6.9 Hz), 4.60 (2H, t, J=6.9 Hz), 7.14-7.56 (7H, m), 7.55 (1H, dd, J=8.8, 3.9 Hz), 7.77 (1H, d, J=5.1 Hz), 8.16 (1H, s, J=5.1 Hz), 9.44 (1H, s), 10.24 (1H, s), 14.09 (1H, br s). [M+H] calc'd for $C_{21}H_{17}FN_4O_2$, 377; found 377.

Preparation 20A and 20B: 7-fluoro-3-iodo-1-propyl-1H-indazole and 7-fluoro-3-iodo-2-propyl-2H-indazole

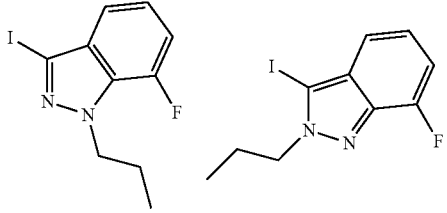

The title compounds were prepared from 7-fluoro-3-iodoindazole and 1-bromopropane according to the procedure for Preparation 4A and 4B.

7-fluoro-3-iodo-1-propyl-1H-indazole (57%) was isolated as the major isomer eluting first. $^1$H NMR (400 MHz, CDCl$_3$): δ 0.91 (3H, t, J=7.4 Hz), 1.89-1.95 (2H, m), 4.49 (2H, t, J=7.1 Hz), 7.04-7.09 (2H, m), 7.20-7.23 (1H, m). [M+H] calc'd for $C_{10}H_{10}FIN_2$, 305; found 305.

7-fluoro-3-iodo-2-propyl-2H-indazole (18%) was isolated as the minor isomer eluting second. $^1$H NMR (400 MHz, CDCl$_3$): δ 0.99 (3H, t, J=7.4 Hz), 2.01-2.07 (2H, m), 4.51 (2H, t, J=7.1 Hz), 6.94-7.06 (2H, m), 7.20 (1H, d, J=8.3 Hz). [M+H] calc'd for $C_{10}H_{10}FIN_2$, 305; found 305.

Example 20C methyl 3-[(7-fluoro-1-propyl-1H-indazol-3-yl)amino]pyridine-4-carboxylate

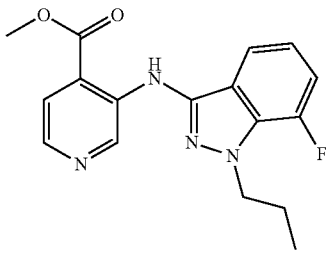 [SMILES: CCCn1nc(Nc2cnccc2C(=O)OC)c2cccc(F)c21]

The title compound was prepared in 67% yield from methyl 3-aminoisonicotinate and Preparation 20A according to the general procedure for Preparation 1A. $^1$H NMR (400 MHz, CDCl$_3$): δ 0.95 (3H, t, J=7.4 Hz), 1.93-1.99 (2H, m), 4.00 (3H, s), 4.43 (2H, t, J=7.0 Hz), 6.98-7.09 (2H, m), 7.45 (1H, d, J=7.9 Hz), 7.76 (1H, d, J=5.1 Hz), 8.17 (1H, d, J=5.1 Hz), 9.78 (1H, s), 10.18 (1H, s). [M+H] calc'd for $C_{17}H_{17}FN_4O_2$, 329; found 329.

Example 20

3-[(7-fluoro-1-propyl-1H-indazol-3-yl)amino]pyridine-4-carboxylic acid

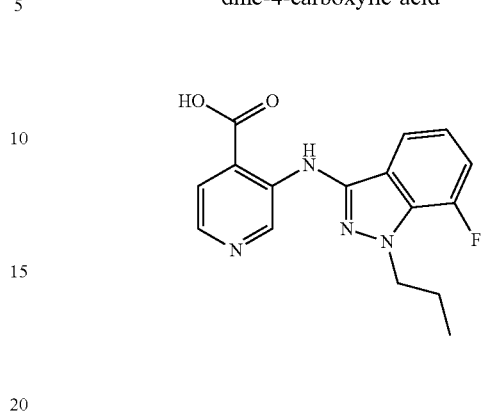

The title compound was prepared in 89% yield from Preparation 20C according to the general hydrolysis procedure for Example 1. $^1$H NMR (400 MHz, DMSO-d$_6$): δ 0.87 (3H, t, J=7.4 Hz), 1.84-1.90 (2H, m), 4.39 (2H, t, J=6.8 Hz), 7.13 (1H, dd, J=7.9, 4.2 Hz), 7.28-7.33 (1H, m), 7.45 (1H, d, J=8.0 Hz), 7.80 (1H, d, J=5.0 Hz), 8.18 (1H, d, J=5.0 Hz), 9.66 (1H, s), 10.29 (1H, s), 14.12 (1H, s). [M+H] calc'd for $C_{16}H_{15}FN_4O_2$, 315; found 315.

Preparation 21A and 21B: 5-fluoro-3-iodo-1-(tetrahydrofuran-2-ylmethyl)-1H-indazole and 5-fluoro-3-iodo-2-(tetrahydrofuran-2-ylmethyl)-2H-indazole

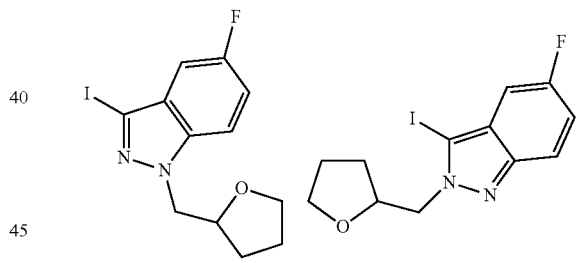

The title compounds were prepared from 5-fluoro-3-iodoindazole and tetrahydrofurfuryl bromide according to the procedure for Preparation 4A and 4B.

5-fluoro-3-iodo-1-(tetrahydrofuran-2-ylmethyl)-1H-indazole (55%) was isolated as the major isomer eluting first. $^1$H NMR (400 MHz, CDCl$_3$): δ 1.67-1.87 (3H, m), 1.98-2.05 (1H, m), 3.70-3.76 (2H, m), 4.30-4.53 (3H, m), 7.08 (1H, dd, J=8.3, 2.3 Hz), 7.19 (1H, td, J=9.0, 2.4 Hz), 7.48 (1H, dd, J=9.1, 4.0 Hz). [M+H] calc'd for $C_{12}H_{12}FIN_2O$, 347. found 347.

5-fluoro-3-iodo-2-(tetrahydrofuran-2-ylmethyl)-2H-indazole (19%) was isolated as the minor isomer eluting second. $^1$H NMR (400 MHz, CDCl$_3$): δ 1.78-2.07 (4H, m), 3.75-3.96 (2H, m), 4.49-4.59 (3H, m), 7.00 (1H, dd, J=8.3, 2.3 Hz), 7.10 (1H, td, J=9.2, 2.4 Hz), 7.66 (1H, dd, J=9.3, 4.2 Hz). [M+H] calc'd for $C_{12}H_{12}FIN_2O$, 347. found 347.

Example 21C methyl 3-{[5-fluoro-1-(tetrahydrofuran-2-ylmethyl)-1H-indazol-3-yl]amino}pyridine-4-carboxylate

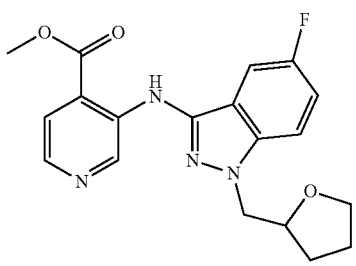 [SMILES: COC(=O)c1ccncc1Nc1nn(CC2CCCO2)c2ccc(F)cc12]

The title compound was prepared in 60% yield from methyl 3-aminoisonicotinate and Preparation 21A according to the general procedure for Preparation 1A. [M+H] calc'd for $C_{19}H_{19}FN_4O_3$, 371; found 371.

Example 21

3-{[5-fluoro-1-(tetrahydrofuran-2-ylmethyl)-1H-indazol-3-yl]amino}pyridine-4-carboxylic acid

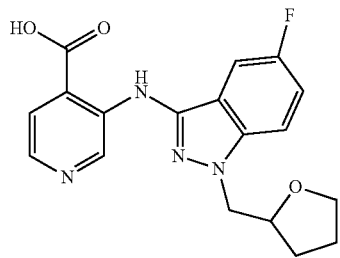 [SMILES: O=C(O)c1ccncc1Nc1nn(CC2CCCO2)c2ccc(F)cc12]

The title compound was prepared in 78% yield from Preparation 21C according to the general hydrolysis procedure for Example 1. $^1$H NMR (400 MHz, DMSO-$d_6$): δ 1.67-2.00 (4H, m), 3.58-3.71 (2H, m), 4.25-4.29 (1H, m), 4.41 (2H, d, J=5.0 Hz), 7.31-7.38 (2H, m), 7.70 (1H, dd, J=9.2, 4.2 Hz), 7.78 (1H, d, J=5.1 Hz), 8.16 (1H, d, J=5.1 Hz), 9.52 (1H, s), 10.33 (1H, s), 14.16 (1H, br s). [M+H] calc'd for $C_{18}H_{17}FN_4O_3$, 357; found 357.

Preparation 22A and 22B: 1-(5-bromopentyl)-5-fluoro-3-iodo-1H-indazole and 2-(5-bromopentyl)-5-fluoro-3-iodo-2H-indazole

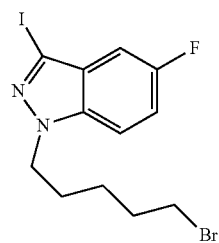

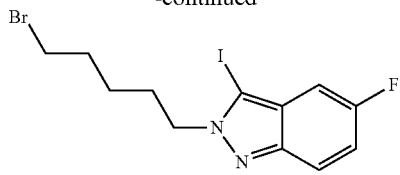

The title compounds were prepared from 5-fluoro-3-iodo-indazole and 1,5-dibromopentane according to the general procedure for Preparation 11A.

1-(5-bromopentyl)-5-fluoro-3-iodo-1H-indazole (57%) was isolated as the major isomer eluting first. $^1$H NMR (400 MHz, CDCl$_3$): δ 1.45-1.51 (2H, m), 1.84-1.99 (4H, m), 3.37 (2H, t, J=6.7 Hz), 4.38 (2H, t, J=7.1 Hz), 7.12 (1H, dd, J=8.3, 2.3 Hz), 7.21 (1H, td, J=8.9, 2.4 Hz), 7.33 (1H, dd, J=9.2, 4.0 Hz). [M+H] calc'd for $C_{12}H_{13}BrFIN_2$, 412; found 412.

2-(5-bromopentyl)-5-fluoro-3-iodo-2H-indazole (14%) was isolated as the minor isomer eluting second. $^1$H NMR (400 MHz, CDCl$_3$): δ 1.48-1.56 (2H, m), 1.88-2.06 (4H, m), 3.40 (2H, t, J=6.7 Hz), 4.51 (2H, t, J=7.2 Hz), 7.00 (1H, dd, J=8.6, 2.4 Hz), 7.11 (1H, td, J=9.2, 2.4 Hz), 7.64 (1H, dd, J=9.2, 4.5 Hz). [M+H] calc'd for $C_{12}H_{13}BrFIN_2$, 412; found 412.

Preparation 22C: 5-(5-fluoro-3-iodo-1H-indazol-1-yl)-N,N-dimethylpentan-1-amine

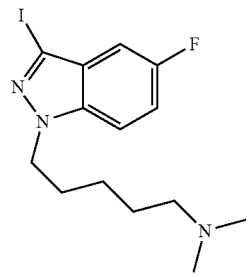 [SMILES: CN(C)CCCCCn1nc(I)c2cc(F)ccc21]

Potassium carbonate (4.84 g, 35 mmol) was added to a solution of Preparation 22A (900 mg, 2.19 mmol) and dimethylamine hydrochloride (1.79 g, 21.9 mmol) in THF (60 mL) at rt. The reaction was heated to 90° C. for 5 h in a sealed tube and then allowed to cool to rt. The reaction was filtered and concentrated. Purification by silica gel chromatography (5% to 15% MeOH/DCM) gave 750 mg (91%) of the title compound as a clear oil. $^1$H NMR (400 MHz, CDCl$_3$): δ 1.30-1.37 (2H, m), 1.46-1.54 (2H, m), 1.91-1.97 (2H, m), 2.20-2.26 (8H, m), 4.36 (2H, t, J=7.1 Hz), 7.09 (1H, dd, J=8.3, 2.3 Hz), 7.18 (1H, td, J=8.9, 2.4 Hz), 7.32 (1H, dd, J=9.1, 4.0 Hz). [M+H] calc'd for $C_{14}H_{19}FIN_3$, 376; found 376.

Preparation 22D: methyl 3-({1-[2-(dimethylamino)pentyl]-5-fluoro-1H-indazol-3-yl}amino)pyridine-4-carboxylate

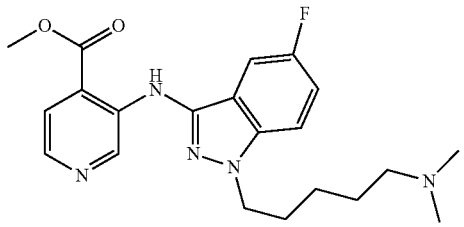

The title compound was prepared in 64% yield from methyl 3-aminoisonicotinate and Preparation 22C according to the general procedure for Preparation 1A. $^{1}$H NMR (400 MHz, DMSO-$d_6$): δ 1.34-1.40 (2H, m), 1.52-1.60 (2H, m), 1.93-2.00 (2H, m), 2.22-2.32 (8H, m), 4.00 (3H, s), 4.28 (2H, t, J=7.0 Hz), 7.17 (1H, td, J=8.8, 2.3 Hz), 7.28-7.32 (2H, m), 7.74 (1H, dd, J=5.1 Hz), 8.15 (1H, d, J=5.1 Hz), 9.61 (1H, s), 10.01 (1H, s). [M+H] calc'd for $C_{21}H_{26}FN_5O_2$, 400; found 400.

Example 22

3-({1-[2-(dimethylamino)pentyl]-5-fluoro-1H-indazol-3-yl}amino)pyridine-4-carboxylic acid

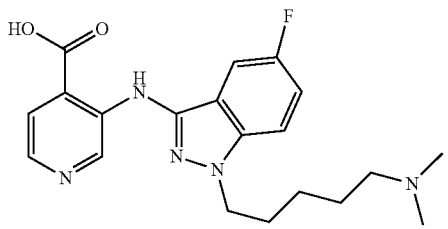 [SMILES: CN(C)CCCCCn1nc(Nc2cnccc2C(=O)O)c2cc(F)ccc21]

The hydrolysis of Preparation 22D (220 mg, 0.55 mmol) was carried out in MeOH (5 mL) with 1N NaOH (1.5 mL) at 40° C. for 2 h. The solution was neutralized with HOAc and concentrated. The residue was dissolved in 5% EtOH/DCM and filtered to remove any inorganic salts, and the solution was concentrated. The residue was precipitated from MeOH and the solid was collected by filtration to give 128 mg (60%) of the title compound as a light yellow solid. $^{1}$H NMR (400 MHz, DMSO-$d_6$): δ 1.23-1.31 (2H, m), 1.62-1.70 (2H, m), 1.83-1.87 (2H, m), 2.70 (6H, s), 2.94 (2H, t, J=7.9 Hz), 4.29 (2H, t, J=6.6 Hz), 7.18-7.25 (2H, m), 7.56 (1H, dd, J=9.0, 4.0 Hz), 7.73 (1H, d, J=4.8 Hz), 8.00 (1H, d, J=4.8 Hz), 9.48 (1H, s), 10.25 (1H, br s), 12.93 (1H, s). [M+H] calc'd for $C_{20}H_{24}FN_5O_2$, 386; found, 386.

Preparation 23A: 5-fluoro-3-iodo-1-(2,2,2-trifluoroethyl)-1H-indazole

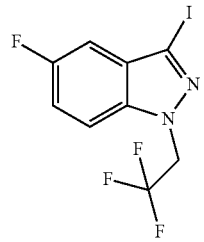 [SMILES: Fc1ccc2c(c1)c(I)nn2CC(F)(F)F]

The title compound was prepared in 46% yield from 5-fluoro-3-iodo-indazole and 1,1,1-trifluoro-2-iodoethane according to the general procedure for Preparation 10A. The minor isomer was not isolated or characterized. $^{1}$H NMR (400 MHz, CDCl$_3$): δ 4.91-4.97 (2H, m), 7.17 (1H, dd, J=2.0, 8.0 Hz), 7.30 (1H, td, J=2.0, 8.4 Hz), 7.38 (1H, dd, J=3.6, 9.2 Hz).

Example 23

3-{[5-fluoro-1-(2,2,2-trifluoroethyl)-1H-indazol-3-yl]amino}pyridine-4-carboxylic acid

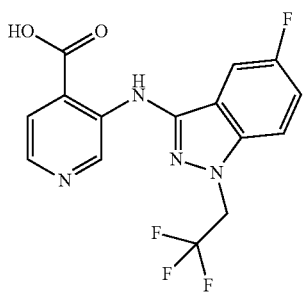 [SMILES: O=C(O)c1ccncc1Nc1nn(CC(F)(F)F)c2ccc(F)cc12]

The title compound was prepared in 22% yield from methyl 3-aminoisonicotinate and Preparation 23A according to the general procedure for Example 9. $^{1}$H NMR (400 MHz, DMSO-$d_6$): δ 5.37-5.43 (2H, m), 7.41-7.51 (2H, m), 7.82-7.86 (2H, m), 8.22 (1H, d, J=5.1 Hz), 9.64 (1H, s), 10.49 (1H, s). [M+H] calc'd for $C_{15}H_{10}F_4N_4O_2$, 355; found, 355.

Preparation 24A: 1-benzyl-5-fluoro-3-iodo-1H-indazole

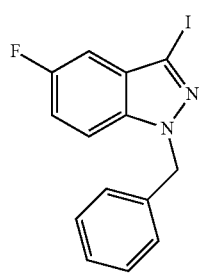 [SMILES: Fc1ccc2c(c1)c(I)nn2Cc1ccccc1]

The title compound was prepared in 75% yield from 5-fluoro-3-iodo-indazole and benzyl bromide according to the general procedure for Preparation 10A. The minor isomer was not isolated or characterized. ¹H NMR (400 MHz, CDCl₃): δ 5.59 (2H, s), 7.11-7.21 (5H, m), 7.23-7.31 (3H, m).

Example 24

3-[(1-benzyl-5-fluoro-1H-indazol-3-yl)amino]pyridine-4-carboxylic acid

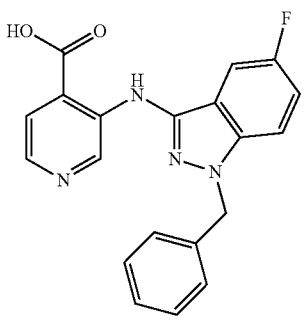 [SMILES: O=C(O)c1ccncc1Nc1nn(Cc2ccccc2)c2ccc(F)cc12]

The title compound was prepared in 45% yield from methyl 3-aminoisonicotinate and Preparation 24A according to the general procedure for Example 9. ¹H NMR (400 MHz, DMSO-d₆): δ 5.62 (2H, s), 7.25-7.41 (7H, m), 7.76-7.82 (2H, m), 8.17 (1H, d, J=5.1 Hz), 9.53 (1H, s), 10.39 (1H, s). [M+H] calc'd for $C_{20}H_{15}FN_4O_2$, 363; found, 363.

Preparation 25A:
5-fluoro-3-iodo-1-(2-methylpropyl)-1H-indazole

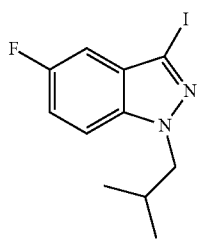

The title compound was prepared in 70% yield from 5-fluoro-3-iodo-indazole and 1-bromo-2-methylpropane according to the general procedure for Preparation 10A. The minor isomer was not isolated or characterized. ¹H NMR (400 MHz, CDCl₃): δ 0.92 (6H, d, J=6.8 Hz), 2.30-2.37 (1H, m), 4.16 (2H, d, J=7.2 Hz), 7.11 (1H, dd, J=2.4, 8.8 Hz), 7.19 (1H, td, J=2.4, 8.8 Hz), 7.32 (1H, dd, J=4.0, 8.8 Hz).

Example 25

3-{[5-fluoro-1-(2-methylpropyl)-1H-indazol-3-yl]amino}pyridine-4-carboxylic acid

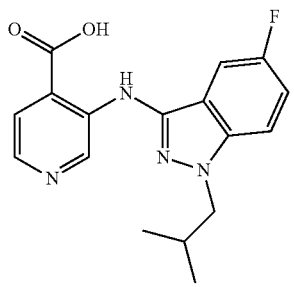 [SMILES: CC(C)Cn1nc(Nc2cnccc2C(=O)O)c2cc(F)ccc21]

The title compound was prepared in 34% yield from methyl 3-aminoisonicotinate and Preparation 25A according to the general procedure for Example 9. ¹H NMR (400 MHz, DMSO-d₆): δ 0.88 (6H, d, J=6.6 Hz), 2.20-2.30 (1H, m), 4.18 (2H, d, J=7.2 Hz), 7.32-7.39 (2H, m), 7.70-7.78 (2H, m), 8.15 (1H, d, J=5.1 Hz), 9.48 (1H, s), 10.30 (1H, br s). [M+H] calc'd for $C_{17}H_{17}FN_4O_2$, 329; found, 329.

Preparation 26A: 5-fluoro-3-iodo-1-(butan-2-yl)-1H-indazole

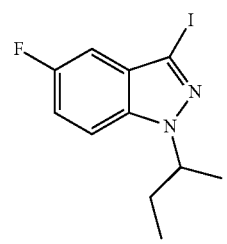

The title compound was prepared in 41% yield from 5-fluoro-3-iodo-indazole and 2-bromobutane according to the general procedure for Preparation 10A. The minor isomer was not isolated or characterized. ¹H NMR (400 MHz, CDCl₃): δ 0.79 (3H, t, J=7.2 Hz), 1.57 (3H, d, J=6.9 Hz), 1.88-1.95 (1H, m), 2.06-2.13 (1H, m), 4.48-4.55 (1H, m), 7.13 (1H, dd, J=2.1, 8.4 Hz), 7.20 (1H, dd, J=2.4, 9.0 Hz), 7.36 (1H, dd, J=3.9, 9.0 Hz).

Example 26

3-{[5-fluoro-1-(butan-2-yl)-1H-indazol-3-yl]amino}pyridine-4-carboxylic acid

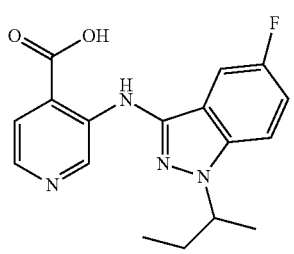 [SMILES: CCC(C)n1nc(Nc2cnccc2C(=O)O)c2cc(F)ccc21]

The title compound was prepared in 8% yield from methyl 3-aminoisonicotinate and Preparation 26A according to the general procedure for Example 9. $^1$H NMR (400 MHz, DMSO-$d_6$): δ 0.72 (3H, t, J=7.2 Hz), 1.47 (3H, d, J=6.6 Hz), 1.81-1.98 (2H, m), 4.69-4.73 (1H, m), 7.32-7.38 (2H, m), 7.74-7.80 (2H, m), 8.15 (1H, d, J=5.1 Hz), 9.45 (1H, s), 10.30 (1H, br s). [M+H] calc'd for $C_{17}H_{17}FN_4O_2$, 329; found, 329.

Preparation 27A and 27B: 1-{2-(2-chloroethoxy)ethyl}-5-fluoro-3-iodo-1H-indazole and 2-{2-(2-chloroethoxy)ethyl}-5-fluoro-3-iodo-2H-indazole

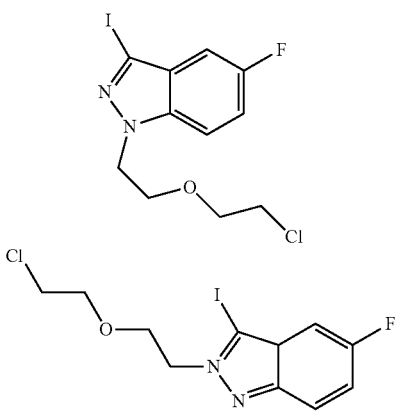

The title compounds were prepared from 5-fluoro-3-iodo-indazole and bis(2-chloroethyl)ether according to the general procedure for Preparation 11A.

1-{2-(2-chloroethoxy)ethyl}-5-fluoro-3-iodo-1H-indazole (69%) was isolated as the major isomer eluting first. $^1$H NMR (400 MHz, CDCl$_3$): δ 3.47 (2H, t, J=5.8 Hz), 3.60 (2H, t, J=5.2 Hz), 3.92 (2H, t, J=5.2 Hz), 4.56 (2H, t, J=5.2 Hz), 7.09 (1H, dd, J=8.3, 2.4 Hz), 7.21 (1H, td, J=9.0, 2.4 Hz), 7.47 (1H, dd, J=9.2, 4.0 Hz). [M+H] calc'd for $C_{11}H_{11}ClFIN_2O$, 369, 371. found 369, 371.

2-{2-(2-chloroethoxy)ethyl}-5-fluoro-3-iodo-2H-indazole (16%) was isolated as the minor isomer eluting second. $^1$H NMR (400 MHz, CDCl$_3$): δ 3.53 (2H, t, J=5.8 Hz), 3.66 (2H, t, J=5.6 Hz), 4.05 (2H, t, J=5.8 Hz), 4.69 (2H, t, J=5.8 Hz), 7.01 (1H, dd, J=8.7, 2.4 Hz), 7.12 (1H, td, J=9.2, 2.4 Hz), 7.64 (1H, dd, J=9.3, 4.5 Hz). [M+H] calc'd for $C_{11}H_{11}ClFIN_2O$, 369, 371. found 369, 371.

Preparation 27C: 2-{2-(5-fluoro-3-iodo-1H-indazol-1-yl)ethoxy}-N,N-dimethylethanamine

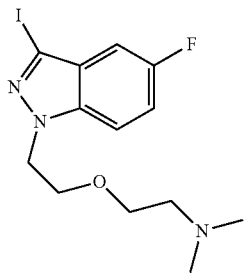 [SMILES: CN(C)CCOCCn1nc(I)c2cc(F)ccc21]

The title compound was prepared in 89% yield from Preparation 27A according to the general procedure for Preparation 11B. $^1$H NMR (400 MHz, CDCl$_3$): δ 2.73 (6H, s), 3.23 (2H, t, J=4.7 Hz), 3.91 (2H, t, J=4.7 Hz), 4.00 (2H, t, J=5.1 Hz), 4.66 (2H, t, J=5.1 Hz), 7.11 (1H, dd, J=8.2, 2.3 Hz), 7.25 (1H, td, J=8.9, 2.4 Hz), 7.58 (1H, dd, J=9.1, 4.0 Hz). [M+H] calc'd for $C_{13}H_{17}FIN_3O$, 378. found 378.

Preparation 27D: methyl 3-[(1-{2-[2-(dimethylamino)ethoxy]ethyl}-5-fluoro-1H-indazol-3-yl)amino]pyridine-4-carboxylate

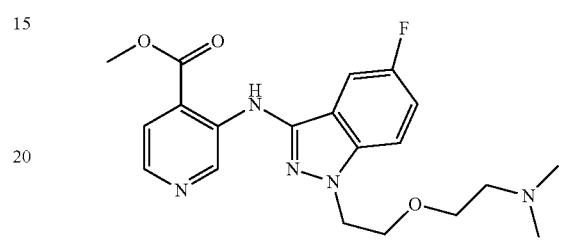

The title compound was prepared in 67% yield from methyl 3-aminoisonicotinate and Preparation 27C according to the general procedure for Preparation 1A. $^1$H NMR (400 MHz, CDCl$_3$): δ 2.21 (6H, s), 2.44 (2H, t, J=5.6 Hz), 3.50 (2H, t, J=5.5 Hz), 3.91 (2H, t, J=5.5 Hz), 4.00 (3H, s), 4.47 (2H, t, J=5.6 Hz), 7.17 (1H, td, J=9.0, 2.3 Hz), 7.28 (1H, dd, J=8.3, 2.3 Hz), 7.40 (1H, dd, J=9.1, 4.0 Hz), 7.75 (1H, dd, J=5.2 Hz), 8.16 (1H, d, J=5.2 Hz), 9.61 (1H, s), 10.01 (1H, s). [M+H] calc'd for $C_{20}H_{24}FN_5O_3$, 402; found 402.

Example 27

3-[(1-{2-[2-(dimethylamino)ethoxy]ethyl}-5-fluoro-1H-indazol-3-yl)amino]pyridine-4-carboxylic acid, acetic acid salt

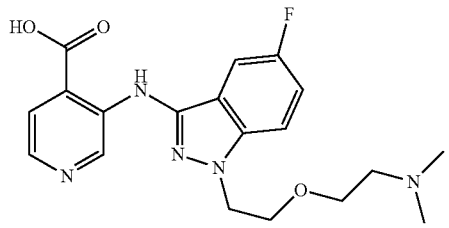 [SMILES: CN(C)CCOCCn1nc(Nc2cnccc2C(=O)O)c2cc(F)ccc21]

The hydrolysis of Preparation 27D (200 mg, 0.50 mmol) was carried out in MeOH (5 mL) with 1N NaOH (1 mL) at 40° C. for 1 h. The solution was cooled, neutralized with HOAc, and concentrated. The residue was taken up 5% EtOH/DCM and filtered to remove any inorganic salts. The solution was concentrated and precipitated from 50% DCM/hexanes. The liquid was decanted off, and the remaining sticky orange solid was dried under vacuum to give 100 mg (46%) of the title compound as its HOAc salt. $^1$H NMR (400 MHz, MeOD): δ 1.94 (3H, s), 2.67 (6H, s), 3.17 (2H, t, J=4.9 Hz), 3.70 (2H, t, J=4.9 Hz), 3.99 (2H, t, J=5.0 Hz), 4.47 (2H, t, J=5.0 Hz), 7.15 (1H, td, J=9.0, 2.4 Hz), 7.31 (1H, dd, J=8.5, 2.2 Hz), 7.43 (1H, dd, J=9.1, 3.8 Hz), 7.90 (1H, d, J=4.8 Hz), 8.02 (1H, d, J=4.8 Hz), 9.57 (1H, s). [M+H] calc'd for $C_{19}H_{22}FN_5O_3$, 388; found, 388.

Preparation 28A and 28B: 1-(cyclobutylmethyl)-5-fluoro-3-iodo-1H-indazole and 2-(cyclobutylmethyl)-5-fluoro-3-iodo-2H-indazole

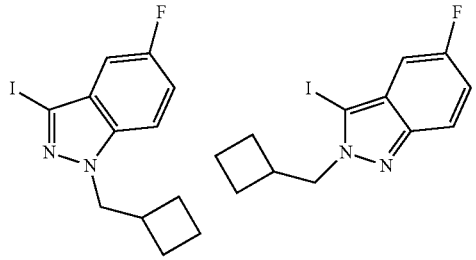

The title compounds were prepared from 5-fluoro-3-iodo-indazole and (bromomethyl)cyclobutane according to the procedure for Preparation 4A and 4B.

1-(cyclobutylmethyl)-5-fluoro-3-iodo-1H-indazole (71%) was isolated as the major isomer eluting first. ¹H NMR (400 MHz, CDCl₃): δ 1.78-1.93 (4H, m), 1.98-2.06 (2H, m), 2.85-2.93 (1H, m), 4.36 (2H, d, J=7.2 Hz), 7.09 (1H, dd, J=8.3, 2.3 Hz), 7.18 (1H, J=8.9, 2.4 Hz), 7.33 (1H, dd, J=9.1, 4.0 Hz). [M+H] calc'd for C₁₂H₁₂FIN₂, 331; found 331.

2-(cyclobutylmethyl)-5-fluoro-3-iodo-2H-indazole (18%) was isolated as the minor isomer eluting second. ¹H NMR (400 MHz, CDCl₃): δ 1.88-1.96 (4H, m), 2.02-2.10 (2H, m), 2.98-3.06 (1H, m), 4.51 (2H, d, J=7.3 Hz), 7.00 (1H, dd, J=8.7, 2.3 Hz), 7.10 (1H, J=9.2, 2.4 Hz), 7.65 (1H, dd, J=9.3, 4.5 Hz). [M+H] calc'd for C₁₂H₁₂FIN₂, 331; found 331.

Example 28C methyl 3-{[1-(cyclobutylmethyl)-5-fluoro-1H-indazol-3-yl]amino}pyridine-4-carboxylate

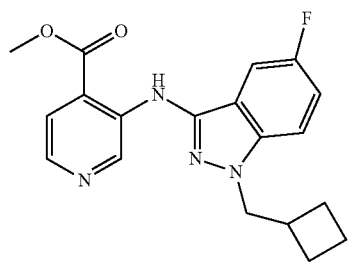 [SMILES: COC(=O)c1ccncc1Nc1nn(CC2CCC2)c2ccc(F)cc12]

The title compound was prepared in 74% yield from methyl 3-aminoisonicotinate and Preparation 28A according to the general procedure for Preparation 1A. ¹H NMR (400 MHz, CDCl₃): δ 1.87-1.94 (4H, m), 2.04-2.10 (2H, m), 2.90-2.98 (1H, m), 4.00 (3H, s), 4.29 (2H, d, J=7.2 Hz), 7.17 (1H, td, J=8.9, 2.3 Hz), 7.29-7.33 (2H, m), 7.77 (1H, d, J=5.1 Hz), 8.15 (1H, d, J=5.1 Hz), 9.63 (1H, s), 10.02 (1H, s). [M+H] calc'd for C₁₉H₁₉FN₄O₂, 355; found 355.

Example 28

3-{[1-(cyclobutylmethyl)-5-fluoro-1H-indazol-3-yl]amino}pyridine-4-carboxylic acid

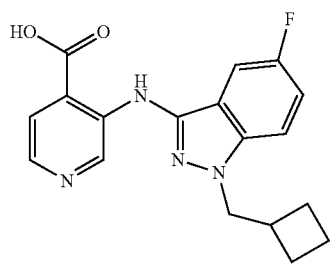 [SMILES: O=C(O)c1ccncc1Nc1nn(CC2CCC2)c2ccc(F)cc12]

The title compound was prepared in 70% yield from Preparation 28C according to the general hydrolysis procedure for Example 1. ¹H NMR (400 MHz, DMSO-d₆): δ 1.83-1.89 (4H, m), 1.96-2.01 (2H, m), 2.80-2.89 (1H, m), 4.38 (2H, d, J=7.1 Hz), 7.31-7.38 (2H, m), 7.73-7.79 (2H, m), 8.15 (1H, d, J=5.1 Hz), 9.51 (1H, s), 10.32 (1H, s), 14.11 (1H, br s). [M+H] calc'd for C₁₈H₁₇FN₄O₂, 341; found 341.

Preparation 29A:
1-cyclopentyl-5-fluoro-3-iodo-1H-indazole

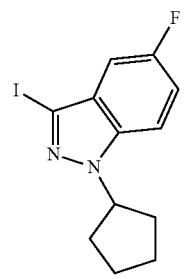 [SMILES: Fc1ccc2c(c1)c(I)nn2C1CCCC1]

The title compound was prepared in 71% yield from 5-fluoro-3-iodo-indazole and bromocyclopentane according to the procedure for Preparation 11A. The minor isomer was not isolated cleanly. ¹H NMR (400 MHz, CDCl₃): δ 1.69-1.76 (2H, m), 1.92-1.98 (2H, m), 2.12-2.18 (4H, m), 4.87-4.95 (1H, m), 7.08 (1H, dd, J=8.2, 2.3 Hz), 7.17 (1H, td, J=8.9, 2.4 Hz), 7.35 (1H, dd, J=9.1, 4.0 Hz). [M+H] calc'd for C₁₂H₁₂FIN₂, 331; found 331.

Example 29B methyl 3-[(1-cyclopentyl-5-fluoro-1H-indazol-3-yl)amino]pyridine-4-carboxylate

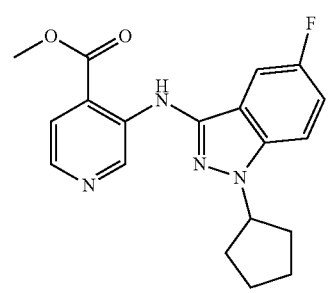 [SMILES: COC(=O)c1ccncc1Nc1nn(C2CCCC2)c2ccc(F)cc12]

The title compound was prepared in 50% yield from methyl 3-aminoisonicotinate and Preparation 29A according to the general procedure for Preparation 1A. ¹H NMR (400 MHz, CDCl₃): δ 1.71-1.77 (2H, m), 1.98-2.03 (2H, m), 2.12-2.21 (4H, m), 4.00 (3H, s), 4.86-4.94 (1H, m), 7.17 (1H, td, J=8.9, 2.4 Hz), 7.29-7.38 (2H, m), 7.75 (1H, d, J=5.1 Hz), 8.14 (1H, d, J=5.1 Hz), 9.67 (1H, s), 10.06 (1H, s). [M+H] calc'd for $C_{19}H_{19}FN_4O_2$, 355; found 355.

Example 29

3-[(1-cyclopentyl-5-fluoro-1H-indazol-3-yl)amino]pyridine-4-carboxylic acid

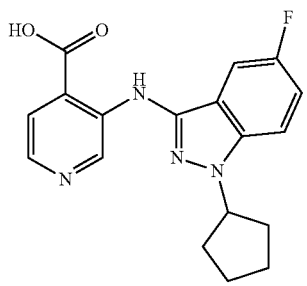 [SMILES: O=C(O)c1ccncc1Nc1nn(C2CCCC2)c2ccc(F)cc12]

The title compound was prepared in 75% yield from Preparation 29B according to the general hydrolysis procedure for Example 1. ¹H NMR (400 MHz, DMSO-d₆): δ 1.69-1.73 (2H, m), 1.89-2.17 (6H, m), 5.11-5.19 (1H, m), 7.31-7.38 (2H, m), 7.72-7.79 (2H, m), 8.15 (1H, d, J=5.0 Hz), 9.49 (1H, s), 10.34 (1H, s), 14.08 (1H, br s). [M+H] calc'd for $C_{18}H_{17}FN_4O_2$, 341; found 341.

Preparation 30A and 30B: 1-(cyclopentylmethyl)-5-fluoro-3-iodo-1H-indazole and 2-(cyclopentylmethyl)-5-fluoro-3-iodo-2H-indazole

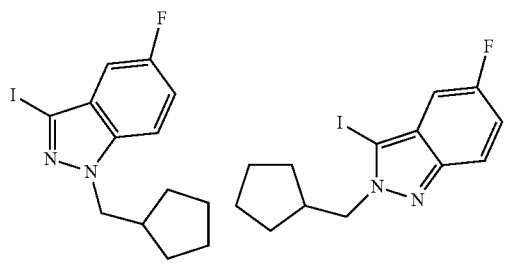

The title compounds were prepared from 5-fluoro-3-iodoindazole and (bromomethyl)cyclopentane according to the procedure for Preparation 10A.

1-(cyclopentylmethyl)-5-fluoro-3-iodo-1H-indazole (72%) was isolated as the major isomer eluting first. ¹H NMR (400 MHz, CDCl₃): δ 1.25-1.32 (2H, m), 1.50-1.65 (6H, m), 2.48-2.56 (1H, m), 4.27 (2H, d, J=7.5 Hz), 7.09 (1H, dd, J=8.3, 2.3 Hz), 7.18 (1H, td, J=8.9, 2.4 Hz), 7.32 (1H, dd, J=9.1, 4.0 Hz). [M+H] calc'd for $C_{13}H_{14}FIN_2$, 345; found 345.

2-(cyclopentylmethyl)-5-fluoro-3-iodo-2H-indazole (18%) was isolated as the minor isomer eluting second. ¹H NMR (400 MHz, CDCl₃): δ 1.33-1.42 (2H, m), 1.56-1.73 (6H, m), 2.62-2.70 (1H, m), 4.41 (2H, d, J=7.6 Hz), 7.00 (1H, dd, J=8.8, 2.4 Hz), 7.09 (1H, td, J=9.2, 2.4 Hz), 7.65 (1H, dd, J=9.3, 4.5 Hz). [M+H] calc'd for $C_{13}H_{14}FIN_2$, 345; found 345.

Example 30C methyl 3-{[1-(cyclopentylmethyl)-5-fluoro-1H-indazol-3-yl]amino}pyridine-4-carboxylate

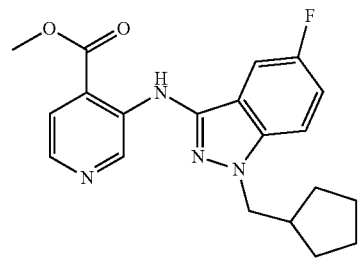 [SMILES: COC(=O)c1ccncc1Nc1nn(CC2CCCC2)c2ccc(F)cc12]

The title compound was prepared in 67% yield from methyl 3-aminoisonicotinate and Preparation 30A according to the general procedure for Preparation 1A. [M+H] calc'd for $C_{20}H_{21}FN_4O_2$, 369; found 369.

Example 30

3-{[1-(cyclopentylmethyl)-5-fluoro-1H-indazol-3-yl]amino}pyridine-4-carboxylic acid

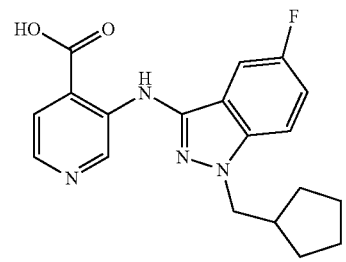 [SMILES: O=C(O)c1ccncc1Nc1nn(CC2CCCC2)c2ccc(F)cc12]

The title compound was prepared in 71% yield from Preparation 30C according to the general hydrolysis procedure for Example 1. ¹H NMR (400 MHz, DMSO-d₆): δ 1.26-1.33 (2H, m), 1.49-1.64 (6H, m), 2.45-2.49 (1H, m), 4.29 (2H, d, J=7.4 Hz), 7.32-7.38 (2H, m), 7.72-7.79 (2H, m), 8.15 (1H, d, J=5.0 Hz), 9.50 (1H, s), 10.32 (1H, s), 14.08 (1H, br s). [M+H] calc'd for $C_{19}H_{19}FN_4O_2$, 355; found 355.

Preparation 31A and 31B: 1-(cyclopropylethyl)-5-fluoro-3-iodo-1H-indazole and 2-(cyclopropylethyl)-5-fluoro-3-iodo-2H-indazole

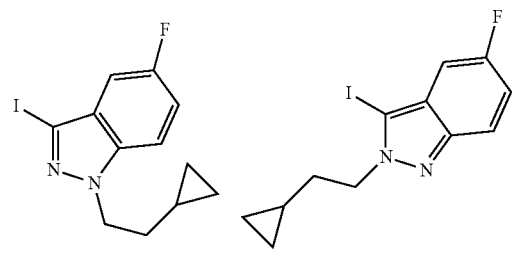

5-Fluoro-3-iodo-indazole (524 mg, 2.0 mmol), 2-cylcopropylethanol (344 mg, 4.0 mmol), and triphenylphosphine (1.05 g, 4.0 mmol) were combined in dry THF (40 mL). Di-tert-butyl azodicarboxylate (921 mg, 4.0 mmol) was added, and the reaction was stirred for 16 h at rt. The solution was concentrated and purified by silica gel chromatography (0% to 20% EtOAc/hexanes) to give two product isomers:

1-(cyclopropylethyl)-5-fluoro-3-iodo-1H-indazole (390 mg, 59%) was isolated as the major isomer eluting first. $^1$H NMR (400 MHz, CDCl$_3$): δ 0.03-0.01 (2H, m), 0.29-0.41 (2H, m), 0.55-0.62 (1H, m), 1.76-1.82 (2H, m), 4.45 (2H, t, J=7.0 Hz), 7.09 (1H, dd, J=8.4, 2.3 Hz), 7.19 (1H, td, J=8.9, 2.4 Hz), 7.35 (1H, dd, J=9.1, 4.0 Hz). [M+H] calc'd for C$_{12}$H$_{12}$FIN$_2$, 331; found 331.

2-(cyclopropylethyl)-5-fluoro-3-iodo-2H-indazole (216 mg, 33%) was isolated as the minor isomer eluting second. $^1$H NMR (400 MHz, CDCl$_3$): δ 0.03-0.01 (2H, m), 0.29-0.42 (2H, m), 0.61-0.69 (1H, m), 1.79-1.85 (2H, m), 4.53 (2H, t, J=7.2 Hz), 6.95 (1H, dd, J=8.7, 2.4 Hz), 7.06 (1H, td, J=9.2, 2.4 Hz), 7.59 (1H, dd, J=9.3, 4.55 Hz). [M+H] calc'd for C$_{12}$H$_{12}$FIN$_2$, 331; found 331.

Example 31C methyl 3-{[1-(cyclopropylethyl)-5-fluoro-1H-indazol-3-yl]amino}pyridine-4-carboxylate

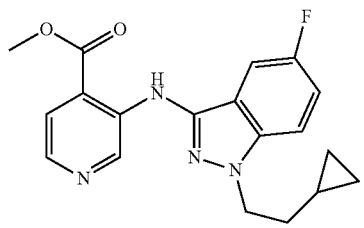 [SMILES: COC(=O)c1ccncc1Nc1nn(CCC2CC2)c2ccc(F)cc12]

The title compound was prepared in 71% yield from methyl 3-aminoisonicotinate and Preparation 31A according to the general procedure for Preparation 1A. [M+H] calc'd for C$_{19}$H$_{19}$FN$_4$O$_2$, 355; found 355.

Example 31

3-{[1-(cyclopropylethyl)-5-fluoro-1H-indazol-3-yl]amino}pyridine-4-carboxylic acid

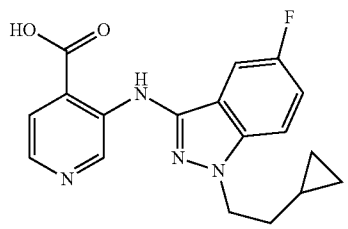 [SMILES: O=C(O)c1ccncc1Nc1nn(CCC2CC2)c2ccc(F)cc12]

The title compound was prepared in 74% yield from Preparation 31C according to the general hydrolysis procedure for Example 1. $^1$H NMR (400 MHz, DMSO-d$_6$): δ 0.04-0.01 (2H, m), 0.26-0.30 (2H, m), 0.57-0.63 (1H, m), 1.70-1.76 (2H, m), 4.43 (2H, t, J=6.6 Hz), 7.31-7.38 (2H, m), 7.72-7.79 (2H, m), 8.15 (1H, d, J=5.0 Hz), 9.48 (1H, s), 10.30 (1H, s), 14.13 (1H, br s). [M+H] calc'd for C$_{18}$H$_{17}$FN$_4$O$_2$, 341; found 341.

Preparation 32A: 5-fluoro-3-iodo-1-(3,3,3-trifluoropropyl)-1H-indazole

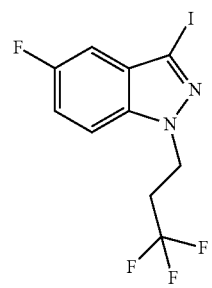 [SMILES: Fc1ccc2c(c1)c(I)nn2CCC(F)(F)F]

The title compound was prepared in 46% yield from 5-fluoro-3-iodo-indazole and 1,1,1-trifluoro-3-iodopropane according to the general procedure for Preparation 10A. The minor isomer was not isolated or characterized. $^1$H NMR (400 MHz, CDCl$_3$): δ 2.75-2.83 (2H, m), 4.60 (2H, t, J=7.2 Hz), 7.14 (1H, dd, J=2.0, 8.0 Hz), 7.26 (1H, td, J=2.4, 9.2 Hz), 7.34 (1H, dd, J=4.0, 9.2 Hz).

Example 32

3-{[5-fluoro-1-(3,3,3-trifluoropropyl)-1H-indazol-3-yl]amino}pyridine-4-carboxylic acid

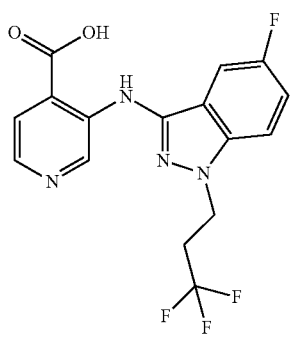 [SMILES: O=C(O)c1ccncc1Nc1nn(CCC(F)(F)F)c2ccc(F)cc12]

The title compound was prepared in 32% yield from methyl 3-aminoisonicotinate and Preparation 32A according to the general procedure for Example 9. $^1$H NMR (400 MHz, DMSO-d$_6$): δ 2.91-2.99 (2H, m), 4.67 (2H, t, J=6.4 Hz), 7.41-7.46 (2H, m), 7.79 (1H, dd, J=3.6, 9.2 Hz), 8.03 (1H, d, J=5.2 Hz), 8.29 (1H, d, J=5.6 Hz), 9.56 (1H, s), 10.52 (1H, s). [M+H] calc'd for C$_{16}$H$_{12}$F$_4$N$_4$O$_2$, 369; found, 369.

Preparation 33A:
5-chloro-3-iodo-1-propyl-1H-indazole

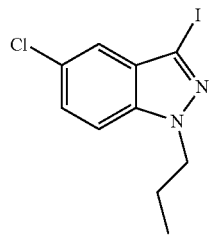

The title compound was prepared in 75% yield from 5-chloro-3-iodo-indazole and 1-bromopropane according to the general procedure for Preparation 10A. The minor isomer was not isolated or characterized. $^1$H NMR (400 MHz, CDCl$_3$): δ 0.92 (3H, t, J=7.6 Hz), 1.91-1.97 (2H, m), 4.33 (2H, t, J=7.2 Hz), 7.31 (1H, d, J=8.8 Hz), 7.37 (1H, dd, J=2.0, 8.8 Hz), 7.46 (1H, d, J=1.2 Hz).

Example 33

3-[(5-chloro-1-propyl-1H-indazol-3-yl)amino]pyridine-4-carboxylic acid

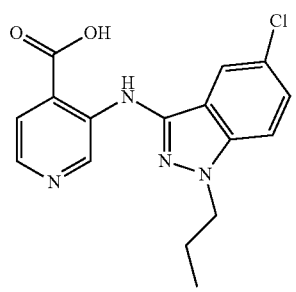 [SMILES: CCCn1nc(Nc2cnccc2C(=O)O)c2cc(Cl)ccc21]

The title compound was prepared in 23% yield from methyl 3-aminoisonicotinate and Preparation 33A according to the general procedure for Example 9. $^1$H NMR (400 MHz, DMSO-d$_6$): δ 0.85 (3H, t, J=7.2 Hz), 1.82-1.90 (2H, m), 4.33 (2H, t, J=6.8 Hz), 7.46 (1H, dd, J=2.0, 9.2 Hz), 7.63 (1H, d, J=1.6 Hz), 7.73 (1H, d, J=9.2 Hz), 7.80 (1H, d, J=5.2 Hz), 8.17 (1H, d, J=4.8 Hz), 9.56 (1H, s), 10.41 (1H, br s). [M+H] calc'd for C$_{16}$H$_{15}$ClN$_4$O$_2$, 331; found, 331.

Preparation 34A:
5-chloro-1-(cyclopropylmethyl-3-iodo-1H-indazole

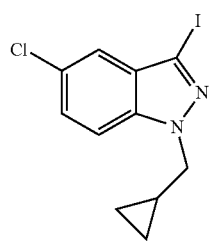 [SMILES: Clc1ccc2c(c1)c(I)nn2CC1CC1]

The title compound was prepared in 69% yield from 5-chloro-3-iodo-indazole and (bromomethyl)cyclopropane according to the general procedure for Preparation 10A. The minor isomer was not isolated or characterized. $^1$H NMR (400 MHz, CDCl$_3$): δ 0.39-0.42 (2H, m), 0.57-0.62 (2H, m), 1.31-1.33 (1H, m), 4.25 (2H, d, J=7.2 Hz), 7.32-7.39 (2H, m), 7.47 (1H, d, J=2.0 Hz).

Example 34

3-{[5-chloro-1-(cyclopropylmethyl)-1H-indazol-3-yl]amino}pyridine-4-carboxylic acid

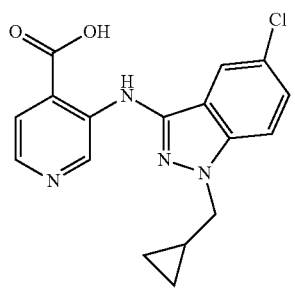 [SMILES: O=C(O)c1ccncc1Nc1nn(CC2CC2)c2ccc(Cl)cc12]

The title compound was prepared in 24% yield from methyl 3-aminoisonicotinate and Preparation 34A according to the general procedure for Example 9. $^1$H NMR (400 MHz, DMSO-d$_6$): δ 0.40-0.44 (2H, m), 0.49-0.53 (2H, m), 1.26-1.32 (1H, m), 4.27 (2H, d, J=6.8 Hz), 7.45 (1H, dd, J=1.6, 9.2 Hz), 7.64 (1H, d, J=2.0 Hz), 7.74 (1H, d, J=9.2 Hz), 7.80 (1H, d, J=5.2 Hz), 8.18 (1H, d, J=4.8 Hz), 9.60 (1H, s), 10.44 (1H, br s). [M+H] calc'd for C$_{17}$H$_{15}$ClN$_4$O$_2$, 343; found, 343.

Preparation 35A: 5-chloro-3-iodo-1-(3,3,3-trifluoro-propyl)-1H-indazole

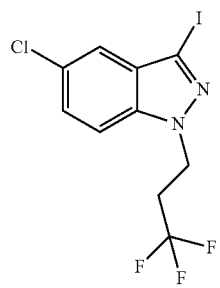 [SMILES: FC(F)(F)CCn1nc(I)c2cc(Cl)ccc21]

The title compound was prepared in 39% yield from 5-chloro-3-iodo-indazole and 1,1,1-trifluoro-3-iodopropane according to the general procedure for Preparation 10A. The minor isomer was not isolated or characterized. $^1$H NMR (400 MHz, CDCl$_3$): δ 2.73-2.85 (2H, m), 4.59 (2H, t, J=7.2 Hz), 7.31 (1H, d, J=9.2 Hz), 7.43 (1H, dd, J=1.6, 8.4 Hz), 7.48 (1H, d, J=1.2 Hz).

Example 35

3-{[5-chloro-1-(3,3,3-trifluoropropyl)-1H-indazol-3-yl]amino}pyridine-4-carboxylic acid

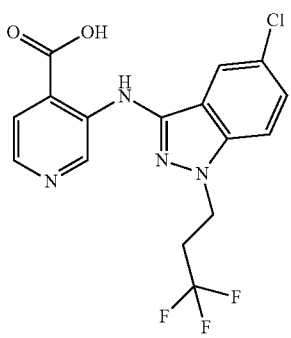

The title compound was prepared in 37% yield from methyl 3-aminoisonicotinate and Preparation 35A according to the general procedure for Example 9. $^1$H NMR (400 MHz, DMSO-$d_6$): δ 2.87-2.99 (2H, m), 4.65 (2H, d, J=5.6 Hz), 7.50 (1H, dd, J=2.0, 8.8 Hz), 7.66 (1H, d, J=2.0 Hz), 7.74 (1H, d, J=8.8 Hz), 7.80 (1H, d, J=5.2 Hz), 8.20 (1H, d, J=4.8 Hz), 9.59 (1H, s), 10.45 (1H, br s). [M+H] calc'd for $C_{16}H_{12}ClF_3N_4O_2$, 385; found, 385.

Preparation 36A and 36B: 1-ethyl-3-iodo-5-methyl-1H-indazole and 2-ethyl-3-iodo-5-methyl-2H-indazole

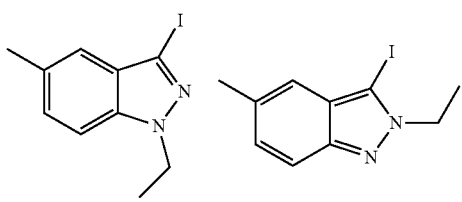

The title compounds were prepared from 3-iodo-5-methyl-indazole and bromoethane according to the general procedure for Preparation 4A and 4B.

1-ethyl-3-iodo-5-methyl-1H-indazole (73%) was isolated as the major isomer eluting first. $^1$H NMR (400 MHz, CDCl$_3$): δ 1.49 (3H, t, J=7.2 Hz), 2.47 (3H, s), 4.40 (2H, q, J=7.2 Hz), 7.22-7.26 (3H, m). [M+H] calc'd for $C_{10}H_{11}IN_2$, 287; found 287.

2-ethyl-3-iodo-5-methyl-2H-indazole (17%) was isolated as the minor isomer eluting second. $^1$H NMR (400 MHz, CDCl$_3$): δ 1.55 (3H, t, J=7.2 Hz), 2.44 (3H, s), 4.54 (2H, q, J=7.2 Hz), 7.13-7.17 (2H, m), 7.56 (1H, dd, J=8.3, 3.3 Hz). [M+H] calc'd for $C_{10}H_{11}IN_2$, 287; found 287.

Preparation 36C: methyl 3-[(1-ethyl-5-methyl-1H-indazol-3-yl)amino]pyridine-4-carboxylate

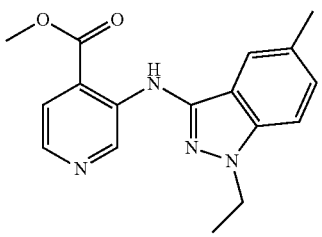 [SMILES: CCn1nc(Nc2cnccc2C(=O)OC)c2cc(C)ccc21]

The title compound was prepared in 82% yield from methyl 3-aminoisonicotinate and Preparation 36A according to the general procedure for Preparation 1A. $^1$H NMR (400 MHz, CDCl$_3$): δ 1.50 (3H, t, J=7.2 Hz), 2.46 (3H, s), 4.00 (3H, s), 4.33 (2H, q, J=7.0 Hz), 7.24-7.27 (2H, m), 7.44 (1H, s), 7.74 (1H, d, J=5.1 Hz), 8.14 (1H, d, J=5.1 Hz), 9.70 (1H, s), 10.03 (1H, s). [M+H] calc'd for $C_{17}H_{18}N_4O_2$, 311; found 311.

Example 36

3-[(1-ethyl-5-methyl-1H-indazol-3-yl)amino]pyridine-4-carboxylic acid

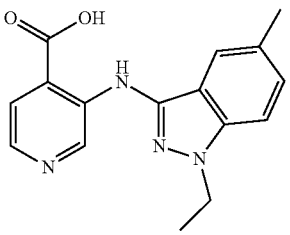 [SMILES: CCn1nc(Nc2cnccc2C(=O)O)c2cc(C)ccc21]

The title compound was prepared in 63% yield using Preparation 36C in the general procedure for the preparation of Example 9. $^1$H NMR (400 MHz, DMSO-$d_6$): δ 1.39 (3H, t, J=7.2 Hz), 2.43 (3H, s), 4.36 (2H, q, J=7.2 Hz), 7.28 (1H, dd, J=7.7, 1.0 Hz), 7.37 (1H, s), 7.54 (1H, d, J=8.6 Hz), 7.79 (1H, d, J=5.1 Hz), 8.15 (1H, d, J=5.1 Hz), 9.63 (1H, s), 10.50 (1H, br s), 14.13 (1H, br s). [M+H] calc'd for $C_{16}H_{16}N_4O_2$, 297; found, 297.

Preparation 37A: 1-(cyclopropylmethyl)-3-iodo-5-methyl-1H-indazole

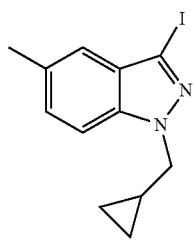

The title compound was prepared in 66% yield from 3-iodo-5-methyl-indazole and (bromomethyl)cyclopropane according to the general procedure for Preparation 10A. The minor isomer was not isolated or characterized. $^1$H NMR (400 MHz, CDCl$_3$): δ 0.38-0.41 (2H, m), 0.54-0.59 (2H, m), 1.31-1.34 (1H, s), 2.48 (3H, s), 4.24 (2H, d, J=7.2 Hz), 7.23-7.29 (3H, m).

Example 37

3-{[1-(cyclopropylmethyl)-5-methyl-1H-indazol-3-yl]amino}pyridine-4-carboxylic acid

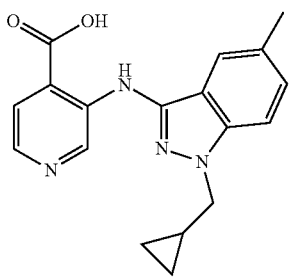 [SMILES: Cc1ccc2c(c1)c(Nc1cnccc1C(=O)O)nn2CC1CC1]

The title compound was prepared in 24% yield using Preparation 37A in the general procedure for the preparation of Example 9. $^1$H NMR (400 MHz, DMSO-d$_6$): δ 0.39-0.42 (2H, m), 0.47-0.51 (2H, m), 1.25-1.29 (1H, m), 2.43 (3H, s), 4.23 (2H, d, J=6.8 Hz), 7.28 (1H, dd, J=1.2, 8.4 Hz), 7.37 (1H, s), 7.57 (1H, d, J=8.8 Hz), 7.80 (1H, d, J=4.8 Hz), 8.16 (1H, d, J=4.8 Hz), 9.66 (1H, s), 10.49 (1H, br s). [M+H] calc'd for C$_{18}$H$_{18}$N$_4$O$_2$, 323; found, 323.

Preparation 38A:
3-iodo-5-methyl-1-propyl-1H-indazole

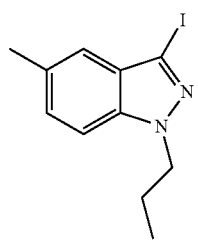

The title compound was prepared in 60% yield from 3-iodo-5-methyl-indazole and 1-bromopropane according to the general procedure for Preparation 10A. The minor isomer was not isolated or characterized. $^1$H NMR (400 MHz, CDCl$_3$): δ 0.92 (3H, t, J=7.2 Hz), 1.90-1.96 (2H, m), 4.32 (2H, t, J=7.2 Hz), 7.22-7.28 (3H, m).

Example 38

3-[(5-methyl-1-propyl-1H-indazol-3-yl)amino]pyridine-4-carboxylic acid

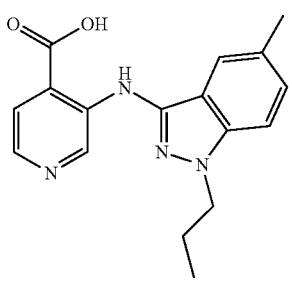 [SMILES: CCCn1nc(Nc2cnccc2C(=O)O)c2cc(C)ccc21]

The title compound was prepared in 28% yield using Preparation 38A in the general procedure for the preparation of Example 9. $^1$H NMR (400 MHz, DMSO-d$_6$): δ 0.85 (3H, t, J=7.6 Hz), 1.83-1.88 (2H, m), 2.43 (3H, s), 4.30 (2H, t, J=6.8 Hz), 7.26 (1H, d, J=8.8 Hz), 7.38 (1H, s), 7.56 (1H, d, J=8.4 Hz), 7.89 (1H, d, J=5.2 Hz), 8.20 (1H, d, J=4.8 Hz), 9.64 (1H, s), 10.52 (1H, br s). [M+H] calc'd for C$_{17}$H$_{18}$N$_4$O$_2$, 311; found, 311.

Preparation 39A: 3-iodo-5-methyl-1-(3,3,3-trifluoropropyl)-1H-indazole

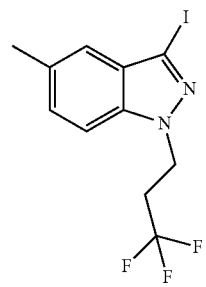 [SMILES: Cc1ccc2c(c1)c(I)nn2CCC(F)(F)F]

The title compound was prepared in 29% yield from 3-iodo-5-methyl-indazole and 1,1,1-trifluoro-3-iodopropane according to the general procedure for Preparation 10A. The minor isomer was not isolated or characterized. $^1$H NMR (400 MHz, CDCl$_3$): δ 2.49 (3H, s), 2.72-2.83 (2H, m), 4.59 (2H, t, J=7.2 Hz), 7.25-7.32 (3H, m).

Example 39

3-{[5-methyl-1-(3,3,3-trifluoropropyl)-1H-indazol-3-yl]amino}pyridine-4-carboxylic acid

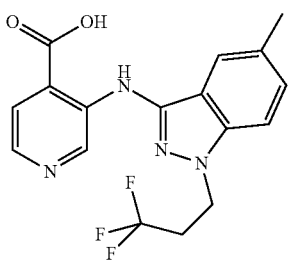 [SMILES: Cc1ccc2c(c1)c(Nc1cnccc1C(=O)O)nn2CCC(F)(F)F]

The title compound was prepared in 2% yield using Preparation 39A in the general procedure for the preparation of Example 9. $^1$H NMR (400 MHz, DMSO-d$_6$): δ 2.43 (3H, s), 2.87-2.95 (2H, m), 4.61 (2H, d, J=5.6 Hz), 7.32 (1H, d, J=9.2 Hz), 7.39 (1H, s), 7.57 (1H, d, J=8.8 Hz), 7.84 (1H, d, J=4.8 Hz), 8.19 (1H, d, J=4.8 Hz), 9.65 (1H, s), 10.55 (1H, br s). [M+H] calc'd for C$_{17}$H$_{15}$F$_3$N$_4$O$_2$, 365; found, 365.

Preparation 40A: 1-{2-(2-chloroethoxy)ethyl}-5-chloro-3-iodo-1H-indazole

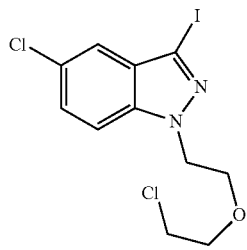 [SMILES: ClCCOCCn1nc(I)c2cc(Cl)ccc21]

The title compound was prepared from 5-chloro-3-iodo-indazole and bis(2-chloroethyl)ether in 54% yield according to the general procedure for Preparation 11A. The minor isomer was not isolated or characterized. $^1$H NMR (400 MHz, CDCl$_3$): δ 3.47 (2H, t, J=5.2 Hz), 3.60 (2H, t, J=5.2 Hz), 3.92 (2H, t, J=5.2 Hz), 4.56 (2H, t, J=5.2 Hz), 7.37 (1H, dd, J=2.0, 9.2 Hz), 7.44-7.46 (2H, m).

Preparation 40B: 2-{2-(5-chloro-3-iodo-1H-indazol-1-yl)ethoxy}-N,N-dimethylethanamine

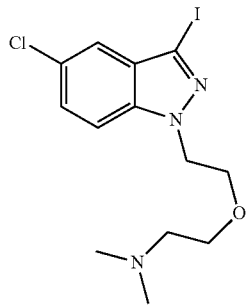 [SMILES: CN(C)CCOCCn1nc(I)c2cc(Cl)ccc21]

The title compound was prepared in 92% yield from Preparation 40A according to the general procedure for Preparation 11B. $^1$H NMR (400 MHz, CDCl$_3$): δ 2.19 (6H, s), 2.39 (2H, t, J=5.6 Hz), 3.45 (2H, t, J=5.6 Hz), 3.87 (2H, t, J=5.2 Hz), 4.55 (2H, t, J=5.2 Hz), 7.36 (1H, dd, J=2.0, 9.2 Hz), 7.44-7.46 (2H, m).

Preparation 40C: methyl 3-[(1-{2-[2-(dimethylamino)ethoxy]ethyl}-5-chloro-1H-indazol-3-yl)amino]pyridine-4-carboxylate, trifluoroacetic acid salt

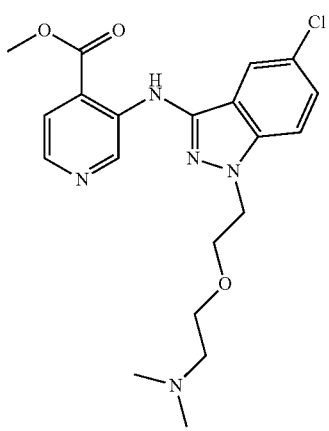 [SMILES: COC(=O)c1ccncc1Nc1nn(CCOCCN(C)C)c2ccc(Cl)cc12]

The title compound was prepared from methyl 3-aminoisonicotinate and Preparation 68B according to the general procedure for Preparation 1A. The product was isolated as the TFA salt in 22% yield using prep-HPLC purification. $^1$H NMR (400 MHz, CD$_3$OD): δ 2.74 (6H, s), 3.24 (2H, t, J=4.8 Hz), 3.75 (2H, t, J=4.8 Hz), 4.04 (2H, t, J=4.8 Hz), 4.09 (3H, s), 4.61 (2H, t, J=4.8 Hz), 7.45 (1H, dd, J=1.6, 9.2 Hz), 7.61 (1H, d, J=8.8 Hz), 7.71 (1H, d, J=1.6 Hz), 8.09 (1H, d, J=5.6 Hz), 8.22 (1H, d, J=5.2 Hz), 9.74 (1H, s). [M+H] calc'd for C$_{20}$H$_{24}$ClN$_5$O$_3$, 418; found, 418.

Example 40

3-[(1-{2-[2-(dimethylamino)ethoxy]ethyl}-5-chloro-1H-indazol-3-yl)amino]pyridine-4-carboxylic acid, trifluoroacetic acid salt

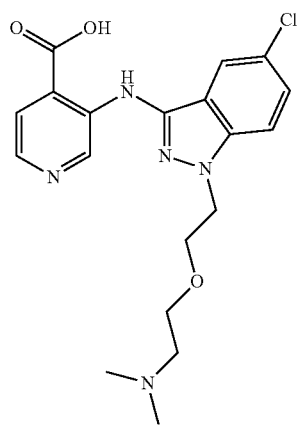 [SMILES: CN(C)CCOCCn1nc(Nc2cnccc2C(=O)O)c2cc(Cl)ccc21]

The title compound was prepared in from Preparation 40C according to the general hydrolysis procedure for Example 1. The product was isolated as the TFA salt in 69% yield using prep-HPLC purification. $^1$H NMR (400 MHz, CD$_3$OD): δ 2.76 (6H, s), 3.26 (2H, t, J=4.8 Hz), 3.77 (2H, t, J=4.8 Hz), 4.07 (2H, t, J=4.8 Hz), 4.62 (2H, t, J=4.8 Hz), 7.45 (1H, dd, J=1.6, 9.2 Hz), 7.60 (1H, d, J=8.8 Hz), 7.69 (1H, d, J=1.6 Hz), 8.27 (2H, d, J=1.6 Hz), 9.86 (1H, s). [M+H] calc'd for C$_{19}$H$_{22}$ClN$_5$O$_3$, 404; found, 404.

Preparation 41A: 5-fluoro-3-iodo-1-[2-(4-methylpiperidin-1yl)ethyl]-1H-indazole

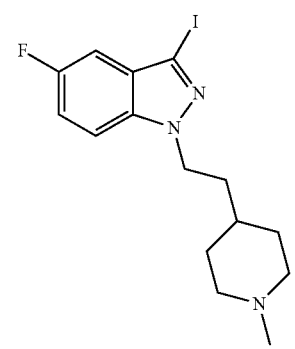 [SMILES: CN1CCC(CCn2nc(I)c3cc(F)ccc32)CC1]

The title compound was prepared from 5-fluoro-3-iodo-indazole and 1-methyl-4-(hydroxyethyl)piperidine in 30% yield according to the general procedure for Preparation 31A. The minor isomer was not isolated or characterized. $^1$H NMR (300 MHz, CDCl$_3$): δ 1.23-1.42 (3H, m), 1.72-1.76 (2H, m), 1.84-1.91 (4H, m), 2.56 (3H, s), 2.82-2.86 (2H, m), 4.41 (2H, t, J=7.8 Hz), 7.13 (1H, dd, J=2.4, 8.4 Hz), 7.22 (1H, td, J=2.4, 8.7 Hz), 7.33 (1H, dd, J=3.9, 9.0 Hz).

Preparation 41B: methyl 3-({5-fluoro-1-{2-(1-methylpiperidin-4-yl)ethyl]-1H-indazol-3-yl]amino)pyridine-4-carboxylate, trifluoroacetic acid salt

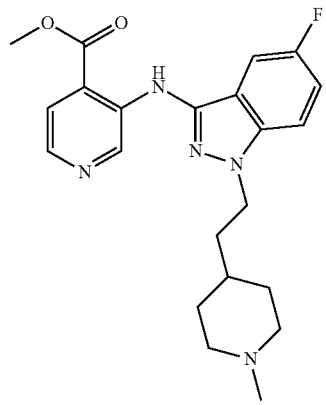 [SMILES: COC(=O)c1ccncc1Nc1nn(CCC2CCN(C)CC2)c2ccc(F)cc12]

The title compound was prepared from methyl 3-aminoisonicotinate and Preparation 41A according to the general procedure for Preparation 1A. The product was isolated as the TFA salt in 59% yield using prep-HPLC purification. $^1$H NMR (400 MHz, CD$_3$OD): δ 1.46-1.62 (3H, m), 1.95-2.00 (2H, m), 2.09-2.13 (2H, m), 2.84 (3H, s), 2.90-2.97 (2H, m), 3.50-3.53 (2H, m), 4.09 (3H, s), 4.49 (2H, t, J=7.2 Hz), 7.33 (1H, td, J=2.0, 8.8 Hz), 7.38 (1H, dd, J=2.0, 8.0 Hz), 7.61 (1H, dd, J=4.0, 8.8 Hz), 8.10 (1H, d, J=5.2 Hz), 8.20 (1H, d, J=5.2 Hz), 9.72 (1H, s). [M+H] calc'd for C$_{22}$H$_{26}$FN$_5$O$_2$, 412; found, 412.

Example 41

3-({5-fluoro-1-{2-(1-methylpiperidin-4-yl)ethyl]-1H-indazol-3-yl]amino)pyridine-4-carboxylic acid, trifluroacetic acid salt

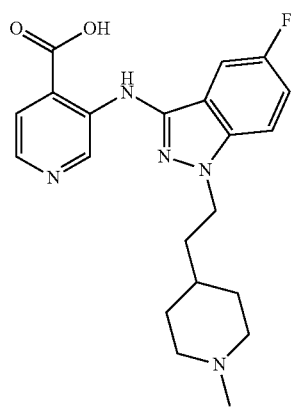 [SMILES: CN1CCC(CCn2nc(Nc3cnccc3C(=O)O)c3cc(F)ccc32)CC1]

The title compound was prepared in from Preparation 41C according to the general hydrolysis procedure for Example 1. The product was isolated as the TFA salt in 76% yield using prep-HPLC purification. $^1$H NMR (400 MHz, CD$_3$OD): δ 1.46-1.62 (3H, m), 1.95-2.00 (2H, m), 2.09-2.13 (2H, m), 2.84 (3H, s), 2.90-2.97 (2H, m), 3.50-3.53 (2H, m), 4.09 (3H, s), 4.49 (2H, t, J=7.2 Hz), 7.33 (1H, td, J=2.0, 8.8 Hz), 7.38 (1H, dd, J=2.0, 8.0 Hz), 7.61 (1H, dd, J=4.0, 8.8 Hz), 8.10 (1H, d, J=5.2 Hz), 8.20 (1H, d, J=5.2 Hz), 9.72 (1H, s). [M+H] calc'd for C$_{21}$H$_{24}$FN$_5$O$_2$, 398; found, 398.

Preparation 42A: 1-(3-tert-butyldimethylsiloxypropyl)-5-fluoro-3-iodo-1H-indazole

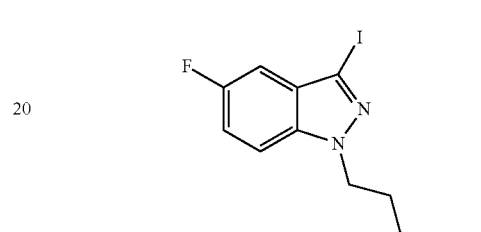

The title compound was prepared from 5-fluoro-3-iodoindazole and (3-chloropropoxy)tert-butyldimethylsilane (Org. Lett., 2000, 3473) in 79% yield according to the general procedure for Preparation 31A. The minor isomer was not isolated or characterized. $^1$H NMR (400 MHz, CDCl$_3$): δ 0.06 (6H, s), 0.89 (9H, s), 2.07-2.13 (2H, m), 3.55 (2H, t, J=6.0 Hz), 4.49 (2H, t, J=6.0 Hz), 7.10 (1H, dd, J=2.4, 8.4 Hz), 7.18 (1H, td, J=2.4, 8.8 Hz), 7.40 (1H, dd, J=4.0, 8.8 Hz).

Preparation 42B: methyl 3-{[5-fluoro-1-(3-hydroxypropyl)-1H-indazol-3-yl]amino}pyridine-4-carboxylic acid

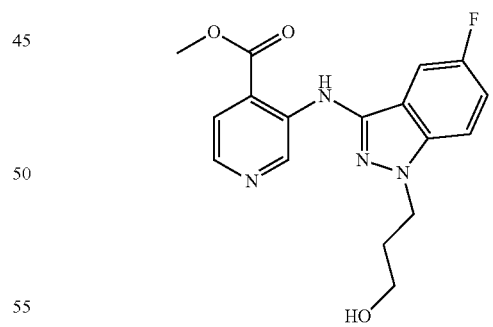

The title compound was prepared from methyl 3-aminoisonicotinate and Preparation 42A according to the general procedure for Preparation 1A, followed by alcohol deprotection in 10% 3N HCl/MeOH at 50° C. for 3 h. The product was isolated from prep-HPLC purification in 58% yield. $^1$H NMR (400 MHz, DMSO-d$_6$): δ 1.96-2.00 (2H, m), 3.41-3.42 (2H, m), 3.95 (3H, s), 4.41 (2H, t, J=6.4 Hz), 4.62 (1H, t, J=4.4 Hz), 7.35-7.39 (2H, m), 7.67-7.54 (2H, m), 8.16 (1H, d, J=4.4 Hz), 9.42 (1H, s), 9.76 (1H, s). [M+H] calc'd for C$_{17}$H$_{17}$FN$_4$O$_3$, 345; found, 345.

Example 42

3-{[5-fluoro-1-(3-hydroxypropyl)-1H-indazol-3-yl]amino}pyridine-4-carboxylic acid

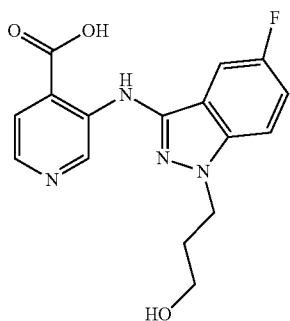 [SMILES: O=C(O)c1ccncc1Nc1nn(CCCO)c2ccc(F)cc12]

The title compound was prepared in 70% yield from Preparation 42B according to the general hydrolysis procedure for Example 1. $^1$H NMR (400 MHz, DMSO-d$_6$): δ 1.96-2.02 (2H, m), 3.41 (2H, t, J=6.0 Hz), 4.42 (2H, t, J=6.4 Hz), 7.33-7.40 (2H, m), 7.69 (1H, dd, J=4.0, 9.2 Hz), 7.79 (1H, d, J=5.2 Hz), 8.16 (1H, d, J=4.8 Hz), 9.50 (1H, s), 10.33 (1H, br s). [M+H] calc'd for C$_{16}$H$_{15}$FN$_4$O$_3$, 331; found, 331.

Preparation 43A: 1-(4-bromobutyl)-5-fluoro-3-iodo-1H-indazole

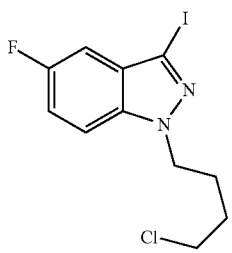 [SMILES: Fc1ccc2c(c1)c(I)nn2CCCCCl]

The title compound was prepared from 5-fluoro-3-iodoindazole and 1-bromo-4-chlorobutane in 74% yield according to the general procedure for Preparation 11A. The minor isomer was not isolated or characterized. $^1$H NMR (400 MHz, CDCl$_3$): δ 1.76-1.80 (2H, m), 2.07-2.11 (2H, m), 3.55 (2H, t, J=6.4 Hz), 4.42 (2H, t, J=6.8 Hz), 7.11 (1H, dd, J=2.0, 8.4 Hz), 7.22 (1H, td, J=2.4, 8.8 Hz), 7.33 (1H, dd, J=4.0, 9.2 Hz).

Preparation 43B: 4-(5-fluoro-3-iodo-1H-indazol-1-yl)-N,N-dimethylbutan-1-amine

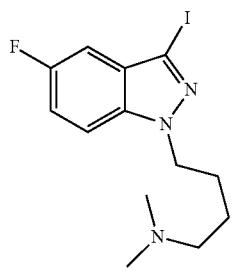 [SMILES: CN(C)CCCCn1nc(I)c2cc(F)ccc21]

The title compound was prepared in 98% yield from Preparation 43A according to the general procedure for Preparation 11B. $^1$H NMR (400 MHz, CDCl$_3$): δ 1.49-1.57 (2H, m), 1.92-1.99 (2H, m), 2.26 (6H, s), 2.38 (2H, t, J=7.2 Hz), 4.40 (2H, t, J=7.2 Hz), 7.11 (1H, dd, J=2.4, 8.0 Hz), 7.21 (1H, td, J=2.4, 8.8 Hz), 7.35 (1H, dd, J=4.0, 9.2 Hz).

Preparation 43C: methyl 3-({1-[4-(dimethylamino)butyl]-5-fluoro-1H-indazol-3-yl}amino)pyridine-4-carboxylate, trifluoroacetic acid salt

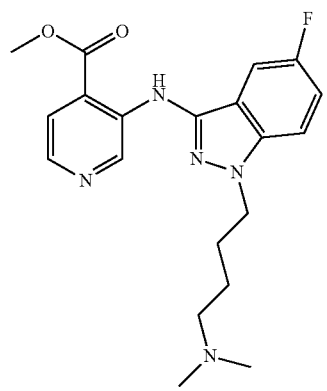 [SMILES: COC(=O)c1ccncc1Nc1nn(CCCCN(C)C)c2ccc(F)cc12]

The title compound was prepared from methyl 3-aminoisonicotinate and Preparation 43B according to the general procedure for Preparation 1A. The product was isolated as the TFA salt in 35% yield using prep-HPLC purification. $^1$H NMR (400 MHz, DMSO-d$_6$): δ 1.60-1.68 (2H, m), 1.83-1.90 (2H, m), 2.73 (3H, s), 2.74 (3H, s), 3.07-3.12 (2H, m), 3.95 (3H, s), 4.41 (2H, t, J=6.4 Hz), 7.38-7.43 (2H, m), 7.74-7.79 (2H, m), 8.19 (1H, d, J=5.2 Hz), 9.39 (1H, br s), 9.46 (1H, s), 9.80 (1H, s). [M+H] calc'd for C$_{20}$H$_{24}$FN$_5$O$_2$, 386; found, 386.

Example 43

3-({1-[4-(dimethylamino)butyl]-5-fluoro-1H-indazol-3-yl}amino)pyridine-4-carboxylic acid, trifluoroacetic acid salt

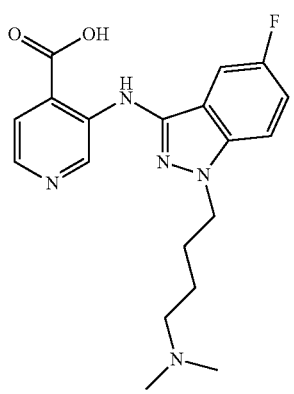 [SMILES: CN(C)CCCCn1nc(Nc2cnccc2C(=O)O)c2cc(F)ccc21]

The title compound was prepared in from Preparation 43C according to the general hydrolysis procedure for Example 1. The product was isolated as the TFA salt in 71% yield using prep-HPLC purification. $^1$H NMR (400 MHz, DMSO-d$_6$): δ 1.60-1.68 (2H, m), 1.84-1.91 (2H, m), 2.73 (3H, s), 2.74 (3H, s), 3.07-3.12 (2H, m), 4.42 (2H, t, J=6.4 Hz), 7.37-7.43 (2H, m), 7.75 (1H, dd, J=4.0, 8.8 Hz), 7.85 (1H, d, J=5.2 Hz), 8.20 (1H, d, J=5.2 Hz), 9.40 (1H, br s), 9.55 (1H, s), 10.39 (1H, s). [M+H] calc'd for C$_{19}$H$_{22}$FN$_5$O$_2$, 372; found, 372.

Preparation 44A: 1-(5-tert-butyldimethylsiloxypentyl)-5-fluoro-3-iodo-1H-indazole

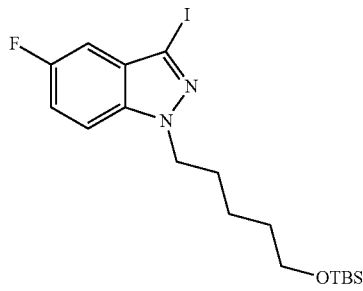 [SMILES: CC(C)(C)[Si](C)(C)OCCCCCn1nc(I)c2cc(F)ccc21]

The title compound was prepared from 5-fluoro-3-iodo-indazole and (5-chloropentoxy)tert-butyldimethylsilane in 79% yield according to the general procedure for Preparation 31A. The minor isomer was not isolated or characterized. $^1$H NMR (400 MHz, CDCl$_3$): δ 0.06 (6H, s), 0.90 (9H, s), 1.34-1.37 (2H, m), 1.50-1.55 (2H, m), 1.90-1.94 (2H, m), 3.55 (2H, t, J=6.4 Hz), 4.37 (2H, t, J=7.2 Hz), 7.10 (1H, dd, J=2.0, 8.0 Hz), 7.19 (1H, td, J=2.4, 8.8 Hz), 7.432 (1H, dd, J=4.0, 9.2 Hz).

Preparation 44B: methyl 3-{[5-fluoro-1-(5-hydroxypentyl)-1H-indazol-3-yl]amino}pyridine-4-carboxylate

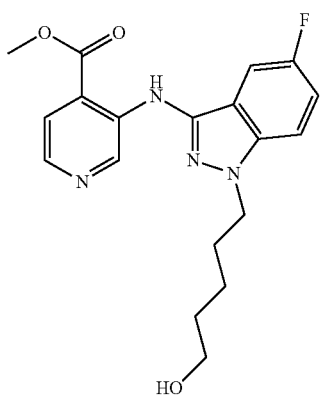 [SMILES: COC(=O)c1ccncc1Nc1nn(CCCCCO)c2ccc(F)cc12]

The title compound was prepared from methyl 3-aminoisonicotinate and Preparation 44A according to the general procedure for Preparation 1A, followed by alcohol deprotection in 10% 3N HCl/MeOH at 50° C. for 3 h. The product was isolated from prep-HPLC purification in 39% yield. $^1$H NMR (400 MHz, DMSO-d$_6$): δ 1.26-1.32 (2H, m), 1.41-1.46 (2H, m), 1.81-1.86 (2H, m), 3.35 (2H, t, J=6.4 Hz), 3.96 (3H, s), 4.36 (2H, t, J=6.4 Hz), 7.34-7.41 (2H, m), 7.73 (1H, dd, J=4.0, 9.2 Hz), 7.83 (1H, d, J=4.8 Hz), 8.20 (1H, d, J=4.8 Hz), 9.42 (1H, s), 9.81 (1H, s). [M+H] calc'd for C$_{19}$H$_{21}$FN$_4$O$_3$, 373; found, 373.

Example 44

3-{[5-fluoro-1-(5-hydroxypentyl)-1H-indazol-3-yl]amino}pyridine-4-carboxylic acid

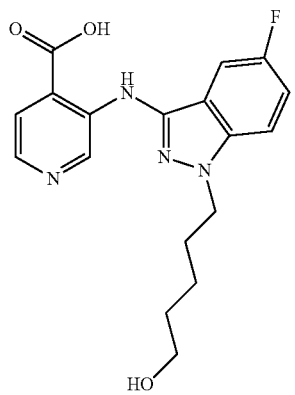 [SMILES: O=C(O)c1ccncc1Nc1nn(CCCCCO)c2ccc(F)cc12]

The title compound was prepared in 70% yield from Preparation 44B according to the general hydrolysis procedure for Example 1. $^1$H NMR (400 MHz, DMSO-d$_6$): δ 1.26-1.32 (2H, m), 1.41-1.46 (2H, m), 1.81-1.88 (2H, m), 3.35 (2H, t, J=6.4 Hz), 4.36 (2H, t, J=6.4 Hz), 7.34-7.39 (2H, m), 7.72 (1H, dd, J=4.0, 9.2 Hz), 7.83 (1H, d, J=4.8 Hz), 8.17 (1H, d, J=5.2 Hz), 9.50 (1H, s), 10.38 (1H, br s). [M+H] calc'd for C$_{18}$H$_{19}$FN$_4$O$_3$, 359; found, 359.

Preparation 45A: 3-iodo-7-methyl-1-propyl-1H-indazole

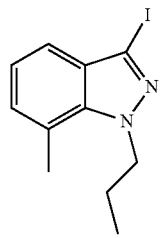

The title compound was prepared in 62% yield from 3-iodo-7-methyl-indazole and 1-bromopropane according to the general procedure for Preparation 4A. The minor isomer was not isolated or characterized. $^1$H NMR (400 MHz, CDCl$_3$): δ 0.94 (3H, t, J=7.4 Hz), 1.84-1.90 (2H, m), 2.66 (3H, s), 4.50 (2H, t, J=7.4 Hz), 7.01 (1H, t, J=7.1 Hz), 7.11 (1H, d, J=6.9 Hz), 7.28 (1H, d, J=8.0 Hz). [M+H] calc'd for C$_{11}$H$_{13}$IN$_2$, 301; found 301.

Preparation 45B: methyl 3-[(7-methyl-1-propyl-1H-indazol-3-yl)amino]pyridine-4-carboxylate

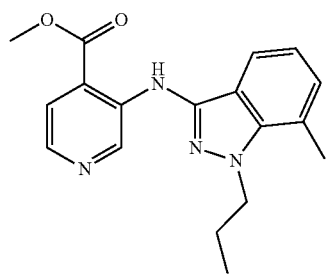

The title compound was prepared in 60% yield from methyl 3-aminoisonicotinate and Preparation 45A according to the general procedure for Preparation 1A. ¹H NMR (400 MHz, CDCl₃): δ 0.98 (3H, t, J=7.4 Hz), 1.89-1.95 (2H, m), 2.71 (3H, s), 4.00 (3H, s), 4.47 (2H, t, J=7.4 Hz), 7.01 (1H, t, J=7.8 Hz), 7.12 (1H, d, J=6.9 Hz), 7.53 (1H, d, J=8.0 Hz), 7.75 (1H, d, J=5.2 Hz), 8.14 (1H, d, J=5.2 Hz), 9.78 (1H, s), 10.11 (1H, s). [M+H] calc'd for C₁₈H₂₀N₄O₂, 325; found 325.

Example 45

3-[(5-methyl-1-propyl-1H-indazol-3-yl)amino]pyridine-4-carboxylic acid

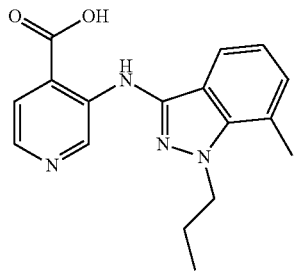 [SMILES: CCCn1nc(Nc2cnccc2C(=O)O)c2cccc(C)c21]

The title compound was prepared in 70% yield from Preparation 45B according to the general hydrolysis procedure for Example 1. ¹H NMR (400 MHz, DMSO-d₆): δ 0.91 (3H, t, J=7.4 Hz), 1.80-1.87 (2H, m), 2.69 (3H, s), 4.46 (2H, t, J=7.2 Hz), 7.05 (1H, t, J=7.2 Hz), 7.20 (1H, d, J=7.0 Hz), 7.44 (1H, d, J=8.0 Hz), 7.79 (1H, d, J=5.1 Hz), 8.16 (1H, d, J=5.1 Hz), 9.70 (1H, s), 10.57 (1H, br s), 14.14 (1H, br s). [M+H] calc'd for C₁₇H₁₈N₄O₂, 311; found, 311.

Preparation 46A: 5-(5-fluoro-3-iodo-1H-indazol-1-yl)-N-methylpentan-1-amine

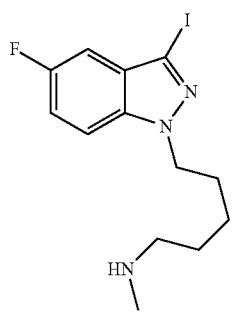 [SMILES: CNCCCCCn1nc(I)c2cc(F)ccc21]

The title compound was prepared in quantitative yield from Preparation 22A and methylamine hydrochloride according to the general procedure for Preparation 11B. ¹H NMR (400 MHz, CDCl₃): δ 1.31-1.38 (2H, m), 1.47-1.55 (2H, m), 1.90-1.97 (2H, m), 2.40 (3H, s), 2.54 (2H, t, J=7.2 Hz), 4.37 (2H, t, J=7.2 Hz), 7.11 (1H, dd, J=2.0, 8.4 Hz), 7.20 (1H, td, J=2.0, 8.8 Hz), 7.33 (1H, dd, J=4.0, 8.8 Hz).

Preparation 46B: tert-butyl N-[5-(5-fluoro-3-iodo-1H-indazol-1-yl)-pentyl-N-methylcarbamate

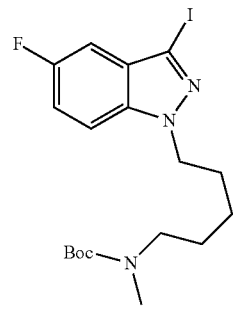 [SMILES: CN(CCCCCn1nc(I)c2cc(F)ccc21)C(=O)OC(C)(C)C]

BOC₂O (651 mg, 3.0 mmol) was added to a solution of Preparation 46A (900 mg, 2.5 mmol) and triethylamine (0.7 mL, 5.0 mmol) in DCM (30 mL) at rt, and the reaction stirred overnight. The solution was concentrated, and the residue was purified by silica gel chromatography to give 850 mg (74%) of the title compound as a yellow oil. ¹H NMR (400 MHz, CDCl₃): δ 1.24-1.32 (2H, m), 1.43 (9H, s), 1.49-1.56 (2H, m), 1.91-1.98 (2H, m), 2.80 (3H, s), 3.17 (2H, s), 4.37 (2H, t, J=7.2 Hz), 7.12 (1H, dd, J=1.6, 8.4 Hz), 7.20 (1H, td, J=2.4, 8.8 Hz), 7.33 (1H, s).

Preparation 46C: methyl 3-({5-fluoro-1-[5-(methylamino)pentyl]-1H-indazol-3-yl}amino)pyridine-4-carboxylate, trifluoroacetic acid salt

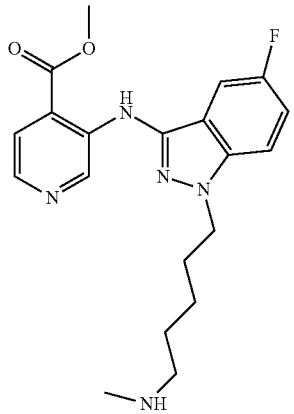 [SMILES: CNCCCCCn1nc(Nc2cnccc2C(=O)OC)c2cc(F)ccc21]

The title compound was prepared from methyl 3-aminoisonicotinate and Preparation 46B according to the general procedure for Preparation 1A, followed by BOC deprotection in 10% 3N HCl/MeOH at 50° C. for 3 h. The product was isolated as the TFA salt in 48% yield using prep-HPLC purification. ¹H NMR (400 MHz, CD₃OD): δ 1.40-1.45 (2H, m), 1.68-1.74 (2H, m), 1.99-2.03 (2H, m), 2.65 (3H, s), 2.94 (2H, t, J=7.6 Hz), 4.12 (3H, s), 4.42 (2H, t, J=6.8 Hz), 7.31 (1H, td, J=2.0, 9.2 Hz), 7.40 (1H, dd, J=2.4, 8.8 Hz), 7.61 (1H, dd, J=4.0, 9.2 Hz), 8.23-8.27 (2H, m), 9.79 (1H, s). [M+H] calc'd for C₂₀H₂₄FN₅O₂, 386; found, 386.

Example 46

3-({5-fluoro-1-[5-(methylamino)pentyl]-1H-indazol-3-yl}amino)pyridine-4-carboxylic acid, trifluoroacetic acid salt

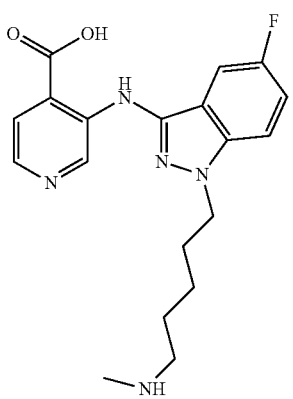 [SMILES: CNCCCCCn1nc(Nc2cnccc2C(=O)O)c2cc(F)ccc21]

The title compound was prepared in from Preparation 46C according to the general hydrolysis procedure for Example 1. The product was isolated as the TFA salt in 69% yield using prep-HPLC purification. $^1$H NMR (400 MHz, CD$_3$OD): δ 1.39-1.45 (2H, m), 1.67-1.73 (2H, m), 1.99-2.03 (2H, m), 2.65 (3H, s), 2.94 (2H, t, J=7.6 Hz), 4.41 (2H, t, J=6.8 Hz), 7.26-7.35 (2H, m), 7.56 (1H, dd, J=4.0, 9.2 Hz), 8.24 (1H, d, J=5.6 Hz), 8.32 (1H, d, J=6.0 Hz), 9.84 (1H, s). [M+H] calc'd for C$_{19}$H$_{22}$FN$_5$O$_2$, 372; found, 372.

Preparation 47A: tert-butyl 3-[2-(5-fluoro-3-iodo-1H-indazol-1-yl)ethyl]piperidine-1-carboxylate

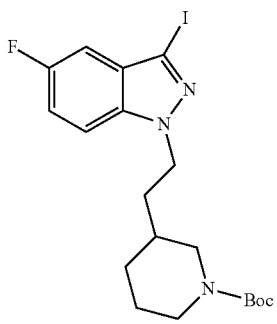 [SMILES: CC(C)(C)OC(=O)N1CCCC(CCn2nc(I)c3cc(F)ccc32)C1]

The title compound was prepared in 56% yield from 5-fluoro-3-iodo-indazole and tert-butyl 3-(2-bromoethyl)piperidine-1-carboxylate according to the general procedure for Preparation 10A. $^1$H NMR (400 MHz, CDCl$_3$): δ 1.16-1.32 (2H, m), 1.37-1.62 (11H, m), 1.78-1.87 (3H, m), 2.70-2.76 (1H, m), 2.90-2.93 (1H, m), 3.75-3.88 (2H, m), 4.42 (2H, t, J=2.0, 7.2 Hz), 7.11 (1H, d, J=8.4 Hz), 7.21 (1H, td, J=2.0, 8.8 Hz), 7.38 (1H, dd, J=4.0, 9.2 Hz).

Preparation 47B: methyl 3-({5-fluoro-1-[2-(piperidin-3-yl)ethyl]-1H-indazol-3-yl}amino)pyridine-4-carboxylate, trifluoroacetic acid salt

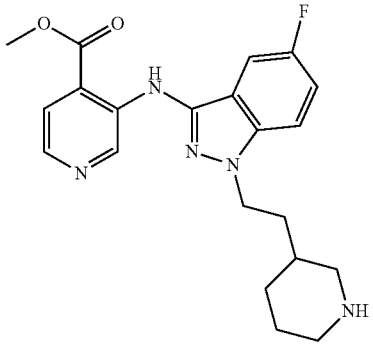 [SMILES: COC(=O)c1ccncc1Nc1nn(CCC2CCCNC2)c2ccc(F)cc12]

The title compound was prepared from methyl 3-aminoisonicotinate and Preparation 47A according to the general procedure for Preparation 1A, followed by BOC deprotection in 10% 3N HCl/MeOH at rt for 3 h. The product was isolated as the TFA salt in 41% yield using prep-HPLC purification. $^1$H NMR (400 MHz, CD$_3$OD): δ 1.30-1.40 (1H, m), 1.65-1.80 (2H, m), 1.91-2.11 (4H, m), 2.74 (1H, t, J=12.0 Hz), 2.91 (1H, td, J=2.8, 12.8 Hz), 3.31-3.38 (2H, m), 4.10 (3H, s), 4.50 (2H, t, J=6.8 Hz), 7.32-7.41 (2H, m), 7.62 (1H, dd, J=4.0, 9.2 Hz), 8.12 (1H, d, J=4.8 Hz), 8.21 (1H, d, J=5.2 Hz), 9.75 (1H, s). [M+H] calc'd for C$_{21}$H$_{24}$FN$_5$O$_2$, 398; found, 398.

Example 47

3-({5-fluoro-1-[2-(piperidin-3-yl)ethyl]-1H-indazol-3-yl}amino)pyridine-4-carboxylic acid, trifluoroacetic acid salt

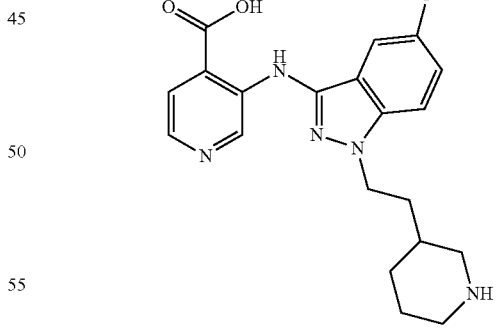

The title compound was prepared in 74% yield from Preparation 47B according to the general hydrolysis procedure for Example 1. $^1$H NMR (400 MHz, DMSO-d$_6$): δ 1.17-1.27 (1H, m), 1.48-1.64 (2H, m), 1.72-1.96 (4H, m), 2.57-2.77 (2H, m), 3.17-3.22 (2H, m), 4.44 (2H, t, J=6.0 Hz), 7.37-7.43 (2H, m), 7.77 (1H, dd, J=4.0, 8.8 Hz), 7.83 (1H, d, J=5.2 Hz), 8.19-8.24 (2H, m), 8.53-8.57 (1H, m), 9.55 (1H, s), 10.38 (1H, s). [M+H] calc'd for C$_{20}$H$_{22}$FN$_5$O$_2$, 384; found, 384.

Preparation 48A: 3-iodo-1-[(2,2-dimethyl-1,3-dioxolan-4-yl)methyl]-5-fluoro-1H-indazole

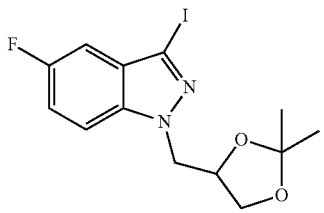 [SMILES: CC1(C)OCC(Cn2nc(I)c3cc(F)ccc32)O1]

The title compound was prepared from 5-fluoro-3-iodo-indazole and 1,2-isopropylideneglycerol in 52% yield according to the general procedure for Preparation 31A. The minor isomer was not isolated or characterized. $^1$H NMR (300 MHz, CDCl$_3$): δ 1.27 (3H, s), 1.31 (3H, s), 3.83-3.87 (1H, m), 4.07-4.11 (1H, m), 4.48-4.55 (3H, m), 7.10 (1H, dd, J=8.3, 2.3 Hz), 7.22 (1H, td, J=8.9, 2.3 Hz), 7.45 (1H, dd, J=9.1, 4.0 Hz). [M+H] calc'd for C$_{13}$H$_{14}$FN$_2$O$_2$, 377; found, 377.

Preparation 48B: methyl 3-{[1-(2,3-dihydroxypropyl)-5-fluoro-1H-indazol-3-yl]amino}pyridine-4-carboxylate

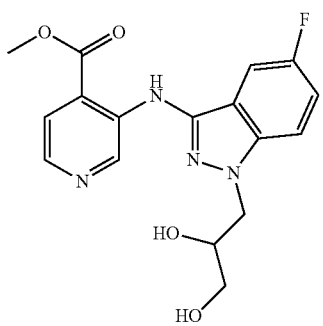 [SMILES: COC(=O)c1ccncc1Nc1nn(CC(O)CO)c2ccc(F)cc12]

The title compound was prepared from methyl 3-aminoisonicotinate and Preparation 48A according to the general procedure for Preparation 1A, followed by diol deprotection in 20% 1N HCl/THF overnight. The product was isolated in 52% yield by silica gel chromatography (10% MeOH/DCM). $^1$H NMR (400 MHz, CDCl$_3$): δ 3.67-3.81 (2H, m), 4.03 (3H, s), 4.31 (1H, t, J=5.0 Hz), 4.41 (2H, br s), 7.19-7.29 (2H, m), 7.38 (1H, dd, J=8.7, 3.4 Hz), 7.78 (1H, d, J=5.2 Hz), 8.03 (1H, d, J=5.2 Hz), 9.67 (1H, s), 10.16 (1H, s). [M+H] calc'd for C$_{17}$H$_{17}$FN$_4$O$_4$, 361; found, 361.

Example 48

3-{[1-(2,3-dihydroxypropyl)-5-fluoro-1H-indazol-3-yl]amino}pyridine-4-carboxylic acid

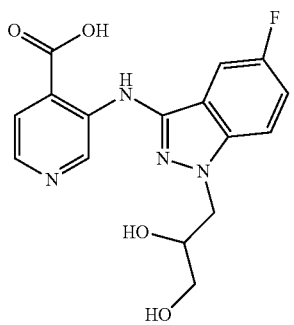 [SMILES: O=C(O)c1ccncc1Nc1nn(CC(O)CO)c2ccc(F)cc12]

The title compound was prepared in from Preparation 48B in 82% yield according to the general hydrolysis procedure for Example 1. $^1$H NMR (400 MHz, DMSO-d$_6$): δ 3.40 (2H, d, J=5.4 Hz), 3.95 (1H, br s), 4.23-4.44 (2H, m), 4.76 (1H, br s), 4.95 (1H, br s), 7.30-7.37 (2H, m), 7.65 (1H, dd, J=9.1, 4.1 Hz), 7.78 (1H, d, J=5.1 Hz), 8.15 (1H, d, J=5.1 Hz), 9.51 (1H, s), 10.35 (1H, br s), 14.11 (1H, br s). [M+H] calc'd for C$_{16}$H$_{15}$FN$_4$O$_4$, 347; found, 347.

Preparation 49A: 1-(4-chlorobut-2-yn-1-yl)-5-fluoro-3-iodo-1H-indazole

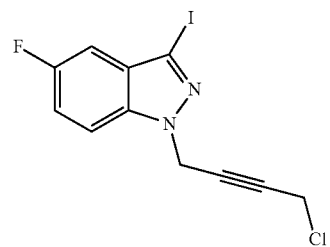 [SMILES: Fc1ccc2c(c1)c(I)nn2CC#CCCl]

The title compound was prepared from 5-fluoro-3-iodo-indazole and 4-chloro-2-butyn-1-ol in 58% yield according to the general procedure for Preparation 31A. The minor isomer was not isolated or characterized.

Preparation 49B: 4-5-fluoro-3-iodo-1H-indazol-1-yl)-N,N-dimethylbut-2-yn-1-amine

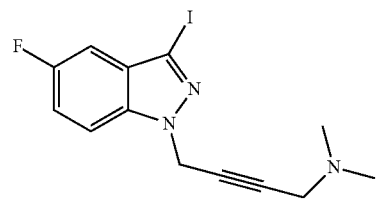 [SMILES: CN(C)CC#CCn1nc(I)c2cc(F)ccc21]

The title compound was prepared in 85% yield from Preparation 49A according to the general procedure for Preparation 11B. $^1$H NMR (400 MHz, CDCl$_3$): δ 2.29 (6H, s), 3.30 (2H, s), 5.23 (2H, t, J=2.0 Hz), 7.14 (1H, dd, J=2.0, 8.0 Hz), 7.25 (1H, td, J=2.4, 9.2 Hz), 7.51 (1H, dd, J=4.0, 9.2 Hz).

Preparation 49C: 3-({1-[4-(dimethylamino)but-2-yn-1-yl]-5-fluoro-1H-indazol-3-yl}amino)pyridine-4-carboxylic acid, trifluoroacetic acid salt

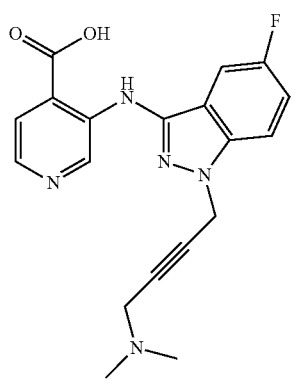 [SMILES: CN(C)CC#CCn1nc(Nc2cnccc2C(=O)O)c2cc(F)ccc21]

To a suspension of Preparation 49B (450 mg, 1.3 mmol), methyl 3-aminoisonicotinate (230 mg, 1.5 mmol), Cs$_2$CO$_3$ (821 mg, 2.5 mmol), Xantphos (109 mg, 0.19 mmol) in dioxane (20 mL) was added Pd$_2$(dba)$_3$ (58 mg, 0.063 mmol) under N$_2$ at rt. The suspension was heated at 100° C. overnight. The reaction mixture was filtered and concentrated. The residue stirred in 1N NaOH/MeOH for 1 h, and then was concentrated and purified by prep-HPLC to give 5 mg (1%) of the title compound as an orange solid. $^1$H NMR (400 MHz, CD$_3$OD): δ 2.91 (6H, s), 4.12 (2H, s), 5.40 (2H, s), 7.37 (1H, td, J=2.0, 8.8 Hz), 7.41 (1H, dd, J=2.0, 8.0 Hz), 7.66 (1H, dd, J=3.6, 8.8 Hz), 8.22-8.27 (2H, m), 9.87 (1H, s). [M+H] calc'd for C$_{19}$H$_{18}$FN$_5$O$_2$, 368; found, 368.

Preparation 50A: 5-fluoro-3-iodo-1-[2-(pyrrolidin-1-yl)ethyl]-1H-indazole

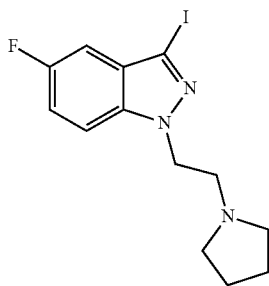 [SMILES: Fc1ccc2c(c1)c(I)nn2CCN1CCCC1]

Potassium carbonate (950 mg, 6.9 mmol) and potassium iodide (380 mg, 2.3 mmol) were added to a solution of 5-fluoro-3-iodo-indazole (600 mg, 2.3 mmol) and 1-(2-chloroethyl)pyrrolidine hydrochloride (779 mg, 4.6 mmol) in DMF (15 mL) at rt. The reaction was heated to 68° C. for 3 h and then allowed to cool to rt. The reaction was filtered, washing with MeOH, and the solution was concentrated. Purification by silica gel chromatography (10% MeOH/DCM) gave 720 mg (88%) of the title compound as a clear oil. This material contained a slight (minor isomer) impurity. $^1$H NMR (400 MHz, CDCl$_3$): δ 1.76-1.81 (4H, m), 2.58-2.64 (4H, m), 3.05 (2H, t, J=7.3 Hz), 4.56 (2H, t, J=7.3 Hz), 7.10 (1H, dd, J=8.2, 4.7 Hz), 7.21 (1H, td, J=8.9, 2.3 Hz), 7.42 (1H, dd, J=9.1, 4.0 Hz). [M+H] calc'd for C$_{13}$H$_{15}$FIN$_3$, 360; found, 360.

Preparation 50B: methyl 3-({5-fluoro-1-[2-(pyrrolidin-1-yl)ethyl]-1H-indazol-3-yl}amino)pyridine-4-carboxylate

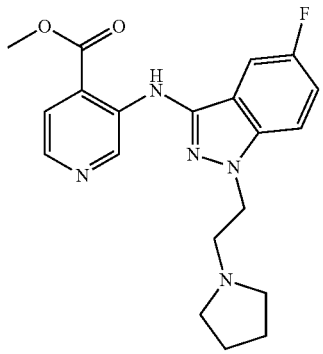 [SMILES: COC(=O)c1ccncc1Nc1nn(CCN2CCCC2)c2ccc(F)cc12]

The title compound was prepared from methyl 3-aminoisonicotinate and Preparation 50A in 50% yield according to the general procedure for Preparation 1A. $^1$H NMR (400 MHz, CDCl$_3$): δ 1.75-1.80 (4H, m), 2.56-2.61 (4H, m), 3.02 (2H, t, J=7.3 Hz), 3.99 (3H, s), 4.43 (2H, t, J=7.1 Hz), 7.17 (1H, td, J=8.9, 2.4 Hz), 7.27-7.35 (2H, m), 7.74 (1H, d, J=5.1 Hz), 8.15 (1H, d, J=5.1 Hz), 9.66 (s, 1H), 10.04 (s, 1H). [M+H] calc'd for C$_{20}$H$_{22}$FN$_5$O$_2$, 384; found, 384.

Example 50

3-({5-fluoro-1-[2-(pyrrolidin-1-yl)ethyl]-1H-indazol-3-yl}amino)pyridine-4-carboxylic acid

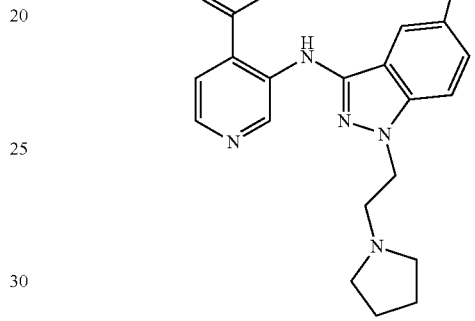

The title compound was prepared in from Preparation 50B in 52% yield according to the general hydrolysis procedure for Example 1. $^1$H NMR (400 MHz, DMSO-d$_6$): δ 1.97-2.01 (4H, m), 3.10-3.30 (4H, br s), 3.71-3.75 (2H, br s), 4.67 (2H, t, J=5.5 Hz), 6.64 (1H, d, J=8.4 Hz), 7.03 (1H, dd, J=9.1, 2.2 Hz), 7.35 (1H, d, J=4.8 Hz), 7.45 (1H, dd, J=9.1, 4.0 Hz), 7.88 (1H, d, J=4.8 Hz), 9.59 (1H, s), 12.01 (1H, s). [M+H] calc'd for C$_{19}$H$_{20}$FN$_5$O$_2$, 370; found, 370.

Preparation 51A: 1-(2-tert-butyldimethylsiloxypropyl)-5-fluoro-3-iodo-1H-indazole

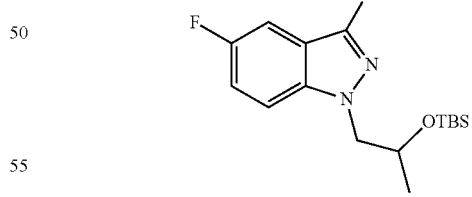

The title compound was prepared in 31% yield from 5-fluoro-3-iodo-indazole and 1-bromo-2-propanol according to the general procedure for Preparation 11A, followed by alcohol protection using TBDMS chloride (1.1 eq) and DMAP (1.1 eq) in DCM. The minor isomer was not isolated or characterized. $^1$H NMR (400 MHz, CDCl$_3$): δ 0.06 (6H, s), 0.89 (9H, s), 2.07-2.13 (2H, m), 3.55 (2H, t, J=6.0 Hz), 4.49 (2H, t, J=6.0 Hz), 7.10 (1H, dd, J=2.4, 8.4 Hz), 7.18 (1H, td, J=2.4, 8.8 Hz), 7.40 (1H, dd, J=4.0, 8.8 Hz).

Preparation 51B: methyl 3-{[5-fluoro-1-(2-hydroxy-propyl)-1H-indazol-3-yl]amino}pyridine-4-carboxylic acid

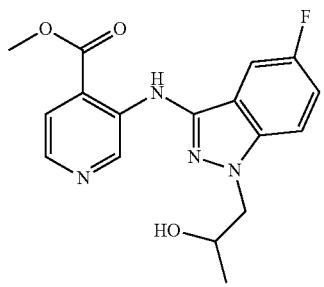 [SMILES: COC(=O)c1ccncc1Nc1nn(CC(C)O)c2ccc(F)cc12]

The title compound was prepared from methyl 3-aminoisonicotinate and Preparation 51A according to the general procedure for Preparation 1A, followed by alcohol deprotection in 10% 3N HCl/MeOH at 50° C. for 3 h. The product was isolated from silica gel chromatography (10% MeOH/DCM) in 52% yield. $^1$H NMR (400 MHz, DMSO-d$_6$): δ 1.96-2.00 (2H, m), 3.41-3.42 (2H, m), 3.95 (3H, s), 4.41 (2H, t, J=6.4 Hz), 4.62 (1H, t, J=4.4 Hz), 7.35-7.39 (2H, m), 7.67-7.54 (2H, m), 8.16 (1H, d, J=4.4 Hz), 9.42 (1H, s), 9.76 (1H, s). [M+H] calc'd for C$_{17}$H$_{17}$FN$_4$O$_3$, 345; found, 345.

Example 51

3-{[5-fluoro-1-(2-hydroxypropyl)-1H-indazol-3-yl]amino}pyridine-4-carboxylic acid

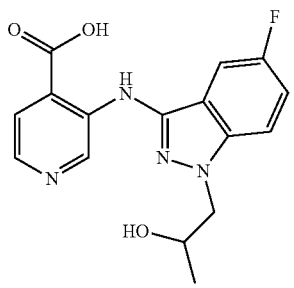 [SMILES: CC(O)Cn1nc(Nc2cnccc2C(=O)O)c2cc(F)ccc21]

The title compound was prepared in 68% yield from Preparation 51B according to the general hydrolysis procedure for Example 1. $^1$H NMR (400 MHz, DMSO-d$_6$): δ 1.96-2.02 (2H, m), 3.41 (2H, t, J=6.0 Hz), 4.42 (2H, t, J=6.4 Hz), 7.33-7.40 (2H, m), 7.69 (1H, dd, J=4.0, 9.2 Hz), 7.79 (1H, d, J=5.2 Hz), 8.16 (1H, d, J=4.8 Hz), 9.50 (1H, s), 10.33 (1H, br s). [M+H] calc'd for C$_{16}$H$_{15}$FN$_4$O$_3$, 331; found, 331.

Preparation 52A: 1-methyl-3-nitro-1H-pyrrolo[2,3-b]pyridine

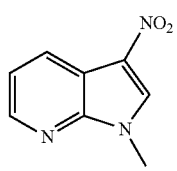

Sodium hydride (236 mg, 60%, 5.9 mmol) was added to a solution of compound 3-nitro-7-azaidole (800 mg, 4.9 mmol) in THF (20 mL) and DMF (10 mL) at 0° C. After stirring for 30 min, iodomethane (837 mg, 5.9 mmol) was added, and the reaction was stirred overnight at rt. The reaction was diluted with water (40 mL), and the precipitate was collected by filtration to give 600 mg (69%) of the title compound as a white solid. $^1$H NMR (400 MHz, DMSO-d$_6$): δ 3.94 (3H, s), 7.48 (1H, dd, J=4.4, 8.4 Hz), 8.46 (1H, dd, J=2.4, 8.0 Hz), 8.50 (1H, dd, J=2.0, 4.8 Hz), 8.94 (1H, s).

Preparation 52B: 1-methyl-1H-pyrrolo[2,3-b]pyridine-3-amine

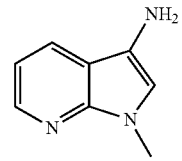

10% Pd/C (50 mg) was added to a solution of Preparation 52A (241 mg, 1.4 mmol) and triethylamine (137 mg, 1.4 mmol) in MeOH (10 mL) at rt under N$_2$. The reaction was stirred under H$_2$ at rt overnight. The mixture was filtered through Celite and concentrated to give 208 mg of the title compound as a yellow oil, which was carried on directly to the next step without purification.

Preparation 52C: 3-[(1-methyl-1H-pyrrolo[2,3-b]pyridine-3-yl)amino]pyridine-4-carboxylate

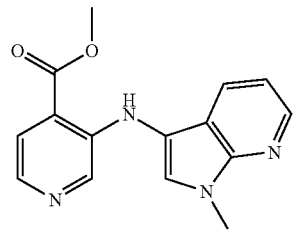 [SMILES: COC(=O)c1ccncc1Nc1cn(C)c2ncccc12]

To a suspension of Preparation 52B (208 mg, 1.4 mmol), methyl 3-bromo-isonicotinate (350 mg, 1.6 mmol), Cs$_2$CO$_3$ (887 mg, 2.7 mmol), and Xantphos (118 mg, 0.20 mmol) in dioxane (20 mL) was added Pd$_2$(dba)$_3$ (62 mg, 0.068 mmol) under N$_2$ at rt. The suspension was heated at 100° C. overnight. Solids were removed by filtration, and the solution was concentrated and purified by prep-HPLC to give 80 mg (15%) of the title compound as a yellow solid. $^1$H NMR (400 MHz, DMSO-d$_6$): δ 3.97 (3H, s), 4.09 (3H, s), 7.22 (1H, dd, J=4.8, 7.6 Hz), 7.60 (1H, s), 7.91 (1H, d, J=8.0 Hz), 8.03 (1H, d, J=9.2 Hz), 8.14 (1H, s), 8.22 (1H, d, J=5.6 Hz), 8.39 (1H, d, J=5.2 Hz).

Example 52

3-[(1-methyl-1H-pyrrolo[2,3-b]pyridine-3-yl)amino]pyridine-4-carboxylic acid

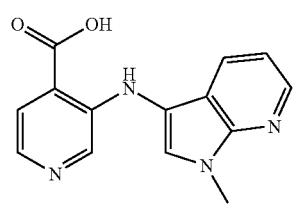

The title compound was prepared in from Preparation 52C in 47% yield according to the general hydrolysis procedure for Example 1. $^1$H NMR (400 MHz, DMSO-d$_6$): δ 3.56 (3H, s), 7.12 (1H, dd, J=4.8, 8.0 Hz), 7.71 (1H, s), 7.77 (1H, d, J=8.4 Hz), 7.81 (1H, d, J=5.2 Hz), 7.98 (1H, d, J=5.2 Hz), 8.12 (1H, s), 8.34 (1H, d, J=3.6 Hz), 9.10 (1H, s). [M+H] calc'd for C$_{14}$H$_{12}$N$_4$O$_2$, 269; found, 269.

Preparation 53A: 1H-indazole-5-carbonitrile

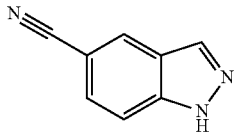 [SMILES: N#Cc1ccc2[nH]ncc2c1]

To a suspension of 5-bromo-indazole (2.0 g, 10.2 mmol), Zn(CN)$_2$ (1.4 g, 12.2 mmol), and Xantphos (0.9 g, 1.5 mmol), in DMF (10 mL) and water (0.1 mL) was added Pd$_2$(dba)$_3$ (417 mg, 0.51 mmol) under N$_2$ at rt. The suspension was heated at 150° C. for 1.5 h in the microwave. The solution was filtered and concentrated, and the residue was purified by silica gel chromatography (10-20% MeOH/DCM) to give 350 mg (24%) of the title compound as a white solid. $^1$H NMR (400 MHz, CDCl$_3$): δ 7.62 (2H, s), 8.20 (2H, d, J=8.0 Hz), 10.56 (1H, br s).

Preparation 53B: 3-iodo-1H-indazole-5-carbonitrile

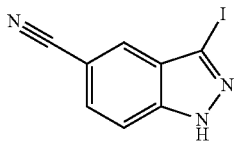 [SMILES: N#Cc1ccc2[nH]nc(I)c2c1]

To a solution of Preparation 53A (350 mg, 2.4 mmol) and I$_2$ (1.2 g, 4.7 mmol) in DMF (20 mL) was added KOH (493 mg, 8.8 mmol), and the reaction was stirred overnight at rt. The solution was diluted with water (50 mL), extracted with EtOAc (40 mL×3), washed with brine (40 mL), dried (Na$_2$SO$_4$), and concentrated to give 500 mg (77%) of the title compound as a yellow solid. $^1$H NMR (400 MHz, CD$_3$OD): δ 7.61 (1H, d, J=8.8 Hz), 7.67 (1H, d, J=8.8 Hz), 7.95 (1H, s), 10.87 (1H, br s).

Preparation 53C: 3-iodo-1-propyl-1H-indazole-5-carbonitrile

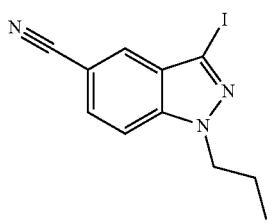

The title compound was prepared from Preparation 53B and 1-bromo-propane in 72% yield according to the general procedure for Preparation 11A. The minor isomer was not isolated or characterized. $^1$H NMR (400 MHz, CD$_3$OD): δ 0.94 (3H, t, J=7.2 Hz), 1.95-2.00 (2H, m), 4.38 (2H, t, J=7.2 Hz), 7.46 (1H, d, J=8.4 Hz), 7.61 (1H, dd, J=0.9, 8.8 Hz), 7.89 (1H, s).

Preparation 53D: methyl 3-[(5-cyano-1H-indol-3-yl)amino]pyridine-4-carboxylate

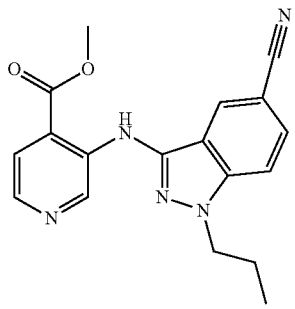 [SMILES: CCCn1nc(Nc2cnccc2C(=O)OC)c2cc(C#N)ccc21]

The title compound was prepared in 58% yield from methyl 3-aminoisonicotinate and Preparation 53C according to the general procedure for Preparation 1A. $^1$H NMR (300 MHz, DMSO-d$_6$): δ 0.85 (3H, t, J=7.2 Hz), 1.83-1.90 (2H, m), 3.95 (3H, s), 4.35 (2H, t, J=6.9 Hz), 7.74-7.77 (2H, m), 7.84 (1H, d, J=9.0 Hz), 8.24 (1H, d, J=5.1 Hz), 8.28 (1H, s), 9.59 (1H, s), 9.97 (1H, s). [M+H] calc'd for C$_{18}$H$_{17}$N$_5$O$_2$, 336; found, 336.

Example 53

3-[(5-cyano-1H-indol-3-yl)amino]pyridine-4-carboxylic acid

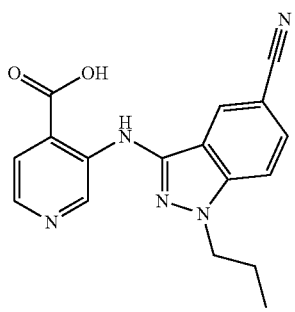 [SMILES: CCCn1nc(Nc2cnccc2C(=O)O)c2cc(C#N)ccc21]

The title compound was prepared in 78% yield from Preparation 53D according to the general hydrolysis procedure for Example 1. $^1$H NMR (300 MHz, DMSO-d$_6$): δ 0.85 (3H, t, J=7.2 Hz), 1.84-1.91 (2H, m), 4.38 (2H, t, J=5.4 Hz), 7.76-7.78 (1H, m), 7.85-7.88 (1H, m), 7.95 (1H, d, J=5.1 Hz), 8.27 (1H, s), 8.28 (1H, d, J=6.8 Hz), 9.66 (1H, s), 10.66 (1H, s). [M+H] calc'd for C$_{17}$H$_{15}$N$_5$O$_2$, 322; found, 322.

Preparation 54A: 5-fluoro-3-iodo-1-(tetrahydrofuran-3-yl)-1H-indazole

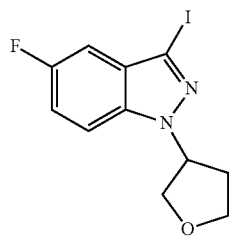 [SMILES: Fc1ccc2c(c1)c(I)nn2C1CCOC1]

The title compound was prepared from 5-fluoro-3-iodo-indazole and 3-hydroxytetrahydrofuran in 56% yield according to the general procedure for Preparation 31A. The minor isomer was not isolated or characterized. ¹H NMR (400 MHz, CDCl₃): δ 2.47-2.52 (2H, m), 3.95-4.00 (1H, m), 4.12-4.19 (2H, m), 4.19-4.28 (1H, m), 5.24-5.30 (1H, m), 7.12 (1H, dd, J=2.0, 8.4 Hz), 7.21 (1H, td, J=1.6, 8.8 Hz), 7.45 (1H, dd, J=4.0, 9.2 Hz).

Preparation 54B: methyl 3-{[5-fluoro-1-(tetrahydrofuran-3-yl)-1H-indazol-3-yl]amino}pyridine-4-carboxylate

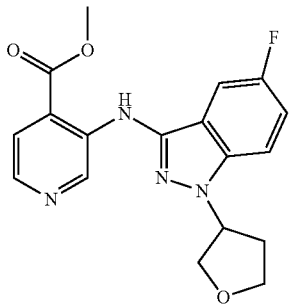 [SMILES: COC(=O)c1ccncc1Nc1nn(C2CCOC2)c2ccc(F)cc12]

The title compound was prepared in 35% yield from methyl 3-aminoisonicotinate and Preparation 54A according to the general procedure for Preparation 1A. ¹H NMR (400 MHz, DMSO-d₆): δ 2.30-2.45 (2H, m), 3.88-3.95 (5H, m), 4.08-4.13 (2H, m), 5.49-5.50 (1H, m), 7.38-7.43 (2H, m), 7.77-7.83 (2H, m), 8.21 (1H, d, J=5.2 Hz), 9.45 (1H, s), 9.84 (1H, s). [M+H] calc'd for $C_{18}H_{17}FN_4O_3$, 357; found, 357.

Example 54

3-{[5-fluoro-1-(tetrahydrofuran-3-yl)-1H-indazol-3-yl]amino}pyridine-4-carboxylic acid

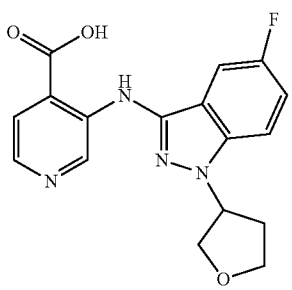 [SMILES: O=C(O)c1ccncc1Nc1nn(C2CCOC2)c2ccc(F)cc12]

The title compound was prepared in 73% yield from Preparation 54B according to the general hydrolysis procedure for Example 1. ¹H NMR (400 MHz, DMSO-d₆): δ 2.29-2.45 (2H, m), 3.91-3.92 (2H, m), 4.01-4.13 (2H, m), 5.48-5.49 (1H, m), 7.35-7.41 (2H, m), 7.77-7.79 (2H, m), 8.17 (1H, d, J=4.0 Hz), 9.52 (1H, s), 10.37 (1H, br s), 14.05 (1H, br s). [M+H] calc'd for $C_{17}H_{15}FN_4O_3$, 343; found, 343.

Preparation 55A: 3-(5-fluoro-3-iodo-1H-indazol-1-yl)-1,1,1-trifluoropropan-2-ol

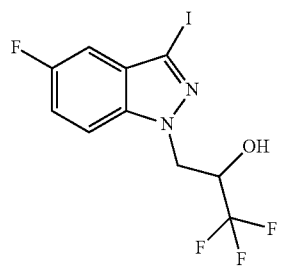 [SMILES: OC(Cn1nc(I)c2cc(F)ccc21)C(F)(F)F]

The title compound was prepared in 70% yield from 5-fluoro-3-iodo-indazole and 3-bromo-1,1,1-trifluoro-2-propanol according to the general procedure for Preparation 11A. The minor isomer was not isolated or characterized. ¹H NMR (400 MHz, CDCl₃): δ 3.47 (1H, d, J=4.0 Hz), 4.51-4.57 (2H, m), 4.64-4.68 (1H, m), 7.14 (1H, dd, J=2.4, 8.4 Hz), 7.27 (1H, td, J=2.4, 8.8 Hz), 7.40 (1H, dd, J=3.6, 9.2 Hz).

Preparation 55B: methyl 3-{[5-fluoro-1-(3,3,3-trifluoro-2-hydroxypropyl)-1H-indazol-3-yl]amino}pyridine-4-carboxylate

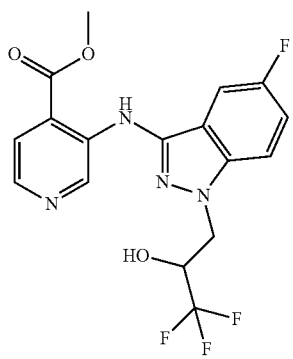 [SMILES: COC(=O)c1ccncc1Nc1nn(CC(O)C(F)(F)F)c2ccc(F)cc12]

The title compound was prepared in 36% yield from methyl 3-aminoisonicotinate and Preparation 55A according to the general procedure for Preparation 1A. ¹H NMR (400 MHz, CD₃OD): δ 4.09 (3H, s), 4.52-4.61 (3H, m), 7.29-7.39 (2H, m), 7.62 (1H, dd, J=4.0, 9.2 Hz), 8.17-8.22 (2H, m), 9.82 (1H, s). [M+H] calc'd for $C_{17}H_{14}F_4N_4O_3$, 399; found, 399.

Example 55

3-{[5-fluoro-1-(3,3,3-trifluoro-2-hydroxypropyl)-1H-indazol-3-yl]amino}pyridine-4-carboxylic acid

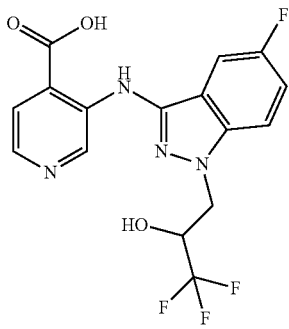 [SMILES: O=C(O)c1ccncc1Nc1nn(CC(O)C(F)(F)F)c2ccc(F)cc12]

The title compound was prepared in 70% yield from Preparation 55B according to the general hydrolysis procedure for Example 1. $^1$H NMR (400 MHz, DMSO-d$_6$): δ 4.49-4.57 (3H, m), 6.61-6.64 (1H, m), 7.35-7.41 (2H, m), 7.72 (1H, dd, J=4.0, 9.2 Hz), 7.79 (1H, d, J=5.2 Hz), 8.18 (1H, d, J=4.8 Hz), 9.55 (1H, s), 10.38 (1H, br s), 14.17 (1H, br s). [M+H] calc'd for C$_{16}$H$_{12}$F$_4$N$_4$O$_3$, 385; found, 385.

Preparation 56A: 5-fluoro-3-iodo-1-[2-(morpholin-1-yl)ethyl]-1H-indazole

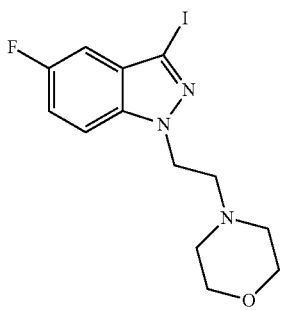 [SMILES: Fc1ccc2c(c1)c(I)nn2CCN1CCOCC1]

The title compound was prepared in 70% yield from 5-fluoro-3-iodo-indazole and 4-(2-chloroethyl)morpholine according to the general procedure for Preparation 50A. $^1$H NMR (400 MHz, CDCl$_3$): δ 2.46-2.52 (4H, m), 2.82-2.89 (2H, m), 3.57-3.67 (4H, m), 4.49 (2H, t, J=6.7 Hz), 7.11 (1H, dd, J=8.2, 2.3 Hz), 7.21 (1H, td, J=8.9, 2.3 Hz), 7.36 (1H, dd, J=9.0, 3.9 Hz). [M+H] calc'd for C$_{13}$H$_{15}$FIN$_3$O, 376. found, 376.

Preparation 56B: methyl 3-({5-fluoro-1-[2-(morpholin-1-yl)ethyl]-1H-indazol-3-yl}amino)pyridine-4-carboxylate

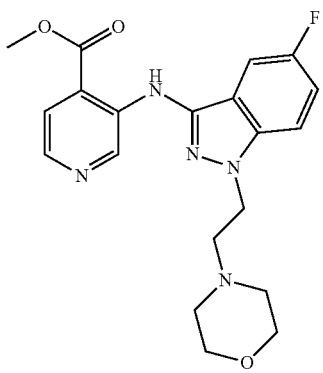 [SMILES: COC(=O)c1ccncc1Nc1nn(CCN2CCOCC2)c2ccc(F)cc12]

The title compound was prepared from methyl 3-aminoisonicotinate and Preparation 56A in 72% yield according to the general procedure for Preparation 1A. $^1$H NMR (400 MHz, CDCl$_3$): δ 2.48-2.54 (4H, m), 2.89 (2H, t, J=6.8 Hz), 3.63-3.69 (4H, m), 4.01 (3H, s), 4.41 (2H, t, J=6.8 Hz), 7.18 (1H, td, J=8.9, 2.3 Hz), 7.26-7.34 (2H, m), 7.75 (1H, d, J=5.1 Hz), 8.16 (1H, d, J=5.1 Hz), 9.66 (s, 1H), 10.05 (s, 1H). [M+H] calc'd for C$_{20}$H$_{22}$FN$_5$O$_2$, 400; found, 400.

Example 56

3-({5-fluoro-1-[2-(morpholin-1-yl)ethyl]-1H-indazol-3-y}amino)pyridine-4-carboxylic acid

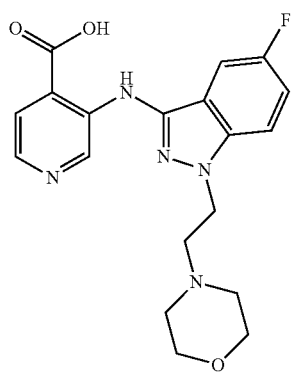 [SMILES: O=C(O)c1ccncc1Nc1nn(CCN2CCOCC2)c2ccc(F)cc12]

The title compound was prepared in from Preparation 56B in 68% yield according to the general hydrolysis procedure for Example 1. $^1$H NMR (400 MHz, DMSO-d$_6$): δ 2.79 (4H, br s), 3.05 (2H, br s), 3.63 (4H, br s), 4.57 (2H, t, J=6.1 Hz), 7.13 (1H, d, J=7.6 Hz), 7.26 (1H, dd, J=9.0, 2.3 Hz), 7.63-7.68 (2H, m), 8.05 (1H, d, J=4.8 Hz), 9.52 (1H, s), 11.16 (1H, br s), 12.98 (1H, br s). [M+H] calc'd for C$_{19}$H$_{20}$FN$_5$O$_3$, 386; found, 386.

Preparation 57A: 5-fluoro-3-nitro-1-propyl-1H-indole

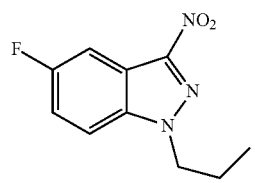

Potassium carbonate (1.5 g, 11.1 mmol) was added to a solution of 5-fluoro-3-nitro-indole (1.0 g, 5.6 mmol) and 1-bromo-propane (820 mg, 6.7 mmol) in ACN (20 mL) at rt. The reaction was heated to 80° C. and stirred overnight. The solution was filtered and concentrated, and the residue was purified by silica gel chromatography to give 520 mg (42%) of the title compound as a brown solid. $^1$H NMR (400 MHz, DMSO-d$_6$): δ 0.86 (3H, t, J=7.2 Hz), 1.81-1.87 (2H, m), 4.30 (2H, t, J=7.2 Hz), 7.28 (1H, td, J=2.4, 9.2 Hz), 7.77-7.86 (2H, m), 8.84 (1H, s).

Preparation 57B: 5-fluoro-1-propyl-1H-indol-3-amine

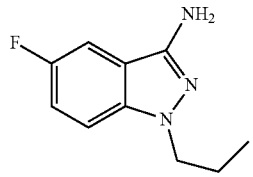

10% Pd/C (20 mg) was added to a solution of Preparation 57A (200 mg, 1.2 mmol) and triethylamine (142 mg, 1.4 mmol) in MeOH (10 mL). The reaction stirred under a balloon of H$_2$ at rt overnight. The reaction was filtered through Celite and concentrated to give the crude title compound, which was used in the next step without purification.

Preparation 57C: methyl 3-[(5-fluoro-1-propyl-1H-indol-3-yl)amino]pyridine-4-carboxylate

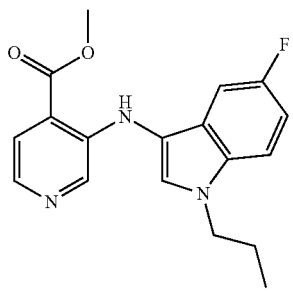 [SMILES: CCCn1cc(Nc2cnccc2C(=O)OC)c2cc(F)ccc21]

The title compound was prepared in 23% yield from methyl 3-bromoisonicotinate and Preparation 57B according to the general procedure for Preparation 1A. $^1$H NMR (400 MHz, CD$_3$OD): δ 0.98 (3H, t, J=7.2 Hz), 1.90-1.96 (2H, m), 4.08 (3H, s), 4.23 (2H, t, J=6.8 Hz), 7.03-7.06 (2H, m), 7.50-7.56 (2H, m), 7.99-8.02 (2H, m), 8.20 (1H, d, J=5.2 Hz). [M+H] calc'd for C$_{18}$H$_{18}$FN$_3$O$_2$, 328; found, 328.

Example 57

3-[(5-fluoro-1-propyl-1H-indol-3-yl)amino]pyridine-4-carboxylic acid

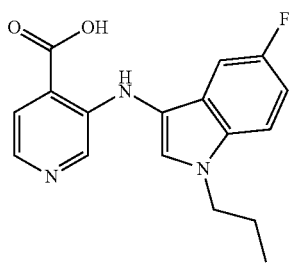 [SMILES: CCCn1cc(Nc2cnccc2C(=O)O)c2cc(F)ccc21]

The title compound was prepared in 79% yield from Preparation 57C according to the general hydrolysis procedure for Example 1. $^1$H NMR (400 MHz, DMSO-d$_6$): δ 0.85 (3H, t, J=7.2 Hz), 1.78-1.83 (2H, m), 4.18 (2H, t, J=7.2 Hz), 6.99-7.07 (2H, m), 7.58-7.66 (3H, m), 7.91 (1H, d, J=4.8 Hz), 8.02 (1H, s), 8.89 (1H, s), 13.68 (1H, br s). [M+H] calc'd for C$_{17}$H$_{16}$FN$_3$O$_2$, 314; found, 314.

Preparation 58A: 3-iodo-5-fluoro-1-[2-(4-methylmorpholin-2-yl)ethyl]-1H-indazole

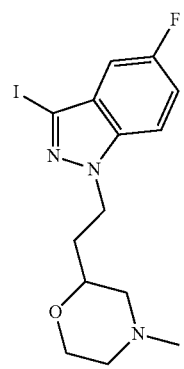 [SMILES: CN1CCOC(CCn2nc(I)c3cc(F)ccc32)C1]

The title compound was prepared from 5-fluoro-3-iodo-indazole and 2-(4-methylmorpholin-2-yl)ethanol in 80% yield according to the general procedure for Preparation 31A. The minor isomer was not isolated or characterized.

Preparation 58B: ethyl 3-({5-fluoro-1-[2-(4-methylmorpholin-2-yl)ethyl]-1H-indazol-3-yl}amino)pyridine-4-carboxylate, TFA salt

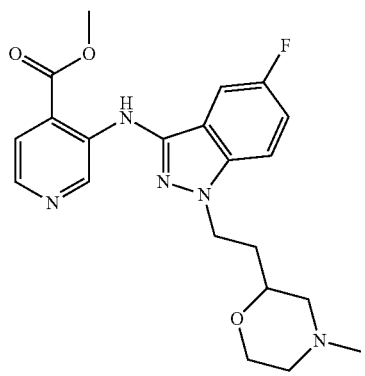 [SMILES: COC(=O)c1ccncc1Nc1nn(CCC2CN(C)CCO2)c2ccc(F)cc12]

The title compound was prepared in 38% yield from methyl 3-aminoisonicotinate and Preparation 58A according to the general procedure for Preparation 1A. The TFA salt was isolated as an orange solid after prep-HPLC purification. $^1$H NMR (400 MHz, CD$_3$OD): δ 2.04-2.07 (1H, m), 2.23-2.25 (1H, m), 2.87 (3H, s), 2.88-2.95 (1H, m), 3.11-3.13 (1H, m), 3.40-3.45 (2H, m), 3.51-3.61 (2H, m), 4.11 (3H, s), 4.14-4.19 (1H, m), 4.50-4.55 (1H, m), 4.61-4.66 (1H, m), 7.32-7.42 (2H, m), 7.60 (1H, dd, J=4.0, 9.2 Hz), 8.17 (1H, d, J=6.0 Hz), 8.24 (1H, d, J=5.6 Hz), 9.79 (1H, s). [M+H] Calc'd for C$_{21}$H$_{24}$FN$_5$O$_3$, 414; Found, 414.

Example 58

3-({5-fluoro-1-[2-(4-methylmorpholin-2-yl)ethyl]-1H-indazol-3-yl}amino)pyridine-4-carboxylic acid, TFA salt

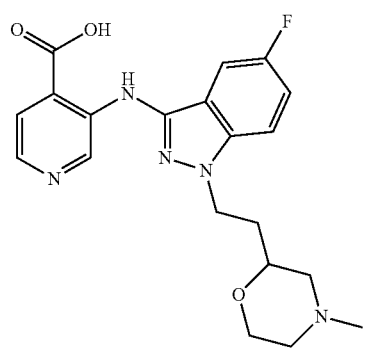 [SMILES: CN1CCOC(CCn2nc(Nc3cnccc3C(=O)O)c3cc(F)ccc32)C1]

The title compound was prepared in 90% yield from Preparation 58B according to the general hydrolysis procedure for Example 1. The TFA salt was isolated as an orange solid after prep-HPLC purification. $^1$H NMR (400 MHz, CD$_3$OD): δ 2.04-2.07 (1H, m), 2.23-2.25 (1H, m), 2.86 (3H, s), 2.87-2.97 (1H, m), 3.11-3.16 (1H, m), 3.41-3.48 (2H, m), 3.58-3.71 (2H, m), 4.18-22 (1H, m), 4.47-4.53 (1H, m), 4.61-4.68 (1H, m), 7.20 (1H, d, J=6.8 Hz), 7.28 (1H, td, J=2.0, 8.8 Hz), 7.56 (1H, dd, J=4.0, 9.2 Hz), 8.18-8.22 (2H, m), 9.83 (1H, s). [M+H] Calc'd for C$_{20}$H$_{22}$FN$_5$O$_3$, 400; Found, 400.

Preparation 59A: 5-chloro-3-nitro-indole

To a solution of 5-chloroindole (2.2 g, 14.8 mmol) and AgNO$_3$ (2.8 g, 16.3 mmol) in ACN (30 mL) was added PhCOCl (1.9 mL, 16.3 mmol) at 0° C., and the mixture was stirred for 2 h. The mixture was diluted with EtOAc (50 mL), filtered, and the filtrate was washed with sat. Na$_2$CO$_3$. Organics were dried over Na$_2$SO$_4$, filtered, concentrated, and the residue was washed with hexanes/EtOAc (10 mL, 1/1) to give 1.5 g (50%) of the title compound as a brown solid. $^1$H NMR (400 MHz, DMSO-d$_6$): δ 7.38 (1H, dd, J=2.0, 8.4 Hz), 7.60 (1H, d, J=8.8 Hz), 8.05 (1H, d, J=2.0 Hz), 8.73 (1H, s), 12.85 (1H, br s).

Preparation 59B: 5-chloro-3-nitro-1-(3,3,3-trifluoropropyl)-1H-indole

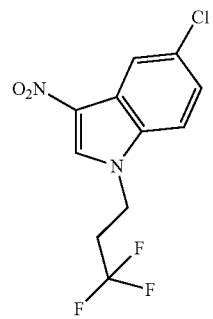 [SMILES: O=[N+]([O-])c1cn(CCC(F)(F)F)c2ccc(Cl)cc12]

Potassium carbonate (1.5 g, 11.1 mmol) was added to a solution of 5-chloro-3-nitro-indole (1.1 g, 5.6 mmol) and 3-bromo-1,1,1-trifluoropropane (1.2 g, 6.7 mmol) in ACN (20 mL) at rt. The mixture was heated to 80° C. and stirred overnight. The reaction mixture was filtered and concentrated to give 1.6 g (100%) of the title compound as a brown solid. $^1$H NMR (400 MHz, CDCl$_3$): δ 2.69-2.76 (2H, m), 4.47 (2H, t, J=7.2 Hz), 7.31 (1H, d, J=8.8 Hz), 7.38 (1H, dd, J=2.0, 8.8 Hz), 8.11 (1H, s), 8.30 (1H, d, J=2.0 Hz).

Preparation 59C: 5-chloro-1-(3,3,3-trifluoropropyl)-1H-indol-3-amine

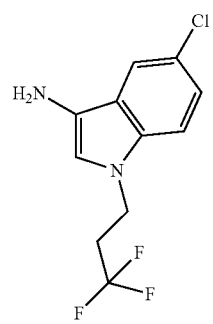

10% Pd/C (20 mg) was added to a solution of Preparation 59B (350 mg, 1.2 mmol) and triethylamine (142 mg, 1.4 mmol) in MeOH (10 mL) at rt under N$_2$. The reaction was charged with H$_2$ and stirred overnight. The reaction mixture was filtered through Celite and concentrated to give the crude title compound, which was used in the next step without purification.

Example 59

3-{[5-chloro-1-(3,3,3-trifluoropropyl)-1H-indol-3-yl]amino}pyridine-4-carboxylic acid

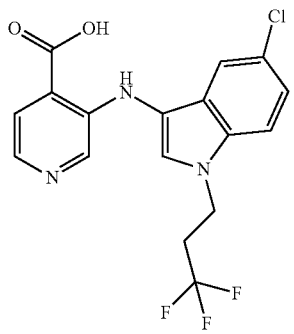 [SMILES: O=C(O)c1ccncc1Nc1cn(CCC(F)(F)F)c2ccc(Cl)cc12]

The title compound was prepared from methyl 3-bromoisonicotinate and Preparation 59C according to the general procedure for Example 6. Purification by prep-HPLC gave the title compound in 9% yield as a yellow solid. $^1$H NMR (400 MHz, DMSO-$d_6$): δ 2.86-2.93 (2H, m), 4.50 (2H, t, J=6.8 Hz), 7.23 (1H, dd, J=1.6, 8.8 Hz), 7.31 (1H, d, J=2.0 Hz), 7.64-7.69 (2H, m), 7.72 (1H, s), 7.94 (1H, d, J=5.2 Hz), 8.07 (1H, s), 8.96 (1H, s). [M+H] Calc'd for $C_{17}H_{13}ClF_3N_3O_2$, 384; Found, 384.

Preparation 60A: BOC-(R)-3-pyrrolidinol

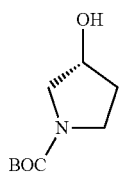

Di-tert-butyl dicarbonate (1.6 g, 7.3 mmol) was added to a solution of (R)-3-pyrrolidinol hydrochloride (1.0 g, 8.1 mmol) in MeOH (20 mL) and triethylamine (3.4 mL, 24.3 mmol) at 0° C. The reaction was stirred overnight while warming to rt. Solvent was removed in vacuo. The residue was diluted with EtOAc (50 mL), washed with water (40 mL×3), washed with brine (50 mL), dried (Na$_2$SO$_4$), and concentrated to give 950 mg (70%) of the title compound as a white solid. $^1$H NMR (400 MHz, DMSO-$d_6$): δ 1.37 (9H, s), 1.60-1.90 (2H, m), 3.00-3.30 (4H, m), 4.19 (1H, m), 4.87 (1H, d, J=2.8 Hz).

Preparation 60B: tert-butyl (3S)-3-(5-fluoro-3-iodo-1H-indazol-1-yl)pyrrolidine-1-carboxylate

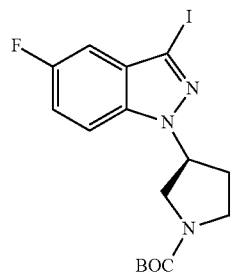 [SMILES: CC(C)(C)OC(=O)N1CC[C@H](n2nc(I)c3cc(F)ccc32)C1]

The title compound was prepared from 5-fluoro-3-iodoindazole and BOC-(R)-3-pyrrolidinol in 32% yield according to the general procedure for Preparation 31A. The minor isomer was not isolated or characterized. $^1$H NMR (400 MHz, CDCl$_3$): δ 1.43 (9H, s), 2.38-2.40 (1H, m), 2.56-2.66 (1H, m), 3.51-3.57 (1H, m), 3.74-3.78 (2H, m), 3.85-3.94 (1H, m), 5.12-5.15 (1H, m), 7.13 (1H, d, J=8.0 Hz), 7.23-7.27 (1H, m), 7.35-7.37 (1H, m).

Preparation 60C: ethyl 3-({5-fluoro-1-[(3S)-pyrrolidin-3-yl]-1H-indazol-3-yl}amino)pyridine-4-carboxylate, TFA salt

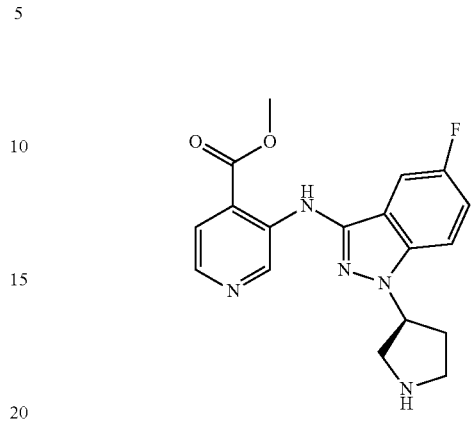

The title compound was prepared in 13% yield from methyl 3-aminoisonicotinate and Preparation 60B according to the general procedure for Preparation 1A, followed by BOC deprotection in 10% 3N HCl/MeOH at 50° C. for 3 h. The TFA salt was isolated after prep-HPLC purification. $^1$H NMR (400 MHz, CD$_3$OD): δ=2.49-2.55 (1H, m), 2.59-2.66 (1H, m), 3.57-3.63 (1H, m), 3.78-3.83 (1H, m), 3.86-3.87 (2H, m), 4.11 (3H, s), 5.67-5.68 (1H, m), 7.38-7.47 (2H, m), 7.70 (1H, dd, J=4.0/9.2 Hz), 8.16 (1H, d, J=5.2 Hz), 8.27 (1H, d, J=5.6 Hz), 9.82 (1H, s) ppm. [M+H] Calc'd for $C_{17}H_{15}F_3N_4O_2$, 356; Found, 356. ee %: >99%.

Example 60

3-({5-fluoro-1-[(3S)-pyrrolidin-3-yl]-1H-indazol-3-yl}amino)pyridine-4-carboxylic acid, TFA salt

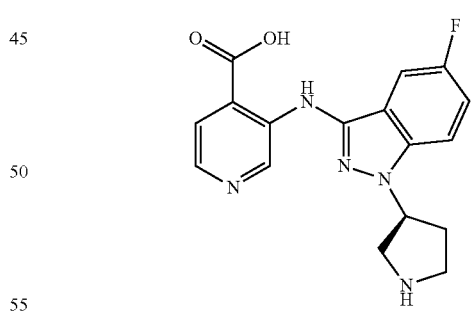

The title compound was prepared in 86% yield from Preparation 60C according to the general hydrolysis procedure for Example 1. The TFA salt was isolated as a yellow solid after prep-HPLC purification. $^1$H NMR (400 MHz, DMSO-$d_6$): δ 2.32-2.40 (1H, m), 2.42-2.50 (1H, m), 3.43-3.47 (1H, m), 3.55-3.61 (2H, m), 3.73-3.75 (1H, m), 5.60-5.63 (1H, m), 7.38-7.48 (2H, m), 7.76-7.80 (2H, m), 8.19 (1H, d, J=4.8 Hz), 9.11-9.22 (2H, m), 9.49 (1H, s), 10.47 (1H, br s). [M+H] Calc'd for $C_{17}H_{16}FN_5O_2$, 342; Found, 342.

Preparation 61A: BOC-(S)-3-pyrrolidinol

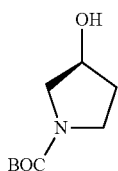

The title compound was prepared in 70% yield from (S)-pyrrolidinol according to the procedure outlined for Preparation 88A. $^1$H NMR (400 MHz, DMSO-d$_6$): δ 1.37 (9H, s), 1.60-1.90 (2H, m), 3.00-3.30 (4H, m), 4.19 (1H, m), 4.87 (1H, d, J=2.8 Hz).

Preparation 61B: tert-butyl (3R)-3-(5-fluoro-3-iodo-1H-indazol-1-yl)pyrrolidine-1-carboxylate

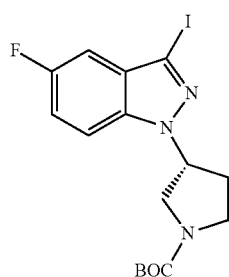 [SMILES: CC(C)(C)OC(=O)N1CC[C@@H](n2nc(I)c3cc(F)ccc32)C1]

The title compound was prepared from 5-fluoro-3-iodoindazole and BOC-(S)-3-pyrrolidinol in 32% yield according to the general procedure for Preparation 31A. The minor isomer was not isolated or characterized. $^1$H NMR (400 MHz, CDCl$_3$): δ 1.43 (9H, s), 2.38-2.40 (1H, m), 2.56-2.66 (1H, m), 3.51-3.57 (1H, m), 3.74-3.78 (2H, m), 3.85-3.94 (1H, m), 5.12-5.15 (1H, m), 7.13 (1H, d, J=8.0 Hz), 7.23-7.27 (1H, m), 7.35-7.37 (1H, m).

Preparation 61C: ethyl 3-({5-fluoro-1-[(3S)-pyrrolidin-3-yl]-1H-indazol-3-yl}amino)pyridine-4-carboxylate, TFA salt

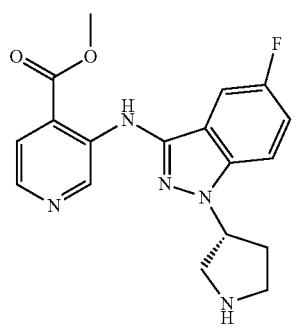 [SMILES: COC(=O)c1ccncc1Nc1nn([C@@H]2CCNC2)c2ccc(F)cc12]

The title compound was prepared in 12% yield from methyl 3-aminoisonicotinate and Preparation 61B according to the general procedure for Preparation 1A, followed by BOC deprotection in 10% 3N HCl/MeOH at 50° C. for 3 h. The TFA salt was isolated after prep-HPLC purification. $^1$H NMR (400 MHz, CD$_3$OD): δ=2.39-2.40 (1H, m) 2.48-2.52 (1H, m), 3.46-3.51 (1H, m), 3.65-3.70 (1H, m) 3.72-3.74 (2H, m), 3.97 (3H, s), 5.52-5.55 (1H, m), 7.24-7.33 (2H, m), 7.55-7.58 (1H, m), 7.99 (1H, d, J=5.2 Hz), 8.13 (1H, d, J=5.6 Hz), 9.65 (1H, s). [M+H] Calc'd for C$_{17}$H$_{15}$F$_3$N$_4$O$_2$, 356; Found, 356. ee %: >99%.

Example 61

3-({5-fluoro-1-[(3S)-pyrrolidin-3-yl]-1H-indazol-3-yl}amino)pyridine-4-carboxylic acid, TFA salt

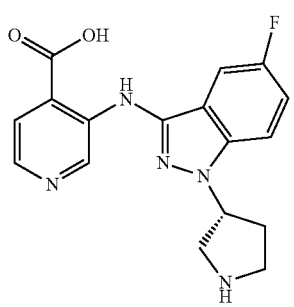 [SMILES: O=C(O)c1ccncc1Nc1nn([C@@H]2CCNC2)c2ccc(F)cc12]

The title compound was prepared in 84% yield from Preparation 61C according to the general hydrolysis procedure for Example 1. The TFA salt was isolated as a yellow solid after prep-HPLC purification. $^1$H NMR (400 MHz, DMSO-d$_6$): δ 2.32-2.40 (1H, m), 2.42-2.50 (1H, m), 3.43-3.47 (1H, m), 3.55-3.61 (2H, m), 3.73-3.75 (1H, m), 5.60-5.63 (1H, m), 7.38-7.48 (2H, m), 7.76-7.80 (2H, m), 8.19 (1H, d, J=4.8 Hz), 9.11-9.22 (2H, m), 9.49 (1H, s), 10.47 (1H, br s). [M+H] Calc'd for C$_{17}$H$_{16}$FN$_5$O$_2$, 342; Found, 342.

Preparation 62A: 5-fluoro-3-iodo-1-(tetrahydro-2H-pyran-4-yl)-1H-indazole

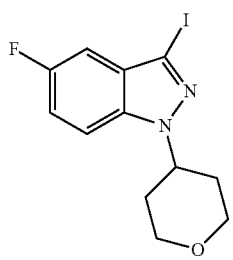 [SMILES: Fc1ccc2c(c1)c(I)nn2C1CCOCC1]

The title compound was prepared from 5-fluoro-3-iodoindazole and tetrahydro-4-pyranol in 56% yield according to the general procedure for Preparation 31A. The minor isomer was not isolated or characterized.

Example 62

3-{[5-fluoro-1-(tetrahydro-2H-pyran-4-yl)-1H-indazol-3-yl]amino}pyridine-4-carboxylic acid

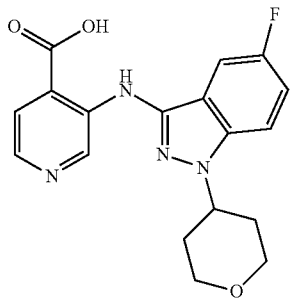 [SMILES: O=C(O)c1ccncc1Nc1nn(C2CCOCC2)c2ccc(F)cc12]

The title compound was prepared from methyl 3-aminoisonicotinate and Preparation 62A according to the general procedure for Example 9. Purification by prep-HPLC gave the title compound in 14% yield as a yellow solid. $^1$H NMR (400 MHz, DMSO-d$_6$): δ 1.87-1.93 (2H, m), 2.08-2.18 (2H, m), 3.52-3.60 (2H, m), 4.02-4.07 (2H, m), 4.83-4.91 (1H, m), 7.34-7.40 (2H, m), 7.79-7.82 (2H, m), 8.17 (1H, d, J=4.8 Hz), 9.54 (1H, s), 10.35 (1H, br s). [M+H] Calc'd for $C_{18}H_{17}FN_4O_3$, 357; Found, 357.

Preparation 63A: 5-fluoro-3-iodo-1-(tetrahydro-2H-pyran-3-yl)-1H-indazole

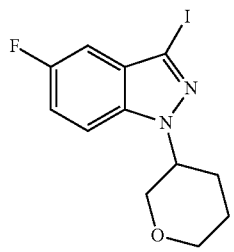 [SMILES: Fc1ccc2c(c1)c(I)nn2C1CCCOC1]

The title compound was prepared from 5-fluoro-3-iodo-indazole and tetrahydro-3-pyranol in 23% yield according to the general procedure for Preparation 31A. The minor isomer was not isolated or characterized. $^1$H NMR (400 MHz, CDCl$_3$): δ 1.86-1.93 (2H, m), 2.20-2.23 (1H, m), 2.34-2.41 (1H, m), 3.48-3.55 (1H, m), 3.80 (1H, t, J=10.4 Hz), 4.00-4.07 (2H, m), 4.50-4.58 (1H, m), 7.12 (1H, dd, J=2.4, 8.0 Hz), 7.21 (1H, td, J=2.4, 8.8 Hz), 7.39 (1H, dd, J=4.0, 8.8 Hz).

Example 63

3-{[5-fluoro-1-(tetrahydro-2H-pyran-3-yl)-1H-indazol-3-yl]amino}pyridine-4-carboxylic acid

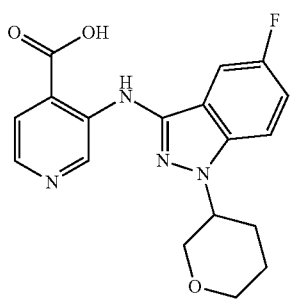 [SMILES: O=C(O)c1ccncc1Nc1nn(C2CCCOC2)c2ccc(F)cc12]

The title compound was prepared from methyl 3-aminoisonicotinate and Preparation 63A according to the general procedure for Example 9. Purification by prep-HPLC gave the title compound in 16% yield as a yellow solid. $^1$H NMR (400 MHz, DMSO-d$_6$): δ 1.80-1.87 (2H, m), 2.16-2.22 (2H, m), 3.43-3.47 (1H, m), 3.68 (1H, t, J=10.0 Hz), 3.90-4.00 (2H, m), 4.71-4.73 (1H, m), 7.34-7.40 (2H, m), 7.78-7.84 (2H, m), 8.17 (1H, d, J=4.4 Hz), 9.48 (1H, s), 10.34 (1H, br s). [M+H] Calc'd for $C_{18}H_{17}FN_4O_3$, 357; Found, 357.

Preparation 64A: 1-(4,4,-difluorocyclohexyl)-5-fluoro-3-iodo-1H-indazole

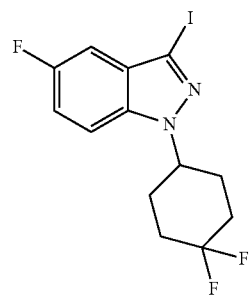 [SMILES: Fc1ccc2c(c1)c(I)nn2C1CCC(F)(F)CC1]

The title compound was prepared from 5-fluoro-3-iodo-indazole and 4,4-difluorocyclohexanol in 17% yield according to the general procedure for Preparation 31A. The minor isomer was not isolated or characterized. $^1$H NMR (400 MHz, CDCl$_3$): δ 1.94-2.17 (4H, m), 2.34-2.52 (4H, m), 4.67-4.73 (1H, m), 7.02 (1H, dd, J=2.4, 8.4 Hz), 7.11 (1H, td, J=2.4, 9.2 Hz), 7.67 (1H, dd, J=4.0, 9.2 Hz).

Example 64

3-{[1-(4,4-difluorocyclohexyl)-5-fluoro-1H-indazol-3-yl]amino}pyridine-4-carboxylic acid

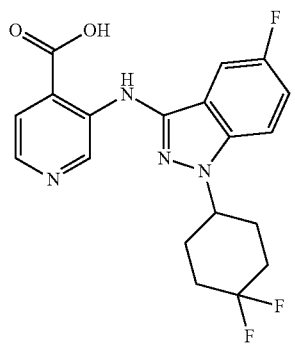 [SMILES: O=C(O)c1ccncc1Nc1nn(C2CCC(F)(F)CC2)c2ccc(F)cc12]

The title compound was prepared from methyl 3-aminoisonicotinate and Preparation 64A according to the general procedure for Example 9. Purification by prep-HPLC gave the title compound in 10% yield as an orange solid. $^1$H NMR (400 MHz, DMSO-d$_6$): δ 2.06-2.33 (8H, m), 4.84-4.89 (1H, m), 7.10-7.13 (1H, m), 7.22-7.29 (1H, m), 7.70 (1H, s), 7.79-7.83 (2H, m), 8.15 (1H, d, J=3.6 Hz), 9.28 (1H, s). [M+H] Calc'd for $C_{19}H_{17}F_3N_4O_3$, 391; Found, 391.

Preparation 65A:
3-iodo-4,5,6,7-tetrahydro-1H-indazole

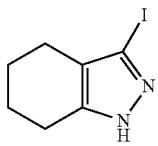

To a suspension of 4,5,6,7-tetrahydroindazole (700 mg, 5.7 mmol) and KOH (1.2 g, 21.5 mmol) in DMF (20 mL) was added $I_2$ (2.9 g, 11.5 mmol) at 0° C., and the reaction was stirred overnight while warming to rt. The reaction mixture was diluted with sat. $Na_2S_2O_3$, extracted with EtOAc (50 mL×3), washed with brine (50 mL), dried ($MgSO_4$), and concentrated to give 1.2 g (83%) of the title compound as a yellow oil. $^1$H NMR (400 MHz, $CDCl_3$): δ 1.73-1.84 (4H, m), 2.40 (2H, t, J=5.6 Hz), 2.54 (2H, t, J=6.0 Hz).

Preparation 65B: 3-iodo-1-(tetrahydrofuran-3-yl)-4,5,6,7-tetrahydro-1H-indazole

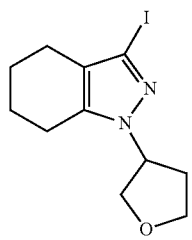 [SMILES: Ic1nn(C2CCOC2)c2c1CCCC2]

The title compound was prepared from Preparation 65A and 3-hydroxytetrahydrofuran in 40% yield according to the general procedure for Preparation 31A. The minor isomer was not isolated or characterized. $^1$H NMR (400 MHz, $CDCl_3$): δ 1.72-1.85 (4H, m), 2.29-2.39 (3H, m), 2.41-2.58 (2H, m), 2.64 (1H, t, J=6.0 Hz), 3.92-3.98 (2H, m), 4.07-4.20 (2H, m), 4.72-4.76 (1H, m).

Example 65

3-{[1-(tetrahydrofuran-3-yl)-4,5,6,7-tetrahydro-1H-indazol-3-yl]amino}pyridine-4-carboxylic acid

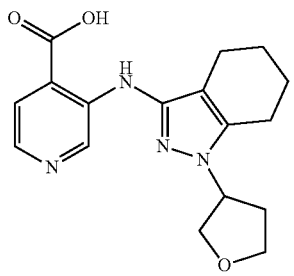 [SMILES: O=C(O)c1ccncc1Nc1nn(C2CCOC2)c2c1CCCC2]

The title compound was prepared from methyl 3-aminoisonicotinate and Preparation 65B according to the general procedure for Example 9. Purification by prep-HPLC gave the title compound in 10% yield as an orange solid. $^1$H NMR (400 MHz, DMSO-$d_6$): δ 1.68-1.77 (4H, m), 2.23-2.33 (4H, m), 2.50 (1H, m), 2.61-2.64 (1H, m), 3.79-3.89 (2H, m), 4.00-4.06 (2H, m), 4.88-4.91 (1H, m), 7.82 (1H, d, J=5.2 Hz), 8.10 (1H, d, J=5.2 Hz), 9.50 (1H, s), 9.87 (1H, br s). [M+H] Calc'd for $C_{17}H_{20}N_4O_3$, 329; Found, 329.

Preparation 66A: 5-fluoro-3-iodo-1-[(3S)-tetrahydrofuran-3-yl]-1H-indazole

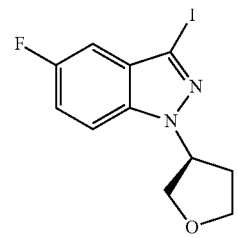 [SMILES: Fc1ccc2c(c1)c(I)nn2[C@H]1CCOC1]

The title compound was prepared from 5-fluoro-3-iodoindazole and (R)-3-hydroxytetrahydrofuran in 56% yield according to the general procedure for Preparation 31A. The minor isomer was not isolated or characterized. $^1$H NMR (400 MHz, $CDCl_3$): δ 2.47-2.52 (2H, m), 3.95-4.00 (1H, m), 4.12-4.19 (2H, m), 4.19-4.28 (1H, m), 5.24-5.30 (1H, m), 7.12 (1H, dd, J=2.0, 8.4 Hz), 7.21 (1H, td, J=1.6, 8.8 Hz), 7.45 (1H, dd, J=4.0, 9.2 Hz).

Example 66

3-({5-fluoro-1-[(3S)-tetrahydrofuran-3-yl]-1H-indazol-3-yl}amino)pyridine-4-carboxylic acid

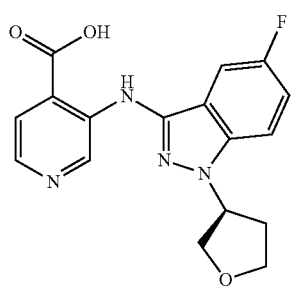 [SMILES: O=C(O)c1ccncc1Nc1nn([C@H]2CCOC2)c2ccc(F)cc12]

The title compound was prepared from methyl 3-aminoisonicotinate and Preparation 66A according to the general procedure for Example 9. Purification by prep-HPLC gave the title compound in 19% yield as a yellow solid. $^1$H NMR (400 MHz, DMSO-$d_6$): δ 2.29-2.45 (2H, m), 3.91-3.92 (2H, m), 4.01-4.13 (2H, m), 5.48-5.49 (1H, m), 7.35-7.41 (2H, m), 7.77-7.79 (2H, m), 8.17 (1H, d, J=4.0 Hz), 9.52 (1H, s), 10.37 (1H, br s), 14.05 (1H, br s). [M+H] Calc'd for $C_{17}H_{15}FN_4O_3$, 343; Found, 343.

Preparation 67A: 5-fluoro-3-iodo-1-[(3R)-tetrahydrofuran-3-yl]-1H-indazole

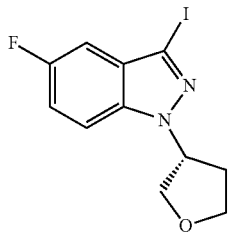 [SMILES: Fc1ccc2c(c1)c(I)nn2[C@@H]1CCOC1]

The title compound was prepared from 5-fluoro-3-iodoindazole and (S)-3-hydroxytetrahydrofuran in 56% yield according to the general procedure for Preparation 31A. The minor isomer was not isolated or characterized. $^1$H NMR (400 MHz, CDCl$_3$): δ 2.47-2.52 (2H, m), 3.95-4.00 (1H, m), 4.12-4.19 (2H, m), 4.19-4.28 (1H, m), 5.24-5.30 (1H, m), 7.12 (1H, dd, J=2.0, 8.4 Hz), 7.21 (1H, td, J=1.6, 8.8 Hz), 7.45 (1H, dd, J=4.0, 9.2 Hz).

Example 67

3-({5-fluoro-1-[(3R)-tetrahydrofuran-3-yl]-1H-indazol-3-yl}amino)pyridine-4-carboxylic acid

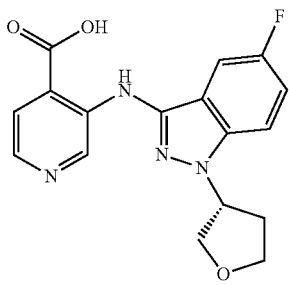 [SMILES: O=C(O)c1ccncc1Nc1nn([C@@H]2CCOC2)c2ccc(F)cc12]

The title compound was prepared from methyl 3-aminoisonicotinate and Preparation 67A according to the general procedure for Example 9. Purification by prep-HPLC gave the title compound in 19% yield as a yellow solid. $^1$H NMR (400 MHz, DMSO-d$_6$): δ 2.29-2.45 (2H, m), 3.91-3.92 (2H, m), 4.01-4.13 (2H, m), 5.48-5.49 (1H, m), 7.35-7.41 (2H, m), 7.77-7.79 (2H, m), 8.17 (1H, d, J=4.0 Hz), 9.52 (1H, s), 10.37 (1H, br s), 14.05 (1H, br s). [M+H] Calc'd for C$_{17}$H$_{15}$FN$_4$O$_3$, 343; Found, 343.

Preparation 68A: 5-fluoro-3-nitro-indole

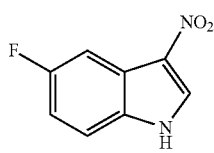 [SMILES: O=[N+]([O-])c1c[nH]c2ccc(F)cc12]

To a solution of 5-fluoroindole (2.0 g, 14.8 mmol) and AgNO$_3$ (2.8 g, 16.3 mmol) in ACN (30 mL) was added PhCOCl (1.9 mL, 16.3 mmol) at 0° C., and the reaction mixture stirred for 2 h at 0° C. The reaction mixture was diluted with EtOAc (50 mL) and filtered. The filtrate was washed with sat. Na$_2$CO$_3$, dried (Na$_2$SO$_4$), and concentrated. The resulting solid was washed with hexanes/EtOAc (10 mL, 1/1) to give the title compound (1.2 g, 45%) as a brown solid.

Preparation 68B: 5-fluoro-3-nitro-1-(tetrahydrofuran-3-yl)-1H-indole

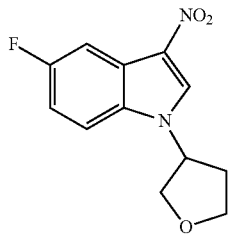 [SMILES: O=[N+]([O-])c1cn(C2CCOC2)c2ccc(F)cc12]

The title compound was prepared from 5-fluoro-3-nitro-indole and 3-hydroxytetrahydrofuran in 18% yield according to the general procedure for Preparation 31A. The minor isomer was not isolated or characterized. $^1$H NMR (400 MHz, CDCl$_3$): δ 2.21-2.27 (1H, m), 2.60-2.69 (1H, m), 3.95-4.01 (1H, m), 4.05-4.09 (1H, m), 4.20-4.25 (2H, m), 5.07-5.10 (1H, m), 7.13 (1H, td, J=2.4, 8.8 Hz), 7.44 (1H, dd, J=4.0, 8.8 Hz), 7.98 (1H, dd, J=2.4, 9.2 Hz), 8.28 (1H, s).

Preparation 68C: 5-fluoro-1-(tetrahydrofuran-3-yl)-1H-indol-3-amine

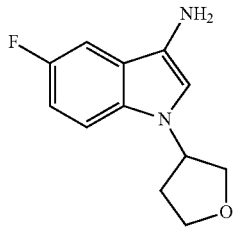 [SMILES: Nc1cn(C2CCOC2)c2ccc(F)cc12]

The title compound was prepared from Preparation 68B according to the general nitro-group reduction procedure for Preparation 59C. The product was used in the next step without purification.

Example 68

3-{[5-fluoro-1-(tetrahydrofuran-3-yl)-1H-indol-3-yl]amino}pyridine-4-carboxylic acid

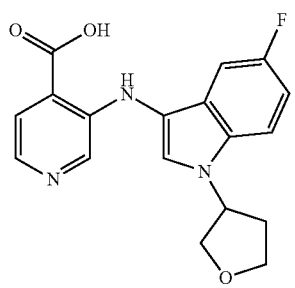 [SMILES: O=C(O)c1ccncc1Nc1cn(C2CCOC2)c2ccc(F)cc12]

The title compound was prepared from methyl 3-bromo-isonicotinate and Preparation 68C according to the general procedure for Example 6. Purification by prep-HPLC gave the title compound in 17% yield as a yellow solid. $^1$H NMR (400 MHz, DMSO-$d_6$): δ 2.12-2.18 (1H, m), 2.50-2.55 (1H, m), 3.80-3.85 (1H, m), 3.91-4.01 (2H, m), 4.04-4.12 (1H, m), 5.29-5.31 (1H, m), 6.97-7.11 (2H, m), 7.62-7.69 (3H, M), 7.90-7.93 (1H, m), 8.02 (1H, d, J=6.8 Hz), 8.91 (1H, s), 13.71 (1H, br s). [M+H] Calc'd for $C_{18}H_{16}FN_3O_3$, 342; Found, 342.

Preparation 69A: 5-chloro-1-(tetrahydrofuran-3-yl)-1H-indazol-3-amine

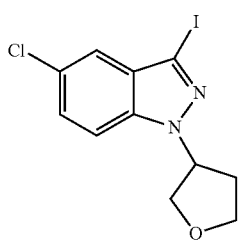 [SMILES: Clc1ccc2c(c1)c(I)nn2C1CCOC1]

The title compound was prepared from 5-chloro-3-iodo-indazole and 3-hydroxytetrahydrofuran in 55% yield according to the general procedure for Preparation 31A. The minor isomer was not isolated or characterized. $^1$H NMR (400 MHz, CDCl$_3$): δ 2.46-2.52 (2H, m), 3.97-4.01 (1H, m), 4.14-4.17 (2H, m), 4.23-4.26 (1H, m), 5.24-5.28 (1H, m), 7.37-7.45 (2H, m), 7.47 (1H, s).

Example 69

3-{[5-chloro-1-(tetrahydrofuran-3-yl)-1H-indazol-3-yl]amino}pyridine-4-carboxylic acid

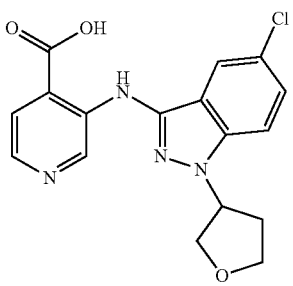 [SMILES: O=C(O)c1ccncc1Nc1nn(C2CCOC2)c2ccc(Cl)cc12]

The title compound was prepared from methyl 3-aminoisonicotinate and Preparation 69A according to the general procedure for Example 9. Purification by prep-HPLC gave the title compound in 18% yield as a yellow solid. $^1$H NMR (400 MHz, DMSO-$d_6$): δ 2.30-2.45 (2H, m), 3.89-3.94 (2H, m), 4.08-4.14 (2H, m), 5.46-5.26 (1H, m), 7.49 (1H, d, J=8.8 Hz), 7.65 (1H, s), 7.76-7.82 (2H, m), 8.19 (1H, d, J=5.2 Hz), 9.58 (1H, s), 10.47 (1H, br s). [M+H] Calc'd for $C_{17}H_{15}ClN_4O_3$, 359; Found, 359.

Preparation 70A

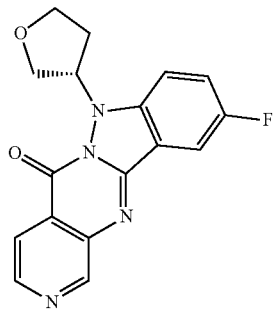 [SMILES: O=c1c2ccncc2nc2c3cc(F)ccc3n([C@H]3CCOC3)n12]

To a suspension of Example 66 (100 mg, 0.29 mmol) in DCM (5 mL) was added oxalyl chloride (74 mg, 0.58 mmol) at 0° C. The solution was stirred for 2 h at rt. Solvent was removed in vacuo to give the crude title compound, which was used in the next step without purification.

Example 70

N-cyano-3-({5-fluoro-1-[(3S)-tetrahydrofuran-3-yl]-1H-indazol-3-yl}amino)pyridine-4-carboxamide

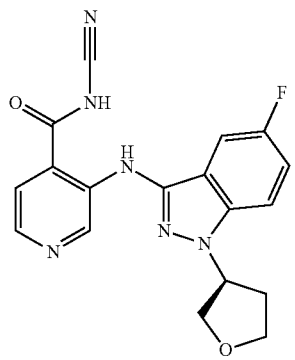 [SMILES: N#CNC(=O)c1ccncc1Nc1nn([C@H]2CCOC2)c2ccc(F)cc12]

To a suspension of Preparation 70A (0.29 mmol) in THF (5 mL) was added cyanamide (122 mg, 2.9 mmol) and t-BuONa (278 mg, 2.9 mmol) at rt, and the reaction stirred overnight. The reaction was concentrated and purified by prep-HPLC to give 40 mg (38%) of the title compound as an orange solid. $^1$H NMR (400 MHz, DMSO-$d_6$): δ 2.28-2.50 (2H, m), 3.94-3.95 (2H, m), 4.11-4.15 (2H, m), 5.49-5.52 (1H, m), 7.30 (1H, d, J=7.2 Hz), 7.41-7.45 (1H, m), 7.79-7.81 (1H, m), 8.32 (1H, d, J=5.6 Hz), 8.40 (1H, d, J=5.6 Hz), 9.67 (1H, s), 12.80 (1H, br s). [M+H] Calc'd for $C_{18}H_{15}FN_6O_2$, 367; Found, 367.

Preparation 71A:
1-(2-chloroethyl)-5-fluoro-3-iodo-1H-indazole

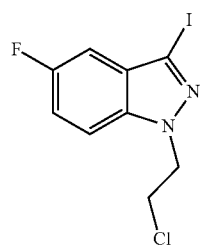 [SMILES: Fc1ccc2c(c1)c(I)nn2CCCl]

To a solution of 5-fluoro-3-iodo-indazole (3.0 g, 11.5 mmol) and 1,2-dichloroethane (5.7 g, 57.3 mmol) in ACN (50 mL) was added K$_2$CO$_3$ (3.2 g, 22.9 mmol) at rt. The reaction was stirred overnight at reflux. The reaction mixture was filtered and concentrated in vacuo. Purification by silica gel chromatography (30:1:5 hexanes/EtOAc/DCM) gave 2.5 g (67%) of the title compound as a yellow solid. $^1$H NMR (300 MHz, CDCl$_3$): δ 3.97 (2H, t, J=6.0 Hz), 4.69 (2H, t, J=6.0 Hz), 7.13 (1H, dd, J=1.8, 7.8 Hz), 7.22-7.29 (1H, m), 7.42 (1H, dd, J=3.9, 9.3 Hz).

Preparation 71B: 1-[2-(3,3-difluoropyrrolidin-1yl)ethyl]-5-fluoro-3-iodo-1H-indazole

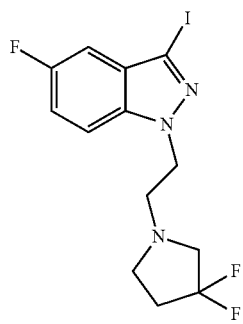 [SMILES: Fc1ccc2c(c1)c(I)nn2CCN1CCC(F)(F)C1]

To a solution of Preparation 71A (904 mg, 2.8 mmol) and 3,3-difluoropyrrolidine hydrochloride (1.0 g, 7.0 mmol) in ACN (30 mL) was added K$_2$CO$_3$ (2.1 g, 15.4 mmol) at rt. The reaction was stirred overnight at reflux. The reaction mixture was filtered and concentrated in vacuo. Purification by silica gel chromatography (5%-10% MeOH/DCM) gave 250 mg (23%) of the title compound as a yellow oil. $^1$H NMR (400 MHz, CDCl$_3$): δ 2.16-2.27 (2H, m), 2.75 (2H, t, J=7.2 Hz), 2.91 (2H, t, J=13.2 Hz), 3.01 (2H, t, J=6.8 Hz), 4.47 (2H, t, J=6.8 Hz), 7.11 (1H, dd, J=2.0, 8.0 Hz), 7.22 (1H, td, J=2.0, 8.8 Hz), 7.35 (1H, dd, J=4.0, 9.2 Hz).

Example 71

3-({1-[2-(3,3-difluoropyrrolidin-1yl)ethyl]-5-fluoro-1H-indazol-3-yl}amino)pyridine-4-carboxylic acid, TFA salt

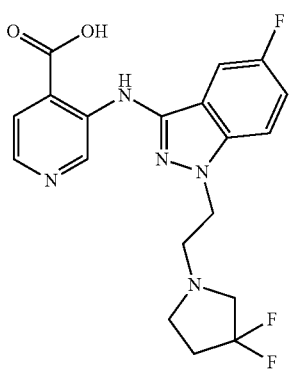 [SMILES: O=C(O)c1ccncc1Nc1nn(CCN2CCC(F)(F)C2)c2ccc(F)cc12]

The title compound was prepared from methyl 3-aminoisonicotinate and Preparation 71B according to the general procedure for Example 9. Purification by prep-HPLC gave the title compound in 55% yield (TFA salt) as a yellow solid. $^1$H NMR (400 MHz, DMSO-d$_6$): δ 2.38-2.48 (2H, m), 3.27-3.31 (2H, m), 3.39-3.60 (4H, m), 4.63 (2H, t, J=6.0 Hz), 7.36-7.45 (2H, m), 7.76-7.82 (2H, m), 8.19 (1H, d, J=4.8 Hz), 9.57 (1H, s), 10.42 (1H, br s). [M+H] Calc'd for C$_{19}$H$_{18}$F$_3$N$_5$O$_2$, 406; Found, 406.

Example 72

N-cyano-3-({1-[2-(3,3-difluoropyrrolidin-1yl)ethyl]-5-fluoro-1H-indazol-3-yl}amino)pyridine-4-carboxamide, TFA salt

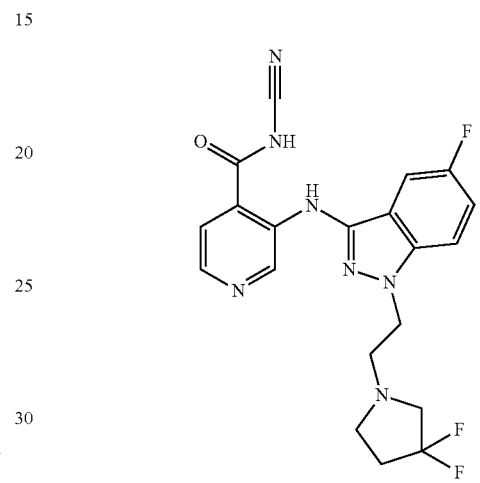

The title compound was prepared in 27% yield from Example 71 according to the general procedures for Preparation 70A and Example 70. $^1$H NMR (400 MHz, DMSO-d$_6$): δ 2.41-2.50 (2H, m), 3.35-3.37 (2H, m), 3.53-3.68 (4H, m), 4.65 (2H, t, J=6.0 Hz), 7.33 (1H, dd, J=2.0, 8.4 Hz), 7.46 (1H, td, J=2.4, 9.2 Hz), 7.80 (1H, dd, J=4.0, 8.8 Hz), 8.29 (2H, dd, J=5.6, 8.0 Hz), 9.62 (1H, s), 12.70 (1H, br s). [M+H] Calc'd for C$_{20}$H$_{18}$F$_3$N$_7$O, 430. Found, 430.

Preparation 73A: 1-[2-(4,4-difluoropiperidin-1yl)ethyl]-5-fluoro-3-iodo-1H-indazole

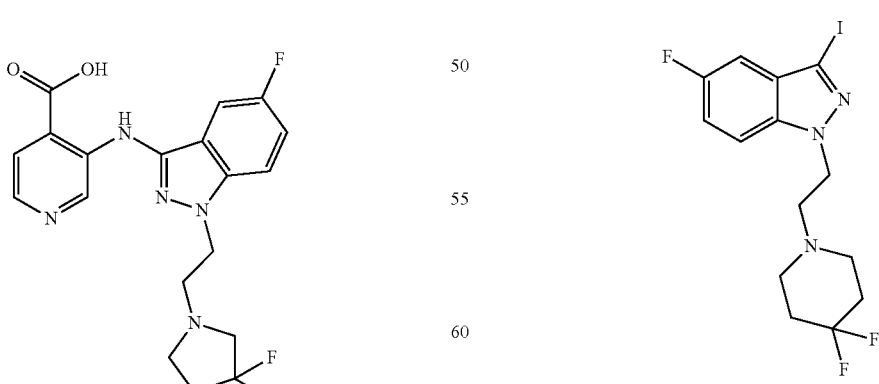

The title compound was prepared in 45% yield from Preparation 71A and 4,4-difluoropiperidine according to the procedure for Preparation 71B. $^1$H NMR (400 MHz, CDCl$_3$): δ 1.86-1.95 (4H, m), 2.58 (4H, t, J=5.2 Hz), 2.90

(2H, t, J=6.8 Hz), 4.47 (2H, t, J=6.4 Hz), 7.11 (1H, d, J=8.0 Hz), 7.21 (1H, t, J=8.4 Hz), 7.35 (1H, dd, J=4.0, 9.2 Hz).

Example 73

3-({1-[2-(4,4-difluoropiperidin-1yl)ethyl]-5-fluoro-1H-indazol-3-yl}amino)pyridine-4-carboxylic acid, TFA salt

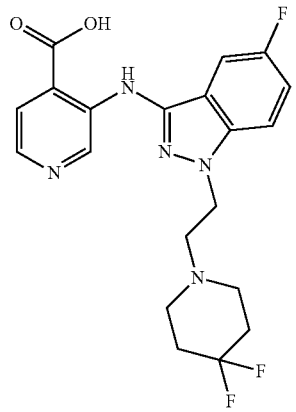 [SMILES: O=C(O)c1ccncc1Nc1nn(CCN2CCC(F)(F)CC2)c2ccc(F)cc12]

The title compound was prepared from methyl 3-aminoisonicotinate and Preparation 73A according to the general procedure for Example 9. Purification by prep-HPLC gave the title compound in 49% yield (TFA salt) as a yellow solid. $^1$H NMR (400 MHz, DMSO-d$_6$): δ 2.27-2.30 (4H, m), 3.40-3.44 (4H, m), 3.60-3.64 (2H, m), 4.76 (2H, t, J=5.6 Hz), 7.33 (1H, d, J=8.0 Hz), 7.43 (1H, td, J=2.0, 8.8 Hz), 7.76-7.79 (2H, m), 8.20 (1H, d, J=5.2 Hz), 9.59 (1H, s), 10.53 (1H, br s). [M+H] Calc'd for C$_{20}$H$_{20}$F$_3$N$_5$O$_2$, 420; Found, 420.

Example 74

N-cyano-3-({1-[2-(4,4-difluoropiperidin-1yl)ethyl]-5-fluoro-1H-indazol-3-yl}amino)pyridine-4-carboxamide, TFA salt

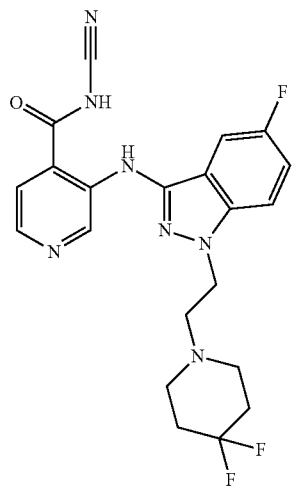 [SMILES: N#CNC(=O)c1ccncc1Nc1nn(CCN2CCC(F)(F)CC2)c2ccc(F)cc12]

The title compound was prepared in 24% yield from Example 73 according to the general procedures for Preparation 70A and Example 70. $^1$H NMR (400 MHz, DMSO-d$_6$): δ 2.2-2.33 (4H, m), 3.17-3.71 (6H, m), 4.77 (2H, t, J=5.6 Hz), 7.34 (1H, dd, J=2.0, 8.4 Hz), 7.49 (1H, td, J=2.0, 8.8 Hz), 7.79 (1H, dd, J=4.0, 9.2 Hz), 8.17 (1H, d, J=5.2 Hz), 8.22 (1H, d, J=5.2 Hz), 9.60 (1H, s), 10.63 (1H, br s). [M+H] Calc'd for C$_{21}$H$_{20}$F$_3$N$_7$O, 444. Found, 444.

Example 75

N-cyano-3-{[5-fluoro-1-(2-methylpropyl)-1H-indazol-3-yl]amino}pyridine-4-carboxamide

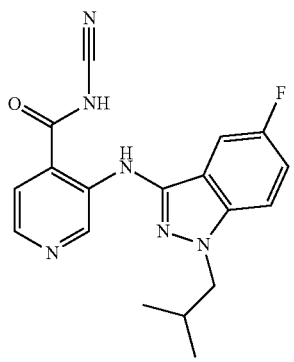 [SMILES: CC(C)Cn1nc(Nc2cnccc2C(=O)NC#N)c2cc(F)ccc21]

The title compound was prepared in 13% yield from Example 25 according to the general procedures for Preparation 70A and Example 70. $^1$H NMR (400 MHz, DMSO-d$_6$): δ 0.89 (6H, d, J=6.7 Hz), 2.25-2.32 (1H, m), 4.17 (2H, d, J=7.1 Hz), 7.27 (1H, dd, J=2.3, 8.5 Hz), 7.36 (1H, td, J=2.4, 9.1 Hz), 7.73 (1H, dd, J=4.1, 9.2 Hz), 8.20-8.24 (2H, m), 9.61 (1H, s), 12.55 (1H, s). [M+H] Calc'd for C$_{18}$H$_{17}$FN$_6$O, 353. Found, 353.

Example 76

N-cyano-3-({1-[4-(dimethylamino)butyl]-5-fluoro-1H-indazol-3-yl}amino)pyridine-4-carboxamide, formic acid salt

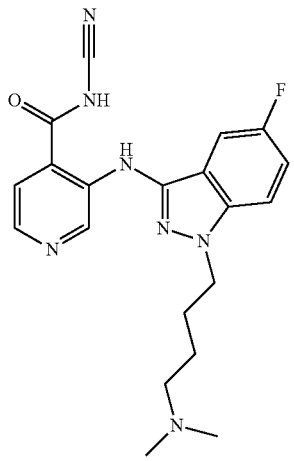 [SMILES: CN(C)CCCCn1nc(Nc2cnccc2C(=O)NC#N)c2cc(F)ccc21]

The title compound was prepared in 13% yield from Example 43 according to the general procedures for Preparation 70A and Example 70. The product was isolated as the formic acid salt after prep-HPLC purification. $^1$H NMR (400 MHz, DMSO-d$_6$): δ 1.59-1.65 (2H, m), 1.83-1.89 (2H, m), 2.65 (6H, s), 3.00 (2H, t, J=7.9 Hz), 4.37 (2H, t, J=6.5 Hz), 7.26 (1H, dd, J=2.0, 8.5 Hz), 7.46 (1H, td, J=2.1, 9.1 Hz), 7.68 (1H, dd, J=4.0, 9.1 Hz), 7.86 (1H, br s), 8.04 (1H, br s), 8.17 (1H, br s), 9.58 (1H, br s), 12.21 (1H, s). [M+H] Calc'd for C$_{20}$H$_{22}$FN$_7$O, 396. Found, 396.

Example 77

N-cyano-3-({5-fluoro-1-[2-(pyrrolidin-1-yl)ethyl]-1H-indazol-3-yl}amino)pyridine-4-carboxamide, formic acid salt

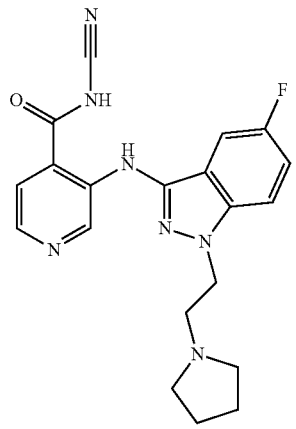 [SMILES: N#CNC(=O)c1ccncc1Nc1nn(CCN2CCCC2)c2ccc(F)cc12]

The title compound was prepared in 66% yield from Example 50 according to the general procedures for Preparation 70A and Example 70. The product was isolated as the formic acid salt after prep-HPLC purification. $^1$H NMR (400 MHz, DMSO-d$_6$): δ 1.77-1.90 (2H, m), 1.91-2.06 (2H, m), 3.09-3.19 (2H, m), 3.55-3.61 (2H, m), 3.69-3.73 (2H, m), 4.69 (2H, t, J=6.0 Hz), 7.30 (1H, dd, J=2.3, 8.4 Hz), 7.44 (1H, td, J=2.3, 9.1 Hz), 7.73 (1H, dd, J=4.1, 9.2 Hz), 7.86 (1H, d, J=5.0 Hz), 8.06 (1H, d, J=5.0 Hz), 8.69 (1H, br s), 9.39 (1H, s), 9.59 (1H, s), 12.38 (1H, s). [M+H] Calc'd for C$_{20}$H$_{20}$FN$_7$O, 394. Found, 394.

Preparation 78A: 5-chloro-3-iodo-1-[2-(pyrrolidin-1-yl)ethyl]-1H-indazole

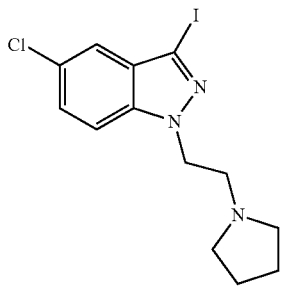 [SMILES: Clc1ccc2c(c1)c(I)nn2CCN1CCCC1]

The title compound was prepared from 5-chloro-3-iodo-indazole and 1-(2-chloroethyl)pyrrolidine hydrochloride in 60% yield according to the procedure for Preparation 50A. $^1$H NMR (400 MHz, CDCl$_3$): δ 1.75-1.80 (4H, m), 2.54-2.59 (4H, m), 2.99 (2H, t, J=7.3 Hz), 4.52 (2H, t, J=7.1 Hz), 7.35-7.39 (2H, m), 7.45 (1H, s). [M+H] Calc'd for C$_{13}$H$_{15}$ClIN$_3$, 376; Found, 376.

Preparation 78B: methyl 3-({5-chloro-1-[2-(pyrrolidin-1-yl)ethyl]-1H-indazol-3-yl}amino)pyridine-4-carboxylate

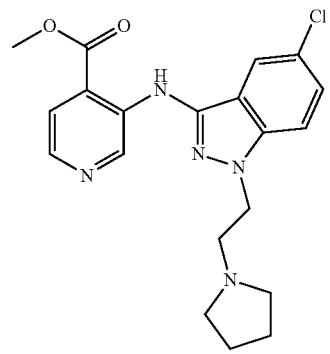 [SMILES: COC(=O)c1ccncc1Nc1nn(CCN2CCCC2)c2ccc(Cl)cc12]

The title compound was prepared from methyl 3-aminoisonicotinate and Preparation 78A in 71% yield according to the general procedure for Preparation 1A. $^1$H NMR (400 MHz, CDCl$_3$): δ 1.75-1.81 (4H, m), 2.56-2.61 (4H, m), 3.03 (2H, t, J=7.2 Hz), 4.00 (3H, s), 4.43 (2H, t, J=7.0 Hz), 7.29-7.37 (2H, m), 7.66 (1H, s), 7.75 (1H, d, J=5.1 Hz), 8.17 (1H, d, J=5.1 Hz), 9.76 (1H, s), 10.14 (1H, s). [M+H] Calc'd for C$_{20}$H$_{22}$ClN$_5$O$_2$, 400; Found, 400.

Example 78

3-({5-chloro-1-[2-(pyrrolidin-1-yl)ethyl]-1H-indazol-3-yl}amino)pyridine-4-carboxylic acid

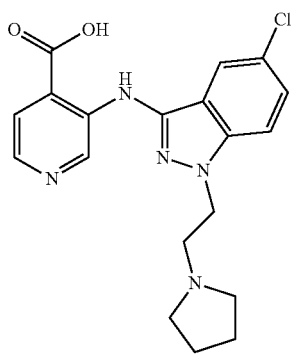 [SMILES: O=C(O)c1ccncc1Nc1nn(CCN2CCCC2)c2ccc(Cl)cc12]

The title compound was prepared in from Preparation 78B in 47% yield according to the general hydrolysis procedure for Example 1. $^1$H NMR (400 MHz, DMSO-d$_6$): δ 1.90-2.01 (4H, m), 3.37-3.49 (4H, m), 3.60-3.71 (2H, m), 4.63-4.469 (2H, m), 7.00 (1H, s), 7.12 (1H, d, J=9.0 Hz), 7.36 (1H, d, J=4.2 Hz), 7.45 (1H, d, J=8.9 Hz), 7.91 (1H, d, J=4.8 Hz), 9.57 (1H, s), 12.31 (1H, s). [M+H] Calc'd for C$_{19}$H$_{20}$ClN$_5$O$_2$, 386; Found, 386.

Example 79

N-cyano-3-({5-chloro-1-[2-(pyrrolidin-1-yl)ethyl]-1H-indazol-3-yl}amino)pyridine-4-carboxamide, formic acid salt

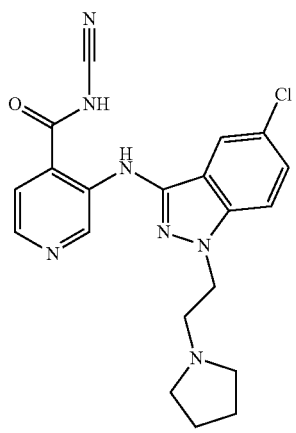 [SMILES: N#CNC(=O)c1ccncc1Nc1nn(CCN2CCCC2)c2ccc(Cl)cc12]

The title compound was prepared in 47% yield from Example 78 according to the general procedures for Preparation 70A and Example 70. The product was isolated as the formic acid salt after prep-HPLC purification. $^1$H NMR (400 MHz, DMSO-d$_6$): δ 1.78-1.90 (2H, m), 1.92-2.07 (2H, m), 3.10-3.20 (2H, m), 3.54-3.61 (2H, m), 3.69-3.73 (2H, m), 4.69 (2H, t, J=5.9 Hz), 7.54 (1H, dd, J=1.9, 8.9 Hz), 7.61 (1H, d, J=1.7 Hz), 7.73 (1H, d, J=8.9 Hz), 7.86 (1H, d, J=4.9 Hz), 8.07 (1H, d, J=4.9 Hz), 8.68 (1H, br s), 9.39 (1H, s), 9.62 (1H, s), 12.51 (1H, s). [M+H] Calc'd for C$_{20}$H$_{20}$ClN$_7$O, 410. Found, 410.

II. Biological Evaluation

Example 1

In Vitro Enzyme Inhibition Assay

This assay determines the ability of a test compound to inhibit Jarid1A, Jarid1B, and JMJD2C demethylase activity. Baculovirus expressed Jarid1A (GenBank Accession #NM_001042603, AA1-1090) was purchased from BPS Bioscience (Cat #50110). Baculovirus expressed Jarid1B (GenBank Accession #NM_006618, AA 2-751) was purchased from BPS Bioscience (Cat #50121) or custom made by MolecularThroughput. Baculovirus expressed JMJD2C (GenBank Accession #BC143571, AA 2-372) was purchased from BPS Bioscience (Cat #50105).

Jarid1A Assay

The enzymatic assay of Jarid1A activity is based upon Time Resolved-Fluorescence Resonance Energy Transfer (TR-FRET) detection. The ability of test compounds to inhibit the activity of Jarid1A was determined in 384-well plate format under the following reaction conditions: 1 nM Jarid1A, 300 nM H3K4me3-biotin labeled peptide (Anaspec cat #64357), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-mono- or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 µl of the mixture of 900 nM H3K4me3-biotin labeled peptide and 6 µM alpha-ketoglutaric acid with 2 µl of 11-point serial diluted inhibitor in 3% DMSO was added to each well of plate, followed by the addition of 2 µl of 3 nM Jarid1A to initiate the reaction. The reaction mixture was incubated at room temperature for 30 minutes, and terminated by the addition of 6 µl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant (IC$_{50}$).

Jarid1B Assay

The ability of test compounds to inhibit the activity of Jarid1B was determined in 384-well plate format under the following reaction conditions: 0.8 nM Jarid1B, 300 nM H3K4me3-biotin labeled peptide (Anaspec cat #64357), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-mono- or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 µl of the mixture of 900 nM H3K4me3-biotin labeled peptide and 6 µM alpha-ketoglutaric acid with 2 µl of 11-point serial diluted inhibitor in 3% DMSO was added to each well of the plate, followed by the addition of 2 µl of 2.4 nM Jarid1B to initiate the reaction. The reaction mixture was incubated at room temperature for 30 minutes, and terminated by the addition of 6 µl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant (IC$_{50}$).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 µl of the mixture of 900 nM H3K9me3-biotin labeled peptide and 6 μM alpha-ketoglutaric acid with 2 μl of 11-point serial diluted inhibitor in 3% DMSO were added to each well of the plate, followed by the addition of 2 μl of 0.9 nM JMJD2C to initiate the reaction. The reaction mixture was incubated at room temperature for 30 minutes, and terminated by the addition of 6 μl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

The ability of the compounds disclosed herein to inhibit demethylase activity was quantified and the respective $IC_{50}$ value was determined. Table 3 provides the $IC_{50}$ values of various compounds disclosed herein.

TABLE 3

| Chemical Synthesis Example | Name | JARID1A $IC_{50}$ (μM) | JARID1B $IC_{50}$ (μM) | JMJD2C $IC_{50}$ (μM) |
|---|---|---|---|---|
| 1 | 3-[(1-methyl-1H-indazol-3-yl)amino]pyridine-4-carboxylic acid | A | A | A |
| 2 | 3-[(2-methyl-2H-indazol-3-yl)amino]pyridine-4-carboxylic acid | C | C | B |
| 3 | 3-(1,2-benzoxazol-3-ylamino]pyridine-4-carboxylic acid | A | A | A |
| 4 | 3-[(5-chloro-1-methyl-1H-indazol-3-yl)amino]pyridine-4-carboxylic acid | A | A | B |
| 5 | 3-[(1,6-dimethyl-1H-indazol-3-yl)amino]pyridine-4-carboxylic acid | A | A | B |
| 6 | 3-[(6-fluoro-1-methyl-1H-indazol-3-yl)amino]pyridine-4-carboxylic acid | A | A | A |
| 7 | 3-[(5-fluoro-1-methyl-1H-indazol-3-yl)amino]pyridine-4-carboxylic acid | A | A | A |
| 8 | 3-[(6-methoxy-1-methyl-1H-indazol-3-yl)amino]pyridine-4-carboxylic acid | A | A | B |
| 9 | 3-[(1-propyl-1H-indazol-3-yl)amino]pyridine-4-carboxylic acid | A | A | B |
| 10 | 3-{[1-(2-methoxyethyl)-1H-indazol-3-yl]amino}pyridine-4-carboxylic acid | A | A | B |
| 11 | 3-[(1-{2-[2-(dimethylamino)ethoxy]ethyl}-1H-indazol-3-yl)amino]pyridine-4-carboxylic acid | A | A | A |
| 12 | 3-[(1,5-dimethyl-1H-indazol-3-yl)amino]pyridine-4-carboxylic acid | A | A | A |
| 13 | 3-[(4-fluoro-1-methyl-1H-indazol-3-yl)amino]pyridine-4-carboxylic acid | A | A | A |
| 14 | 3-[(5-trifluoromethyl-1-methyl-1H-indazol-3-yl)amino]pyridine-4-carboxylic acid | A | A | A |
| 15 | 3-[(5-fluoro-1-propyl-1H-indazol-3-yl)amino]pyridine-4-carboxylic acid | A | A | B |
| 16 | 3-{[1-(cyclopropylmethyl)-5-fluoro-1H-indazol-3-yl]amino}pyridine-4-carboxylic acid | A | A | B |
| 17 | 3-{[5-fluoro-1-(methoxypropyl)-1H-indazol-3-yl]amino}pyridine-4-carboxylic acid | A | A | A |
| 18 | 3-[(5-fluoro-1-pentyl-1H-indazol-3-yl)amino]pyridine-4-carboxylic acid | A | A | B |
| 19 | 3-{[5-fluoro-1-(2-phenethyl)-1H-indazol-3-yl]amino}pyridine-4-carboxylic acid | A | A | B |
| 20 | 3-[(7-fluoro-1-propyl-1H-indazol-3-yl)amino]pyridine-4-carboxylic acid | A | A | A |
| 21 | 3-{[5-fluoro-1-(tetrahydrofuran-2-ylmethyl)-1H-indazol-3-yl]amino}pyridine-4-carboxylic acid | A | A | B |
| 22 | 3-({1-[2-(dimethylamino)pentyl]-5-fluoro-1H-indazol-3-yl}amino)pyridine-4-carboxylic acid | A | A | B |
| 23 | 3-{[5-fluoro-1-(2,2,2-trifluoroethyl)-1H-indazol-3-yl]amino}pyridine-4-carboxylic acid | A | A | B |
| 24 | 3-[(1-benzyl-5-fluoro-1H-indazol-3-yl)amino]pyridine-4-carboxylic acid | A | A | B |
| 25 | 3-{[5-fluoro-1-(2-methylpropyl)-1H-indazol-3-yl]amino}pyridine-4-carboxylic acid | A | A | B |
| 26 | 3-{[5-fluoro-1-(butan-2-yl)-1H-indazol-3-yl]amino}pyridine-4-carboxylic acid | A | A | B |

TABLE 3-continued

| Chemical Synthesis Example | Name | JARID1A IC$_{50}$ (μM) | JARID1B IC$_{50}$ (μM) | JMJD2C IC$_{50}$ (μM) |
|---|---|---|---|---|
| 27 | 3-[(1-{2-[2-(dimethylamino)ethoxy]ethyl}-5-fluoro-1H-indazol-3-yl)amino]pyridine-4-carboxylic acid | A | A | A |
| 28 | 3-{[1-(cyclobutylmethyl)-5-fluoro-1H-indazol-3-yl]amino}pyridine-4-carboxylic acid | A | A | B |
| 29 | 3-[(1-cyclopentyl-5-fluoro-1H-indazol-3-yl)amino]pyridine-4-carboxylic acid | A | A | B |
| 30 | 3-{[1-(cyclopentylmethyl)-5-fluoro-1H-indazol-3-yl]amino}pyridine-4-carboxylic acid | A | A | B |
| 31 | 3-{[1-(cyclopropylethyl)-5-fluoro-1H-indazol-3-yl]amino}pyridine-4-carboxylic acid | A | A | B |
| 32 | 3-{[5-fluoro-1-(3,3,3-trifluoropropyl)-1H-indazol-3-yl]amino}pyridine-4-carboxylic acid | A | A | B |
| 33 | 3-[(5-chloro-1-propyl-1H-indazol-3-yl)amino]pyridine-4-carboxylic acid | A | A | B |
| 34 | 3-{[5-chloro-1-(cyclopropylmethyl)-1H-indazol-3-yl]amino}pyridine-4-carboxylic acid | A | A | B |
| 35 | 3-{[5-chloro-1-(3,3,3-trifluoropropyl)-1H-indazol-3-yl]amino}pyridine-4-carboxylic acid | A | A | B |
| 36 | 3-[(1-ethyl-5-methyl-1H-indazol-3-yl)amino]pyridine-4-carboxylic acid | A | A | B |
| 37 | 3-{[1-(cyclopropylmethyl)-5-methyl-1H-indazol-3-yl]amino}pyridine-4-carboxylic acid | A | A | B |
| 38 | 3-[(5-methyl-1-propyl-1H-indazol-3-yl)amino]pyridine-4-carboxylic acid | A | A | B |
| 39 | 3-{[5-methyl-1-(3,3,3-trifluoropropyl)-1H-indazol-3-yl]amino}pyridine-4-carboxylic acid | A | A | B |
| 40 | 3-[(1-{2-[2-(dimethylamino)ethoxy]ethyl}-5-chloro-1H-indazol-3-yl)amino]pyridine-4-carboxylic acid | A | A | A |
| 41 | 3-({5-fluoro-1-{2-(1-methylpiperidin-4-yl]ethyl}-1H-indazol-3-yl]amino)pyridine-4-carboxylic acid | A | A | A |
| 42 | 3-{[5-fluoro-1-(3-hydroxypropyl)-1H-indazol-3-yl]amino}pyridine-4-carboxylic acid | A | A | A |
| 43 | 3-({1-[4-(dimethylamino)butyl]-5-fluoro-1H-indazol-3-yl}amino)pyridine-4-carboxylic acid | A | A | A |
| 44 | 3-{[5-fluoro-1-(5-hydroxypentyl)-1H-indazol-3-yl]amino}pyridine-4-carboxylic acid | A | A | A |
| 45 | 3-[(5-methyl-1-propyl-1H-indazol-3-yl)amino]pyridine-4-carboxylic acid | A | A | B |
| 46 | 3-({5-fluoro-1-[5-(methylamino)pentyl]-1H-indazol-3-yl}amino)pyridine-4-carboxylic acid | A | A | A |
| 47 | 3-({5-fluoro-1-[2-(piperidin-3-yl)ethyl]-1H-indazol-3-yl}amino)pyridine-4-carboxylic acid | A | A | A |
| 48 | 3-{[1-(2,3-dihydroxypropyl)-5-fluoro-1H-indazol-3-yl]amino}pyridine-4-carboxylic acid | A | A | A |
| 49 | 3-({1-[4-(dimethylamino)but-2-yn-1-yl]-5-fluoro-1H-indazol-3-yl}amino)pyridine-4-carboxylic acid | A | A | A |
| 50 | 3-({5-fluoro-1-[2-(pyrrolidin-1-yl)ethyl]-1H-indazol-3-yl}amino)pyridine-4-carboxylic acid | A | A | A |
| 51 | 3-{[5-fluoro-1-(2-hydroxypropyl)-1H-indazol-3-yl]amino}pyridine-4-carboxylic acid | A | A | A |
| 52 | 3-[(1-methyl-1H-pyrrolo[2,3-b]pyridin-3-yl)amino]pyridine-4-carboxylic acid | A | A | B |

TABLE 3-continued

| Chemical Synthesis Example | Name | JARID1A IC$_{50}$ (μM) | JARID1B IC$_{50}$ (μM) | JMJD2C IC$_{50}$ (μM) |
|---|---|---|---|---|
| 53 | 3-[(5-cyano-1H-indol-3-yl)amino]pyridine-4-carboxylic acid | A | A | A |
| 54 | 3-{[5-fluoro-1-(tetrahydrofuran-3-yl)-1H-indazol-3-yl]amino}pyridine-4-carboxylic acid | A | A | A |
| 55 | 3-{[5-fluoro-1-(3,3,3-trifluoro-2-hydroxypropyl)-1H-indazol-3-yl]amino}pyridine-4-carboxylic acid | A | A | A |
| 56 | 3-({5-fluoro-1-[2-(morpholin-1-yl)ethyl]-1H-indazol-3-yl}amino)pyridine-4-carboxylic acid | A | A | A |
| 57 | 3-[(5-fluoro-1-propyl-1H-indol-3-yl)amino]pyridine-4-carboxylic acid | A | A | B |
| 58 | 3-({5-fluoro-1-[2-(4-methylmorpholin-2-yl)ethyl]-1H-indazol-3-yl}amino)pyridine-4-carboxylic acid | A | A | A |
| 59 | 3-{[5-chloro-1-(3,3,3-trifluoropropyl)-1H-indol-3-yl]amino}pyridine-4-carboxylic acid | A | A | B |
| 60 | 3-({5-fluoro-1-[(3S)-pyrrolidin-3-yl]-1H-indazol-3-yl}amino)pyridine-4-carboxylic acid | A | A | A |
| 61 | 3-({5-fluoro-1-[(3R)-pyrrolidin-3-yl]-1H-indazol-3-yl}amino)pyridine-4-carboxylic acid | A | A | A |
| 62 | 3-{[5-fluoro-1-(tetrahydro-2H-pyran-4-yl)-1H-indazol-3-yl]amino}pyridine-4-carboxylic acid | A | A | B |
| 63 | 3-{[5-fluoro-1-(tetrahydro-2H-pyran-3-yl)-1H-indazol-3-yl]amino}pyridine-4-carboxylic acid | A | A | B |
| 64 | 3-{[1-(4,4-difluorocyclohexyl)-5-fluoro-1H-indazol-3-yl]amino}pyridine-4-carboxylic acid | C | C | C |
| 65 | 3-{[1-(tetrahydro furan-3-yl)-4,5,6,7-tetrahydro-1H-indazol-3-yl]amino}pyridine-4-carboxylic acid | A | A | B |
| 66 | 3-({5-fluoro-1-[(3S)-tetrahydrofuran-3-yl]-1H-indazol-3-yl}amino)pyridine-4-carboxylic acid | A | A | A |
| 67 | 3-({5-fluoro-1-[(3R)-tetrahydrofuran-3-yl]-1H-indazol-3-yl}amino)pyridine-4-carboxylic acid | A | A | A |
| 68 | 3-{[5-fluoro-1-(tetrahydrofuran-3-yl)-1H-indol-3-yl]amino}pyridine-4-carboxylic acid | A | A | B |
| 69 | 3-{[5-chloro-1-(tetrahydrofuran-3-yl)-1H-indazol-3-yl]amino}pyridine-4-carboxylic acid | A | A | B |
| 70 | N-cyano-3-({5-fluoro-1-[(3S)-tetrahydrofuran-3-yl]-1H-indazol-3-yl}amino)pyridine-4-carboxamide | A | A | C |
| 71 | 3-({1-[2-(3,3-difluoropyrrolidin-1yl)ethyl]-5-fluoro-1H-indazol-3-yl}amino)pyridine-4-carboxylic acid | A | A | A |
| 72 | N-cyano-3-({1-[2-(3,3-difluoropyrrolidin-1yl)ethyl]-5-fluoro-1H-indazol-3-yl}amino)pyridine-4-carboxamide | A | A | C |
| 73 | 3-({1-[2-(4,4-difluoropiperidin-1yl)ethyl]-5-fluoro-1H-indazol-3-yl}amino)pyridine-4-carboxylic acid | A | A | A |
| 74 | N-cyano-3-({1-[2-(4,4-difluoropiperidin-1yl)ethyl]-5-fluoro-1H-indazol-3-yl}amino)pyridine-4-carboxamide | A | A | C |
| 75 | N-cyano-3-{[5-fluoro-1-(2-methylpropyl)-1H-indazol-3-yl]amino}pyridine-4-carboxamide | A | A | C |
| 76 | N-cyano-3-({1-[4-(dimethylamino)butyl]-5-fluoro-1H-indazol-3-yl}amino)pyridine-4-carboxamide | A | A | B |

TABLE 3-continued

| Chemical Synthesis Example | Name | JARID1A IC$_{50}$ (μM) | JARID1B IC$_{50}$ (μM) | JMJD2C IC$_{50}$ (μM) |
|---|---|---|---|---|
| 77 | N-cyano-3-({5-fluoro-1-[2-(pyrrolidin-1-yl)ethyl]-1H-indazol-3-yl}amino)pyridine-4-carboxamide | A | A | A |
| 78 | 3-({5-chloro-1-[2-(pyrrolidin-1-yl)ethyl]-1H-indazol-3-yl}amino)pyridine-4-carboxylic acid | A | A | A |
| 79 | N-cyano-3-({5-chloro-1-[2-(pyrrolidin-1-yl)ethyl]-1H-indazol-3-yl}amino)pyridine-4-carboxamide | A | A | B |

Note:
Biochemical assay IC$_{50}$ data are designated within the following ranges:
A: ≤0.10 μM
B: >0.10 μM to ≤1.0 μM
C: >1.0 μM to ≤10 μM
D: >10 μM

Example 2

In Vitro Cell-Based Assay

An assay to measure the degree of cellular inhibition of KDM5A and 5B was developed. This quantitative immuno-blotting assay measures the amount tri-methylated histone H3 at amino acid Lysine number 4, a specific substrate and product of the direct enzymatic activity of the histone demethylases KDM5A and KDM5B from extracts of the ZR-75-1 breast cancer cell line. Upon analysis a correlation was observed between the between inhibition of these enzymes in a biochemical assay and the degree of inhibition of these enzymes within cancer cell lines.

Assay Principle

This assay is a fluorometric immunoassay for the quantification of tri-methyl H3K4 extracted from cells treated with test compound and is used as a measure of the cellular inhibition of KDM5A/B.

Assay Method

ZR-75-1 (PTEN null, ER+) breast cancer cells numbering 50,000 (ATCC) were seeded into each well of a 96-well tissue culture treated plate and then exposed to an 11 point dilution of test compound with final concentration ranges of test compound ranging from 2000 uM to 10 nM. Cells were left in the presence of test compound for 72 hours. Extracts were prepared containing all of the cellular histone material using detergent based lysis and sonication methods. These lysates were subsequently normalized for total protein content using a colorimetric bicinchonic acid assay (MicroBCA Pierce/Thermo Scientific). Normalized cell extracts were then subjected to typical immuno-blotting procedures using NuPage reagents (Life Technologies). Electrophoretically separated histones were then transferred and immobilized using polyvinylidene difluoride membrane (Immobilon-FL Millipore). The amount of tri-methylated lysine 4 of histone H3 was detected using an antibody specific to the tri-methylated state (Cell Signaling Technologies) and quantified on an infrared imager using a densitometry software package (Odyssey CLx, Image Studio, Li-Cor). This background subtracted densitometry value was reported as a ration of the GAPDH amount for that sample and then calculated as a percent of the DMSO treated sample. The software package XL-fit (IDBS) was then used to calculate a relative IC$_{50}$ value for the dilution series of a given test compound according to the equation:

$$\text{fit}=(D+((V\text{max}*(x\char`\^n))/((x\char`\^n)+(Km\char`\^n)))).$$

Table 4 provides the cellular IC$_{50}$ values of various compounds disclosed herein.

TABLE 4

| Chemical Synthesis Example | Cellular IC$_{50}$ (μM) |
|---|---|
| 1 | C |
| 4 | B |
| 5 | C |
| 6 | C |
| 7 | C |
| 8 | C |
| 9 | B |
| 10 | C |
| 11 | D |
| 12 | B |
| 14 | C |
| 15 | C |
| 16 | C |
| 17 | D |
| 18 | C |
| 19 | D |
| 20 | C |
| 21 | C |
| 22 | C |
| 23 | C |
| 24 | D |
| 25 | C |
| 26 | C |
| 27 | D |
| 28 | B |
| 29 | B |
| 30 | C |
| 31 | C |
| 32 | B |
| 33 | B |
| 34 | C |
| 35 | B |
| 37 | B |
| 42 | C |
| 43 | C |
| 45 | C |
| 46 | D |
| 47 | D |
| 48 | D |
| 49 | D |
| 50 | C |
| 51 | C |
| 52 | B |
| 53 | C |
| 54 | C |
| 58 | C |
| 59 | C |
| 60 | C |
| 61 | C |

TABLE 4-continued

| Chemical Synthesis Example | Cellular IC$_{50}$ (μM) |
|---|---|
| 66 | C |
| 67 | C |
| 68 | C |
| 69 | C |
| 71 | C |
| 73 | B |

Note:
Cellular assay IC$_{50}$ data are designated within the following ranges:
A: ≤0.10 μM
B: >0.10 μM to ≤1.0 μM
C: >1.0 μM to ≤10 μM
D: >10 μM Example 3

In Vivo Xenograph Study

Time release pellets containing 0.72 mg 17-β Estradiol are subcutaneously implanted into nu/nu mice. MCF-7 cells are grown in RPMI containing 10% FBS at 5% CO$_2$, 37° C. Cells are spun down and re-suspended in 50% RPMI (serum free) and 50% Matrigel at 1×10$^7$ cells/mL. MCF-7 cells are subcutaneously injected (100 μL/animal) on the right flank 2-3 days post pellet implantation and tumor volume (length× width$^2$/2) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1

Oral Tablet

A tablet is prepared by mixing 48% by weigh of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound, or pharmaceutically acceptable salt thereof, chosen from:
3-({5-fluoro-1-[2-(4-methylmorpholin-2-yl)ethyl]-1H-indazol-3-yl}amino)pyridine-4-carboxylic acid,
3-{[5-chloro-1-(3,3,3-trifluoropropyl)-1H-indol-3-yl]amino}pyridine-4-carboxylic acid,
3-({5-fluoro-1-[(3S)-pyrrolidin-3-yl]-1H-indazol-3-yl}amino)pyridine-4-carboxylic acid,
3-({5-fluoro-1-[(3R)-pyrrolidin-3-yl]-1H-indazol-3-yl}amino)pyridine-4-carboxylic acid,
3-{[5-fluoro-1-(tetrahydro-2H-pyran-4-yl)-1H-indazol-3-yl]amino}pyridine-4-carboxylic acid,
3-{[5-fluoro-1-(tetrahydro-2H-pyran-3-yl)-1H-indazol-3-yl]amino}pyridine-4-carboxylic acid,
3-{[1-(4,4-difluorocyclohexyl)-5-fluoro-1H-indazol-3-yl]amino}pyridine-4-carboxylic acid,
3-{[1-(tetrahydrofuran-3-yl)-4,5,6,7-tetrahydro-1H-indazol-3-yl]amino}pyridine-4-carboxylic acid,
3-({5-fluoro-1-[(3S)-tetrahydrofuran-3-yl]-1H-indazol-3-yl}amino)pyridine-4-carboxylic acid,
3-({5-fluoro-1-[(3R)-tetrahydrofuran-3-yl]-1H-indazol-3-yl}amino)pyridine-4-carboxylic acid,
3-{[5-fluoro-1-(tetrahydrofuran-3-yl)-1H-indol-3-yl]amino}pyridine-4-carboxylic acid,
3-{[5-chloro-1-(tetrahydrofuran-3-yl)-1H-indazol-3-yl]amino}pyridine-4-carboxylic acid,
N-cyano-3-({5-fluoro-1-[(3S)-tetrahydrofuran-3-yl]-1H-indazol-3-yl}amino)pyridine-4-carboxamide,
3-({1-[2-(3,3-difluoropyrrolidin-1yl)ethyl]-5-fluoro-1H-indazol-3-yl}amino)pyridine-4-carboxylic acid,
N-cyano-3-({1-[2-(3,3-difluoropyrrolidin-1 yl)ethyl]-5-fluoro-1H-indazol-3-yl}amino)pyridine-4-carboxamide,
3-({1-[2-(4,4-difluoropiperidin-1 yl)ethyl]-5-fluoro-1H-indazol-3-yl}amino)pyridine-4-carboxylic acid,
N-cyano-3-({1-[2-(4,4-difluoropiperidin-1 yl)ethyl]-5-fluoro-1H-indazol-3-yl}amino)pyridine-4-carboxamide,
N-cyano-3-{[5-fluoro-1-(2-methylpropyl)-1H-indazol-3-yl]amino}pyridine-4-carboxamide,
N-cyano-3-({1-[4-(dimethylamino)butyl]-5-fluoro-1H-indazol-3-yl}amino)pyridine-4-carboxamide,
N-cyano-3-({5-fluoro-1-[2-(pyrrolidin-1-yl)ethyl]-1H-indazol-3-yl}amino)pyridine-4-carboxamide,
3-({5-chloro-1-[2-(pyrrolidin-1-yl)ethyl]-1H-indazol-3-yl}amino)pyridine-4-carboxylic acid, and
N-cyano-3-({5-chloro-1-[2-(pyrrolidin-1-yl)ethyl]-1H-indazol-3-yl}amino)pyridine-4-carboxamide.

2. A pharmaceutical composition comprising a pharmaceutically acceptable carrier and a compound of claim 1, or a pharmaceutically acceptable salt thereof.

3. A method for treating cancer in a subject in need thereof, comprising administering to the subject a composition comprising a compound of claim 1, or a pharmaceutically acceptable salt thereof.

* * * * *